(12) United States Patent
Terrett et al.

(10) Patent No.: US 12,146,157 B2
(45) Date of Patent: *Nov. 19, 2024

(54) ANTI-PTK7 IMMUNE CELL CANCER THERAPY

(71) Applicant: CRISPR THERAPEUTICS AG, Zug (CH)

(72) Inventors: Jonathan Alexander Terrett, Cambridge, MA (US); Jason Sagert, Cambridge, MA (US)

(*) Notice: Subject to any disclaimer, the term of this patent is extended or adjusted under 35 U.S.C. 154(b) by 817 days.

This patent is subject to a terminal disclaimer.

(21) Appl. No.: 16/677,207

(22) Filed: Nov. 7, 2019

(65) Prior Publication Data

US 2020/0140815 A1 May 7, 2020

Related U.S. Application Data

(60) Provisional application No. 62/910,586, filed on Oct. 4, 2019, provisional application No. 62/756,638, filed on Nov. 7, 2018.

(51) Int. Cl.
| | | |
|---|---|---|
| *C12N 5/0783* | (2010.01) | |
| *A61K 35/17* | (2015.01) | |
| *A61K 39/00* | (2006.01) | |
| *A61P 35/00* | (2006.01) | |
| *C07K 14/705* | (2006.01) | |
| *C07K 14/725* | (2006.01) | |
| *C07K 16/40* | (2006.01) | |
| *C12N 15/11* | (2006.01) | |
| *C12N 15/86* | (2006.01) | |

(52) U.S. Cl.
CPC ............ *C12N 5/0636* (2013.01); *A61K 35/17* (2013.01); *A61P 35/00* (2018.01); *C07K 14/7051* (2013.01); *C07K 14/70521* (2013.01); *C07K 14/70575* (2013.01); *C07K 16/40* (2013.01); *C12N 15/11* (2013.01); *C12N 15/86* (2013.01); *A61K 2039/505* (2013.01); *C07K 2317/565* (2013.01); *C07K 2317/622* (2013.01); *C07K 2319/02* (2013.01); *C12N 2750/14143* (2013.01)

(58) Field of Classification Search
CPC ....... C12N 5/0636; A61K 35/17; A61P 35/00; C07K 14/7051; C07K 14/70575; C07K 16/40; C07K 2317/622

See application file for complete search history.

(56) References Cited

U.S. PATENT DOCUMENTS

| | | | |
|---|---|---|---|
| 5,858,358 A | 1/1999 | June et al. | |
| 5,883,223 A | 3/1999 | Gray | |
| 6,140,081 A | 10/2000 | Barbas | |
| 6,352,694 B1 | 3/2002 | June et al. | |
| 6,453,242 B1 | 9/2002 | Eisenberg et al. | |
| 6,534,055 B1 | 3/2003 | June et al. | |
| 6,534,261 B1 | 3/2003 | Cox et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 7,888,121 B2 | 2/2011 | Urnov et al. | |
| 7,972,854 B2 | 7/2011 | Miller et al. | |
| 9,102,738 B2 | 8/2015 | Terrett et al. | |
| 9,409,995 B2 | 8/2016 | Foord et al. | |
| 2011/0145940 A1 | 6/2011 | Voytas et al. | |
| 2016/0152723 A1* | 6/2016 | Chen | C07K 16/2803 435/254.2 |

FOREIGN PATENT DOCUMENTS

| | | | |
|---|---|---|---|
| WO | 98/53058 A1 | 11/1998 | |
| WO | 98/53059 A1 | 11/1998 | |
| WO | 98/53060 A1 | 11/1998 | |
| WO | 02/16536 A1 | 2/2002 | |
| WO | 03/16496 A2 | 2/2003 | |
| WO | 2007/067730 A2 | 6/2007 | |
| WO | 2016/069282 A1 | 5/2016 | |
| WO | 2016/069283 | 5/2016 | |
| WO | WO-2017172981 A2 * | 10/2017 | ............ A61K 35/17 |
| WO | 2018/027036 A1 | 2/2018 | |
| WO | WO-2019067805 A1 * | 4/2019 | ............ A61K 35/17 |

OTHER PUBLICATIONS

Eyquem et al. Targeting a CAR to the TRAC locus with CRISPR/Cas9 enhances tumour rejection. Nature Mar. 2, 2017 vol. 543 p. 113—OF Record (Year: 2017).*

Ren et al. Multiplex Genome Editing to Generate Universal CAR T Cells Resistant to PD1 Inhibition. Clin Cancer Res; 23(9) May 1, 2017. OF Record (Year: 2016).*

SEQ alignment. Instant Seq ID No. 50. (Year: 2022).*

Fujiwara. Hinge and Transmembrane Domains of Chimeric Antigen Receptor Regulate Receptor Expression and Signaling Threshold. Cells 2020, 9, 1182 (Year: 2020).*

Al-Lazikani et al., Standard conformations for the canonical structures of immunoglobulins, J. Mol. Biol., 273:927-948 (1997).

Almagro, Identification of differences in the specificity-determining residues of antibodies that recognize antigens of different size: implications for the rational design of antibody repertoires, J. Mol. Recognit., 17:132-143 (2004).

(Continued)

*Primary Examiner* — Amy E Juedes
*Assistant Examiner* — Brian Hartnett
(74) *Attorney, Agent, or Firm* — Casimir Jones, S.C.; J. Mitchell Jones

(57) ABSTRACT

Provided herein, in some embodiments, are methods and compositions (e.g., cell compositions) for the treatment of cancer, such as $PTK7^+$ malignancies.

24 Claims, 34 Drawing Sheets

Specification includes a Sequence Listing.

(56) References Cited

OTHER PUBLICATIONS

Bauer et al., Generation of genomic deletions in mammalian cell lines via CRISPR/Cas9, J. Vis. Exp., 95;e52118 (2015).
Chang et al., Modification of DNA ends can decrease end joining relative to homologous recombination in mammalian cells, Proc. Natl. Acad. Sci. USA., 84:4959-4963 (1987).
Chothia et al., Canonical structures for the hypervariable regions of immunoglobulins, J. Mol. Biol., 196:901-917 (1987).
Chothia et al., Conformations of immunoglobulin hypervariable regions, Nature, 342:877-883 (1989).
Deltcheva et al., Crispr RNA maturation by trans-encoded small RNA and host factor RNase III, Nature, 471:602-607 (2011).
Enblad et al., CAR T-Cell Therapy: The Role of Physical Barriers and Immunosuppression in Lymphoma, Human Gene. Therapy., 26:498-505 (2015).
Eyquem et al., Targeting a CAR to the TRAC locus with CRISPR/Cas9 enhances tumour rejection, Nature, 543:113-117 (2017).
International Application No. PCT/IB2019/059585, International Search Report and Written Opinion, mailed Feb. 10, 2020.
Jinek et al., A programmable dual-RNA-guided DNA endonuclease in adaptive bacterial immunity, Science, 337:816-821 (2012).
Kakarla et al., CAR T cells for solid tumors: armed and ready to go?, Cancer J., 20:151-155 (2014).
Liu et al., CRISPR-Cas9-mediated multiplex gene editing in CAR-T cells, Cell Res., 27(1):154-157 (2017).
Maude et al., CD19-targeted chimeric antigen receptor T-cell therapy for acute lymphoblastic leukemia, Blood, 125:4017-4023 (2015).
Morgan, Risky business: target choice in adoptive cell therapy, R. Blood, 122:3392-3394 (2013).
Nehls et al., Two Genetically Separable Steps in the Differentiation of Thymic Epithelium, Science, 272:886-889 (1996).
Ren et al., A versatile system for rapid multiplex genome-edited Car T cell generation, Oncot., 8(10):17002-17011 (2017).
Ren et al., Multiplex Genome Editing to Generate Universal Car T Cells Resistant to PD1 Inhibition, Clin. Cancer Res., 23(9):2255-2266 (2016).

* cited by examiner

OVARIAN

COLON & SCLC

BREAST

SEQUENCE LISTING

<160> NUMBER OF SEQ ID NOS: 113

<210> SEQ ID NO 1
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 1
aagagcaaca aatctgact                                              19

<210> SEQ ID NO 2
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 2
aagagcaaca gtgctgtgcc tggagcaaca aatctgacta agagcaacaa atctgact    58

<210> SEQ ID NO 3
<211> LENGTH: 52
<212> TYPE: DNA
<213> ORGANISM: Artificial Sequence

```
<220> FEATURE:
<223> OTHER INFORMATION: Synthetic Polynucleotide

<400> SEQUENCE: 3
aagagcaaca gtgctggagc aacaaatctg actaagagca acaaatctga ct            52

<210> SEQ ID NO 4
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 4
aagagcaaca gtgcctggag caacaaatct gactaagagc aacaaatctg act           53

<210> SEQ ID NO 5
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 5
aagagcaaca gtgctgacta agagcaacaa atctgact                            38

<210> SEQ ID NO 6
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 6
aagagcaaca gtgctgtggg cctggagcaa caaatctgac taagagcaac aaatctgact    60

<210> SEQ ID NO 7
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 7
aagagcaaca gtgctggcct ggagcaacaa atctgactaa gagcaacaaa tctgact       57

<210> SEQ ID NO 8
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 8
aagagcaaca gtgctgtgtg cctggagcaa caaatctgac taagagcaac aaatctgact    60

<210> SEQ ID NO 9
<211> LENGTH: 79
<212> TYPE: DNA
<213> ORGANISM: Artificial Sequence
<220> FEATURE:
<223> OTHER INFORMATION: Synthetic Polynucleotide

<400> SEQUENCE: 9
cgtggcctta gctgtgctcg cgctactctc tctttctgcc tggaggctat ccagcgtgag    60
```
tctctcctac cctcccgct                                              79

<210> SEQ ID NO 10
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 10
cgtggcctta gctgtgctcg cgctactctc tctttcgcct ggaggctatc cagcgtgagt    60
ctctcctacc ctcccgct                                                 78

<210> SEQ ID NO 11
<211> LENGTH: 75
<212> TYPE: DNA
<213> ORGANISM: Artificial Sequence
<220> FEATURE:
<223> OTHER INFORMATION: Synthetic Polynucleotide

<400> SEQUENCE: 11
cgtggcctta gctgtgctcg cgctactctc tctttctgga ggctatccag cgtgagtctc    60
tcctaccctc ccgct                                                    75

<210> SEQ ID NO 12
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 12
cgtggcctta gctgtgctcg cgctactctc tctttctgga tagcctggag gctatccagc    60
gtgagtctct cctaccctcc cgct                                          84

<210> SEQ ID NO 13
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 13
cgtggcctta gctgtgctcg cgctatccag cgtgagtctc tcctaccctc ccgct        55

<210> SEQ ID NO 14
<211> LENGTH: 82
<212> TYPE: DNA
<213> ORGANISM: Artificial Sequence
<220> FEATURE:
<223> OTHER INFORMATION: Synthetic Polynucleotide

<400> SEQUENCE: 14
cgtggcctta gctgtgctcg cgctactctc tctttctgtg gcctggaggc tatccagcgt    60
gagtctctcc taccctcccg ct                                            82

<210> SEQ ID NO 15
<211> LENGTH: 100
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature

```
<222> LOCATION: (1)..(20)
<223> OTHER INFORMATION: n is a, c, g, t or u

<400> SEQUENCE: 15
nnnnnnnnnn nnnnnnnnnn guuuuagagc uagaaauagc aaguuaaaau aaggcuaguc    60
cguuaucaac uugaaaaagu ggcaccgagu cggugcuuuu                         100

<210> SEQ ID NO 16
<211> LENGTH: 96
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)
<223> OTHER INFORMATION: n is a, c, g, t or u

<400> SEQUENCE: 16
nnnnnnnnnn nnnnnnnnnn guuuuagagc uagaaauagc aaguuaaaau aaggcuaguc    60
cguuaucaac uugaaaaagu ggcaccgagu cggugc                              96

<210> SEQ ID NO 17
<211> LENGTH: 78
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: repeat_region
<222> LOCATION: (1)..(1)
<223> OTHER INFORMATION: Can be repeated 17-30 times
<220> FEATURE:
<221> NAME/KEY: misc_feature
<222> LOCATION: (1)..(1)
<223> OTHER INFORMATION: n is a, c, g, t or u

<400> SEQUENCE: 17
nguuuuagag cuagaaauag caaguuaaaa uaaggcuagu ccguuaucaa cuugaaaaag    60
uggcaccgag ucggugcu                                                  78

<210> SEQ ID NO 18
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 18
agagcaacag ugcuguggcc guuuuagagc uagaaauagc aaguuaaaau aaggcuaguc    60
cguuaucaac uugaaaaagu ggcaccgagu cggugcuuuu                         100

<210> SEQ ID NO 19
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 19
agagcaacag ugcuguggcc                                                20

<210> SEQ ID NO 20
<211> LENGTH: 100
<212> TYPE: DNA
```

<213> ORGANISM: Artificial Sequence
<220> FEATURE:
<223> OTHER INFORMATION: Synthetic Polynucleotide

<400> SEQUENCE: 20
gcuacucucu cuuucuggcc guuuuagagc uagaaauagc aaguuaaaau aaggcuaguc    60
cguuaucaac uugaaaaagu ggcaccgagu cggugcuuuu                         100

<210> SEQ ID NO 21
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 21
gcuacucucu cuuucuggcc                                               20

<210> SEQ ID NO 22
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 22
cugcagcuuc uccaacacau guuuuagagc uagaaauagc aaguuaaaau aaggcuaguc    60
cguuaucaac uugaaaaagu ggcaccgagu cggugcuuuu                         100

<210> SEQ ID NO 23
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 23
cugcagcuuc uccaacacau                                               20

<210> SEQ ID NO 24
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 24 gcuuggucc cauuggucgc guuuuagagc uagaaauagc aaguuaaaau aaggcuaguc     60
cguuaucaac uugaaaaagu ggcaccgagu cggugcuuuu                         100

<210> SEQ ID NO 25
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 25 gcuuggucc cauuggucgc                                                20

<210> SEQ ID NO 26
<211> LENGTH: 100
<212> TYPE: DNA
<213> ORGANISM: Artificial Sequence

```
<220> FEATURE:
<223> OTHER INFORMATION: Synthetic Polynucleotide

<400> SEQUENCE: 26
gcccgcagga cgcacccaua guuuagagc uagaaauagc aaguuaaaau aaggcuaguc    60
cguuaucaac uugaaaaagu ggcaccgagu cggugcuuuu                        100

<210> SEQ ID NO 27
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 27
gcccgcagga cgcacccaua                                              20

<210> SEQ ID NO 28
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 28
agagcaacag ugcuguggcc guuuagagc uagaaauagc aaguuaaaau aaggcuaguc    60
cguuaucaac uugaaaaagu ggcaccgagu cggugcuuuu                        100

<210> SEQ ID NO 29
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 29
agagcaacag ugcuguggcc                                              20

<210> SEQ ID NO 30
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 30
gcuacucucu cuuucuggcc guuuagagc uagaaauagc aaguuaaaau aaggcuaguc    60
cguuaucaac uugaaaaagu ggcaccgagu cggugcuuuu                        100

<210> SEQ ID NO 31
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 31
gcuacucucu cuuucuggcc                                              20

<210> SEQ ID NO 32
<211> LENGTH: 100
<212> TYPE: DNA
<213> ORGANISM: Artificial Sequence
<220> FEATURE:
```

<223> OTHER INFORMATION: Synthetic Polynucleotide

<400> SEQUENCE: 32
cugcagcuuc uccaacacau guuuuagagc uagaaauagc aaguuaaaau aaggcuaguc    60
cguuaucaac uugaaaaagu ggcaccgagu cggugcuuuu                        100

<210> SEQ ID NO 33
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 33
cugcagcuuc uccaacacau                                               20

<210> SEQ ID NO 34
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 34 gcuuggucc cauuggucgc guuuuagagc uagaaauagc aaguuaaaau aaggcuaguc    60
cguuaucaac uugaaaaagu ggcaccgagu cggugcuuuu                        100

<210> SEQ ID NO 35
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 35 gcuuggucc cauuggucgc                                                20

<210> SEQ ID NO 36
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 36
gcccgcagga cgcacccaua guuuuagagc uagaaauagc aaguuaaaau aaggcuaguc    60
cguuaucaac uugaaaaagu ggcaccgagu cggugcuuuu                        100

<210> SEQ ID NO 37
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 37
gcccgcagga cgcacccaua                                               20

<210> SEQ ID NO 38
<211> LENGTH: 23
<212> TYPE: DNA
<213> ORGANISM: Artificial Sequence
<220> FEATURE:
<223> OTHER INFORMATION: Synthetic Polynucleotide

```
<400> SEQUENCE: 38
gctttggtcc cattggtcgc ggg                                            23

<210> SEQ ID NO 39
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 39
gcccgcagga cgcacccata ggg                                            23

<210> SEQ ID NO 40
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 40
agagcaacag tgctgtggcc tgg                                            23

<210> SEQ ID NO 41
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 41
gctactctct ctttctggcc tgg                                            23

<210> SEQ ID NO 42
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 42
ctgcagcttc tccaacacat cgg                                            23

<210> SEQ ID NO 43
<211> LENGTH: 126
<212> TYPE: DNA
<213> ORGANISM: Artificial Sequence
<220> FEATURE:
<223> OTHER INFORMATION: Synthetic Polynucleotide

<400> SEQUENCE: 43
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

<210> SEQ ID NO 44
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 44
```

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 45
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 45
tcaaagcgga gtaggttgtt gcattccgat tacatgaata tgactcctcg ccggcctggg      60
ccgacaagaa aacattacca accctatgcc cccccacgag acttcgctgc gtacaggtcc     120

<210> SEQ ID NO 46
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 46

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40

<210> SEQ ID NO 47
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 47
cgagtgaagt tttcccgaag cgcagacgct ccggcatatc agcaaggaca gaatcagctg      60
tataacgaac tgaatttggg acgccgcgag gagtatgacg tgcttgataa cgccggggg     120 agagacccgg aaatgggggg taaaccccga agaaagaatc cccaagaagg actctacaat    180
gaactccaga aggataagat ggcggaggcc tactcagaaa taggtatgaa gggcgaacga    240
cgacggggaa aaggtcacga tggcctctac caagggttga gtacggcaac caaagatacg    300
tacgatgcac tgcatatgca ggccctgcct cccaga                              336

<210> SEQ ID NO 48
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 48

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 49
<211> LENGTH: 1530
<212> TYPE: DNA
<213> ORGANISM: Artificial Sequence
<220> FEATURE:
<223> OTHER INFORMATION: Synthetic Polynucleotide

<400> SEQUENCE: 49
atggcgctgc cggtgaccgc gctgctgctg ccgctggcgc tgctgctgca tgcggcgcgc      60
ccgcaggtgc agctggtgga aagcggcggc ggcgtggtgc agccgggccg cagcctgcgc     120
ctgagctgcg cggcgagcgg ctttaccttt agcagctatg catgcattg ggtgcgccag      180
gcgccgggca aaggcctgga atgggtggcg gtgatttggg atgatggcag caacaaatat     240
tatgtggata gcgtgaaagg ccgctttacc attagccgcg ataacagcaa aaacaccctg     300
tatctgcaga tgaacagcct gcgcgcggaa gataccgcgg tgtattattg cgcgcgcgat     360
gattattatg gcagcggcag ctttaacagc tattatggca ccgatgtgtg gggccagggc     420
accaccgtga ccgtgagcag cggcggcggc ggcagcggcg gcggcggcag cggcggcggc     480
ggcagcgaaa ttgtgctgac ccagagcccg gcgaccctga gcctgagccc gggcgaacgc     540
gcgaccctga gctgccgcgc gagccagagc gtgagcattt atctggcgtg gtatcagcag     600
aaaccgggcc aggcgccgcg cctgctgatt tatgatgcga gcaaccgcgc gaccggcatt     660
ccggcgcgct ttagcggcag cggcagcggc accgatttta ccctgaccat tagcagcctg     720
gaaccggaag attttgcggt gtattattgc cagcagcgca gcaactggcc gccgtttacc     780
tttggcccgg gcaccaaagt ggatattaaa gcgcggcgg cgtttgtgcc ggtgtttctg      840
ccggcgaaac cgaccaccac cccggcgccg cgcccgccga cccggcgcc gaccattgcg      900
agccagccgc tgagcctgcg cccggaagcg tgccgcccgg cggcgggcgg cgcggtgcat     960
acccgcggcc tggattttgc gtgcgatatt tatatttggg cgccgctggc gggcacctgc    1020
ggcgtgctgc tgctgagcct ggtgattacc ctgtattgca accatcgcaa ccgcagcaaa    1080
cgcagccgcc tgctgcatag cgattatatg aacatgaccc cgcgccgccc gggcccgacc    1140
cgcaaacatt atcagccgta tgcgccgccg cgcgattttg cggcgtatcg cagccgcgtg    1200
aaatttagcc gcagcgcgga tgcgccggcg tatcagcagg gccagaacca gctgtataac    1260
gaactgaacc tgggccgccg cgaagaatat gatgtgctgg ataaacgccg cggccgcgat    1320
ccggaaatgg gcggcaaacc gcgccgcaaa aacccgcagg aaggcctgta taacgaactg    1380
cagaaagata aaatggcgga agcgtatagc gaaattggca tgaaaggcga acgccgccgc    1440
ggcaaaggcc atgatggcct gtatcagggc ctgagcaccg cgaccaaaga tacctatgat    1500
gcgctgcata tgcaggcgct gccgccgcgc                                    1530

```
<210> SEQ ID NO 50
<211> LENGTH: 510
<212> TYPE: PRT
<213> ORGANISM: Artificial Sequence
<220> FEATURE:
<223> OTHER INFORMATION: Synthetic Polypeptide

<400> SEQUENCE: 50
```

| | | | | | | | | | | | | | | |
|---|---|---|---|---|---|---|---|---|---|---|---|---|---|---|
| Met | Ala | Leu | Pro | Val | Thr | Ala | Leu | Leu | Leu | Pro | Leu | Ala | Leu | Leu |
| 1 | | | | 5 | | | | | 10 | | | | | 15 |
| His | Ala | Ala | Arg | Pro | Gln | Val | Gln | Leu | Val | Glu | Ser | Gly | Gly | Val |
| | | | 20 | | | | | 25 | | | | | 30 | |
| Val | Gln | Pro | Gly | Arg | Ser | Leu | Arg | Leu | Ser | Cys | Ala | Ala | Ser | Gly | Phe |
| | | 35 | | | | | 40 | | | | | 45 | | |
| Thr | Phe | Ser | Ser | Tyr | Gly | Met | His | Trp | Val | Arg | Gln | Ala | Pro | Gly | Lys |
| | | 50 | | | | | 55 | | | | | 60 | | |
| Gly | Leu | Glu | Trp | Val | Ala | Val | Ile | Trp | Asp | Asp | Gly | Ser | Asn | Lys | Tyr |
| 65 | | | | | 70 | | | | | 75 | | | | | 80 |
| Tyr | Val | Asp | Ser | Val | Lys | Gly | Arg | Phe | Thr | Ile | Ser | Arg | Asp | Asn | Ser |
| | | | | 85 | | | | | 90 | | | | | 95 | |
| Lys | Asn | Thr | Leu | Tyr | Leu | Gln | Met | Asn | Ser | Leu | Arg | Ala | Glu | Asp | Thr |
| | | | 100 | | | | | 105 | | | | | 110 | | |
| Ala | Val | Tyr | Tyr | Cys | Ala | Arg | Asp | Asp | Tyr | Tyr | Gly | Ser | Gly | Ser | Phe |
| | | | 115 | | | | | 120 | | | | | 125 | | |
| Asn | Ser | Tyr | Tyr | Gly | Thr | Asp | Val | Trp | Gly | Gln | Gly | Thr | Thr | Val | Thr |
| | | 130 | | | | | 135 | | | | | 140 | | | |
| Val | Ser | Ser | Gly | Gly | Gly | Gly | Ser | Gly | Gly | Gly | Ser | Gly | Gly | Gly |
| 145 | | | | | 150 | | | | | 155 | | | | | 160 |
| Gly | Ser | Glu | Ile | Val | Leu | Thr | Gln | Ser | Pro | Ala | Thr | Leu | Ser | Leu | Ser |
| | | | | 165 | | | | | 170 | | | | | 175 | |
| Pro | Gly | Glu | Arg | Ala | Thr | Leu | Ser | Cys | Arg | Ala | Ser | Gln | Ser | Val | Ser |
| | | | 180 | | | | | 185 | | | | | 190 | | |
| Ile | Tyr | Leu | Ala | Trp | Tyr | Gln | Gln | Lys | Pro | Gly | Gln | Ala | Pro | Arg | Leu |
| | | | 195 | | | | | 200 | | | | | 205 | | |
| Leu | Ile | Tyr | Asp | Ala | Ser | Asn | Arg | Ala | Thr | Gly | Ile | Pro | Ala | Arg | Phe |
| | | 210 | | | | | 215 | | | | | 220 | | | |
| Ser | Gly | Ser | Gly | Ser | Gly | Thr | Asp | Phe | Thr | Leu | Thr | Ile | Ser | Ser | Leu |
| 225 | | | | | 230 | | | | | 235 | | | | | 240 |
| Glu | Pro | Glu | Asp | Phe | Ala | Val | Tyr | Tyr | Cys | Gln | Gln | Arg | Ser | Asn | Trp |
| | | | | 245 | | | | | 250 | | | | | 255 | |
| Pro | Pro | Phe | Thr | Phe | Gly | Pro | Gly | Thr | Lys | Val | Asp | Ile | Lys | Ser | Ala |
| | | | 260 | | | | | 265 | | | | | 270 | | |
| Ala | Ala | Phe | Val | Pro | Val | Phe | Leu | Pro | Ala | Lys | Pro | Thr | Thr | Thr | Pro |
| | | | 275 | | | | | 280 | | | | | 285 | | |
| Ala | Pro | Arg | Pro | Pro | Thr | Pro | Ala | Pro | Thr | Ile | Ala | Ser | Gln | Pro | Leu |
| | | 290 | | | | | 295 | | | | | 300 | | | |
| Ser | Leu | Arg | Pro | Glu | Ala | Cys | Arg | Pro | Ala | Ala | Gly | Gly | Ala | Val | His |
| 305 | | | | | 310 | | | | | 315 | | | | | 320 |
| Thr | Arg | Gly | Leu | Asp | Phe | Ala | Cys | Asp | Ile | Tyr | Ile | Trp | Ala | Pro | Leu |
| | | | | 325 | | | | | 330 | | | | | 335 | |
| Ala | Gly | Thr | Cys | Gly | Val | Leu | Leu | Leu | Ser | Leu | Val | Ile | Thr | Leu | Tyr |
| | | | 340 | | | | | 345 | | | | | 350 | | |
| Cys | Asn | His | Arg | Asn | Arg | Ser | Lys | Arg | Ser | Arg | Leu | Leu | His | Ser | Asp |
| | | | 355 | | | | | 360 | | | | | 365 | | |
| Tyr | Met | Asn | Met | Thr | Pro | Arg | Arg | Pro | Gly | Pro | Thr | Arg | Lys | His | Tyr |

```
                        370                 375                 380
Gln Pro Tyr Ala Pro Pro Arg Asp Phe Ala Ala Tyr Arg Ser Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Gly Arg Asp Pro Glu Met Gly Gly Lys Pro Arg
            435                 440                 445

Arg Lys Asn Pro Gln Glu Gly Leu Tyr Asn Glu Leu Gln Lys Asp Lys
        450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510

<210> SEQ ID NO 51
<211> LENGTH: 1536
<212> TYPE: DNA
<213> ORGANISM: Artificial Sequence
<220> FEATURE:
<223> OTHER INFORMATION: Synthetic Polynucleotide

<400> SEQUENCE: 51
atggcgctgc cggtgaccgc gctgctgctg ccgctggcgc tgctgctgca tgcggcgcgc      60
ccgcaggtgc agctggtgga aagcggcggc ggcgtggtgc agccgggccg cagcctgcgc     120
ctgagctgcg cggcgagcgg ctttaccttt agcagctatg catgcattg ggtgcgccag      180 gcgccgggca aaggcctgga atgggtggcg gtgatttggg atgatggcag caacaaatat     240
tatgtggata gcgtgaaagg ccgctttacc attagccgcg ataacagcaa aaacaccctg     300
tatctgcaga tgaacagcct gcgcgcggaa gataccgcgg tgtattattg cgcgcgcgat     360
gattattatg gcagcggcag ctttaacagc tattatggca ccgatgtgtg gggccagggc     420
accaccgtga ccgtgagcag cggcggcggc ggcagcggcg gcggcggcag cggcggcggc     480
ggcagcgaaa ttgtgctgac ccagagcccg gcgaccctga gcctgagccc gggcgaacgc     540
gcgaccctga gctgccgcgc gagccagagc gtgagcattt atctggcgtg gtatcagcag     600
aaaccgggcc aggcgccgcg cctgctgatt tatgatgcga gcaaccgcgc gaccggcatt     660
ccggcgcgct ttagcggcag cggcagcggc accgatttta ccctgaccat tagcagcctg     720
gaaccggaag attttgcggt gtattattgc agcagcgca gcaactggcc gccgtttacc      780
tttggcccgg gcaccaaagt ggatattaaa agcgcggcgg cgtttgtgcc ggtgtttctg     840
ccggcgaaac cgaccaccac cccggcgccg cgcccgccga ccccggcgcc gaccattgcg     900
agccagccgc tgagcctgcg cccggaagcg tgccgcccgg cggcgggcgg cgcggtgcat     960
acccgcggcc tggattttgc gtgcgatatt tatatttggg cgccgctggc gggcacctgc    1020
ggcgtgctgc tgctgagcct ggtgattacc ctgtattgca accatcgcaa ccgcaaacgc    1080
ggccgcaaaa aactgctgta tatttttaaa cagccgttta tgcgcccggt gcagaccacc    1140
caggaagaag atggctgcag ctgccgcttt ccggaagaag aagaaggcgg ctgcgaactg    1200
cgcgtgaaat ttagccgcag cgcggatgcg ccggcgtatc agcagggcca gaaccagctg    1260
tataacgaac tgaacctggg ccgccgcgaa gaatatgatg tgctggataa cgccgcggc     1320
```

```
cgcgatccgg aaatgggcgg caaaccgcgc cgcaaaaacc cgcaggaagg cctgtataac    1380
gaactgcaga aagataaaat ggcggaagcg tatagcgaaa ttggcatgaa aggcgaacgc    1440
cgccgcggca aaggccatga tggcctgtat cagggcctga gcaccgcgac caaagatacc    1500
tatgatgcgc tgcatatgca ggcgctgccg ccgcgc                              1536
```

<210> SEQ ID NO 52
<211> LENGTH: 512
<212> TYPE: PRT
<213> ORGANISM: Artificial Sequence
<220> FEATURE:
<223> OTHER INFORMATION: Synthetic Polypeptide

<400> SEQUENCE: 52

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Trp Asp Asp Gly Ser Asn Lys Tyr
65                  70                  75                  80

Tyr Val Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Asp Asp Tyr Tyr Gly Ser Gly Ser Phe
        115                 120                 125

Asn Ser Tyr Tyr Gly Thr Asp Val Trp Gly Gln Gly Thr Thr Val Thr
    130                 135                 140

Val Ser Ser Gly Gly Gly Gly Ser Gly Gly Gly Ser Gly Gly Gly
145                 150                 155                 160

Gly Ser Glu Ile Val Leu Thr Gln Ser Pro Ala Thr Leu Ser Leu Ser
                165                 170                 175

Pro Gly Glu Arg Ala Thr Leu Ser Cys Arg Ala Ser Gln Ser Val Ser
            180                 185                 190

Ile Tyr Leu Ala Trp Tyr Gln Gln Lys Pro Gly Gln Ala Pro Arg Leu
        195                 200                 205

Leu Ile Tyr Asp Ala Ser Asn Arg Ala Thr Gly Ile Pro Ala Arg Phe
    210                 215                 220

Ser Gly Ser Gly Ser Gly Thr Asp Phe Thr Leu Thr Ile Ser Ser Leu
225                 230                 235                 240

Glu Pro Glu Asp Phe Ala Val Tyr Tyr Cys Gln Gln Arg Ser Asn Trp
                245                 250                 255

Pro Pro Phe Thr Phe Gly Pro Gly Thr Lys Val Asp Ile Lys Ser Ala
            260                 265                 270

Ala Ala Phe Val Pro Val Phe Leu Pro Ala Lys Pro Thr Thr Thr Pro
        275                 280                 285

Ala Pro Arg Pro Pro Thr Pro Ala Pro Thr Ile Ala Ser Gln Pro Leu
    290                 295                 300

Ser Leu Arg Pro Glu Ala Cys Arg Pro Ala Ala Gly Gly Ala Val His
305                 310                 315                 320
```

```
Thr Arg Gly Leu Asp Phe Ala Cys Asp Ile Tyr Ile Trp Ala Pro Leu
                325                 330                 335

Ala Gly Thr Cys Gly Val Leu Leu Ser Leu Val Ile Thr Leu Tyr
        340                 345                 350

Cys Asn His Arg Asn Arg Lys Arg Gly Arg Lys Lys Leu Leu Tyr Ile
            355                 360                 365

Phe Lys Gln Pro Phe Met Arg Pro Val Gln Thr Thr Gln Glu Glu Asp
    370                 375                 380

Gly Cys Ser Cys Arg Phe Pro Glu Glu Glu Glu Gly Gly Cys Glu Leu
385                 390                 395                 400

Arg Val Lys Phe Ser Arg Ser Ala Asp Ala Pro Ala Tyr Gln Gln Gly
                405                 410                 415

Gln Asn Gln Leu Tyr Asn Glu Leu Asn Leu Gly Arg Arg Glu Glu Tyr
            420                 425                 430

Asp Val Leu Asp Lys Arg Arg Gly Arg Asp Pro Glu Met Gly Gly Lys
        435                 440                 445

Pro Arg Arg Lys Asn Pro Gln Glu Gly Leu Tyr Asn Glu Leu Gln Lys
    450                 455                 460

Asp Lys Met Ala Glu Ala Tyr Ser Glu Ile Gly Met Lys Gly Glu Arg
465                 470                 475                 480

Arg Arg Gly Lys Gly His Asp Gly Leu Tyr Gln Gly Leu Ser Thr Ala
                485                 490                 495

Thr Lys Asp Thr Tyr Asp Ala Leu His Met Gln Ala Leu Pro Pro Arg
            500                 505                 510

<210> SEQ ID NO 53
<211> LENGTH: 747
<212> TYPE: DNA
<213> ORGANISM: Artificial Sequence
<220> FEATURE:
<223> OTHER INFORMATION: Synthetic Polynucleotide

<400> SEQUENCE: 53
caggtgcagc tggtggaaag cggcggcggc gtggtgcagc cgggccgcag cctgcgcctg      60
agctgcgcgg cgagcggctt tacctttagc agctatggca tgcattgggt gcgccaggcg     120
ccgggcaaag cctggaatg gtggcggtg atttgggatg atggcagcaa caaatattat      180
gtggatagcg tgaaaggccg ctttaccatt agccgcgata caagcaaaaa caccctgtat     240
ctgcagatga acagcctgcg cgcggaagat accgcggtgt attattgcgc gcgcgatgat     300
tattatggca gcggcagctt taacagctat atggcaccg atgtgtgggg ccagggcacc     360
accgtgaccg tgagcagcgg cggcggcggc agcggcggcg gcggcagcgg cggcggcggc     420
agcgaaattg tgctgaccca gagcccggcg accctgagcc tgagcccggg cgaacgcgcg     480
accctgagct gccgcgcgag ccagagcgtg agcatttatc tggcgtggta tcagcagaaa     540
ccgggccagg cgccgcgcct gctgatttat gatgcgagca accgcgcgac cggcattccg     600
gcgcgcttta gcggcagcgg cagcggcacc gatttaccc tgaccattag cagcctggaa     660
ccggaagatt ttgcggtgta ttattgccag cagcgcagca actggccgcc gtttaccttt     720 ggccccgggca ccaaagtgga tattaaa                                        747

<210> SEQ ID NO 54
<211> LENGTH: 249
<212> TYPE: PRT
<213> ORGANISM: Artificial Sequence
<220> FEATURE:
<223> OTHER INFORMATION: Synthetic Polypeptide
```

<400> SEQUENCE: 54

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Asp Asp Gly Ser Asn Lys Tyr Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Tyr Tyr Gly Ser Gly Ser Phe Asn Ser Tyr Tyr Gly
            100                 105                 110

Thr Asp Val Trp Gly Gln Gly Thr Val Thr Val Ser Ser Gly Gly
            115                 120                 125

Gly Gly Ser Gly Gly Gly Ser Gly Gly Gly Ser Glu Ile Val
        130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ile Tyr Leu Ala Trp
                165                 170                 175

Tyr Gln Gln Lys Pro Gly Gln Ala Pro Arg Leu Leu Ile Tyr Asp Ala
            180                 185                 190

Ser Asn Arg Ala Thr Gly Ile Pro Ala Arg Phe Ser Gly Ser Gly Ser
        195                 200                 205

Gly Thr Asp Phe Thr Leu Thr Ile Ser Ser Leu Glu Pro Glu Asp Phe
    210                 215                 220

Ala Val Tyr Tyr Cys Gln Gln Arg Ser Asn Trp Pro Pro Phe Thr Phe
225                 230                 235                 240

Gly Pro Gly Thr Lys Val Asp Ile Lys
            245

<210> SEQ ID NO 55
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 55

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Asp Asp Gly Ser Asn Lys Tyr Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Tyr Tyr Gly Ser Gly Ser Phe Asn Ser Tyr Tyr Gly
            100                 105                 110

Thr Asp Val Trp Gly Gln Gly Thr Thr Val Thr Val Ser Ser
        115                 120                 125

<210> SEQ ID NO 56
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 56

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ile Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
            100                 105

<210> SEQ ID NO 57
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 57

Ser Tyr Gly Met His
1               5

<210> SEQ ID NO 58
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 58

Val Ile Trp Asp Asp Gly Ser Asn Lys Tyr Tyr Val Asp Ser Val Lys
1               5                   10                  15

Gly

<210> SEQ ID NO 59
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 59

Asp Asp Tyr Tyr Gly Ser Gly Ser Phe Asn Ser Tyr Tyr Gly Thr Asp
1               5                   10                  15

Val

<210> SEQ ID NO 60
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 60

Arg Ala Ser Gln Ser Val Ser Ile Tyr Leu Ala
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 61

Asp Ala Ser Asn Arg Ala Thr
1               5

<210> SEQ ID NO 62
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 62

Gln Gln Arg Ser Asn Trp Pro Pro Phe Thr
1               5                   10

<210> SEQ ID NO 63
<211> LENGTH: 4370
<212> TYPE: DNA
<213> ORGANISM: Artificial Sequence
<220> FEATURE:
<223> OTHER INFORMATION: Synthetic Polynucleotide

<400> SEQUENCE: 63

| | | | | | |
|---|---|---|---|---|---|
| gagatgtaag | gagctgctgt | gacttgctca | aggccttata | tcgagtaaac | ggtagtgctg | 60 |
| gggcttagac | gcaggtgttc | tgatttatag | ttcaaaacct | ctatcaatga | gagagcaatc | 120 |
| tcctggtaat | gtgatagatt | tcccaactta | atgccaacat | accataaacc | tcccattctg | 180 |
| ctaatgccca | gcctaagttg | gggagaccac | tccagattcc | aagatgtaca | gtttgctttg | 240 |
| ctgggccttt | ttcccatgcc | tgcctttact | ctgccagagt | tatattgctg | ggttttgaa | 300 |
| gaagatccta | ttaaataaaa | gaataagcag | tattattaag | tagccctgca | tttcaggttt | 360 |
| ccttgagtgg | caggccaggc | ctggccgtga | acgttcactg | aaatcatggc | ctcttggcca | 420 |
| agattgatag | cttgtgcctg | tccctgagtc | ccagtccatc | acgagcagct | ggttctaag | 480 |
| atgctatttc | ccgtataaag | catgagaccg | tgacttgcca | ccccacaga | gccccgccct | 540 |
| tgtccatcac | tggcatctgg | actccagcct | gggttggggc | aaagagggaa | atgagatcat | 600 |
| gtcctaaccc | tgatcctctt | gtcccacaga | tatccagaac | cctgaccctg | ccgtgtacca | 660 |
| gctgagagac | tctaaatcca | gtgacaagtc | tgtctgccta | ttcaccgatt | ttgattctca | 720 |
| aacaaatgtg | tcacaaagta | aggattctga | tgtgtatatc | acagacaaaa | ctgtgctaga | 780 |
| catgaggtct | atggacttca | ggctccggtg | cccgtcagtg | ggcagagcgc | acatcgccca | 840 |
| cagtccccga | gaagttgggg | ggaggggtcg | gcaattgaac | cggtgcctag | agaaggtggc | 900 |

```
gcggggtaaa ctgggaaagt gatgtcgtgt actggctccg ccttttccc gagggtgggg      960
gagaaccgta tataagtgca gtagtcgccg tgaacgttct ttttcgcaac gggtttgccg     1020
ccagaacaca ggtaagtgcc gtgtgtggtt cccgcgggcc tggcctcttt acggggttatg   1080
gcccttgcgt gccttgaatt acttccactg gctgcagtac gtgattcttg atcccgagct   1140
tcgggttgga agtgggtggg agagttcgag gccttgcgct taaggagccc cttcgcctcg    1200
tgcttgagtt gaggcctggc ctgggcgctg gggccgccgc gtgcgaatct ggtggcacct    1260
tcgcgcctgt ctcgctgctt tcgataagtc tctagccatt taaaatttt gatgacctgc     1320
tgcgacgctt tttttctggc aagatagtct tgtaaatgcg ggccaagatc tgcacactgg   1380
tatttcggtt tttggggccg cgggcggcga cggggcccgt gcgtcccagc gcacatgttc   1440
ggcgaggcgg ggcctgcgag cgcggccacc gagaatcgga cggggggtagt ctcaagctgg   1500
ccggcctgct ctggtgcctg gcctcgcgcc gccgtgtatc gccccgcccct gggcggcaag   1560
gctggcccgg tcggcaccag ttgcgtgagc ggaaagatgg ccgcttcccg gccctgctgc   1620
agggagctca aaatggagga cgcggcgctc gggagagcgg gcgggtgagt cacccacaca   1680
aaggaaaagg gccttttccgt cctcagccgt cgcttcatgt gactccacgg agtaccgggc  1740
gccgtccagg cacctcgatt agttctcgag cttttggagt acgtcgtctt taggttgggg   1800
ggaggggttt tatgcgatgg agtttcccca cactgagtgg gtggagactg aagttaggcc   1860
agcttggcac ttgatgtaat tctccttgga atttgccctt tttgagtttg atcttggtt    1920
cattctcaag cctcagacag tggttcaaag ttttttttctt ccatttcagg tgtcgtgacc   1980
accatggcgc ttccggtgac agcactgctc ctccccttgg cgctgttgct ccacgcagca   2040
aggccgcagg tgcagctggt ggagagcggc ggaggagtgg tgcaacccgg aaggtccctg   2100
aggctctcct gtgccgccag cggcttcacc ttctccagct acggtatgca ctgggtgaga   2160
caagccccccg gaaagggcct cgagtgggtg gccgtgatct gggatgatgg ctccaacaag   2220
tactacgtgg acagcgtcaa gggcagattc accatcagca gggacaacag caagaacacc   2280
ctgtacctgc agatgaactc cctgagagcc gaagacaccg ccgtgtacta ttgtgccagg   2340
gacgactact atggctccgg ctccttcaat agctactatg gcaccgacgt gtggggccag   2400
ggcaccacag tgacagtgag cagcggcgga ggaggatccg gaggaggagg aagcggagga   2460
ggaggaagcg agatcgtgct gacacagtcc cccgctaccc tgagcctgag ccccggcgag   2520
agagctaccc tgagctgcag agccagccag agcgtctcca tctacctggc ctggtaccag   2580
cagaagcctg gccaggcccc tagactgctg atctacgacg ccagcaacag ggccaccggc   2640
attcctgcca gattcagcgg ctccggctcc ggcaccgatt tcacactgac catcagctcc   2700
ctggagcctg aggacttcgc cgtgtattac tgccagcaga ggagcaactg gccccccttt   2760
accttcggcc ccggcaccaa ggtcgacatc aagagtgctg ctgcctttgt cccggtattt   2820
ctcccagcca aaccgaccac gactcccgcc ccgcgccctc cgacaccgc tcccaccatc   2880
gcctctcaac ctcttagtct tcgccccgag gcatgccgac ccgccgccgg gggtgctgtt   2940
catacgaggg gcttggactt cgcttgtgat atttacatttt gggctccgtt ggcgggtacg   3000
tgcggcgtcc ttttgttgtc actcgttatt actttgtatt gtaatcacag gaatcgctca    3060
aagcggagta ggttgttgca ttccgattac atgaatatga ctcctcgccg gctgggccg    3120
acaagaaaac attaccaacc ctatgccccc ccacgagact cgctgcgta caggtcccga    3180
gtgaagtttt cccgaagcgc agacgctccg gcatatcagc aaggacagaa tcagctgtat   3240
```

| | |
|---|---|
| aacgaactga atttgggacg ccgcgaggag tatgacgtgc ttgataaacg ccggggggaga | 3300 |
| gacccggaaa tggggggtaa accccgaaga aagaatcccc aagaaggact ctacaatgaa | 3360 |
| ctccagaagg ataagatggc ggaggcctac tcagaaatag gtatgaaggg cgaacgacga | 3420 |
| cggggaaaag gtcacgatgg cctctaccaa gggttgagta cggcaaccaa agatacgtac | 3480 |
| gatgcactgc atatgcaggc cctgcctccc agataataat aaaatcgcta tccatcgaag | 3540 |
| atggatgtgt gttggttttt tgtgtgtgga gcaacaaatc tgactttgca tgtgcaaacg | 3600 |
| ccttcaacaa cagcattatt ccagaagaca ccttcttccc cagcccaggt aagggcagct | 3660 |
| ttggtgcctt cgcaggctgt ttccttgctt caggaatggc caggttctgc ccagagctct | 3720 |
| ggtcaatgat gtctaaaact cctctgattg gtggtctcgg ccttatccat tgccaccaaa | 3780 |
| accctctttt tactaagaaa cagtgagcct tgttctggca gtccagaaa tgacacggga | 3840 |
| aaaaagcaga tgaagagaag gtggcaggag agggcacgtg gcccagcctc agtctctcca | 3900 |
| actgagttcc tgcctgcctg cctttgctca gactgttttgc cccttactgc tcttctaggc | 3960 |
| ctcattctaa gccccttctc caagttgcct ctccttattt ctccctgtct gccaaaaaat | 4020 |
| cttcccagc tcactaagtc agtctcacgc agtcactcat taacccacca atcactgatt | 4080 |
| gtgccggcac atgaatgcac caggtgttga agtggaggaa ttaaaaagtc agatgagggg | 4140 |
| tgtgcccaga ggaagcacca ttctagttgg gggagcccat ctgtcagctg ggaaaagtcc | 4200 |
| aaataacttc agattggaat gtgttttaac tcagggttga gaaaacagct accttcagga | 4260 |
| caaaagtcag ggaagggctc tctgaagaaa tgctacttga agataccagc cctaccaagg | 4320 |
| gcagggagag gaccctatag aggcctggga caggagctca atgagaaagg | 4370 |

<210> SEQ ID NO 64
<211> LENGTH: 4376
<212> TYPE: DNA
<213> ORGANISM: Artificial Sequence
<220> FEATURE:
<223> OTHER INFORMATION: Synthetic Polynucleotide

<400> SEQUENCE: 64

| | |
|---|---|
| gagatgtaag gagctgctgt gacttgctca aggcctttata tcgagtaaac ggtagtgctg | 60 |
| gggcttagac gcaggtgttc tgatttatag ttcaaaacct ctatcaatga gagagcaatc | 120 |
| tcctggtaat gtgatagatt tcccaactta atgccaacat accataaacc tcccattctg | 180 |
| ctaatgccca gcctaagttg gggagaccac tccagattcc aagatgtaca gtttgctttg | 240 |
| ctgggccttt tcccatgcc tgcctttact ctgccagagt tatattgctg gggttttgaa | 300 |
| gaagatccta ttaaataaaa gaataagcag tattattaag tagccctgca tttcaggttt | 360 |
| ccttgagtgg caggccaggc ctggccgtga acgttcactg aaatcatggc ctcttggcca | 420 |
| agattgatag cttgtgcctg tccctgagtc ccagtccatc acgagcagct ggtttctaag | 480 |
| atgctatttc ccgtataaag catgagaccg tgacttgcca gccccacaga gccccgccct | 540 |
| tgtccatcac tggcatctgg actccagcct gggttggggc aaagagggaa atgagatcat | 600 |
| gtcctaaccc tgatcctctt gtcccacaga tatccagaac cctgaccctg ccgtgtacca | 660 |
| gctgagagac tctaaatcca gtgacaagtc tgtctgccta ttcaccgatt ttgattctca | 720 |
| aacaaatgtg tcacaaagta aggattctga tgtgtatatc acagacaaaa ctgtgctaga | 780 |
| catgaggtct atggacttca ggctccggtg cccgtcagtg ggcagagcgc acatcgccca | 840 |
| cagtcccccga gaagttgggg ggaggggtcg gcaattgaac cggtgcctag agaaggtggc | 900 |
| gcggggtaaa ctgggaaagt gatgtcgtgt actggctccg cctttttccc gagggtgggg | 960 |

```
gagaaccgta tataagtgca gtagtcgccg tgaacgttct ttttcgcaac gggtttgccg    1020
ccagaacaca ggtaagtgcc gtgtgtggtt cccgcgggcc tggcctcttt acgggttatg    1080
gcccttgcgt gccttgaatt acttccactg gctgcagtac gtgattcttg atcccgagct    1140
tcgggttgga agtgggtggg agagttcgag gccttgcgct taaggagccc cttcgcctcg    1200
tgcttgagtt gaggcctggc ctgggcgctg gggccgccgc gtgcgaatct ggtggcacct    1260
tcgcgcctgt ctcgctgctt tcgataagtc tctagccatt taaaatttt gatgacctgc    1320 tgcgacgctt tttttctggc aagatagtct tgtaaatgcg ggccaagatc tgcacactgg    1380
tatttcggtt tttggggccg cgggcggcga cggggcccgt gcgtcccagc gcacatgttc    1440
ggcgaggcgg ggcctgcgag cgcggccacc gagaatcgga cggggtagt ctcaagctgg     1500 ccggcctgct ctggtgcctg gcctcgcgcc gccgtgtatc gccccgccct gggcggcaag    1560
gctggcccgg tcggcaccag ttgcgtgagc ggaaagatgg ccgcttcccg gccctgctgc    1620
agggagctca aaatggagga cgcggcgctc gggagagcgg gcgggtgagt cacccacaca    1680
aaggaaaagg gccttccgt cctcagccgt cgcttcatgt gactccacgg agtaccgggc     1740
gccgtccagg cacctcgatt agttctcgag cttttggagt acgtcgtctt taggttgggg    1800
ggaggggttt tatgcgatgg agtttcccca cactgagtgg gtggagactg aagttaggcc    1860
agcttggcac ttgatgtaat tctccttgga atttgccctt tttgagtttg gatcttggtt    1920
cattctcaag cctcagacag tggttcaaag ttttttttctt ccatttcagg tgtcgtgacc   1980
accatggcgc ttccggtgac agcactgctc ctcccctttgg cgctgttgct ccacgcagca   2040
aggccgcagg tgcagctggt ggagagcggc ggaggagtgg tgcaacccgg aaggtccctg    2100
aggctctcct gtgccgccag cggcttcacc ttctccagct acggtatgca ctgggtgaga   2160 caagccccg gaaagggcct cgagtgggtg gccgtgatct gggatgatgg ctccaacaag    2220
tactacgtgg acagcgtcaa gggcagattc accatcagca gggacaacag caagaacacc   2280
ctgtacctgc agatgaactc cctgagagcc gaagacaccg ccgtgtacta ttgtgccagg    2340
gacgactact atggctccgg ctccttcaat agctactatg gcaccgacgt gtggggccag    2400
ggcaccacag tgacagtgag cagcggcgga ggaggatccg gaggaggagg aagcggagga    2460
ggaggaagcg agatcgtgct gacacagtcc cccgctaccc tgagcctgag ccccggcgag    2520
agagctaccc tgagctgcag agccagccag agcgtctcca tctacctggc ctggtaccag    2580
cagaagcctg gccaggcccc tagactgctg atctacgacg ccagcaacag ggccaccggc    2640
attcctgcca gattcagcgg ctccggctcc ggcaccgatt tcacactgac catcagctcc    2700
ctggagcctg aggacttcgc cgtgtattac tgccagcaga ggagcaactg gccccccttt    2760
accttcggcc ccggcaccaa ggtcgacatc aagagtgctg ctgcctttgt cccggtattt   2820
ctcccagcca aaccgaccac gactcccgcc ccgcgccctc cgacacccgc tcccaccatc    2880
gcctctcaac ctcttagtct tcgccccgag gcatgccgac ccgccgccgg gggtgctgtt    2940
catacgaggg gcttggactt cgcttgtgat atttacattt gggctccgtt ggcgggtacg    3000
tgcggcgtcc ttttgttgtc actcgttatt actttgtatt gtaatcacag gaatcgcaaa    3060
cggggcagaa agaaactcct gtatatattc aaacaaccat ttatgagacc agtacaaact    3120
actcaagagg aagatggctg tagctgccga tttccagaag aagaagaagg aggatgtgaa    3180
ctgcgagtga agttttcccg aagcgcagac gctccggcat atcagcaagg acagaatcag    3240
ctgtataacg aactgaattt gggacgccgc gaggagtatg acgtgcttga taaacgccgg    3300
```

-continued

| | | | |
|---|---|---|---|
| gggagagacc | cggaaatggg | gggtaaaccc | cgaagaaaga atccccaaga aggactctac | 3360 |
| aatgaactcc | agaaggataa | gatggcggag | gcctactcag aaataggtat gaagggcgaa | 3420 |
| cgacgacggg | gaaaaggtca | cgatggcctc | taccaagggt tgagtacggc aaccaaagat | 3480 |
| acgtacgatg | cactgcatat | gcaggccctg | cctcccagat aataataaaa tcgctatcca | 3540 |
| tcgaagatgg | atgtgtgttg | gttttttgtg | tgtggagcaa caaatctgac tttgcatgtg | 3600 |
| caaacgcctt | caacaacagc | attattccag | aagacacctt cttccccagc ccaggtaagg | 3660 |
| gcagctttgg | tgccttcgca | ggctgtttcc | ttgcttcagg aatggccagg ttctgcccag | 3720 |
| agctctggtc | aatgatgtct | aaaactcctc | tgattggtgg tctcggcctt atccattgcc | 3780 |
| accaaaaccc | tcttttttact | aagaaacagt | gagccttgtt ctggcagtcc agagaatgac | 3840 |
| acggaaaaaa | agcagatgaa | gagaaggtgg | caggagaggg cacgtggccc agcctcagtc | 3900 |
| tctccaactg | agttcctgcc | tgcctgcctt | tgctcagact gtttgcccct tactgctctt | 3960 |
| ctaggcctca | ttctaagccc | cttctccaag | ttgcctctcc ttatttctcc ctgtctgcca | 4020 |
| aaaaatcttt | cccagctcac | taagtcagtc | tcacgcagtc actcattaac ccaccaatca | 4080 |
| ctgattgtgc | cggcacatga | atgcaccagg | tgttgaagtg gaggaattaa aaagtcagat | 4140 |
| gaggggtgtg | cccagaggaa | gcaccattct | agttggggga gcccatctgt cagctgggaa | 4200 |
| aagtccaaat | aacttcagat | tggaatgtgt | tttaactcag ggttgagaaa acagctacct | 4260 |
| tcaggacaaa | agtcagggaa | gggctctctg | aagaaatgct acttgaagat accagcccta | 4320 |
| ccaagggcag | ggagaggacc | ctatagaggc | ctgggacagg agctcaatga gaaagg | 4376 |

<210> SEQ ID NO 65
<211> LENGTH: 1527
<212> TYPE: DNA
<213> ORGANISM: Artificial Sequence
<220> FEATURE:
<223> OTHER INFORMATION: Synthetic Polynucleotide

<400> SEQUENCE: 65

| | | | |
|---|---|---|---|
| atggcgctgc | cggtgaccgc | gctgctgctg | ccgctggcgc tgctgctgca tgcggcgcgc | 60 |
| ccggaaattg | tgctgaccca | gagcccggcg | accctgagcc tgagcccggg cgaacgcgcg | 120 |
| accctgagct | gccgcgcgag | ccagagcgtg | agcatttatc tggcgtggta tcagcagaaa | 180 |
| ccgggccagg | cgccgcgcct | gctgatttat | gatgcgagca accgcgcgac cggcattccg | 240 |
| gcgcgcttta | gcggcagcgg | cagcggcacc | gattttaccc tgaccattag cagcctggaa | 300 |
| ccggaagatt | ttgcggtgta | ttattgccag | cagcgcagca actggccgcc gtttaccttt | 360 |
| ggccccgggca | ccaaagtgga | tattaaaggc | ggcggcggca gcggcggcgg cggcagcggc | 420 |
| ggcggcggca | gccaggtgca | gctggtggaa | agcggcggcg gcgtggtgca gccgggccgc | 480 |
| agcctgcgcc | tgagctgcgc | ggcgagcggc | tttacccttta gcagctatgg catgcattgg | 540 |
| gtgcgccagg | cgccgggcaa | aggcctggaa | tgggtggcgg tgatttggga tgatggcagc | 600 |
| aacaaatatt | atgtggatag | cgtgaaaggc | cgctttacca ttagccgcga taacagcaaa | 660 |
| aacacctgt | atctgcagat | gaacagcctg | cgcgcggaag ataccgcggt gtattattgc | 720 |
| gcgcgcgatg | attattatgg | cagcggcagc | tttaacagct attatggcac cgatgtgtgg | 780 |
| ggccagggca | ccaccgtgac | cgtgagcagc | gcggcggcgt tgtgccggt gtttctgccg | 840 |
| gcgaaaccga | ccaccacccc | ggccgcgcgc | ccgccgaccc cggcgccgac cattgcgagc | 900 |
| cagccgctga | gcctgcgccc | ggaagcgtgc | cgcccggcgg cggcggcgc ggtgcatacc | 960 |
| cgcggcctgg | attttgcgtg | cgatatttat | atttgggcgc cgctggcggg cacctgcggc | 1020 |

```
gtgctgctgc tgagcctggt gattaccctg tattgcaacc atcgcaaccg cagcaaacgc    1080
agccgcctgc tgcatagcga ttatatgaac atgaccccgc cgcccgg    cccgaccccc    1140 aaacattatc agccgtatgc gccgccgcgc gatttgcgg cgtatcgcag ccgcgtgaaa    1200
tttagccgca gcgcggatgc gccggcgtat cagcagggcc agaaccagct gtataacgaa    1260
ctgaacctgg ccgccgcga agaatatgat gtgctggata acgccgcgg ccgcgatccg    1320 gaaatgggcg gcaaaccgcg ccgcaaaaac ccgcaggaag gcctgtataa cgaactgcag    1380
aaagataaaa tggcggaagc gtatagcgaa attggcatga aggcgaacg ccgccgcggc    1440 aaaggccatg atggcctgta tcagggcctg agcaccgcga ccaaagatac ctatgatgcg    1500
ctgcatatgc aggcgctgcc gccgcgc                                       1527

<210> SEQ ID NO 66
<211> LENGTH: 509
<212> TYPE: PRT
<213> ORGANISM: Artificial Sequence
<220> FEATURE:
<223> OTHER INFORMATION: Synthetic Polypeptide

<400> SEQUENCE: 66

Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Ser Val Ser Ile Tyr Leu Ala Trp Tyr Gln Gln Lys Pro Gly Gln Ala
    50                  55                  60

Pro Arg Leu Leu Ile Tyr Asp Ala Ser Asn Arg Ala Thr Gly Ile Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Gln Arg
            100                 105                 110

Ser Asn Trp Pro Pro Phe Thr Phe Gly Pro Gly Thr Lys Val Asp Ile
        115                 120                 125

Lys Gly Gly Gly Gly Ser Gly Gly Gly Ser Gly Gly Gly Gly Ser
    130                 135                 140

Gln Val Gln Leu Val Glu Ser Gly Gly Gly Val Val Gln Pro Gly Arg
145                 150                 155                 160

Ser Leu Arg Leu Ser Cys Ala Ala Ser Gly Phe Thr Phe Ser Ser Tyr
                165                 170                 175

Gly Met His Trp Val Arg Gln Ala Pro Gly Lys Gly Leu Glu Trp Val
            180                 185                 190

Ala Val Ile Trp Asp Asp Gly Ser Asn Lys Tyr Tyr Val Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Ala Arg Asp Asp Tyr Tyr Gly Ser Gly Ser Phe Asn Ser Tyr Tyr Gly
                245                 250                 255

Thr Asp Val Trp Gly Gln Gly Thr Thr Val Thr Val Ser Ser Ala Ala
            260                 265                 270
```

Ala Phe Val Pro Val Phe Leu Pro Ala Lys Pro Thr Thr Thr Pro Ala
            275                 280                 285

Pro Arg Pro Pro Thr Pro Ala Pro Thr Ile Ala Ser Gln Pro Leu Ser
        290                 295                 300

Leu Arg Pro Glu Ala Cys Arg Pro Ala Ala Gly Gly Ala Val His Thr
305                 310                 315                 320

Arg Gly Leu Asp Phe Ala Cys Asp Ile Tyr Ile Trp Ala Pro Leu Ala
                325                 330                 335

Gly Thr Cys Gly Val Leu Leu Leu Ser Leu Val Ile Thr Leu Tyr Cys
            340                 345                 350

Asn His Arg Asn Arg Ser Lys Arg Ser Arg Leu Leu His Ser Asp Tyr
                355                 360                 365

Met Asn Met Thr Pro Arg Arg Pro Gly Pro Thr Arg Lys His Tyr Gln
        370                 375                 380

Pro Tyr Ala Pro Pro Arg Asp Phe Ala Ala Tyr Arg Ser Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Arg Arg
        435                 440                 445

Lys Asn Pro Gln Glu Gly Leu Tyr Asn Glu Leu Gln Lys Asp Lys Met
        450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505

<210> SEQ ID NO 67
<211> LENGTH: 747
<212> TYPE: DNA
<213> ORGANISM: Artificial Sequence
<220> FEATURE:
<223> OTHER INFORMATION: Synthetic Polynucleotide

<400> SEQUENCE: 67
gaaattgtgc tgacccagag cccggcgacc ctgagcctga gcccgggcga acgcgcgacc        60
ctgagctgcc gcgcgagcca gagcgtgagc atttatctgg cgtggtatca gcagaaaccg       120
ggccaggcgc cgcgcctgct gatttatgat gcgagcaacc gcgcgaccgg cattccggcg       180
cgctttagcg gcagcggcag cggcaccgat tttaccctga ccattagcag cctggaaccg       240
gaagattttg cggtgtatta ttgccagcag cgcagcaact ggccgccgtt tacctttggc       300
ccgggcacca aagtggatat taaaggcggc ggcggcagcg gcggcggcgg cagcggcggc       360
ggcggcagcc aggtgcagct ggtggaaagc ggcggcggcg tggtgcagcc gggccgcagc       420
ctgcgcctga gctgcgcggc gagcggcttt acctttagca gctatggcat gcattgggtg       480
cgccaggcgc cgggcaaagg cctggaatgg gtggcggtga tttgggatga tggcagcaac       540
aaatattatg tggatagcgt gaaaggccgc tttaccatta gccgcgataa cagcaaaaac       600
accctgtatc tgcagatgaa cagcctgcgc gcggaagata ccgcggtgta ttattgcgcg       660
cgcgatgatt attatggcag cggcagcttt aacagctatt atggcaccga tgtgtgggc       720 cagggcacca ccgtgaccgt gagcagc				747

<210> SEQ ID NO 68
<211> LENGTH: 249
<212> TYPE: PRT
<213> ORGANISM: Artificial Sequence
<220> FEATURE:
<223> OTHER INFORMATION: Synthetic Polypeptide

<400> SEQUENCE: 68

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ile Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Gly
            100                 105                 110

Ser Gly Gly Gly Gly Ser Gly Gly Gly Ser Gln Val Gln Leu Val
        115                 120                 125

Glu Ser Gly Gly Gly Val Val Gln Pro Gly Arg Ser Leu Arg Leu Ser
    130                 135                 140

Cys Ala Ala Ser Gly Phe Thr Phe Ser Ser Tyr Gly Met His Trp Val
145                 150                 155                 160

Arg Gln Ala Pro Gly Lys Gly Leu Glu Trp Val Ala Val Ile Trp Asp
                165                 170                 175

Asp Gly Ser Asn Lys Tyr Tyr Val Asp Ser Val Lys Gly Arg Phe Thr
            180                 185                 190

Ile Ser Arg Asp Asn Ser Lys Asn Thr Leu Tyr Leu Gln Met Asn Ser
        195                 200                 205

Leu Arg Ala Glu Asp Thr Ala Val Tyr Tyr Cys Ala Arg Asp Asp Tyr
    210                 215                 220

Tyr Gly Ser Gly Ser Phe Asn Ser Tyr Gly Thr Asp Val Trp Gly
225                 230                 235                 240

Gln Gly Thr Thr Val Thr Val Ser Ser
                245

<210> SEQ ID NO 69
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 69

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Asn Lys Tyr Tyr Val Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Asp Tyr Tyr Gly Ser Gly Ser Phe Asn Ser Tyr Tyr Gly
                100                 105                 110

Thr Asp Val Trp Gly Gln Gly Thr Thr Val Thr Val Ser Ser
                115                 120                 125

<210> SEQ ID NO 70
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 70

Ile Val Leu Thr Gln Ser Pro Ala Thr Leu Ser Leu Ser Pro Gly Glu
 1               5                  10                  15

Arg Ala Thr Leu Ser Cys Arg Ala Ser Gln Ser Val Ser Ile Tyr Leu
                20                  25                  30

Ala Trp Tyr Gln Gln Lys Pro Gly Gln Ala Pro Arg Leu Leu Ile Tyr
                35                  40                  45

Asp Ala Ser Asn Arg Ala Thr Gly Ile Pro Ala Arg Phe Ser Gly Ser
            50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Gln Gln Arg Ser Asn Trp Pro Pro Phe
                85                  90                  95

Thr Phe Gly Pro Gly Thr Lys Val Asp Ile Lys
                100                 105

<210> SEQ ID NO 71
<211> LENGTH: 4370
<212> TYPE: DNA
<213> ORGANISM: Artificial Sequence
<220> FEATURE:
<223> OTHER INFORMATION: Synthetic Polynucleotide

<400> SEQUENCE: 71
gagatgtaag gagctgctgt gacttgctca aggccttata tcgagtaaac ggtagtgctg     60
gggcttagac gcaggtgttc tgatttatag ttcaaaacct ctatcaatga gagagcaatc    120
tcctggtaat gtgatagatt tcccaactta atgccaacat accataaacc tcccattctg    180
ctaatgccca gcctaagttg gggagaccac tccagattcc aagatgtaca gtttgctttg    240
ctgggccttt ttcccatgcc tgcctttact ctgccagagt tatattgctg ggttttgaa     300 gaagatccta ttaaataaaa gaataagcag tattattaag tagccctgca tttcaggttt    360
ccttgagtgg caggccaggc ctggccgtga acgttcactg aaatcatggc ctcttggcca    420
agattgatag cttgtgcctg tccctgagtc ccagtccatc acgagcagct ggtttctaag    480
atgctatttc ccgtataaag catgagaccg tgacttgcca gccccacaga gccccgccct    540
tgtccatcac tggcatctgg actccagcct gggttgggc aaagagggaa atgagatcat    600
gtcctaaccc tgatcctctt gtcccacaga tatccagaac cctgaccctg ccgtgtacca    660

```
gctgagagac tctaaatcca gtgacaagtc tgtctgccta ttcaccgatt ttgattctca    720
aacaaatgtg tcacaaagta aggattctga tgtgtatatc acagacaaaa ctgtgctaga    780
catgaggtct atggacttca ggctccggtg cccgtcagtg ggcagagcgc acatcgccca    840
cagtccccga gaagttgggg ggaggggtcg gcaattgaac cggtgcctag agaaggtggc    900
gcggggtaaa ctgggaaagt gatgtcgtgt actggctccg ccttttcccc gagggtgggg    960
gagaaccgta tataagtgca gtagtcgccg tgaacgttct ttttcgcaac gggtttgccg   1020
ccagaacaca ggtaagtgcc gtgtgtggtt cccgcgggcc tggcctcttt acgggttatg   1080
gcccttgcgt gccttgaatt acttccactg gctgcagtac gtgattcttg atcccgagct   1140
tcgggttgga agtgggtggg agagttcgag gccttgcgct taaggagccc cttcgcctcg   1200
tgcttgagtt gaggcctggc ctgggcgctg gggccgccgc gtgcgaatct ggtggcacct   1260
tcgcgcctgt ctcgctgctt tcgataagtc tctagccatt taaaattttt gatgacctgc   1320
tgcgacgctt ttttttctggc aagatagtct tgtaaatgcg ggccaagatc tgcacactgg   1380
tatttcggtt tttggggccg cgggcggcga cggggcccgt gcgtcccagc gcacatgttc   1440
ggcgaggcgg ggcctgcgag cgcggccacc gagaatcgga cggggtagt ctcaagctgg   1500 ccggcctgct ctggtgcctg gcctcgcgcc gccgtgtatc gccccgccct gggcggcaag   1560
gctggcccgg tcggcaccag ttgcgtgagc ggaaagatgg ccgcttcccg gccctgctgc   1620
agggagctca aaatggagga cgcggcgctc gggagagcgg gcgggtgagt cacccacaca   1680
aaggaaaagg gcctttccgt cctcagccgt cgcttcatgt gactccacgg agtaccgggc   1740
gccgtccagg cacctcgatt agttctcgag cttttggagt acgtcgtctt taggttgggg   1800
ggaggggttt tatgcgatgg agtttcccca cactgagtgg gtggagactg aagttaggcc   1860
agcttggcac ttgatgtaat tctccttgga atttgcccctt tttgagtttg gatcttggtt   1920
cattctcaag cctcagacag tggttcaaag ttttttttctt ccatttcagg tgtcgtgacc   1980
accatggcgc ttccggtgac agcactgctc ctcccccttgg cgctgttgct ccacgcagca   2040
aggccggaga tcgtgctgac ccagagccct gccacactga gcctgagccc cggagagagg   2100
gctaccctga gctgcagggc ctcccagtcc gtgagcatct acctggcctg gtaccagcag   2160
aaacctggcc aggcccccag gctgctgatc tacgacgcca gcaatagggc caccggaatc   2220
cctgccaggt ttagcggctc cggaagcggc accgacttca ccctgaccat ctcctccctg   2280
gagcccgagg atttcgccgt gtactactgc cagcagaggt ccaactggcc tcccttttacc   2340 ttcggccccg gcaccaaggt ggatattaag ggcggcggcg gatccggagg aggaggcagc   2400
ggaggaggag gaagccaggt gcaactggtg gagtccggcg gaggcgtggt gcaacctggc   2460
agaagcctga ggctgagctg tgccgccagc ggcttcacct tcagcagcta cggtatgcac   2520
tgggtgaggc aggctcccgg aaagggcctg gaatgggtgg ccgtgatctg ggacgacggc   2580
tccaacaagt actacgtgga ctccgtgaag ggcaggttca ccatcagcag ggacaactcc   2640
aagaacacac tgtacctgca gatgaacagc ctgagggccg aggataccgc tgtgtattac   2700
tgcgccaggg acgattacta cggcagcggc agcttcaatt cctactacgg aaccgacgtc   2760
tggggccagg gaaccaccgt gaccgtgagc agcagtgctg ctgcctttgt cccggtattt   2820
ctcccagcca aaccgaccac gactcccgcc ccgcgccctc cgacaccgcg tcccaccatc   2880
gcctctcaac ctcttagtct tcgccccgag gcatgccgac ccgccgccgg gggtgctgtt   2940
catacgaggg gcttggactt cgcttgtgat atttacattt gggctccgtt ggcgggtacg   3000
tgcggcgtcc ttttgttgtc actcgttatt actttgtatt gtaatcacag gaatcgctca   3060
```

```
aagcggagta ggttgttgca ttccgattac atgaatatga ctcctcgccg gcctgggccg    3120
acaagaaaac attaccaacc ctatgccccc ccacgagact tcgctgcgta caggtcccga    3180
gtgaagtttt cccgaagcgc agacgctccg gcatatcagc aaggacagaa tcagctgtat    3240
aacgaactga atttgggacg ccgcgaggag tatgacgtgc ttgataaacg ccggggagaa    3300
gacccggaaa tgggggtaa accccgaaga aagatcccc aagaaggact ctacaatgaa    3360
ctccagaagg ataagatggc ggaggcctac tcagaaatag gtatgaaggg cgaacgacga    3420
cggggaaaag gtcacgatgg cctctaccaa gggttgagta cggcaaccaa agatacgtac    3480
gatgcactgc atatgcaggc cctgcctccc agataataat aaaatcgcta tccatcgaag    3540
atggatgtgt gttggttttt tgtgtgtgga gcaacaaatc tgactttgca tgtgcaaacg    3600
ccttcaacaa cagcattatt ccagaagaca ccttcttccc cagcccaggt aagggcagct    3660
ttggtgcctt cgcaggctgt ttccttgctt caggaatggc caggttctgc ccagagctct    3720
ggtcaatgat gtctaaaact cctctgattg gtggtctcgg ccttatccat tgccaccaaa    3780
accctctttt tactaagaaa cagtgagcct tgttctggca gtccagagaa tgacacggga    3840
aaaaagcaga tgaagagaag gtggcaggag agggcacgtg gcccagcctc agtctctcca    3900
actgagttcc tgcctgcctg cctttgctca gactgtttgc cccttactgc tcttctaggc    3960
ctcattctaa gccccttctc caagttgcct ctccttattt ctccctgtct gccaaaaaat    4020
ctttcccagc tcactaagtc agtctcacgc agtcactcat taacccacca atcactgatt    4080
gtgccggcac atgaatgcac caggtgttga agtggaggaa ttaaaaagtc agatgagggg    4140
tgtgcccaga ggaagcacca ttctagttgg gggagcccat ctgtcagctg gaaaagtcc    4200 aaataacttc agattggaat gtgttttaac tcagggttga gaaaacagct accttcagga    4260
caaaagtcag ggaagggctc tctgaagaaa tgctacttga agataccagc cctaccaagg    4320
gcagggagag gaccctatag aggcctggga caggagctca atgagaaagg    4370
```

<210> SEQ ID NO 72
<211> LENGTH: 1488
<212> TYPE: DNA
<213> ORGANISM: Artificial Sequence
<220> FEATURE:
<223> OTHER INFORMATION: Synthetic Polynucleotide

<400> SEQUENCE: 72

```
atggcgctgc cggtgaccgc gctgctgctg ccgctggcgc tgctgctgca tgcggcgcgc      60
ccggaaattg tgctgaccca gagcccgggc accctgagcc tgagcccggg cgaacgcgcg     120
accctgagct gccgcgcgag ccagagcgtg agcagcagct atctggcgtg gtatcagcag     180
aaacggggcc aggcgccgcg cctgctgatt tatggcgcga gcagccgcgc gaccggcatt     240
ccggatcgct ttagcggcag cggcagcggc accgatttta ccctgaccat tagccgcctg     300
gaaccggaag attttgcggt gtattattgc cagcagtatg cagcagccc gatgtatacc     360 tttggccagg gcaccaaact ggaaattaaa ggcggcggcg gcagcggcgg cggcggcagc     420
ggcggcggcg gcagcgaagt gcagctggtg cagagcggcg cgggcctggt gcatccgggc     480
ggcagcctgc gcctgagctg cgcgggcagc ggctttacct ttagcaccta tctgatgtat     540
tgggtgcgcc aggcgccggg caaaaccctg gaatgggtga gcgcgattgg cagcggcggc     600 gataccctatt atgcggatag cgtgaaaggc cgctttacca ttagccgcga taacgcgaaa     660
aacagcctgt atctgcagat gaacagcctg cgcgcggaag atatggcggt gtattattgc     720
```

-continued

```
gcgcgcggcc tgggctattg gggccagggc accctggtga ccgtgagcag cgcggcggcg    780
tttgtgccgg tgtttctgcc ggcgaaaccg accaccaccc cggcgccgcg cccgccgacc    840
ccggcgccga ccattgcgag ccagccgctg agcctgcgcc cggaagcgtg ccgcccggcg    900
gcgggcggcg cggtgcatac ccgcggcctg gattttgcgt gcgatattta tatttgggcg    960
ccgctggcgg gcacctgcgg cgtgctgctg ctgagcctgg tgattaccct gtattgcaac   1020
catcgcaacc gcagcaaacg cagccgcctg ctgcatagcg attatatgaa catgaccccg   1080
cgccgcccgg gcccgacccg caaacattat cagccgtatg cgccgccgcg cgattttgcg   1140
gcgtatcgca ccgcgtgaa atttagccgc agcgcggatg cgccggcgta tcagcagggc    1200
cagaaccagc tgtataacga actgaacctg gccgccgcg aagaatatga tgtgctggat   1260
aaacgccgcg gccgcgatcc ggaaatgggc ggcaaaccgc cgcaaaaa cccgcaggaa    1320 ggcctgtata cgaactgca gaaagataaa atggcggaag cgtatagcga aattggcatg   1380
aaaggcgaac cgccgcgcgg caaaggccat gatggcctgt atcagggcct gagcaccgcg   1440
accaaagata cctatgatgc gctgcatatg caggcgctgc cgccgcgc                1488
```

<210> SEQ ID NO 73
<211> LENGTH: 496
<212> TYPE: PRT
<213> ORGANISM: Artificial Sequence
<220> FEATURE:
<223> OTHER INFORMATION: Synthetic Polypeptide

<400> SEQUENCE: 73

```
Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Gly Thr Leu
            20                  25                  30

Ser Leu Ser Pro Gly Glu Arg Ala Thr Leu Ser Cys Arg Ala Ser Gln
        35                  40                  45

Ser Val Ser Ser Ser Tyr Leu Ala Trp Tyr Gln Gln Lys Pro Gly Gln
    50                  55                  60

Ala Pro Arg Leu Leu Ile Tyr Gly Ala Ser Ser Arg Ala Thr Gly Ile
65                  70                  75                  80

Pro Asp Arg Phe Ser Gly Ser Gly Ser Gly Thr Asp Phe Thr Leu Thr
                85                  90                  95

Ile Ser Arg Leu Glu Pro Glu Asp Phe Ala Val Tyr Tyr Cys Gln Gln
            100                 105                 110

Tyr Gly Ser Ser Pro Met Tyr Thr Phe Gly Gln Gly Thr Lys Leu Glu
        115                 120                 125

Ile Lys Gly Gly Gly Gly Ser Gly Gly Gly Gly Ser Gly Gly Gly Gly
    130                 135                 140

Ser Glu Val Gln Leu Val Gln Ser Gly Gly Gly Leu Val His Pro Gly
145                 150                 155                 160

Gly Ser Leu Arg Leu Ser Cys Ala Gly Ser Gly Phe Thr Phe Ser Thr
                165                 170                 175

Tyr Leu Met Tyr Trp Val Arg Gln Ala Pro Gly Lys Thr Leu Glu Trp
            180                 185                 190

Val Ser Ala Ile Gly Ser Gly Gly Asp Thr Tyr Tyr Ala Asp Ser Val
        195                 200                 205

Lys Gly Arg Phe Thr Ile Ser Arg Asp Asn Ala Lys Asn Ser Leu Tyr
    210                 215                 220

Leu Gln Met Asn Ser Leu Arg Ala Glu Asp Met Ala Val Tyr Tyr Cys
```

```
               225                 230                 235                 240
   Ala Arg Gly Leu Gly Tyr Trp Gly Gln Gly Thr Leu Val Thr Val Ser
                       245                 250                 255

Ser Ala Ala Ala Phe Val Pro Val Phe Leu Pro Ala Lys Pro Thr Thr
                       260                 265                 270

Thr Pro Ala Pro Arg Pro Pro Thr Pro Ala Pro Thr Ile Ala Ser Gln
                       275                 280                 285

Pro Leu Ser Leu Arg Pro Glu Ala Cys Arg Pro Ala Ala Gly Gly Ala
                       290                 295                 300

Val His Thr Arg Gly Leu Asp Phe Ala Cys Asp Ile Tyr Ile Trp Ala
   305                 310                 315                 320

Pro Leu Ala Gly Thr Cys Gly Val Leu Leu Leu Ser Leu Val Ile Thr
                       325                 330                 335

Leu Tyr Cys Asn His Arg Asn Arg Ser Lys Arg Ser Arg Leu Leu His
                       340                 345                 350

Ser Asp Tyr Met Asn Met Thr Pro Arg Arg Pro Gly Pro Thr Arg Lys
                       355                 360                 365

His Tyr Gln Pro Tyr Ala Pro Pro Arg Asp Phe Ala Ala Tyr Arg Ser
                       370                 375                 380

Arg Val Lys Phe Ser Arg Ser Ala Asp Ala Pro Ala Tyr Gln Gln Gly
   385                 390                 395                 400

Gln Asn Gln Leu Tyr Asn Glu Leu Asn Leu Gly Arg Arg Glu Glu Tyr
                       405                 410                 415

Asp Val Leu Asp Lys Arg Arg Gly Arg Asp Pro Glu Met Gly Gly Lys
                       420                 425                 430

Pro Arg Arg Lys Asn Pro Gln Glu Gly Leu Tyr Asn Glu Leu Gln Lys
                       435                 440                 445

Asp Lys Met Ala Glu Ala Tyr Ser Glu Ile Gly Met Lys Gly Glu Arg
                       450                 455                 460

Arg Arg Gly Lys Gly His Asp Gly Leu Tyr Gln Gly Leu Ser Thr Ala
   465                 470                 475                 480

Thr Lys Asp Thr Tyr Asp Ala Leu His Met Gln Ala Leu Pro Pro Arg
                       485                 490                 495

<210> SEQ ID NO 74
<211> LENGTH: 708
<212> TYPE: DNA
<213> ORGANISM: Artificial Sequence
<220> FEATURE:
<223> OTHER INFORMATION: Synthetic Polynucleotide

<400> SEQUENCE: 74
gaaattgtgc tgacccagag cccgggcacc ctgagcctga gcccgggcga acgcgcgacc     60
ctgagctgcc gcgcgagcca gagcgtgagc agcagctatc tggcgtggta tcagcagaaa    120
ccgggccagg cgccgcgcct gctgatttat ggcgcgagca gccgcgcgac cggcattccg    180
gatcgcttta gcggcagcgg cagcggcacc gattttaccc tgaccattag ccgcctggaa    240
ccggaagatt ttgcggtgta ttattgccag cagtatggca gcagcccgat gtataccttt    300
ggccagggca ccaaactgga aattaaaggc ggcggcggca gcggcggcgg cggcagcggc    360
ggcggcggca gcgaagtgca gctggtgcag agcggcggcg gcctggtgca tccgggcggc    420
agcctgcgcc tgagctgcgc gggcagcggc tttaccttta gcacctatct gatgtattgg    480
gtgcgccagg cgccgggcaa acccctggaa tgggtgagcg cgattggcag cggcggcgat    540
acctattatg cggatagcgt gaaaggccgc tttaccatta gccgcgataa cgcgaaaaac    600
```
agcctgtatc tgcagatgaa cagcctgcgc gcggaagata tggcggtgta ttattgcgcg    660
cgcggcctgg gctattgggg ccagggcacc ctggtgaccg tgagcagc                708

<210> SEQ ID NO 75
<211> LENGTH: 236
<212> TYPE: PRT
<213> ORGANISM: Artificial Sequence
<220> FEATURE:
<223> OTHER INFORMATION: Synthetic Polypeptide

<400> SEQUENCE: 75

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Met Tyr Thr Phe Gly Gln Gly Thr Lys Leu Glu Ile Lys Gly Gly Gly
            100                 105                 110

Gly Ser Gly Gly Gly Gly Ser Gly Gly Gly Gly Ser Glu Val Gln Leu
        115                 120                 125

Val Gln Ser Gly Gly Gly Leu Val His Pro Gly Gly Ser Leu Arg Leu
    130                 135                 140

Ser Cys Ala Gly Ser Gly Phe Thr Phe Ser Thr Tyr Leu Met Tyr Trp
145                 150                 155                 160

Val Arg Gln Ala Pro Gly Lys Thr Leu Glu Trp Val Ser Ala Ile Gly
                165                 170                 175

Ser Gly Gly Asp Thr Tyr Tyr Ala Asp Ser Val Lys Gly Arg Phe Thr
            180                 185                 190

Ile Ser Arg Asp Asn Ala Lys Asn Ser Leu Tyr Leu Gln Met Asn Ser
        195                 200                 205

Leu Arg Ala Glu Asp Met Ala Val Tyr Tyr Cys Ala Arg Gly Leu Gly
    210                 215                 220

Tyr Trp Gly Gln Gly Thr Leu Val Thr Val Ser Ser
225                 230                 235
```

<210> SEQ ID NO 76
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 76

```
Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Thr Tyr
            20                  25                  30

Leu Met Tyr Trp Val Arg Gln Ala Pro Gly Lys Thr Leu Glu Trp Val
        35                  40                  45
```

Ser Ala Ile Gly Ser Gly Gly Asp Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Leu Gly Tyr Trp Gly Gln Gly Thr Leu Val Thr Val Ser Ser
            100                 105                 110

<210> SEQ ID NO 77
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 77

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Met Tyr Thr Phe Gly Gln Gly Thr Lys Leu Glu Ile Lys
            100                 105

<210> SEQ ID NO 78
<211> LENGTH: 4331
<212> TYPE: DNA
<213> ORGANISM: Artificial Sequence
<220> FEATURE:
<223> OTHER INFORMATION: Synthetic Polynucleotide

<400> SEQUENCE: 78
gagatgtaag gagctgctgt gacttgctca aggccttata tcgagtaaac ggtagtgctg     60
gggcttagac gcaggtgttc tgatttatag ttcaaaacct ctatcaatga gagagcaatc    120
tcctggtaat gtgatagatt cccaactta atgccaacat accataaacc tcccattctg     180
ctaatgccca gcctaagttg gggagaccac tccagattcc aagatgtaca gtttgctttg    240
ctgggccttt ttcccatgcc tgcctttact ctgccagagt tatattgctg gggttttgaa    300
gaagatccta ttaaataaaa gaataagcag tattattaag tagccctgca tttcaggttt    360
ccttgagtgg caggccaggc ctggccgtga acgttcactg aaatcatggc ctcttggcca    420
agattgatag cttgtgcctg tccctgagtc ccagtccatc acgagcagct ggtttctaag    480
atgctatttc ccgtataaag catgagaccg tgacttgcca gccccacaga gccccgccct    540
tgtccatcac tggcatctgg actccagcct gggttggggc aaagagggaa atgagatcat    600
gtcctaaccc tgatcctctt gtcccacaga tatccagaac cctgaccctg ccgtgtacca    660
gctgagagac tctaaatcca gtgacaagtc tgtctgccta ttcaccgatt ttgattctca    720
aacaaatgtg tcacaaagta aggattctga tgtgtatatc acagacaaaa ctgtgctaga    780

```
catgaggtct atggacttca ggctccggtg cccgtcagtg ggcagagcgc acatcgccca    840
cagtccccga gaagttgggg ggaggggtcg gcaattgaac cggtgcctag agaaggtggc    900
gcggggtaaa ctgggaaagt gatgtcgtgt actggctccg ccttttccc gagggtgggg     960 gagaaccgta tataagtgca gtagtcgccg tgaacgttct ttttcgcaac gggtttgccg   1020
ccagaacaca ggtaagtgcc gtgtgtggtt cccgcgggcc tggcctcttt acgggttatg   1080
gcccttgcgt gccttgaatt acttccactg gctgcagtac gtgattcttg atcccgagct   1140
tcgggttgga agtgggtggg agagttcgag gccttgcgct taaggagccc cttcgcctcg   1200
tgcttgagtt gaggcctggc ctgggcgctg gggccgccgc gtgcgaatct ggtggcacct   1260
tcgcgcctgt ctcgctgctt tcgataagtc tctagccatt taaaattttt gatgacctgc   1320
tgcgacgctt ttttctggc aagatagtct tgtaaatgcg ggccaagatc tgcacactgg    1380
tatttcggtt tttggggccg cgggcggcga cggggcccgt gcgtcccagc gcacatgttc   1440
ggcgaggcgg ggcctgcgag cgcggccacc gagaatcgga cggggtagt ctcaagctgg    1500 ccggcctgct ctggtgcctg gcctcgcgcc gccgtgtatc gccccgccct gggcggcaag   1560
gctggcccgg tcggcaccag ttgcgtgagc ggaaagatgg ccgcttcccg gccctgctgc   1620
agggagctca aaatggagga cgcggcgctc gggagagcgg gcgggtgagt cacccacaca   1680
aaggaaaagg gcctttccgt cctcagccgt cgcttcatgt gactccacgg agtaccgggc   1740
gccgtccagg cacctcgatt agttctcgag cttttggagt acgtcgtctt taggttgggg   1800
ggaggggttt tatgcgatgg agtttcccca cactgagtgg gtggagactg aagttaggcc   1860
agcttggcac ttgatgtaat tctccttgga atttgcccctt tttgagtttg gatcttggtt   1920
cattctcaag cctcagacag tggttcaaag ttttttttctt ccatttcagg tgtcgtgacc   1980 accatgcgc ttccggtgac agcactgctc ctcccccttgg cgctgttgct ccacgcagca    2040
aggccggaga tcgtgctgac ccagagcccc ggaacactga gcctgtcccc cggagaaaga   2100
gccacactgt cctgcagggc cagccagagc gtgagcagct cctacctggc ctggtaccag   2160
cagaagcctg gacaggcccc caggctgctg atttacggcg ccagcagcag ggccaccggc   2220
atccccgaca gattcagcgg atccggcagc ggcaccgact tcaccctgac catcagcagg   2280
ctggagcccg aggacttcgc tgtgtactac tgccagcagt acggcagcag ccccatgtac   2340
accttcggcc agggcaccaa gctggagatc aagggaggag gaggatccgg aggaggcgga   2400
agcggaggag gaggaagcga ggtgcagctg gtgcagagcg gcggaggact ggtgcatccc   2460
ggaggatccc tgagactgag ctgtgccggc agcggattca cattctccac ctacctgatg   2520
tactgggtga ggcaggcccc tggcaagacc ctggagtggg tgtccgccat ggctccggc    2580 ggagacacct attatgccga ctccgtcaag gcaggttca ccatcagcag agacaacgcc     2640
aagaactccc tgtacctgca gatgaacagc ctgagggccg aggatatggc tgtgtactat   2700
tgcgctaggg gcctgggata ctggggccag ggaaccctgg tgaccgtgag ctccagtgct   2760
gctgcctttg tcccggtatt tctcccagcc aaaccgacca cgactcccgc ccgcgcccct   2820
ccgacacccg ctcccaccat cgcctctcaa cctcttagtc ttcgcccga ggcatgccga    2880 cccgccgccg ggggtgctgt tcatacgagg ggcttggact tcgcttgtga tatttacatt   2940
tgggctccgt tggcgggtac gtgcggcgtc cttttgttgt cactcgttat tactttgtat   3000
tgtaatcaca ggaatcgctc aaagcggagt aggttgttgc attccgatta catgaatatg   3060
actcctcgcc ggcctgggcc gacaagaaaa cattaccaac cctatgcccc ccacgagac    3120 ttcgctgcgt acaggtcccg agtgaagttt tcccgaagcg cagacgctcc ggcatatcag   3180
```

```
caaggacaga atcagctgta taacgaactg aatttgggac gccgcgagga gtatgacgtg    3240
cttgataaac gccgggggag agacccggaa atgggggggta accccgaag aaagaatccc    3300 caagaaggac tctacaatga actccagaag gataagatgg cggaggccta ctcagaaata    3360
ggtatgaagg cgaacgacg acggggaaaa ggtcacgatg gcctctacca agggttgagt    3420
acggcaacca agatacgta cgatgcactg catatgcagg ccctgcctcc cagataataa    3480
taaaatcgct atccatcgaa gatggatgtg tgttggtttt ttgtgtgtgg agcaacaaat    3540
ctgactttgc atgtgcaaac gccttcaaca acagcattat tccagaagac accttcttcc    3600
ccagcccagg taagggcagc tttggtgcct tcgcaggctg tttccttgct tcaggaatgg    3660
ccaggttctg cccagagctc tggtcaatga tgtctaaaac tcctctgatt ggtggtctcg    3720
gccttatcca ttgccaccaa aaccctcttt ttactaagaa acagtgagcc ttgttctggc    3780
agtccagaga atgacacggg aaaaaagcag atgaagagaa ggtggcagga gagggcacgt    3840
ggcccagcct cagtctctcc aactgagttc ctgcctgcct gcctttgctc agactgtttg    3900 cccccttactg ctcttctagg cctcattcta agccccttct ccaagttgcc tctccttatt   3960
tctccctgtc tgccaaaaaa tctttcccag ctcactaagt cagtctcacg cagtcactca    4020
ttaacccacc aatcactgat tgtgccggca catgaatgca ccaggtgttg aagtggagga    4080 attaaaagt cagatgaggg gtgtgcccag aggaagcacc attctagttg ggggagccca    4140
tctgtcagct gggaaaagtc caaataactt cagattggaa tgtgttttaa ctcagggttg    4200
agaaaacagc taccttcagg acaaaagtca gggaagggct ctctgaagaa atgctacttg    4260
aagataccag ccctaccaag ggcagggaga ggaccctata gaggcctggg acaggagctc    4320
aatgagaaag g                                                        4331
```

<210> SEQ ID NO 79
<211> LENGTH: 1491
<212> TYPE: DNA
<213> ORGANISM: Artificial Sequence
<220> FEATURE:
<223> OTHER INFORMATION: Synthetic Polynucleotide

<400> SEQUENCE: 79

```
atggcgctgc cggtgaccgc gctgctgctg ccgctggcgc tgctgctgca tgcggcgcgc     60
ccggaagtgc agctggtgca gagcggcggc ggcctggtgc atccgggcgg cagcctgcgc    120
ctgagctgcg cgggcagcgg cttttacctttt agcacctatc tgatgtattg ggtgcgccag    180
gcgccgggca aaaaccctgga atgggtgagc gcgattggca gcggcggcga tacctattat    240
gcggatagcg tgaaaggccg ctttaccatt agccgcgata acgcgaaaaa cagcctgtat    300
ctgcagatga acagcctgcg cgcggaagat atggcggtgt attattgcgc gcgcggcctg    360
ggctattggg gccagggcac cctggtgacc gtgagcagcg gcggcggcgg cagcggcggc    420
ggcggcagcg gcggcggcgg cagcgaaatt gtgctgaccc agagcccggg caccctgagc    480
ctgagcccgg gcgaacgcgc gaccctgagc tgccgcgcga gccagagcgt gagcagcagc    540
tatctggcgt ggtatcagca gaaaccgggc caggcgccgc gcctgctgat ttatggcgcg    600
agcagccgcg cgaccggcat tccggatcgc tttagcggca gcggcagcgg caccgatttt    660
accctgacca ttagccgcct ggaaccggaa gattttgcgg tgtattattg ccagcagtat    720
ggcagcagcc cgatgtatac ctttggccag ggcaccaaac tggaaattaa agcgcggcg    780 gcgtttgtgc cggtgtttct gccggcgaaa ccgaccacca cccggcgcc gcgcccgccg    840
```

```
accccggcgc cgaccattgc gagccagccg ctgagcctgc gcccggaagc gtgccgcccg    900
gcggcgggcg gcgcggtgca tacccgcggc ctggattttg cgtgcgatat ttatatttgg    960
gcgccgctgg cgggcacctg cggcgtgctg ctgctgagcc tggtgattac cctgtattgc   1020
aaccatcgca accgcagcaa acgcagccgc ctgctgcata gcgattatat gaacatgacc   1080
ccgcgccgcc cgggcccgac ccgcaaacat tatcagccgt atgcgccgcc gcgcgatttt   1140
gcggcgtatc gcagccgcgt gaaatttagc cgcagcgcgg atgcgccggc gtatcagcag   1200
ggccagaacc agctgtataa cgaactgaac ctgggccgcc gcaagaata tgatgtgctg    1260 gataaacgcc gcggccgcga tccggaaatg ggcggcaaac cgcgccgcaa aaacccgcag   1320
gaaggcctgt ataacgaact gcagaaagat aaaatggcgg aagcgtatag cgaaattggc   1380
atgaaaggcg aacgccgccg cggcaaaggc catgatggcc tgtatcaggg cctgagcacc   1440
gcgaccaaag atacctatga tgcgctgcat atgcaggcgc tgccgccgcg c            1491
```

<210> SEQ ID NO 80
<211> LENGTH: 497
<212> TYPE: PRT
<213> ORGANISM: Artificial Sequence
<220> FEATURE:
<223> OTHER INFORMATION: Synthetic Polypeptide

<400> SEQUENCE: 80

```
Met Ala Leu Pro Val Thr Ala Leu Leu Pro Leu Ala Leu Leu Leu
1               5                   10                  15

His Ala Ala Arg Pro Glu Val Gln Leu Val Gln Ser Gly Gly Gly Leu
            20                  25                  30

Val His Pro Gly Gly Ser Leu Arg Leu Ser Cys Ala Gly Ser Gly Phe
        35                  40                  45

Thr Phe Ser Thr Tyr Leu Met Tyr Trp Val Arg Gln Ala Pro Gly Lys
    50                  55                  60

Thr Leu Glu Trp Val Ser Ala Ile Gly Ser Gly Gly Asp Thr Tyr Tyr
65                  70                  75                  80

Ala Asp Ser Val Lys Gly Arg Phe Thr Ile Ser Arg Asp Asn Ala Lys
                85                  90                  95

Asn Ser Leu Tyr Leu Gln Met Asn Ser Leu Arg Ala Glu Asp Met Ala
            100                 105                 110

Val Tyr Tyr Cys Ala Arg Gly Leu Gly Tyr Trp Gly Gln Gly Thr Leu
        115                 120                 125

Val Thr Val Ser Ser Gly Gly Gly Ser Gly Gly Gly Ser Gly
    130                 135                 140

Gly Gly Gly Ser Glu Ile Val Leu Thr Gln Ser Pro Gly Thr Leu Ser
145                 150                 155                 160

Leu Ser Pro Gly Glu Arg Ala Thr Leu Ser Cys Arg Ala Ser Gln Ser
                165                 170                 175

Val Ser Ser Ser Tyr Leu Ala Trp Tyr Gln Gln Lys Pro Gly Gln Ala
            180                 185                 190

Pro Arg Leu Leu Ile Tyr Gly Ala Ser Ser Arg Ala Thr Gly Ile Pro
        195                 200                 205

Asp Arg Phe Ser Gly Ser Gly Ser Gly Thr Asp Phe Thr Leu Thr Ile
    210                 215                 220

Ser Arg Leu Glu Pro Glu Asp Phe Ala Val Tyr Tyr Cys Gln Gln Tyr
225                 230                 235                 240

Gly Ser Ser Pro Met Tyr Thr Phe Gly Gln Gly Thr Lys Leu Glu Ile
                245                 250                 255
```

Lys Ser Ala Ala Ala Phe Val Pro Val Phe Leu Pro Ala Lys Pro Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Ser Leu Val Ile
                325                 330                 335

Thr Leu Tyr Cys Asn His Arg Asn Arg Ser Lys Arg Ser Arg Leu Leu
            340                 345                 350

His Ser Asp Tyr Met Asn Met Thr Pro Arg Arg Pro Gly Pro Thr Arg
        355                 360                 365

Lys His Tyr Gln Pro Tyr Ala Pro Pro Arg Asp Phe Ala Ala Tyr Arg
    370                 375                 380

Ser Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 81
<211> LENGTH: 708
<212> TYPE: DNA
<213> ORGANISM: Artificial Sequence
<220> FEATURE:
<223> OTHER INFORMATION: Synthetic Polynucleotide

<400> SEQUENCE: 81
gaagtgcagc tggtgcagag cggcggcggc ctggtgcatc cgggcggcag cctgcgcctg      60
agctgcgcgg gcagcggctt tacctttagc acctatctga tgtattgggt gcgccaggcg     120
ccgggcaaaa ccctggaatg ggtgagcgcg attggcagcg gcggcgatac ctattatgcg     180
gatagcgtga aaggccgctt taccattagc cgcgataacg cgaaaaacag cctgtatctg     240
cagatgaaca gcctgcgcgc ggaagatatg gcggtgtatt attgcgcgcg cggcctgggc     300
tattggggcc agggcaccct ggtgaccgtg agcagcggcg gcggcggcag cggcggcggc     360
ggcagcggcg gcggcggcag cgaaattgtg ctgacccaga gcccgggcac cctgagcctg     420
agcccgggcg aacgcgcgac cctgagctgc cgcgcgagcc agagcgtgag cagcagctat     480
ctggcgtggt atcagcagaa accgggccag gcgccgcgcc tgctgattta tggcgcgagc     540
agccgcgcga ccggcattcc ggatcgcttt agcggcagcg gcagcggcac cgattttacc     600
ctgaccatta gccgcctgga accggaagat tttgcggtgt attattgcca gcagtatggc     660
agcagcccga tgtataccct tggccagggc accaaactgg aaattaaa   708

<210> SEQ ID NO 82
<211> LENGTH: 236
<212> TYPE: PRT
<213> ORGANISM: Artificial Sequence
<220> FEATURE:
<223> OTHER INFORMATION: Synthetic Polypeptide

<400> SEQUENCE: 82

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Thr Tyr
            20                  25                  30

Leu Met Tyr Trp Val Arg Gln Ala Pro Gly Lys Thr Leu Glu Trp Val
        35                  40                  45

Ser Ala Ile Gly Ser Gly Gly Asp Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Leu Gly Tyr Trp Gly Gln Gly Thr Leu Val Thr Val Ser Ser
            100                 105                 110

Gly Gly Gly Gly Ser Gly Gly Gly Gly Ser Gly Gly Gly Gly Ser Glu
        115                 120                 125

Ile Val Leu Thr Gln Ser Pro Gly Thr Leu Ser Leu Ser Pro Gly Glu
    130                 135                 140

Arg Ala Thr Leu Ser Cys Arg Ala Ser Gln Ser Val Ser Ser Ser Tyr
145                 150                 155                 160

Leu Ala Trp Tyr Gln Gln Lys Pro Gly Gln Ala Pro Arg Leu Leu Ile
                165                 170                 175

Tyr Gly Ala Ser Ser Arg Ala Thr Gly Ile Pro Asp Arg Phe Ser Gly
            180                 185                 190

Ser Gly Ser Gly Thr Asp Phe Thr Leu Thr Ile Ser Arg Leu Glu Pro
        195                 200                 205

Glu Asp Phe Ala Val Tyr Tyr Cys Gln Gln Tyr Gly Ser Ser Pro Met
    210                 215                 220

Tyr Thr Phe Gly Gln Gly Thr Lys Leu Glu Ile Lys
225                 230                 235

<210> SEQ ID NO 83
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 83

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Thr Tyr
            20                  25                  30

Leu Met Tyr Trp Val Arg Gln Ala Pro Gly Lys Thr Leu Glu Trp Val
        35                  40                  45

Ser Ala Ile Gly Ser Gly Gly Asp Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Leu Gly Tyr Trp Gly Gln Gly Thr Leu Val Thr Val Ser Ser
            100                 105                 110

<210> SEQ ID NO 84
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 84

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Met Tyr Thr Phe Gly Gln Gly Thr Lys Leu Glu Ile Lys
            100                 105

<210> SEQ ID NO 85
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 85

Thr Tyr Leu Met Tyr
1               5

<210> SEQ ID NO 86
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 86

Ala Ile Gly Ser Gly Gly Asp Thr Tyr Tyr Ala Asp Ser Val Lys Gly
1               5                   10                  15

<210> SEQ ID NO 87
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 87

Gly Leu Gly Tyr
1

<210> SEQ ID NO 88
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 88

Arg Ala Ser Gln Ser Val Ser Ser Ser Tyr Leu Ala
1               5                   10

<210> SEQ ID NO 89
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 89

Gly Ala Ser Ser Arg Ala Thr
1               5

<210> SEQ ID NO 90
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 90

Gln Gln Tyr Gly Ser Ser Pro Met Tyr Thr
1               5                   10

<210> SEQ ID NO 91
<211> LENGTH: 4331
<212> TYPE: DNA
<213> ORGANISM: Artificial Sequence
<220> FEATURE:
<223> OTHER INFORMATION: Synthetic Polynucleotide

<400> SEQUENCE: 91

| | | | | | |
|---|---|---|---|---|---|
| gagatgtaag | gagctgctgt | gacttgctca | aggccttata | tcgagtaaac | ggtagtgctg | 60 |
| gggcttagac | gcaggtgttc | tgatttatag | ttcaaaacct | ctatcaatga | gagagcaatc | 120 |
| tcctggtaat | gtgatagatt | tcccaactta | atgccaacat | accataaacc | tcccattctg | 180 |
| ctaatgccca | gcctaagttg | gggagaccac | tccagattcc | aagatgtaca | gtttgctttg | 240 |
| ctgggccttt | ttcccatgcc | tgcctttact | ctgccagagt | tatattgctg | gggttttgaa | 300 |
| gaagatccta | ttaaataaaa | gaataagcag | tattattaag | tagccctgca | tttcaggttt | 360 |
| ccttgagtgg | caggccaggc | ctggccgtga | acgttcactg | aaatcatggc | ctcttggcca | 420 |
| agattgatag | cttgtgcctg | tccctgagtc | ccagtccatc | acgagcagct | ggttctaag | 480 |
| atgctatttc | ccgtataaag | catgagaccg | tgacttgcca | ccccacaga | gccccgccct | 540 |
| tgtccatcac | tggcatctgg | actccagcct | gggttggggc | aaagagggaa | atgagatcat | 600 |
| gtcctaaccc | tgatcctctt | gtcccacaga | tatccagaac | cctgaccctg | ccgtgtacca | 660 |
| gctgagagac | tctaaatcca | gtgacaagtc | tgtctgccta | ttcaccgatt | ttgattctca | 720 |
| aacaaatgtg | tcacaaagta | aggattctga | tgtgtatatc | acagacaaaa | ctgtgctaga | 780 |
| catgaggtct | atggacttca | ggctccggtg | cccgtcagtg | gcagagcgc | acatcgccca | 840 |
| cagtccccga | gaagttgggg | ggaggggtcg | gcaattgaac | cggtgcctag | agaaggtggc | 900 |

```
gcggggtaaa ctgggaaagt gatgtcgtgt actggctccg cctttttccc gagggtgggg    960
gagaaccgta tataagtgca gtagtcgccg tgaacgttct ttttcgcaac gggtttgccg   1020
ccagaacaca ggtaagtgcc gtgtgtggtt cccgcgggcc tggcctcttt acgggttatg   1080
gcccttgcgt gccttgaatt acttccactg gctgcagtac gtgattcttg atcccgagct   1140
tcgggttgga agtgggtggg agagttcgag gccttgcgct taaggagccc cttcgcctcg   1200
tgcttgagtt gaggcctggc ctgggcgctg ggccgccgc gtgcgaatct ggtggcacct    1260
tcgcgcctgt ctcgctgctt tcgataagtc tctagccatt taaaattttt gatgacctgc   1320
tgcgacgctt ttttctggc aagatagtct tgtaaatgcg ggccaagatc tgcacactgg    1380
tatttcggtt tttggggccg cgggcggcga cggggcccgt gcgtcccagc gcacatgttc   1440
ggcgaggcgg ggcctgcgag cgcggccacc gagaatcgga cggggtagt ctcaagctgg    1500 ccggcctgct ctggtgcctg gcctcgcgcc gccgtgtatc gccccgccct gggcggcaag   1560 gctggcccg tcggcaccag ttgcgtgagc ggaaagatgg ccgcttcccg gccctgctgc    1620
agggagctca aaatggagga cgcggcgctc gggagagcgg gcgggtgagt cacccacaca   1680
aaggaaaagg gccttttccgt cctcagccgt cgcttcatgt gactccacgg agtaccgggc  1740
gccgtccagg cacctcgatt agttctcgag cttttggagt acgtcgtctt taggttgggg   1800
ggaggggttt tatgcgatgg agtttcccca cactgagtgg gtggagactg aagttaggcc   1860
agcttggcac ttgatgtaat tctccttgga atttgccctt tttgagtttg atcttggtt   1920 cattctcaag cctcagacag tggttcaaag ttttttttctt ccatttcagg tgtcgtgacc  1980
accatggcgc ttccggtgac agcactgctc ctcccccttgg cgctgttgct ccacgcagca  2040 aggccgagg tccagctggt gcagagcgga ggcggactgg tgcatcctgg aggctccctg    2100
agactgtcct gtgccggcag cggcttcacc ttcagcacct acctgatgta ctgggtgaga  2160
caggcccccg gcaaaaccct ggagtgggtg agcgctatcg gcagcggcgg agacacatac  2220
tacgccgaca gcgtgaaggg caggttcacc atcagcaggg acaacgccaa gaactccctg  2280
tacctgcaga tgaactccct gagggctgag gacatggccg tgtactactg cgctagaggc  2340
ctgggctact ggggacaggg cacactggtg acagtgagca gcggaggcgg cggcagcgga  2400
ggcggcggca gcggcggcgg aggcagcgag atcgtgctga cacagagccc tggcacctg   2460 tccctgtccc ctgcgaaaag gccaccctg agctgtaggg ccagccagtc cgtgagcagc   2520
agctatctgg cctggtacca gcagaaaccc ggccaggccc ctagactgct gatctacggc  2580
gcctcctcca gagccaccgg aatccccgat agattcagcg gctccggcag cggcaccgat  2640
ttcacactga ccatcagcag gctggagccc gaggacttcg ccgtgtatta ctgccagcag  2700
tacggcagca gccctatgta cacattcggc cagggcacca agctggagat caagagtgct  2760
gctgcctttg tccggtatt tctcccagcc aaaccgacca cgactcccgc ccgcgccct   2820 ccgacacccg ctcccaccat cgcctctcaa cctcttagtc ttcgcccga ggcatgccga   2880 cccgccgccg ggggtgctgt tcatacgagg ggcttggact tcgcttgtga tatttacatt  2940
tgggctccgt tggcgggtac gtgcggcgtc cttttgttgt cactcgttat tactttgtat  3000
tgtaatcaca ggaatcgctc aaagcggagt aggttgttgc attccgatta catgaatatg  3060
actcctcgcc ggcctgggcc gacaagaaaa cattaccaac cctatgcccc cccacgagac  3120
ttcgctgcgt acaggtcccg agtgaagttt tcccgaagcg cagacgctcc ggcatatcag  3180
caaggacaga atcagctgta taacgaactg aatttgggac gccgcgagga gtatgacgtg  3240
```

| | |
|---|---:|
| cttgataaac gccggggag agacccggaa atggggggta aaccccgaag aaagaatccc | 3300 |
| caagaaggac tctacaatga actccagaag gataagatgg cggaggccta ctcagaaata | 3360 |
| ggtatgaagg gcgaacgacg acggggaaaa ggtcacgatg gcctctacca agggttgagt | 3420 |
| acggcaacca aagatacgta cgatgcactg catatgcagg ccctgcctcc cagataataa | 3480 |
| taaaatcgct atccatcgaa gatggatgtg tgttggtttt ttgtgtgtgg agcaacaaat | 3540 |
| ctgactttgc atgtgcaaac gccttcaaca acagcattat tccagaagac accttcttcc | 3600 |
| ccagcccagg taagggcagc tttggtgcct tcgcaggctg tttccttgct tcaggaatgg | 3660 |
| ccaggttctg cccagagctc tggtcaatga tgtctaaaac tcctctgatt ggtggtctcg | 3720 |
| gccttatcca ttgccaccaa accctctttt ttactaagaa acagtgagcc ttgttctggc | 3780 |
| agtccagaga atgacacggg aaaaaagcag atgaagagaa ggtggcagga gagggcacgt | 3840 |
| ggcccagcct cagtctctcc aactgagttc ctgcctgcct gcctttgctc agactgtttg | 3900 |
| ccccttactg ctcttctagg cctcattcta agccccttct ccaagttgcc tctccttatt | 3960 |
| tctccctgtc tgccaaaaaa tctttcccag ctcactaagt cagtctcacg cagtcactca | 4020 |
| ttaacccacc aatcactgat tgtgccggca catgaatgca ccaggtgttg aagtggagga | 4080 |
| attaaaaagt cagatgaggg gtgtgcccag aggaagcacc attctagttg ggggagccca | 4140 |
| tctgtcagct gggaaaagtc caaataactt cagattggaa tgtgttttaa ctcagggttg | 4200 |
| agaaaacagc taccttcagg acaaaagtca gggaagggc tctgaagaa atgctacttg | 4260 |
| aagataccag ccctaccaag ggcagggaga ggaccctata gaggcctggg acaggagctc | 4320 |
| aatgagaaag g | 4331 |

<210> SEQ ID NO 92
<211> LENGTH: 804
<212> TYPE: DNA
<213> ORGANISM: Artificial Sequence
<220> FEATURE:
<223> OTHER INFORMATION: Synthetic Polynucleotide

<400> SEQUENCE: 92

| | |
|---|---:|
| tggagcaaca aatctgactt tgcatgtgca aacgccttca acaacagcat tattccagaa | 60 |
| gacaccttct tccccagccc aggtaagggc agctttggtg ccttcgcagg ctgtttcctt | 120 |
| gcttcaggaa tggccaggtt ctgcccagag ctctggtcaa tgatgtctaa aactcctctg | 180 |
| attggtggtc tcggccttat ccattgccac caaaaccctc tttttactaa gaaacagtga | 240 |
| gccttgttct ggcagtccag agaatgacac gggaaaaaag cagatgaaga gaaggtggca | 300 |
| ggagagggca cgtggcccag cctcagtctc tccaactgag ttcctgcctg cctgcctttg | 360 |
| ctcagactgt ttgccccctta ctgctcttct aggcctcatt ctaagcccct tctccaagtt | 420 |
| gcctctcctt atttctccct gtctgccaaa aaatctttcc cagctcacta agtcagtctc | 480 |
| acgcagtcac tcattaaccc accaatcact gattgtgccg gcacatgaat gcaccaggtg | 540 |
| ttgaagtgga ggaattaaaa agtcagatga ggggtgtgcc cagaggaagc accattctag | 600 |
| ttgggggagc ccatctgtca gctgggaaaa gtccaaataa cttcagattg gaatgtgttt | 660 |
| taactcaggg ttgagaaaac agctaccttc aggacaaaag tcagggaagg gctctctgaa | 720 |
| gaaatgctac ttgaagatac cagccctacc aagggcaggg agaggaccct atagaggcct | 780 |
| gggacaggag ctcaatgaga aagg | 804 |

<210> SEQ ID NO 93
<211> LENGTH: 21

<212> TYPE: PRT
<213> ORGANISM: Artificial Sequence
<220> FEATURE:
<223> OTHER INFORMATION: Synthetic Polypeptide

<400> SEQUENCE: 93

Met Ala Leu Pro Val Thr Ala Leu Leu Pro Leu Ala Leu Leu
1               5                   10                  15

His Ala Ala Arg Pro
            20

<210> SEQ ID NO 94
<211> LENGTH: 261
<212> TYPE: DNA
<213> ORGANISM: Artificial Sequence
<220> FEATURE:
<223> OTHER INFORMATION: Synthetic Polynucleotide

<400> SEQUENCE: 94
gctgctgcct tgtcccggt atttctccca gccaaaccga ccacgactcc cgccccgcgc    60
cctccgacac ccgctcccac catcgcctct caacctctta gtcttcgccc cgaggcatgc   120
cgacccgccg ccgggggtgc tgttcatacg aggggcttgg acttcgcttg tgatatttac   180
atttgggctc cgttggcggg tacgtgcggc gtccttttgt tgtcactcgt tattactttg   240
tattgtaatc acaggaatcg c                                            261

<210> SEQ ID NO 95
<211> LENGTH: 88
<212> TYPE: PRT
<213> ORGANISM: Artificial Sequence
<220> FEATURE:
<223> OTHER INFORMATION: Synthetic Polypeptide

<400> SEQUENCE: 95

Ser Ala Ala Ala Phe Val Pro Val Phe Leu Pro Ala Lys Pro Thr Thr
1               5                   10                  15

Thr Pro Ala Pro Arg Pro Pro Thr Pro Ala Pro Thr Ile Ala Ser Gln
            20                  25                  30

Pro Leu Ser Leu Arg Pro Glu Ala Cys Arg Pro Ala Ala Gly Gly Ala
        35                  40                  45

Val His Thr Arg Gly Leu Asp Phe Ala Cys Asp Ile Tyr Ile Trp Ala
    50                  55                  60

Pro Leu Ala Gly Thr Cys Gly Val Leu Leu Leu Ser Leu Val Ile Thr
65                  70                  75                  80

Leu Tyr Cys Asn His Arg Asn Arg
                85

<210> SEQ ID NO 96
<211> LENGTH: 252
<212> TYPE: DNA
<213> ORGANISM: Artificial Sequence
<220> FEATURE:
<223> OTHER INFORMATION: Synthetic Polynucleotide

<400> SEQUENCE: 96
tttgtcccgg tatttctccc agccaaaccg accacgactc cgccccgcg ccctccgaca    60 cccgctccca ccatcgcctc tcaacctctt agtcttcgcc ccgaggcatg ccgacccgcc   120
gccgggggtg ctgttcatac gaggggcttg gacttcgctt gtgatattta catttgggct   180
ccgttggcgg gtacgtgcgg cgtccttttg ttgtcactcg ttattacttt gtattgtaat   240

-continued cacaggaatc gc                                                      252

<210> SEQ ID NO 97
<211> LENGTH: 84
<212> TYPE: PRT
<213> ORGANISM: Artificial Sequence
<220> FEATURE:
<223> OTHER INFORMATION: Synthetic Polypeptide

<400> SEQUENCE: 97

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg

<210> SEQ ID NO 98
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 98
cgagtgaagt tttcccgaag cgcagacgct ccggcatatc agcaaggaca gaatcagctg     60
tataacgaac tgaatttggg acgccgcgag gagtatgacg tgcttgataa acgccggggg    120
agagacccgg aaatggggggg taaaccccga agaaagaatc cccaagaagg actctacaat    180
gaactccaga aggataagat ggcggaggcc tactcagaaa taggtatgaa gggcgaacga    240
cgacggggaa aaggtcacga tggcctctac caagggttga gtacggcaac caaagatacg    300
tacgatgcac tgcatatgca ggccctgcct cccaga                              336

<210> SEQ ID NO 99
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 99

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 100
<211> LENGTH: 800
<212> TYPE: DNA
<213> ORGANISM: Artificial sequence
<220> FEATURE:
<223> OTHER INFORMATION: Synthetic polynucleotide

<400> SEQUENCE: 100

| | | | | | |
|---|---|---|---|---|---|
| gagatgtaag | gagctgctgt | gacttgctca | aggccttata | tcgagtaaac | ggtagtgctg | 60 |
| gggcttagac | gcaggtgttc | tgatttatag | ttcaaaacct | ctatcaatga | gagagcaatc | 120 |
| tcctggtaat | gtgatagatt | tcccaactta | atgccaacat | accataaacc | tcccattctg | 180 |
| ctaatgccca | gcctaagttg | gggagaccac | tccagattcc | aagatgtaca | gtttgctttg | 240 |
| ctgggccttt | ttcccatgcc | tgcctttact | ctgccagagt | tatattgctg | gggttttgaa | 300 |
| gaagatccta | ttaaataaaa | gaataagcag | tattattaag | tagccctgca | tttcaggttt | 360 |
| ccttgagtgg | caggccaggc | ctggccgtga | acgttcactg | aaatcatggc | ctcttggcca | 420 |
| agattgatag | cttgtgcctg | tccctgagtc | ccagtccatc | acgagcagct | ggtttctaag | 480 |
| atgctatttc | ccgtataaag | catgagaccg | tgacttgcca | gccccacaga | gccccgccct | 540 |
| tgtccatcac | tggcatctgg | actccagcct | gggttgggc | aaagagggaa | atgagatcat | 600 |
| gtcctaaccc | tgatcctctt | gtcccacaga | tatccagaac | cctgaccctg | ccgtgtacca | 660 |
| gctgagagac | tctaaatcca | gtgacaagtc | tgtctgccta | ttcaccgatt | ttgattctca | 720 |
| aacaaatgtg | tcacaaagta | aggattctga | tgtgtatatc | acagacaaaa | ctgtgctaga | 780 |
| catgaggtct | atggacttca | | | | | 800 |

<210> SEQ ID NO 101
<211> LENGTH: 1178
<212> TYPE: DNA
<213> ORGANISM: Artificial Seuqence
<220> FEATURE:
<223> OTHER INFORMATION: Synthetic Polynucleotide

<400> SEQUENCE: 101

| | | | | | |
|---|---|---|---|---|---|
| ggctccggtg | cccgtcagtg | ggcagagcgc | acatcgccca | cagtccccga | gaagttgggg | 60 |
| ggaggggtcg | gcaattgaac | cggtgcctag | agaaggtggc | gcggggtaaa | ctgggaaagt | 120 |
| gatgtcgtgt | actggctccg | ccttttttccc | gagggtgggg | gagaaccgta | tataagtgca | 180 |
| gtagtcgccg | tgaacgttct | ttttcgcaac | gggtttgccg | ccagaacaca | ggtaagtgcc | 240 |
| gtgtgtggtt | cccgcgggcc | tggcctcttt | acgggttatg | gcccttgcgt | gccttgaatt | 300 |
| acttccactg | gctgcagtac | gtgattcttg | atcccgagct | tcgggttgga | agtgggtggg | 360 |
| agagttcgag | gccttgcgct | taaggagccc | cttcgcctcg | tgcttgagtt | gaggcctggc | 420 |
| ctgggcgctg | gggccgccgc | gtgcgaatct | ggtggcacct | tcgcgcctgt | ctcgctgctt | 480 |
| tcgataagtc | tctagccatt | taaaattttt | gatgacctgc | tgcgacgctt | tttttctggc | 540 |
| aagatagtct | tgtaaatgcg | ggccaagatc | tgcacactgg | tatttcggtt | tttggggccg | 600 |
| cgggcggcga | cggggcccgt | gcgtcccagc | gcacatgttc | ggcgaggcgg | ggcctgcgag | 660 |
| cgcggccacc | gagaatcgga | cgggggtagt | ctcaagctgg | ccggcctgct | ctggtgcctg | 720 |
| gcctcgcgcc | gccgtgtatc | gccccgccct | gggcggcaag | gctggcccgg | tcggcaccag | 780 |
| ttgcgtgagc | ggaaagatgg | ccgcttcccg | gccctgctgc | agggagctca | aaatggagga | 840 |

```
cgcggcgctc gggagagcgg gcgggtgagt cacccacaca aaggaaaagg gcctttccgt      900
cctcagccgt cgcttcatgt gactccacgg agtaccgggc gccgtccagg cacctcgatt      960
agttctcgag cttttggagt acgtcgtctt taggttgggg ggaggggttt tatgcgatgg     1020
agtttcccca cactgagtgg gtggagactg aagttaggcc agcttggcac ttgatgtaat     1080
tctccttgga atttgccctt tttgagtttg gatcttggtt cattctcaag cctcagacag     1140
tggttcaaag ttttttttctt ccatttcagg tgtcgtga                             1178
```

<210> SEQ ID NO 102
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 102

```
aataaaatcg ctatccatcg aagatggatg tgtgttggtt ttttgtgtg                   49
```

<210> SEQ ID NO 103

<400> SEQUENCE: 103

000

<210> SEQ ID NO 104
<211> LENGTH: 20
<212> TYPE: DNA
<213> ORGANISM: Artificial Seuqence
<220> FEATURE:
<223> OTHER INFORMATION: Synthetic Polynucleotide

<400> SEQUENCE: 104

```
agagcaacag tgctgtggcc                                                   20
```

<210> SEQ ID NO 105
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 105

```
agagcaacag ugcuguggcc                                                   20
```

<210> SEQ ID NO 106
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 106

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 107
<211> LENGTH: 84
<212> TYPE: PRT
<213> ORGANISM: Artificial Seuqence
<220> FEATURE:
<223> OTHER INFORMATION: Synthetic Polypeptide

<400> SEQUENCE: 107

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg

<210> SEQ ID NO 108
<211> LENGTH: 456
<212> TYPE: PRT
<213> ORGANISM: Artificial Sequence
<220> FEATURE:
<223> OTHER INFORMATION: Synthetic polypeptide

<400> SEQUENCE: 108

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Tyr Tyr Gly Ser Gly Ser Phe Asn Ser Tyr Tyr Gly
            100                 105                 110

Thr Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

```
Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 109
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 109

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ile Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175
```

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 110
<211> LENGTH: 100
<212> TYPE: DNA
<213> ORGANISM: Artificial Seuqence
<220> FEATURE:
<223> OTHER INFORMATION: Synthetic Polynucleotide

<400> SEQUENCE: 110
ccgccgcgau gggagcugcg guuuuagagc uagaaauagc aaguuaaaau aaggcuaguc      60
cguuaucaac uugaaaaagu ggcaccgagu cggugcuuuu                          100

<210> SEQ ID NO 111
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 111
ccgccgcgau gggagcugcg guuuuagagc uagaaauagc aaguuaaaau aaggcuaguc      60
cguuaucaac uugaaaaagu ggcaccgagu cggugcuuuu                          100

<210> SEQ ID NO 112
<211> LENGTH: 1530
<212> TYPE: DNA
<213> ORGANISM: Artificial Seuqence
<220> FEATURE:
<223> OTHER INFORMATION: Synthetic Polynucleotide

<400> SEQUENCE: 112
atggcgcttc cggtgacagc actgctcctc cccttggcgc tgttgctcca cgcagcaagg      60
ccgcaggtgc agctggtgga gagcggcgga ggagtggtgc aacccggaag gtccctgagg     120
ctctcctgtg ccgccagcgg cttcaccttc tccagctacg gtatgcactg ggtgagacaa     180 gccccggaa agggcctcga gtgggtggcc gtgatctggg atgatggctc caacaagtac     240
tacgtggaca cgtcaagggg cagattcacc atcagcaggg acaacagcaa gaacaccctg     300
tacctgcaga tgaactccct gagagccgaa gacaccgccg tgtactattg tgccagggac     360
gactactatg gctccggctc cttcaatagc tactatggca ccgacgtgtg gggcagggc      420 accacagtga cagtgagcag cggcggagga ggatccggag gaggaggaag cggaggagga     480
ggaagcgaga tcgtgctgac acagtccccc gctaccctga gcctgagccc cggcgagaga     540
gctaccctga gctgcagagc cagccagagc gtctccatct acctggcctg gtaccagcag     600
aagcctggcc aggcccctag actgctgatc tacgacgcca gcaacagggc caccggcatt     660
cctgccagat tcagcggctc cggctccggc accgatttca cactgaccat cagctccctg     720
gagcctgagg acttcgccgt gtattactgc cagcagagga gcaactggcc cccctttacc     780
ttcggccccg gcaccaaggt cgacatcaag agtgctgctg cctttgtccc ggtatttctc     840
ccagccaaac cgaccacgac tcccgccccg cgccctccga cacccgctcc caccatcgcc     900
tctcaacctc ttagtcttcg ccccgaggca tgccgacccg ccgcggggg tgctgttcat     960

```
acgaggggct tggacttcgc ttgtgatatt tacatttggg ctccgttggc gggtacgtgc    1020
ggcgtccttt tgttgtcact cgttattact ttgtattgta atcacaggaa tcgctcaaag    1080
cggagtaggt tgttgcattc cgattacatg aatatgactc ctcgccggcc tgggccgaca    1140
agaaaacatt accaaccca tgccccccca cgagacttcg ctgcgtacag gtcccgagtg    1200
aagttttccc gaagcgcaga cgctccggca tatcagcaag gacagaatca gctgtataac    1260
gaactgaatt tgggacgccg cgaggagtat gacgtgcttg ataaacgccg ggggagagac    1320
ccggaaatgg ggggtaaacc ccgaagaaag aatccccaag aaggactcta caatgaactc    1380
cagaaggata agatggcgga ggcctactca gaaataggta tgaagggcga acgacgacgg    1440
ggaaaaggtc acgatggcct ctaccaaggg ttgagtacgg caaccaaaga tacgtacgat    1500
gcactgcata tgcaggccct gcctcccaga                                     1530

<210> SEQ ID NO 113
<211> LENGTH: 747
<212> TYPE: DNA
<213> ORGANISM: Artificial Seuqence
<220> FEATURE:
<223> OTHER INFORMATION: Synthetic Polynucleotide

<400> SEQUENCE: 113
caggtgcagc tggtggaaag cggcggcggc gtggtgcagc cgggccgcag cctgcgcctg      60
agctgcgcgg cgagcggctt tacctttagc agctatggca tgcattgggt gcgccaggcg     120
ccgggcaaag gcctggaatg ggtggcggtg atttgggatg atggcagcaa caaatattat     180
gtggatagcg tgaaaggccg ctttaccatt agccgcgata cagcaaaaa cacctgtat      240 ctgcagatga acagcctgcg cgcggaagat accgcggtgt attattgcgc gcgcgatgat     300
tattatggca gcggcagctt taacagctat tatggcaccg atgtgtgggg ccagggcacc     360
accgtgaccg tgagcagcgg cggcggcggc agcggcggcg gcggcagcgg cggcggcggc     420
agcgaaattg tgctgaccca gagcccggcg accctgagcc tgagcccggg cgaacgcgcg     480
accctgagct gccgcgcgag ccagagcgtg agcatttatc tggcgtggta tcagcagaaa     540
ccgggccagg cgccgcgcct gctgatttat gatgcgagca accgcgcgac cggcattccg     600
gcgcgcttta gcggcagcgg cagcggcacc gatttaccc tgaccattag cagcctggaa     660
ccggaagatt ttgcggtgta ttattgccag cagcgcagca actggccgcc gtttaccttt     720
ggcccgggca ccaaagtgga tattaaa                                        747
```

ANTI-PTK7 IMMUNE CELL CANCER THERAPY

RELATED APPLICATIONS

This application claims the benefit of U.S. Provisional Application No. 62/756,638, filed Nov. 7, 2018, and U.S. Provisional Application No. 62/910,586, filed Oct. 4, 2019, the disclosures of which are hereby incorporated by reference in their entirety.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "CT111_SubSeqlisting.txt", which was created on Jan. 17, 2019 and is 119,853 bytes in size. The subject matter of the Sequence Listing is incorporated herein in its entirety by reference.

BACKGROUND

Chimeric antigen receptor (CAR) T-cell therapy uses genetically-modified T cells to more specifically and efficiently target and kill cancer cells. After T cells have been collected from the blood, the cells are engineered to include CARs on their surface. The CARs may be introduced into the T cells using CRISPR/Cas9 gene editing technology. When these allogeneic CAR T cells are injected into a patient, the receptors enable the T cells to kill cancer cells.

SUMMARY

Multiple tumor-associated antigen targets have been progressed into clinical trials, chosen predominantly using the logic that expression in cancer tissues should be selective over normal tissues to avoid toxicity (Morgan, R. *Blood* 2013; 122(2): 3392-3394). PTK7, however, does not meet this criteria due to its apparent excessive expression in normal tissues including lung, smooth muscle, stomach, kidney and bladder. Thus, PTK7 has not been considered a viable CAR T cell target. Nonetheless, the data provided herein unexpectedly demonstrate that animals do, in fact, tolerate therapy with anti-PTK7 CAR T cells, and these anti-PTK7 CAR T cells effectively and selectively kill cells expressing PTK7.

Some aspects of the present disclosure provide an engineered T cell comprising a nucleic acid encoding a chimeric antigen receptor (CAR), wherein the CAR comprise an ectodomain that binds specifically to PTK7. In some embodiments, the engineered T cell further comprises a disrupted T cell receptor alpha chain constant region (TRAC) gene. For example, the TRAC gene may be disrupted by insertion of the nucleic acid encoding a CAR. In some embodiments, the engineered T cell further comprises a disrupted beta-2-microglobulin (β2M) gene.

The ectodomain of the CAR, in some embodiments, comprises an anti-PTK7 antibody. In some embodiments, the anti-PTK7 antibody is an anti-PTK7 single-chain variable fragment (scFv). The anti-PTK7 scFv, in some embodiments, comprises an amino acid sequence of any one of SEQ ID NO: 54, 68, 75, or 82. In some embodiments, the anti-PTK7 scFv comprises a VH comprising an amino acid sequence of any one of SEQ ID NO: 55, 69, 76, or 83 and/or a VL comprising an amino acid sequence of any one of SEQ ID NO: 56, 70, 77, or 84. In some embodiments, the anti-PTK7 scFv comprises a VH comprising CDR amino acid sequences of SEQ ID NO: 57, SEQ ID NO: 58, and/or SEQ ID NO: 59; and/or the anti-PTK7 scFv comprises a VL sequence comprising CDR amino acid sequences of SEQ ID NO: 60, SEQ ID NO: 61, and/or SEQ ID NO: 62. In some embodiments, the anti-PTK7 scFv comprises a VH comprising CDR amino acid sequences of SEQ ID NO: 85, SEQ ID NO: 86, and/or SEQ ID NO: 87; and/or the anti-PTK7 scFv comprises a VL sequence comprising CDR amino acid sequences of SEQ ID NO: 88, SEQ ID NO: 89, and/or SEQ ID NO: 90.

The CAR, in some embodiments, comprises a CD3ζ cytoplasmic signaling domain. In some embodiments, the CAR comprises a CD28 co-stimulatory domain or a 41 BB co-stimulatory domain.

In some embodiments, the TRAC gene comprises the nucleotide sequence encoding the left homology arm (LHA) and/or right homology arm (RHA) within of any one of SEQ ID NOs: 63, 64, 71, 78, or 91 or the nucleotide sequence of SEQ ID NO: 92 or 100, and/or wherein the CAR is encoded by the nucleotide sequence of any one of SEQ ID NOs: 49, 51, 65, 72, 79, or 112. In some embodiments, the disrupted β2M gene comprises at least one nucleotide sequence selected from any one of SEQ ID NOs: 9-14.

Also provided herein, in some aspects, is an engineered T cell comprising: (i) a disrupted TRAC gene; (ii) a disrupted β2M gene; and (iii) a nucleic acid encoding a CAR comprising an anti-PTK7 antigen-binding fragment.

Also provided herein, in some aspects, is a population of cells comprising engineered T cells, wherein the engineered T cells comprise: (i) a disrupted TRAC gene; (ii) a disrupted β2M gene; and (iii) a nucleic acid encoding a CAR comprising an anti-PTK7 antigen-binding fragment. In other aspects, provided herein is A population of cells comprising engineered T cells, wherein the engineered T cells comprise: (i) a disrupted TRAC gene, wherein the disrupted TRAC gene comprises a nucleic acid encoding a CAR, wherein the nucleic acid sequence is at least 90% identical to SEQ ID NOs: 49, 51, 65, 72, 79, or 112 and encodes the CAR of SEQ ID NOs: 50, 52, 66, 73, or 80; and (ii) a disrupted β2M gene.

Also provided herein, in some aspects, is a population of engineered T cells (e.g., comprising a nucleic acid encoding an anti-PTK7 CAR), wherein at least 25% or at least 50% of engineered T cells of the population express the CAR. For example, at least 70% of engineered T cells of the population express the CAR.

In some embodiments, at least 25% of engineered T cells of the population express the CAR following at least 7 or at least 14 days of in vitro proliferation.

In some embodiments, at least 50% of engineered T cells of the population do not express a detectable level of T cell receptor (TCR) protein. For example, at least 90% of engineered T cells of the population may not express a detectable level of TCR protein.

In some embodiments, at least 50% of engineered T cells of the population do not express a detectable level of β2M protein. For example, at least 70% of engineered T cells of the population may not express a detectable level of β2M protein.

In some embodiments, engineered T cells of the population, when co-cultured in vitro with a population of cancer cells that express PTK7, induce cell lysis of at least 50% of the cancer cells of the population. For example, engineered T cells of the population may induce cell lysis of at least 70%, at least 80%, or at least 90% of the cancer cells of the population. In some embodiments, engineered T cells of the population, when co-cultured in vitro with a population of cancer cells that express PTK7, induce cell lysis of at least 10%, at least 25%, or at least 50% of the cancer cells of the population. In some embodiments, engineered T cells of the population, when co-cultured in vitro with a population of cancer cells, secrete IFNγ. In some embodiments, the ratio of engineered T cells to cancer cells is 1:1 to 2:1. The cancer cells may be, for example, sarcoma cells or breast cancer cells. Other cancer cells may be targeted. In some embodiments, the cancer cells may be breast cancer cells, ovarian cancer cells, small cell lung cancer cells, and/or colon cancer cells In some embodiments, proliferative capacity of engineered T cells of the population is within 10% of proliferative capacity of control cells. In still other embodiments, the population of T cells, when administered in vivo to a subject, does not induce toxicity in the subject.

Other aspects of the present disclosure provide a method that comprises administering the population of engineered T cells as described herein. In some embodiments, percent body weight of the subject, following 5-10 days of administration, is within 10% of initial body weight of the subject, wherein initial body weight of the subject is body weight of the subject at the time of administration. In some embodiments, the subject is a human subject. In some embodiments, the subject has a cancer. The cancer may express PTK7, for example. In various embodiments, the cancer is selected from the group consisting of: pancreatic cancer, gastric cancer, ovarian cancer, uterine cancer, breast cancer, prostate cancer, testicular cancer, thyroid cancer, nasopharyngeal cancer, non-small cell lung (NSCLC), glioblastoma, neuronal, soft tissue sarcomas, leukemia, lymphoma, melanoma, colon cancer, colon adenocarcinoma, brain glioblastoma, hepatocellular carcinoma, liver hepatocholangiocarcinoma, osteosarcoma, gastric cancer, esophagus squamous cell carcinoma, advanced stage pancreas cancer, lung adenocarcinoma, lung squamous cell carcinoma, lung small cell cancer, renal carcinoma, and intrahepatic biliary cancer.

Further aspects of the present disclosure provide a method for producing an engineered T cell, the method comprising (a) delivering to a T cell a RNA-guided nuclease, a gRNA targeting a TRAC gene, and a vector comprising a donor template that comprises a nucleic acid encoding a CAR that comprise an ectodomain that binds specifically to PTK7, wherein the nucleic acid encoding the CAR is flanked by left and right homology arms to the TRAC gene, and (b) producing an engineered T cell. In some embodiments, the gRNA targeting the TRAC gene comprises the nucleotide sequence of SEQ ID NO: 18 or 19, or targets the nucleotide sequence of SEQ ID NO: 40. In one related embodiment, the method is provided wherein the nucleic acid encoding the CAR is flanked by left and right homology arms to the TRAC gene.

In some embodiments, the method further comprises delivering to the T cell a gRNA targeting the β2M gene. In some embodiments, the gRNA targeting the β2M gene comprises the nucleotide sequence of SEQ ID NO: 20 or 21, or targets the nucleotide sequence of SEQ ID NO: 41.

In some embodiments, the RNA-guided nuclease is a Cas9 nuclease, optionally a *S. pyogenes* Cas9 nuclease. In some embodiments, the ectodomain of the CAR is an anti-PTK7 antibody, optionally an anti-PTK7 single-chain variable fragment (scFv).

In some embodiments, the donor template comprises the nucleotide sequence of any one of SEQ ID NOs: 63, 64, 71, 78, or 91.

In some embodiments, the CAR comprises the nucleotide sequence encoding any one of SEQ ID NOs: 50, 52, 66, 73, or 80.

In some embodiments, the method of producing is provided wherein the anti-PTK7 scFv comprises the same heavy chain variable domain (VH) complementarity determining regions (CDRs) and the same light chain variable domain (VL) CDRs as a reference antibody, wherein the reference antibody comprises (i) a VH set forth as SEQ ID NO: 55 and VL set forth as SEQ ID NO: 56, (ii) a VH set forth as SEQ ID NO: 69 and a VL set forth as SEQ ID NO: 70, (iii) a VH set forth as SEQ ID NO: 76 and a VL set forth as SEQ ID NO: 77, or (iv) a VH set forth as SEQ ID NO: 83 and a VL set forth as SEQ ID NO: 84. In one embodiment, the method is provided wherein the anti-PTK7 scFv comprises the same VH and VL chains as the reference antibody. In still another embodiment, the anti-PTK7 scFv comprises the amino acid sequence of any one of SEQ ID NOs: 54, 68, 75, or 82.

In one embodiment, an aforementioned method of producing is provided wherein the CAR comprises a CD28 co-stimulatory domain or a 411BB co-stimulatory domain. In a related embodiment, the CAR further comprises a CD3ζ cytoplasmic signaling domain.

In some embodiments, an aforementioned method of producing is provided wherein the donor template comprises the nucleotide sequence of any one of SEQ ID NOs: 63, 64, 71, 78, or 91. In still other embodiments, the CAR is encoded by a nucleotide sequence of any one of SEQ ID NOs: 49, 51, 65, 72, 79, or 112.

BRIEF DESCRIPTION OF THE DRAWINGS

FIG. 10C shows the PTK7 cell surface expression in the Saos2 cells, PTK7-KO Saos2 cells, A498 cells, and PTK7 overexpressing A498 cells.

DETAILED DESCRIPTION

PTK7 Cancer Antigen

Figure 1:
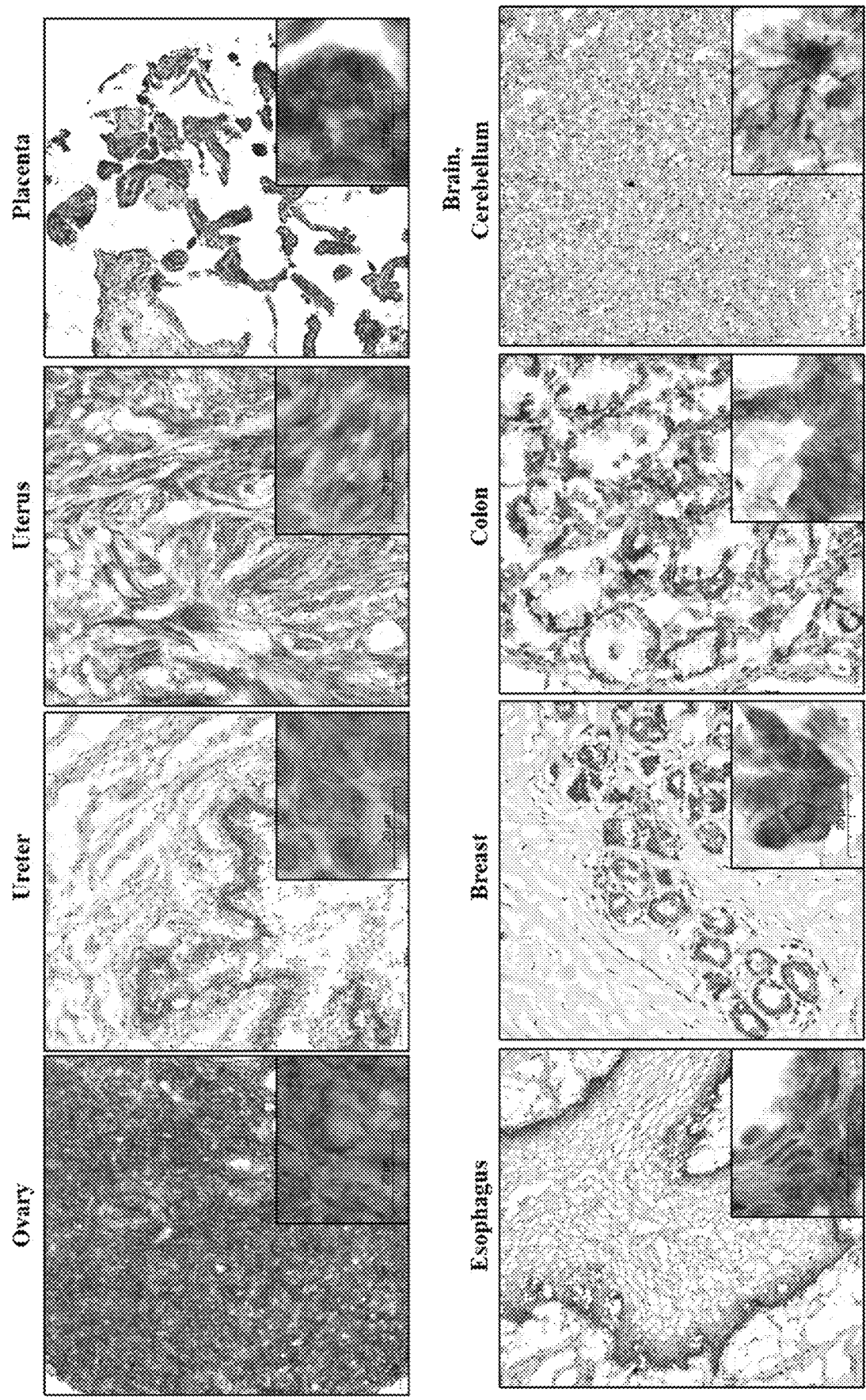
FIG. 1 shows PTK7 expression normal human tissues.

In some embodiments, the T cells of the present disclosure are engineered with a chimeric antigen receptor (CAR) designed to target PTK7. Protein tyrosine kinase 7 (PTK7), also known as colon carcinoma kinase 4 (CCK4), is receptor protein tyrosine kinase that is involved in non-canonical Wnt signaling and comprises an extracellular domain. PTK7 lacks detectable catalytic tyrosine kinase activity; however, it does comprise signal transduction activity and is presumed to function in cellular adhesion. It is further thought that PTK7 is a marker for tumor progression in cancer, as it is expressed in cancer cell lines (e.g., colon and breast cancer cell lines).

Thus, in some embodiments, T cells of the present disclosure are engineered to express a CAR comprising an anti-PTK7 antibody (e.g., anti-PTK7 scFv). In some embodiments, the anti-PTK7 antibody is an anti-PTK7 scFv encoded by the sequence of any one of SEQ ID NOs: 53, 67, 74, or 81. In some embodiments, the anti-PTK7 antibody is an anti-PTK7 scFv encoded by the sequence of any one of SEQ ID NO: 113. In some embodiments, the anti-PTK7 antibody is an anti-PTK7 scFv comprising the sequence of any one of SEQ ID NOs: 54, 68, 75, or 82. In some embodiments, the anti-PTK7 antibody is an anti-PTK7 scFv comprising a VH comprising an amino acid sequence of any one of SEQ ID NO: 55, 69, 76, or 83. In some embodiments, the anti-PTK7 antibody is an anti-PTK7 scFv comprising a VL comprising an amino acid sequence of any one of SEQ ID NO: 56, 70, 77, or 84. In some embodiments, a CAR comprising an anti-PTK7 antibody is encoded by the sequence of any one of SEQ ID NOs: 49, 51, 65, 72, or 79. In some embodiments, a CAR comprising an anti-PTK7 antibody is encoded by a sequence comprising a nucleic acid that is at least 90% identical to SEQ ID NOs: 49, 51, 65, 72, 79, or 112. In some embodiments, a CAR comprising an anti-PTK7 antibody is encoded by the sequence of any one of SEQ ID NO: 112. In some embodiments, a CAR comprising an anti-PTK7 antibody comprises the sequence of any one of SEQ ID NOs: 50, 52, 66, 73, or 80. In some embodiments, a CAR comprising an anti-PTK7 antibody comprises an anti-PTK7 antibody as described in U.S. Pat. No. 9,102,738 or U.S. Pat. No. 9,409,995.

Multi-Gene Editing

The engineered T cells of the present disclosure, in some embodiments, include more than one gene edit, for example, in more than one gene. For example, an engineered T cell may comprise a disrupted T cell receptor alpha chain constant region (TRAC) gene, a disrupted beta-2-microglobulin (β2M) gene, a disrupted programmed cell death-1 (PD-1 or PDCD1) gene, a disrupted CD70 gene, or any combination of two or more of the foregoing disrupted genes. In some embodiments, an engineered T cell comprises a disrupted TRAC gene, a disrupted β2M gene, and a disrupted CD70 gene. In some embodiments, an engineered T cell comprises a disrupted TRAC gene, a disrupted β2M gene, and a disrupted PD-1 gene. In some embodiments, an engineered T cell comprises a disrupted TRAC gene, a disrupted β2M gene, a disrupted CD70 gene and a disrupted PD-1 gene.

It should be understood that gene disruption encompasses gene modification through gene editing (e.g., using CRISPR/Cas gene editing to insert or delete one or more nucleotides). In some embodiments, a disrupted gene is a gene that does not encode functional protein. In some embodiments, a cell that comprises a disrupted gene does not express (e.g., at the cell surface) a detectable level (e.g. by antibody, e.g., by flow cytometry) of the protein encoded by the gene. A cell that does not express a detectable level of the protein may be referred to as a knockout cell. For example, a cell having a β2M gene edit may be considered a β2M knockout cell if A2M protein cannot be detected at the cell surface using an antibody that specifically binds A2M protein.

Provided herein, in some embodiments, are populations of cells in which a certain percentage of the cells has been edited (e.g., β2M gene edited), resulting in a certain percentage of cells not expressing a particular gene and/or protein. In some embodiments, at least 50% (e.g., 50%, 55%, 60%, 65%, 70%, 75%, 80%, 85%, 90%, or 85%) of the cells of a gene-edited population of cells are β2M knockout cells. In some embodiments, at least 50% of the cells (e.g. T cells) of the population do not express detectable levels of β2M protein. In some embodiments, at least 55%, at least 60%, at least 65%, at least 70%, at least 75%, at least 80%, at least 85%, at least 90%, or at least 95% of the cells of a gene-edited population of cells may be β2M knockout cells.

Methods of using CRISPR-Cas gene editing technology to create a genomic deletion in a cell (e.g., to knock out a gene in a cell) are known (Bauer D E et al. Vis. Exp. 2015; 95;e52118).

TRAC Gene Edit

In some embodiments, an engineered T cell comprises a disrupted TRAC gene. This disruption leads to loss of function of the TCR and renders the engineered T cell non-alloreactive and suitable for allogeneic transplantation, minimizing the risk of graft versus host disease. In some embodiments, expression of the endogenous TRAC gene is eliminated to prevent a graft-versus-host response. In some embodiments, a disruption in the TRAC gene expression is created by knocking a chimeric antigen receptor (CAR) into the TRAC gene (e.g., using an adeno-associated viral (AAV) vector and donor template). In some embodiments, a disruption in the TRAC gene expression is created by gRNAs targeting the TRAC genomic region. In some embodiments, a genomic deletion in the TRAC gene is created by knocking a chimeric antigen receptor (CAR) into the TRAC gene (e.g., using an AAV vector and donor template). In some embodiments, a disruption in the TRAC gene expression is created by gRNAs targeting the TRAC genomic region and knocking a chimeric antigen receptor (CAR) into the TRAC gene.

Non-limiting examples of modified and unmodified TRAC gRNA sequences that may be used as provided herein to create a genomic disruption in the TRAC gene are listed in Table 4 (e.g., SEQ ID NOs: 18 and 19). See also International Application No. PCT/US2018/032334, filed May 11, 2018, incorporated herein by reference. Other gRNA sequences may be designed using the TRAC gene sequence located on chromosome 14 (GRCh38: chromosome 14: 22,547,506-22,552,154;. Ensembl; ENSG00000277734). In some embodiments, gRNAs targeting the TRAC genomic region create Indels in the TRAC gene disrupting expression of the mRNA or protein.

In some embodiments, at least 50% of the engineered T cells of a population do not express a detectable level of T cell receptor (TCR) surface protein. For example, at least 55%, at least 60%, at least 70%, at least 75%, at least 80%, at least 85%, at least 90%, or at least 95% of a population may not express a detectable level of TCR surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the population of engineered T cells do not express a detectable level of TCR surface protein.

In some embodiments, gRNAs targeting the TRAC genomic region create Indels in the TRAC gene comprising at least one nucleotide sequence selected from the following sequences in Table 1:

TABLE 1

| Sequence | SEQ ID NO: |
|---|---|
| AAGAGCAACAAATCTGACT | 1 |
| AAGAGCAACAGTGCTGTGCCTGGAGCAACAAAT CTGACTAAGAGCAACAAATCTGACT | 2 |
| AAGAGCAACAGTGCTGGAGCAACAAATCTGACT AAGAGCAACAAATCTGACT | 3 |
| AAGAGCAACAGTGCCTGGAGCAACAAATCTGAC TAAGAGCAACAAATCTGACT | 4 |
| AAGAGCAACAGTGCTGACTAAGAGCAACAAATC TGACT | 5 |
| AAGAGCAACAGTGCTGTGGGCCTGGAGCAACAA ATCTGACTAAGAGCAACAAATCTGACT | 6 |
| AAGAGCAACAGTGCTGGCCTGGAGCAACAAATC TGACTAAGAGCAACAAATCTGACT | 7 |
| AAGAGCAACAGTGCTGTGTGCCTGGAGCAACAA ATCTGACTAAGAGCAACAAATCTGACT | 8 |

In some embodiments, an engineered T cell comprises a deletion in the TRAC gene relative to unmodified T cells. In some embodiments, an engineered T cell comprises a deletion of 15-30 base pairs in the TRAC gene relative to unmodified T cells. In some embodiments, an engineered T cell comprises a deletion of 15, 16, 17, 18, 19, 20, 21, 22, 23, 24, 25, 26, 27, 28, 29 or 30 base pairs in the TRAC gene relative to unmodified T cells. In some embodiments, an engineered T cell comprises a deletion of more than 30 base pairs in the TRAC gene relative to unmodified T cells. In some embodiments, an engineered T cell comprises a deletion of 20 base pairs in the TRAC gene relative to unmodified T cells. In some embodiments, an engineered T cell comprises a deletion of SEQ ID NO: 104 (AGAGCAACAGTGCTGTGGCC) in the TRAC gene relative to unmodified T cells. In some embodiments, an engineered T cell comprises a deletion comprising SEQ ID NO: 104 (AGAGCAACAGTGCTGTGGCC) in the TRAC gene relative to unmodified T cells. In some embodiments, an engineered T cell comprises a deletion of SEQ ID NO: 40 in the TRAC gene relative to unmodified T cells. In some embodiments, an engineered T cell comprises a deletion comprising SEQ ID NO: 40 in the TRAC gene relative to unmodified T cells.

β2M Gene Edit

In some embodiments, an engineered T cell comprises a disrupted β2M gene. β2M is a common (invariant) component of MHC I complexes. Disrupting its expression by gene editing will prevent host versus therapeutic allogeneic T cells responses leading to increased allogeneic T cell persistence. In some embodiments, expression of the endogenous β2M gene is eliminated to prevent a host-versus-graft response.

Non-limiting examples of modified and unmodified β2M gRNA sequences that may be used as provided herein to create a genomic disruption in the β2M gene are listed in Table 4 (e.g., SEQ ID NOs: 20 and 21). See also International Application No. PCT/US2018/032334, filed May 11, 2018, incorporated herein by reference. Other gRNA sequences may be designed using the β2M gene sequence located on Chromosome 15 (GRCh38 coordinates: Chromosome 15: 44,711,477-44,718,877; Ensembl: ENSG00000166710).

In some embodiments, gRNAs targeting the β2M genomic region create Indels in the β2M gene disrupting expression of the mRNA or protein.

In some embodiments, at least 50% of the engineered T cells of a population do not express a detectable level of β2M surface protein. For example, at least 55%, at least 60%, at least 70%, at least 75%, at least 80%, at least 85%, at least 90%, or at least 95% of the engineered T cells of a population may not express a detectable level of β2M surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population do not express a detectable level of β2M surface protein.

In some embodiments, an edited β2M gene comprises at least one nucleotide sequence selected from the following sequences in Table 2.

TABLE 2

| Sequences | SEQ ID NO: |
|---|---|
| CGTGGCCTTAGCTGTGCTCGCGCTACTCTCTTTCTG CCTGGAGGCTATCCAGCGTGAGTCTCTCCTACCCTCCC GCT | 9 |
| CGTGGCCTTAGCTGTGCTCGCGCTACTCTCTTTCGC CTGGAGGCTATCCAGCGTGAGTCTCTCCTACCCTCCCG CT | 10 |
| CGTGGCCTTAGCTGTGCTCGCGCTACTCTCTTTCTG GAGGCTATCCAGCGTGAGTCTCTCCTACCCTCCCGCT | 11 |
| CGTGGCCTTAGCTGTGCTCGCGCTACTCTCTCTTTCTG GATAGCCTGGAGGCTATCCAGCGTGAGTCTCTCCTACC CTCCCGCT | 12 |
| CGTGGCCTTAGCTGTGCTCGCGCTATCCAGCGTGAGTC TCTCCTACCCTCCCGCT | 13 |
| CGTGGCCTTAGCTGTGCTCGCGCTACTCTCTCTTTCTG TGGCCTGGAGGCTATCCAGCGTGAGTCTCTCCTACCCT CCCGCT | 14 |

PD-1 Gene Edit

PD-1 is an immune checkpoint molecule that is upregulated in activated T cells and serves to dampen or stop T cell responses. Disrupting PD-1 by gene editing could lead to more persistent and/or potent therapeutic T cell responses and/or reduce immune suppression in a subject. In some embodiments, an engineered T cell comprises a disrupted PD-1 gene. In some embodiments, expression of the endogenous PD-1 gene is eliminated to enhance anti-tumor efficacy of the CAR T cells of the present disclosure.

Non-limiting examples of modified and unmodified PD-1 gRNA sequences that may be used as provided herein to create a genomic deletion in the PD-1 gene are listed in Table 4 (e.g., SEQ ID NOs: 22 and 23). See also International Application No. PCT/US2018/032334, filed May 11, 2018, incorporated herein by reference. Other gRNA sequences may be designed using the PD-1 gene sequence located on Chromosome 2 (GRCh38 coordinates: Chromosome 2: 241,849,881-241,858,908; Ensembl: ENSG00000188389).

In some embodiments, gRNAs targeting the PD-1 genomic region create Indels in the PD-1 gene disrupting expression of the PD-1 mRNA or protein.

In some embodiments, at least 50% of the engineered T cells of a population do not express a detectable level of PD-1 surface protein. For example, at least 55%, at least 60%, at least 70%, at least 75%, at least 80%, at least 85%, at least 90%, or at least 95% of the engineered T cells of a population may not express a detectable level of PD-1 surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population do not express a detectable level of PD-1 surface protein.

CD70 Gene Edit

Cluster of Differentiation 70 (CD70) is a member of the tumor necrosis factor superfamily and its expression is restricted to activated T and B lymphocytes and mature dendritic cells. CD70 has also been detected on hematological tumors and on carcinomas. CD70 is implicated in tumor cell and regulatory T cell survival through interaction with its ligand, CD27. Disrupting CD70 by gene editing increases cell expansion and reduces cell exhaustion. In some embodiments, an engineered T cell comprises a disrupted CD70 gene. In some embodiments, expression of the endogenous CD70 gene is eliminated to enhance anti-tumor efficacy of the CAR T cells of the present disclosure. In some embodiments, gRNAs targeting the CD70 genomic region create Indels in, or around, the CD70 gene disrupting expression of the CD70 mRNA and/or protein.

Non-limiting examples of modified and unmodified CD70 gRNA sequences that may be used as provided herein to create a genomic disruption in the CD70 gene are listed in Table 4 (e.g., SEQ ID NOs: 24-27). Other gRNA sequences may be designed using the CD70 gene sequence located on Chromosome 19 (GRCh38 coordinates: Chromosome 19: 6,583,183-6,604,103; Ensembl: ENSG00000125726).

In some embodiments, at least 50% of the engineered T cells of a population do not express a detectable level of CD70 surface protein. For example, at least 55%, at least 60%, at least 70%, at least 75%, at least 80%, at least 85%, at least 90%, or at least 95% of the engineered T cells of a population may not express a detectable level of CD70 surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population do not express a detectable level of CD70 surface protein.

Cellular Phenotypes

In some embodiments, one or more gene edits within a population of cells results in a phenotype associated with changes in cellular proliferative capacity, cellular exhaustion, cellular viability, cellular lysis capability (e.g., increase cytokine production and/or release), or any combination thereof.

In some embodiments, engineered T cells of the present disclosure exhibit at least 20% greater cellular proliferative capacity, relative to control T cells. For example, engineered T cells may exhibit at least 25%, at least 30%, at least 35%, at least 40%, at least 45%, at least 50%, at least 55%, at least 60%, at least 65%, at least 70%, at least 75%, at least 80%, or at least 90% greater cellular proliferative capacity, relative to control T cells. In some embodiments, engineered T cells of the present disclosure exhibit 20%-100%, 20%-90%, 20%-80%, 20%-70%, 20%-60%, 20%-50%, 30%-100%, 30%-90%, 30%-80%, 30%-70%, 30%-60%, 30%-50%, 40%-100%, 40%-90%, 40%-80%, 40%-70%, 40%-60%, 40%-50%, 50%-100%, 50%-90%, 50%-80%, 50%-70%, or 50%-60% greater cellular proliferative capacity, relative to control T cells.

In some embodiments, engineered T cells of the present disclosure exhibit an at least 20% increase in cellular viability, relative to control cells. For example, engineered T cells of the present disclosure may exhibit at least 25%, at least 30%, at least 35%, at least 40%, at least 45%, at least 50%, at least 55%, at least 60%, at least 65%, at least 70%, at least 75%, at least 80%, or at least 90% increase in cellular viability, relative to control cells. In some embodiments, engineered T cells of the present disclosure exhibit a 20%-100%, 20%-90%, 20%-80%, 20%-70%, 20%-60%, 20%-50%, 30%-100%, 30%-90%, 30%-80%, 30%-70%, 30%-60%, 30%-50%, 40%-100%, 40%-90%, 40%-80%, 40%-70%, 40%-60%, 40%-50%, 50%-100%, 50%-90%, 50%-80%, 50%-70%, or 50%-60% increase in cellular viability, relative to control cells.

In some embodiments, engineered T cells of the present disclosure exhibit an at least 20% increase in cellular lysis capability (kill at least 20% more target cells), relative to control cells. For example, engineered T cells of the present disclosure may exhibit an at least at least 25%, at least 30%, at least 35%, at least 40%, at least 45%, at least 50%, at least 55%, at least 60%, at least 65%, at least 70%, at least 75%, at least 80%, or at least 90% increase in cellular lysis capability, relative to control cells. In some embodiments, engineered T cells of the present disclosure exhibit a 20%-100%, 20%-90%, 20%-80%, 20%-70%, 20%-60%, 20%-50%, 30%-100%, 30%-90%, 30%-80%, 30%-70%, 30%-60%, 30%-50%, 40%-100%, 40%-90%, 40%-80%, 40%-70%, 40%-60%, 40%-50%, 50%-100%, 50%-90%, 50%-80%, 50%-70%, or 50%-60% increase in cellular lysis capability, relative to control cells. For example, the level of cytokines (e.g., IL-2 and/or IFN-gamma) secreted by the engineered T cells may at least 2-fold (e.g., at least 3-fold, at least 4-fold, or at least 5-fold) greater than the level of cytokines secreted by control T cells.

Control T cells, in some embodiments, are engineered T cells (e.g., gene edited T cells). In some embodiments, control T cells are engineered T cells that comprise a disrupted TRAC gene, a nucleic acid encoding a CAR (e.g., an anti-PTK7 CAR) inserted into the TRAC gene, and/or a disrupted β2M gene. In some embodiments, control T cells are unedited T cells.

Gene Editing Methods

Gene editing (including genomic editing) is a type of genetic engineering in which nucleotide(s)/nucleic acid(s) is/are inserted, deleted, and/or substituted in a DNA sequence, such as in the genome of a targeted cell. Targeted gene editing enables insertion, deletion, and/or substitution at pre-selected sites in the genome of a targeted cell (e.g., in a targeted gene or targeted DNA sequence). When an sequence of an endogenous gene is edited, for example by deletion, insertion or substitution of nucleotide(s)/nucleic acid(s), the endogenous gene comprising the affected sequence may be knocked-out or knocked-down due to the sequence alteration. Therefore, targeted editing may be used to disrupt endogenous gene expression. "Targeted integration" refers to a process involving insertion of one or more exogenous sequences, with or without deletion of an endogenous sequence at the insertion site. Targeted integration can result from targeted gene editing when a donor template containing an exogenous sequence is present.

Targeted editing can be achieved either through a nuclease-independent approach, or through a nuclease-dependent approach. In the nuclease-independent targeted editing approach, homologous recombination is guided by homologous sequences flanking an exogenous polynucleotide to be introduced into an endogenous sequence through the enzymatic machinery of the host cell. The exogenous polynucleotide may introduce deletions, insertions or replacement of nucleotides in the endogenous sequence.

Alternatively, the nuclease-dependent approach can achieve targeted editing with higher frequency through the specific introduction of double strand breaks (DSBs) by specific rare-cutting nucleases (e.g., endonucleases). Such nuclease-dependent targeted editing also utilizes DNA repair mechanisms, for example, non-homologous end joining (NHEJ), which occurs in response to DSBs. DNA repair by NHEJ often leads to random insertions or deletions (indels) of a small number of endogenous nucleotides. In contrast to NHEJ mediated repair, repair can also occur by a homology directed repair (HDR). When a donor template containing exogenous genetic material flanked by a pair of homology arms is present, the exogenous genetic material can be introduced into the genome by HDR, which results in targeted integration of the exogenous genetic material.

Available endonucleases capable of introducing specific and targeted DSBs include, but not limited to, zinc-finger nucleases (ZFN), transcription activator-like effector nucleases (TALEN), and RNA-guided CRISPR-Cas9 nuclease (CRISPR/Cas9; Clustered Regular Interspaced Short Palindromic Repeats Associated 9). Additionally, DICE (dual integrase cassette exchange) system utilizing phiC31 and Bxb1 integrases may also be used for targeted integration.

ZFNs are targeted nucleases comprising a nuclease fused to a zinc finger DNA binding domain (ZFBD), which is a polypeptide domain that binds DNA in a sequence-specific manner through one or more zinc fingers. A zinc finger is a domain of about 30 amino acids within the zinc finger binding domain whose structure is stabilized through coordination of a zinc ion. Examples of zinc fingers include, but not limited to, C2H2 zinc fingers, C3H zinc fingers, and C4 zinc fingers. A designed zinc finger domain is a domain not occurring in nature whose design/composition results principally from rational criteria, e.g., application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496. A selected zinc finger domain is a domain not found in nature whose production results primarily from an empirical process such as phage display, interaction trap or hybrid selection. ZFNs are described in greater detail in U.S. Pat. Nos. 7,888,121 and 7,972,854. The most recognized example of a ZFN is a fusion of the FokI nuclease with a zinc finger DNA binding domain.

A TALEN is a targeted nuclease comprising a nuclease fused to a TAL effector DNA binding domain. A "transcription activator-like effector DNA binding domain", "TAL effector DNA binding domain", or "TALE DNA binding domain" is a polypeptide domain of TAL effector proteins that is responsible for binding of the TAL effector protein to DNA. TAL effector proteins are secreted by plant pathogens of the genus *Xanthomonas* during infection. These proteins enter the nucleus of the plant cell, bind effector-specific DNA sequences via their DNA binding domain, and activate gene transcription at these sequences via their transactivation domains. TAL effector DNA binding domain specificity depends on an effector-variable number of imperfect 34 amino acid repeats, which comprise polymorphisms at select repeat positions called repeat variable-diresidues (RVD). TALENs are described in greater detail in US Patent Application No. 2011/0145940. The most recognized example of a TALEN in the art is a fusion polypeptide of the FokI nuclease to a TAL effector DNA binding domain.

Additional examples of targeted nucleases suitable for use as provided herein include, but are not limited to, Bxb1, phiC31, R4, PhiBT1, and WP/SPBc/TP901-1, whether used individually or in combination.

Other non-limiting examples of targeted nucleases include naturally-occurring and recombinant nucleases, e.g., CRISPR/Cas9, restriction endonucleases, meganucleases homing endonucleases, and the like.

CRISPR-Cas9 Gene Editing

The CRISPR-Cas9 system is a naturally-occurring defense mechanism in prokaryotes that has been repurposed as a RNA-guided DNA-targeting platform used for gene editing. It relies on the DNA nuclease Cas9, and two noncoding RNAs-crisprRNA (crRNA) and trans-activating RNA (tracrRNA)—to target the cleavage of DNA.

crRNA drives sequence recognition and specificity of the CRISPR-Cas9 complex through Watson-Crick base pairing typically with a 20 nucleotide (nt) sequence in the target DNA. Changing the sequence of the 5' 20 nt in the crRNA allows targeting of the CRISPR-Cas9 complex to specific loci. The CRISPR-Cas9 complex only binds DNA sequences that contain a sequence match to the first 20 nt of the crRNA, single-guide RNA (sgRNA), if the target sequence is followed by a specific short DNA motif (with the sequence NGG) referred to as a protospacer adjacent motif (PAM).

TracrRNA hybridizes with the 3' end of crRNA to form an RNA-duplex structure that is bound by the Cas9 endonuclease to form the catalytically active CRISPR-Cas9 complex, which can then cleave the target DNA.

Once the CRISPR-Cas9 complex is bound to DNA at a target site, two independent nuclease domains within the Cas9 enzyme each cleave one of the DNA strands upstream of the PAM site, leaving a double-strand break (DSB) where both strands of the DNA terminate in a base pair (a blunt end).

After binding of CRISPR-Cas9 complex to DNA at a specific target site and formation of the site-specific DSB, the next key step is repair of the DSB. Cells use two main DNA repair pathways to repair the DSB: non-homologous end-joining (NHEJ) and homology-directed repair (HDR).

NHEJ is a robust repair mechanism that appears highly active in the majority of cell types, including non-dividing cells. NHEJ is error-prone and can often result in the removal or addition of between one and several hundred nucleotides at the site of the DSB, though such modifications are typically <20 nt. The resulting insertions and deletions (indels) can disrupt coding or noncoding regions of genes. Alternatively, HDR uses a long stretch of homologous donor DNA, provided endogenously or exogenously, to repair the DSB with high fidelity. HDR is active only in dividing cells, and occurs at a relatively low frequency in most cell types. In many embodiments of the present disclosure, NHEJ is utilized as the repair operant.

In some embodiments, the Cas9 (CRISPR associated protein 9) endonuclease is from *Streptococcus pyogenes*, although other Cas9 homologs may be used. It should be understood, that wild-type Cas9 may be used or modified versions of Cas9 may be used (e.g., evolved versions of Cas9, or Cas9 orthologues or variants), as provided herein. In some embodiments, Cas9 may be substituted with another RNA-guided endonuclease, such as Cpf1 (of a class II CRISPR/Cas system).

Guide RNAs

The present disclosure provides a genome-targeting nucleic acid that can direct the activities of an associated polypeptide (e.g., a site-directed polypeptide) to a specific target sequence within a target nucleic acid. The genome-targeting nucleic acid can be an RNA. A genome-targeting RNA is referred to as a "guide RNA" or "gRNA" herein. A guide RNA comprises at least a spacer sequence that hybridizes to a target nucleic acid sequence of interest, and a CRISPR repeat sequence. In Type II systems, the gRNA also comprises a second RNA called the tracrRNA sequence. In the Type II guide RNA (gRNA), the CRISPR repeat sequence and tracrRNA sequence hybridize to each other to form a duplex. In the Type V guide RNA (gRNA), the crRNA forms a duplex. In both systems, the duplex binds a site-directed polypeptide, such that the guide RNA and site-direct polypeptide form a complex. In some embodiments, the genome-targeting nucleic acid provides target specificity to the complex by virtue of its association with the site-directed polypeptide. The genome-targeting nucleic acid thus directs the activity of the site-directed polypeptide.

As is understood by the person of ordinary skill in the art, each guide RNA is designed to include a spacer sequence complementary to its genomic target sequence. See Jinek et al., Science, 337, 816-821 (2012) and Deltcheva et al., Nature, 471, 602-607 (2011).

In some embodiments, the genome-targeting nucleic acid is a double-molecule guide RNA. In some embodiments, the genome-targeting nucleic acid is a single-molecule guide RNA.

A double-molecule guide RNA comprises two strands of RNA. The first strand comprises in the 5' to 3' direction, an optional spacer extension sequence, a spacer sequence and a minimum CRISPR repeat sequence. The second strand comprises a minimum tracrRNA sequence (complementary to the minimum CRISPR repeat sequence), a 3' tracrRNA sequence and an optional tracrRNA extension sequence.

A single-molecule guide RNA (sgRNA) in a Type II system comprises, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may comprise elements that contribute additional functionality (e.g., stability) to the guide RNA. The single-molecule guide linker links the minimum CRISPR repeat and the minimum tracrRNA sequence to form a hairpin structure. The optional tracrRNA extension comprises one or more hairpins.

A single-molecule guide RNA (referred to as a "sgRNA" or "gRNA") in a Type V system comprises, in the 5' to 3' direction, a minimum CRISPR repeat sequence and a spacer sequence.

The sgRNA can comprise a 20 nucleotide spacer sequence at the 5' end of the sgRNA sequence. The sgRNA can comprise a less than 20 nucleotide spacer sequence at the 5' end of the sgRNA sequence. The sgRNA can comprise a more than 20 nucleotide spacer sequence at the 5' end of the sgRNA sequence. The sgRNA can comprise a variable length spacer sequence with 17-30 nucleotides at the 5' end of the sgRNA sequence (see Table 3).

The sgRNA can comprise no uracil at the 3' end of the sgRNA sequence. The sgRNA can comprise one or more uracil at the 3' end of the sgRNA sequence. For example, the sgRNA can comprise 1 uracil (U) at the 3' end of the sgRNA sequence. The sgRNA can comprise 2 uracil (UU) at the 3' end of the sgRNA sequence. The sgRNA can comprise 3 uracil (UUU) at the 3' end of the sgRNA sequence. The sgRNA can comprise 4 uracil (UUUU) at the 3' end of the sgRNA sequence. The sgRNA can comprise 5 uracil (UUUUU) at the 3' end of the sgRNA sequence. The sgRNA can comprise 6 uracil (UUUUUU) at the 3' end of the sgRNA sequence. The sgRNA can comprise 7 uracil (UUUUUUU) at the 3' end of the sgRNA sequence. The sgRNA can comprise 8 uracil (UUUUUUUU) at the 3' end of the sgRNA sequence.

The sgRNA can be unmodified or modified. For example, modified sgRNAs can comprise one or more 2'-O-methyl phosphorothioate nucleotides.

TABLE 3

| SEQ ID NO. | sgRNA sequence |
|---|---|
| 15 | nnnnnnnnnnnnnnnnnnnnguuuuagagcuagaaaua gcaaguuaaaauaaggcuaguccguuaucaacuugaaa aaguggcaccgagucggugcuuuu |

TABLE 3-continued

| SEQ ID NO. | sgRNA sequence |
|---|---|
| 16 | nnnnnnnnnnnnnnnnnnnnguuuuagagcuagaaaua gcaaguuaaaauaaggcuaguccguuaucaacuugaaa aaguggcaccgagucggugc |
| 17 | n$_{(17-30)}$guuuuagagcuagaaauagcaaguuaaaauaa ggcuaguccguuaucaacuugaaaaaguggcaccgagu cggugcu$_{(1-8)}$ |

By way of illustration, guide RNAs used in the CRISPR/Cas/Cpf1 system, or other smaller RNAs can be readily synthesized by chemical means, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 or Cpf1 endonuclease, are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

Spacer Sequence

A gRNA comprises a spacer sequence. A spacer sequence is a sequence (e.g., a 20 nucleotide sequence) that defines the target sequence (e.g., a DNA target sequences, such as a genomic target sequence) of a target nucleic acid of interest. In some embodiments, the spacer sequence is 15 to 30 nucleotides. In some embodiments, the spacer sequence is 15, 16, 17, 18, 19, 29, 21, 22, 23, 24, 25, 26, 27, 28, 29, or 30 nucleotides. In some embodiments, a spacer sequence is 20 nucleotides.

The "target sequence" is adjacent to a PAM sequence and is the sequence modified by an RNA-guided nuclease (e.g., Cas9). The "target nucleic acid" is a double-stranded molecule: one strand comprises the target sequence and is referred to as the "PAM strand," and the other complementary strand is referred to as the "non-PAM strand." One of skill in the art recognizes that the gRNA spacer sequence hybridizes to the reverse complement of the target sequence, which is located in the non-PAM strand of the target nucleic acid of interest. Thus, the gRNA spacer sequence is the RNA equivalent of the target sequence. For example, if the target sequence is 5'-AGAGCAACAGTGCTGTGGCC-3' (SEQ ID NO: 104), then the gRNA spacer sequence is 5'-AGAGCAACAGUGCUGUGGCC-3' (SEQ ID NO: 105). The spacer of a gRNA interacts with a target nucleic acid of interest in a sequence-specific manner via hybridization (i.e., base pairing). The nucleotide sequence of the spacer thus varies depending on the target sequence of the target nucleic acid of interest.

In a CRISPR/Cas system herein, the spacer sequence is designed to hybridize to a region of the target nucleic acid that is located 5' of a PAM of the Cas9 enzyme used in the system. The spacer may perfectly match the target sequence or may have mismatches. Each Cas9 enzyme has a particular PAM sequence that it recognizes in a target DNA. For example, S. pyogenes recognizes in a target nucleic acid a PAM that comprises the sequence 5'-NRG-3', where R comprises either A or G, where N is any nucleotide and N is immediately 3' of the target nucleic acid sequence targeted by the spacer sequence.

In some embodiments, the target nucleic acid sequence comprises 20 nucleotides. In some embodiments, the target nucleic acid comprises less than 20 nucleotides. In some embodiments, the target nucleic acid comprises more than 20 nucleotides. In some embodiments, the target nucleic acid comprises at least: 5, 10, 15, 16, 17, 18, 19, 20, 21, 22, 23, 24, 25, 30 or more nucleotides. In some embodiments, the target nucleic acid comprises at most: 5, 10, 15, 16, 17, 18, 19, 20, 21, 22, 23, 24, 25, 30 or more nucleotides. In some embodiments, the target nucleic acid sequence comprises 20 bases immediately 5' of the first nucleotide of the PAM. For example, in a sequence comprising 5'-NNNNNNNNNNNNNNNNNNNNNRG-3', the target nucleic acid comprises the sequence that corresponds to the Ns, wherein N is any nucleotide, and the underlined NRG sequence is the S. pyogenes PAM.

Non-limiting examples of gRNAs that may be used as provided herein are provided in Table 4 and PCT/US2018/032334, filed May 11, 2018.

TABLE 4 gRNA Sequences/Target Sequences gRNA Sequences

| Name | Unmodified Sequence | Modified Sequence |
|---|---|---|
| TRAC sgRNA | AGAGCAACAGUGCUG UGGCCguuuuagagc uagaaauagcaaguu aaaauaaggcuaguc cguuaucaacuugaa aaaguggcaccgagu cggugcUUUU (SEQ ID NO: 18) | A*G*A*GCAACAGUG CUGUGGCCguuuuag agcuagaaauagcaa guuaaaauaaggcua guccguuaucaacuu gaaaaaguggcaccg agucggugcU*U*U*U (SEQ ID NO: 28) |
| TRAC sgRNA spacer | AGAGCAACAGUGCUG UGGCC (SEQ ID NO: 19) | A*G*A*GCAACAGUG CUGUGGCC (SEQ ID NO: 29) |
| β2M sgRNA | GCUACUCUCUCUUUC UGGCCguuuuagagc uagaaauagcaaguu aaaauaaggcuaguc cguuaucaacuugaa aaaguggcaccgagu cggugcUUUU (SEQ ID NO: 20) | G*C*U*ACUCUCUCU UUCUGGCCguuuuag agcuagaaauagcaa guuaaaauaaggcua guccguuaucaacuu gaaaaaguggcaccg agucggugcU*U*U*U (SEQ ID NO: 30) |
| β2M sgRNA spacer | GCUACUCUCUCUUUC UGGCC (SEQ ID NO: 21) | G*C*U*ACUCUCUCU UUCUGGCC (SEQ ID NO: 31) |
| PD-1 sgRNA | CUGCAGCUUCUCCAA CACAUguuuuagagc uagaaauagcaaguu aaaauaaggcuaguc cguuaucaacuugaa aaaguggcaccgagu cggugcUUUU (SEQ ID NO: 22) | C*U*G*CAGCUUCUC CAACACAUguuuuag agcuagaaauagcaa guuaaaauaaggcua guccguuaucaacuu gaaaaaguggcaccg agucggugcU*U*U*U (SEQ ID NO: 32) |

TABLE 4-continued gRNA Sequences/Target Sequences

| | | |
|---|---|---|
| PD-1 sgRNA spacer | CUGCAGCUUCUCCAA CACAU (SEQ ID NO: 23) | C*U*G*CAGCUUCUC CAACACAU (SEQ ID NO: 33) |
| CD70 sgRNA (E1_T7) | GCUUUGGUCCCAUUG GUCGCguuuuagagc uagaaauagcaaguu aaaauaaggcuaguc cguuaucaacuugaa aaaguggcaccgagu cggugcUUUU (SEQ ID NO: 24) | G*C*U*UUGGUCCCA UUGGUCGCguuuuag agcuagaaauagcaa guuaaaauaaggcua guccguuaucaacuu gaaaaaguggcaccg agucggugcU*U*U* U (SEQ ID NO: 34), T7 |
| CD70 sgRNA (E1_T7) spacer | GCUUUGGUCCCAUUG GUCGC (SEQ ID NO: 25) | G*C*U*UUGGUCCCA UUGGUCGC (SEQ ID NO: 35) |
| CD70 sgRNA (E1_T8) | GCCCGCAGGACGCAC CCAUAguuuuagagc uagaaauagcaaguu aaaauaaggcuaguc cguuaucaacuugaa aaaguggcaccgagu cggugcUUUU (SEQ ID NO: 26) | G*C*C*CGCAGGACG CACCCAUAguuuuag agcuagaaauagcaa guuaaaauaaggcua guccguuaucaacuu gaaaaaguggcaccg agucggugcU*U*U* U (SEQ ID NO: 36), T8 |
| CD70 sgRNA (E1_T8) spacer | GCCCGCAGGACGCAC CCAUA (SEQ ID NO: 27) | G*C*C*CGCAGGACG CACCCAUA (SEQ ID NO: 37) |

Target Sequences

| Guide Name | Target Sequence | (PAM) |
|---|---|---|
| CD70 sgRNA (E1_T7) | GCTTTGGTCCCATTGGTCGC (GGG) | (SEQ ID NO: 38) |
| CD70 sgRNA (E1_T8) | GCCCGCAGGACGCACCCATA (GGG) | (SEQ ID NO: 39) |
| TRAC sgRNA | AGAGCAACAGTGCTGTGGCC (TGG) | (SEQ ID NO: 40) |
| β2M sgRNA | GCTACTCTCTCTTTCTGGCC (TGG) | (SEQ ID NO: 41) |
| PD-1 sgRNA | CTGCAGCTTCTCCAACACAT (CGG) | (SEQ ID NO: 42) |

*: 2'-O-methyl phosphorothioate residue

Chimeric Antigen Receptor (CAR) T Cells

A chimeric antigen receptor refers to an artificial immune cell receptor that is engineered to recognize and bind to an antigen expressed by tumor cells. Generally, a CAR is designed for a T cell and is a chimera of a signaling domain of the T-cell receptor (TCR) complex and an antigen-recognizing domain (e.g., a single chain fragment (scFv) of an antibody or other antibody fragment) (Enblad et al., Human Gene Therapy. 2015; 26(8):498-505). A T cell that expresses a CAR is referred to as a CAR T cell. CARs have the ability to redirect T-cell specificity and reactivity toward a selected target in a non-MHC-restricted manner. The non-MHC-restricted antigen recognition gives T-cells expressing CARs the ability to recognize an antigen independent of antigen processing, thus bypassing a major mechanism of tumor escape. Moreover, when expressed in T-cells, CARs advantageously do not dimerize with endogenous T-cell receptor (TCR) alpha and beta chains.

There are four generations of CARs, each of which contains different components. First generation CARs join an antibody-derived scFv to the CD3ζ eta ((or z) intracellular signaling domain of the T-cell receptor through hinge and transmembrane domains. Second generation CARs incorporate an additional domain, e.g., CD28, 4-11BB (411BB), or ICOS, to supply a costimulatory signal. Third-generation CARs contain two costimulatory domains fused with the TCR CD3ζ chain. Third-generation costimulatory domains may include, e.g., a combination of CD3ζ, CD27, CD28, 4-11BB, ICOS, or OX40. CARs, in some embodiments, contain an ectodomain (e.g., CD3), commonly derived from a single chain variable fragment (scFv), a hinge, a transmembrane domain, and an endodomain with one (first generation), two (second generation), or three (third generation) signaling domains derived from CD3Z and/or co-stimulatory molecules (Maude et al., Blood. 2015; 125(26):4017-4023; Kakarla and Gottschalk, Cancer J. 2014; 20(2):151-155).

CARs typically differ in their functional properties. The CD3ζ signaling domain of the T-cell receptor, when engaged, will activate and induce proliferation of T-cells but can lead to anergy (a lack of reaction by the body's defense mechanisms, resulting in direct induction of peripheral lymphocyte tolerance). Lymphocytes are considered anergic when they fail to respond to a specific antigen. The addition of a costimulatory domain in second-generation CARs improved replicative capacity and persistence of modified T-cells. Similar antitumor effects are observed in vitro with CD28 or 4-11BB CARs, but preclinical in vivo studies suggest that 4-11BB CARs may produce superior proliferation and/or persistence. Clinical trials suggest that both of these second-generation CARs are capable of inducing substantial T-cell proliferation in vivo, but CARs containing the 4-11BB costimulatory domain appear to persist longer. Third generation CARs combine multiple signaling domains (costimulatory) to augment potency.

In some embodiments, a chimeric antigen receptor is a first generation CAR. In other embodiments, a chimeric antigen receptor is a second generation CAR. In yet other embodiments, a chimeric antigen receptor is a third generation CAR.

A CAR, in some embodiments, comprises an extracellular (ecto) domain comprising an antigen binding domain (e.g., an antibody, such as an scFv), a transmembrane domain, and a cytoplasmic (endo) domain.

Ectodomain

The ectodomain is the region of the CAR that is exposed to the extracellular fluid and, in some embodiments, includes an antigen binding domain, and optionally a signal peptide, a spacer domain, and/or a hinge domain. In some embodiments, the antigen binding domain is a single-chain variable fragment (scFv) that include the VL and VH of immunoglobulins connected with a short linker peptide. The linker, in some embodiments, includes hydrophilic residues with stretches of glycine and serine for flexibility as well as stretches of glutamate and lysine for added solubility. A single-chain variable fragment (scFv) is not actually a fragment of an antibody, but instead is a fusion protein of the variable regions of the heavy chain (VH) and light chain (VL) of immunoglobulins, connected with a short linker peptide of ten to about 25 amino acids. The linker is usually rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. Non-limiting examples of VH and VL protein sequences that may be used to create an anti-PTK7 scFv may include the amino acid sequence of SEQ ID NOs: 55, 69, 76, or 83 (VH) and SEQ ID NOs: 56, 70, 77, or 83 (VL). In some embodiments, the scFv of the present disclosure is humanized. In other embodiments, the scFv is fully human. In yet other embodiments, the scFv is a chimera (e.g., of mouse and human sequence). In some embodiments, the scFv is an anti-PTK7 scFv (binds specifically to PTK7). Non-limiting examples of anti-PTK7 scFv proteins that may be used as provided herein may include the amino acid sequence of any one of SEQ ID NOs: 54, 68, 75, 82. Other scFv proteins may be used.

The signal peptide can enhance the antigen specificity of CAR binding. Signal peptides can be derived from antibodies, such as, but not limited to, CD8, as well as epitope tags such as, but not limited to, GST or FLAG. Examples of signal peptides include MLLLVTSLLLCELPHPAFLLIP (SEQ ID NO: 106) and MALPVTALLLPLALLLHAARP (SEQ ID NO: 93). Other signal peptides may be used.

In some embodiments, a spacer domain or hinge domain is located between an extracellular domain (comprising the antigen binding domain) and a transmembrane domain of a CAR, or between a cytoplasmic domain and a transmembrane domain of the CAR. A spacer domain is any oligopeptide or polypeptide that functions to link the transmembrane domain to the extracellular domain and/or the cytoplasmic domain in the polypeptide chain. A hinge domain is any oligopeptide or polypeptide that functions to provide flexibility to the CAR, or domains thereof, or to prevent steric hindrance of the CAR, or domains thereof. In some embodiments, a spacer domain or a hinge domain may comprise up to 300 amino acids (e.g., 10 to 100 amino acids, or 5 to 20 amino acids). In some embodiments, one or more spacer domain(s) may be included in other regions of a CAR. In some embodiments, the hinge domain is a CD8 hinge domain. Other hinge domains may be used.

Transmembrane Domain

The transmembrane domain is a hydrophobic alpha helix that spans the membrane.

The transmembrane domain provides stability of the CAR. In some embodiments, the transmembrane domain of a CAR as provided herein is a CD8 transmembrane domain. In other embodiments, the transmembrane domain is a CD28 transmembrane domain. In yet other embodiments, the transmembrane domain is a chimera of a CD8 and CD28 transmembrane domain. Other transmembrane domains may be used as provided herein. In some embodiments, the transmembrane domain is a CD8a transmembrane domain: FVPVFLPAKPTTTPAPRPPTPAPTIASQPLSLRPEACR-PAAGG AVHTRGLDFACDIYI-WAPLAGTCGVLLLSLVITLYCNHRNR (SEQ ID NO: 107). Other transmembrane domains may be used.

Endodomain

The endodomain is the functional end of the receptor. Following antigen recognition, receptors cluster and a signal is transmitted to the cell. The most commonly used endodomain component is CD3-zeta, which contains three (3) immunoreceptor tyrosine-based activation motif (ITAM)s. This transmits an activation signal to the T cell after the antigen is bound. In many cases, CD3-zeta may not provide a fully competent activation signal and, thus, a co-stimulatory signaling is used. For example, CD28 and/or 4-1 BB may be used with CD3-zeta (CD3ζ) to transmit a proliferative/survival signal. Thus, in some embodiments, the co-stimulatory molecule of a CAR as provided herein is a CD28 co-stimulatory molecule. In other embodiments, the co-stimulatory molecule is a 4-1 BB co-stimulatory molecule. In some embodiments, a CAR includes CD3ζ and CD28. In other embodiments, a CAR includes CD3-zeta and 4-1 BB. In still other embodiments, a CAR includes CD3ζ, CD28, and 4-1 BB. Table 5 provides examples of signaling molecules that may be used as provided herein.

TABLE 5

| Name | Sequence | SEQ ID NO: |
|---|---|---|
| 4-1BB | AAACGGGGCAGAAAGAAACTCCTGTATATATT CAAACAACCATTTATGAGACCAGTACAAACTA CTCAAGAGGAAGATGGCTGTAGCTGCCGATTT CCAGAAGAAGAAGAAGGAGGATGTGAACTG | 43 |
| | KRGRKKLLYIFKQPFMRPVQTTQEEDGCSCRF PEEEEGGCEL | 44 |
| CD28 | TCAAAGCGGAGTAGGTTGTTGCATTCCGATTA CATGAATATGACTCCTCGCCGGCCTGGGCCGA CAAGAAAACATTACCAACCCTATGCCCCCCCA CGAGACTTCGCTGCGTACAGGTCC | 45 |
| | SKRSRLLHSDYMNMTPRRPGPTRKHYQPYAPP RDFAAYRS | 46 |
| CD3-zeta | CGAGTGAAGTTTTCCCGAAGCGCAGACGCTCC GGCATATCAGCAAGGACAGAATCAGCTGTATA ACGAACTGAATTTGGGACGCCGCGAGGAGTAT GACGTGCTTGATAAACGCCGGGGGAGAGACCC GGAAATGGGGGGTAAACCCCGAAGAAAGAATC CCCAAGAAGGACTCTACAATGAACTCCAGAAG GATAAGATGGCGGAGGCCTACTCAGAAATAGG TATGAAGGGCGAACGACGACGGGGAAAAGGTC ACGATGGCCTCTACCAAGGGTTGAGTACGGCA ACCAAAGATACGTACGATGCACTGCATATGCA GGCCCTGCCTCCCAGA | 47 |
| | RVKFSRSADAPAYQQGQNQLYNELNLGRREEY DVLDKRRGRDPEMGGKPRRKNPQEGLYNELQK DKMAEAYSEIGMKGERRRGKGHDGLYQGLSTA TKDTYDALHMQALPPR | 48 |

Antibodies

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) monoclonal antibodies, but also antigen-binding fragments (such as Fab, Fab', F(ab')2, Fv), single chain variable fragment (scFv), mutants thereof, fusion proteins comprising an antibody portion, humanized antibodies, chimeric antibodies, diabodies, linear antibodies, single chain antibodies, single domain antibodies (e.g., camel or llama VHH antibodies), multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies.

A typical antibody molecule comprises a heavy chain variable region (VH) and a light chain variable region (VL), which are usually involved in antigen binding. These regions/residues that are responsible for antigen-binding can be identified from amino acid sequences of the VH/VL sequences of a reference antibody (e.g., an anti-PTK7 antibody as described herein) by methods known in the art. The VH and VL regions can be further subdivided into regions of hypervariability, also known as "complementarity determining regions" ("CDR"), interspersed with regions that are more conserved, which are known as "framework regions" ("FR"). Each VH and VL is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the Chothia definition, the AbM definition, and/or the contact definition, all of which are well known in the art. As used herein, a CDR may refer to the CDR defined by any method known in the art. Two antibodies having the same CDR means that the two antibodies have the same amino acid sequence of that CDR as determined by the same method. See, e.g., Kabat, E. A., et al. (1991) Sequences of Proteins of Immunological Interest, Fifth Edition, U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). See also hgmp.mrc.ac.uk and bioinf.org.uk/abs.

In some embodiments, an antibody is an scFv, such as an anti-PTK7 scFv. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The antibodies to be used as provided herein can be murine, rat, human, or any other origin (including chimeric or humanized antibodies). In some examples, the antibody comprises a modified constant region, such as a constant region that is immunologically inert, e.g., does not trigger complement mediated lysis, or does not stimulate antibody-dependent cell mediated cytotoxicity (ADCC).

In some embodiments, an antibody of the present disclosure is a humanized antibody. Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. A humanized antibody optimally also will comprise at least a portion of an immunoglobulin constant region or domain (Fc), typically that of a human immunoglobulin. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

In some embodiments, an antibody of the present disclosure is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, an antibody of the present disclosure specifically binds a target antigen, such as human PTK7. An antibody that "specifically binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically (or preferentially) binds to a PTK7 epitope is an antibody that binds this PTK7 epitope with greater affinity, avidity, more readily, and/or with greater duration than it binds to other PTK7 epitopes or non-PTK7 epitopes. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

In some embodiments, the equilibrium dissociation constant ($K_D$) between the antibody and PTK7 is 100 pM to 1 µM. In some embodiments, the $K_D$ between the antibody and PTK7 is 1 nM to 100 nM.

Also within the scope of the present disclosure are functional variants of any of the exemplary antibodies as disclosed herein. A functional variant may contain one or more amino acid residue variations in the VH and/or VL, or in one or more of the VH CDRs and/or one or more of the VL CDRs as relative to a reference antibody, while retaining substantially similar binding and biological activities (e.g., substantially similar binding affinity, binding specificity, inhibitory activity, anti-tumor activity, or a combination thereof) as the reference antibody.

In some examples, an antibody disclosed herein comprises a VH CDR1, a VH CDR2, and a VH CDR3, which collectively contains no more than 10 amino acid variations (e.g., no more than 9, 8, 7, 6, 5, 4, 3, 2, or 1 amino acid variation) as compared with the VH CDR1, VH CDR2, and VH CDR3 of a reference antibody such as Antibody A (VH: SEQ ID NO: 55; VL: SEQ ID NO: 56). "Collectively" means that the total number of amino acid variations in all of the three VH CDRs is within the defined range. Alternatively or in addition, antibody may comprise a VL CDR1, a VL CDR2, and a VL CDR3, which collectively contains no more than 10 amino acid variations (e.g., no more than 9, 8, 7, 6, 5, 4, 3, 2 or 1 amino acid variation) as compared with the VL CDR1, VL CDR2, and VL CDR3 of the reference antibody.

In some examples, an antibody disclosed herein may comprise a VH CDR1, a VH CDR2, and a VH CDR3, at least one of which contains no more than 5 amino acid variations (e.g., no more than 4, 3, 2, or 1 amino acid variation) as the counterpart VH CDR of a reference antibody such as Antibody A (VH: SEQ ID NO: 55; VL: SEQ ID NO: 56). In specific examples, the antibody comprises a VH CDR3, which contains no more than 5 amino acid variations (e.g., no more than 4, 3, 2, or 1 amino acid variation) as the VH CDR3 of a reference antibody such as Antibody A (VH: SEQ ID NO: 55; VL: SEQ ID NO: 56). Alternatively or in addition, an antibody may comprise a VL CDR1, a VL CDR2, and a VL CDR3, at least one of which contains no more than 5 amino acid variations (e.g., no more than 4, 3, 2, or 1 amino acid variation) as the counterpart VL CDR of the reference antibody. In specific examples, the antibody comprises a VL CDR3, which contains no more than 5 amino acid variations (e.g., no more than 4, 3, 2, or 1 amino acid variation) as the VL CDR3 of the reference antibody.

In some instances, the amino acid residue variations can be conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) A→G, S; (b) R→K, H; (c) N→Q, H; (d) D→E, N; (e) C→S, A; (f) Q→N; (g) E→D, Q; (h) G→A; (i) H→N, Q; (j) I→L, V; (k) L→I, V; (l) K→R, H; (m) M→L, I, Y; (n) F→Y, M, L; (o) P→A; (p) S→T; (q) T→S; (r) W→Y, F; (s) Y→W, F; and (t) V→I, L.

In some embodiments, an antibody disclosed herein may comprise VH CDRs that collectively are at least 80% (e.g., 85%, 90%, 95%, or 98%) identical to the VH CDRs of a reference antibody such as Antibody A (VH: SEQ ID NO: 55; VL: SEQ ID NO: 56). Alternatively or in addition, the antibody may comprise VL CDRs that collectively are at least 80% (e.g., 85%, 90%, 95%, or 98%) identical to the VL CDRs of the reference antibody. In some embodiments, an antibody may comprise a VH that is at least 80% (e.g., 85%, 90%, 95%, or 98%) identical to the VH of a reference antibody such as Antibody A (VH: SEQ ID NO: 55; VL: SEQ ID NO: 56) and/or a VL that is at least 80% (e.g., 85%, 90%, 95%, or 98%) identical to the VL of the reference antibody.

Donor Template

The nucleic acid encoding a CAR may be delivered to a T cell that comprises what is referred to herein as a donor template (also referred to as a donor polynucleotide). A donor template can contain a non-homologous sequence, such as the nucleic acid encoding a CAR, flanked by two regions of homology to allow for efficient HDR at a genomic location of interest. In some embodiments, the region of homology can comprise a nucleotide sequence of SEQ ID NO: 92 or 100. In some embodiments, the non-homologous sequence is flanked by a nucleotide sequence of SEQ ID NO: 92 and a nucleotide sequence of SEQ ID NO: 100. Alternatively, a donor template may have no regions of homology to the targeted location in the DNA and may be integrated by NHEJ-dependent end joining following cleavage at the target site.

A donor template can be DNA or RNA, single-stranded and/or double-stranded, and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al., (1987) Proc. Natl. Acad. Sci. USA 84:4959-4963; Nehls et al., (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A donor template can be introduced into a cell as part of a vector molecule having additional sequences such as, for example, replication origins, promoters and genes encoding antibiotic resistance. Moreover, a donor template can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

A donor template, in some embodiments, is inserted so that its expression is driven by the endogenous promoter at the integration site, namely the promoter that drives expression of the endogenous gene into which the donor is inserted. However, in some embodiments, the donor template comprises an exogenous promoter and/or enhancer, for example a constitutive promoter, an inducible promoter, or tissue-specific promoter. In some embodiments, the exogenous promoter is an EF1α promoter comprising a sequence of SEQ ID NO: 101. Other promoters may be used.

Furthermore, exogenous sequences may also include transcriptional or translational regulatory sequences, for example, promoters, enhancers, insulators, internal ribosome entry sites, sequences encoding 2A peptides and/or polyadenylation signals.

In some embodiments, the donor template comprises the nucleotide sequence of any one of SEQ ID NOs: 63, 64, 71, 78, or 91.

Delivery Methods and Constructs

Nucleases and/or donor templates may be delivered using a vector system, including, but not limited to, plasmid vectors, DNA minicircles, retroviral vectors, lentiviral vectors, adenovirus vectors, poxvirus vectors; herpesvirus vectors and adeno-associated virus vectors, and combinations thereof.

Conventional viral and non-viral based gene transfer methods can be used to introduce nucleic acids encoding nucleases and donor templates in cells (e.g., T cells). Non-viral vector delivery systems include DNA plasmids, DNA minicircles, naked nucleic acid, and nucleic acid complexed with a delivery vehicle such as a liposome or poloxamer. Viral vector delivery systems include DNA and RNA viruses, which have either episomal or integrated genomes after delivery to the cell.

Methods of non-viral delivery of nucleic acids include electroporation, lipofection, microinjection, biolistics, virosomes, liposomes, immunoliposomes, polycation or lipid:nucleic acid conjugates, naked DNA, naked RNA, capped RNA, artificial virions, and agent-enhanced uptake of DNA. Sonoporation using, e.g., the Sonitron® 2000 system (RichMar) can also be used for delivery of nucleic acids.

Adeno-Associated Viral Delivery

The donor nucleic acid encoding a CAR construct can be delivered to a cell using an adeno-associated virus (AAV). AAVs are small viruses which integrate site-specifically into the host genome and can therefore deliver a transgene, such as CAR. Inverted terminal repeats (ITRs) are present flanking the AAV genome and/or the transgene of interest and serve as origins of replication. Also present in the AAV genome are rep and cap proteins which, when transcribed, form capsids which encapsulate the AAV genome for delivery into target cells. Surface receptors on these capsids which confer AAV serotype, which determines which target organs the capsids will primarily bind and thus what cells the AAV will most efficiently infect. There are twelve currently known human AAV serotypes. In some embodiments, the AAV is AAV serotype 6 (AAV6).

Adeno-associated viruses are among the most frequently used viruses for gene therapy for several reasons. First, AAVs do not provoke an immune response upon administration to mammals, including humans. Second, AAVs are effectively delivered to target cells, particularly when consideration is given to selecting the appropriate AAV serotype. Finally, AAVs have the ability to infect both dividing and non-dividing cells because the genome can persist in the host cell without integration. This trait makes them an ideal candidate for gene therapy.

Homology-Directed Repair (HDR)

The donor nucleic acid encoding a CAR is inserted by homology directed repair (HDR) into the target gene locus. Both strands of the DNA at the target locus are cut by a CRISPR Cas9 enzyme. HDR then occurs to repair the double-strand break (DSB) and insert the donor DNA. For this to occur correctly, the donor sequence is designed with flanking residues which are complementary to the sequence surrounding the DSB site in the target gene (hereinafter "homology arms"). These homology arms serve as the template for DSB repair and allow HDR to be an essentially error-free mechanism. The rate of homology directed repair (HDR) is a function of the distance between the mutation and the cut site so choosing overlapping or nearby target sites is important. Templates can include extra sequences flanked by the homologous regions or can contain a sequence that differs from the genomic sequence, thus allowing sequence editing.

The target gene can be associated with an immune response in a subject, wherein permanently deleting at least a portion of the target gene will modulate the immune response. For example, to generate a CAR T cell, the target gene can be the TCRα constant region (TRAC). Disruption of TRAC leads to loss of function of the endogenous TCR.

In some embodiments, the target gene is in a safe harbor locus.

Engineered T Cells

Engineered (gene edited) CAR T cells of the present disclosure may be autologous ("self") or non-autologous ("non-self," e.g., allogeneic, syngeneic or xenogeneic). "Autologous" refers to cells from the same subject. "Allogeneic" refers to cells of the same species as a subject, but that differ genetically to the cells in the subject. In some embodiments, the T cells are obtained from a mammalian subject. In some embodiments, the T cells are obtained from a human subject.

T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation.

In some embodiments, an isolated population of T cells is used. In some embodiments, after isolation of peripheral blood mononuclear cells (PBMC), both cytotoxic and helper T lymphocytes can be sorted into naive, memory, and effector T cell subpopulations either before or after activation, expansion, and/or genetic modification.

A specific subpopulation of T cells, expressing one or more of the following cell surface markers: TCRab, CD3, CD4, CD8, CD27 CD28, CD38 CD45RA, CD45RO, CD62L, CD127, CD122, CD95, CD197, CCR7, KLRG1, MCH-1 proteins and/or MCH-II proteins, can be further isolated by positive or negative selection techniques. In some embodiments, a specific subpopulation of T cells, expressing one or more of the markers selected from the group consisting of TCRab, CD4 and/or CD8, is further isolated by positive or negative selection techniques. In some embodiments, the engineered T cell populations do not express or do not substantially express one or more of the following markers: CD70, CD57, CD244, CD160, PD-1, CTLA4, HM3, and LAG3. In some embodiments, subpopulations of T cells may be isolated by positive or negative selection prior to genetic engineering and/or post genetic engineering.

In some embodiments, an isolated population of T cells expresses one or more of the markers including, but not limited to a CD3+, CD4+, CD8+, or a combination thereof. In some embodiments, the T cells are isolated from a subject and first activated and stimulated to proliferate in vitro prior to undergoing gene editing.

To achieve sufficient therapeutic doses of T cell compositions, T cells are often subjected to one or more rounds of stimulation, activation and/or expansion. T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041. In some embodiments, T cells are activated and expanded for about 1 day to about 4 days, about 1 day to about 3 days, about 1 day to about 2 days, about 2 days to about 3 days, about 2 days to about 4 days, about 3 days to about 4 days, or about 1 day, about 2 days, about 3 days, or about 4 days prior to introduction of the genome editing compositions into the T cells.

In some embodiments, T cells are activated and expanded for about 4 hours, about 6 hours, about 12 hours, about 18 hours, about 24 hours, about 36 hours, about 48 hours, about 60 hours, or about 72 hours prior to introduction of the gene editing compositions into the T cells.

In some embodiments, T cells are activated at the same time that genome editing compositions are introduced into the T cells.

Also provided are populations of engineered T cells described herein. In some embodiments, at least 25% to 100% of the engineered T cells of the population express the CAR. In some embodiments, at least 25% or at least 50% of the engineered T cells of the population express the CAR. In some embodiments, at least 70% of the engineered T cells of the population express the CAR. In some embodiments, at least 25% of engineered T cells of the population express the CAR following at least 7 or at least 14 days of in vitro proliferation.

Treatment Methods and Compositions

Provided herein, in some embodiments, are methods for treating cancer (e.g.: solid tumors). Non-limiting examples of solid tumors that may be treated as provided herein include: pancreatic cancer, gastric cancer, ovarian cancer, uterine cancer, breast cancer, prostate cancer, testicular cancer, thyroid cancer, nasopharyngeal cancer, non-small cell lung (NSCLC), glioblastoma, neuronal, soft tissue sarcomas and/or melanoma. In some embodiments, the cancer is selected from the group consisting of: pancreatic cancer, gastric cancer, ovarian cancer, uterine cancer, breast cancer, prostate cancer, testicular cancer, thyroid cancer, nasopharyngeal cancer, non-small cell lung (NSCLC), glioblastoma, neuronal, soft tissue sarcomas, leukemia, lymphoma, melanoma, colon cancer, colon adenocarcinoma, brain glioblastoma, hepatocellular carcinoma, liver hepatocholangiocarcinoma, osteosarcoma, gastric cancer, esophagus squamous cell carcinoma, advanced stage pancreas cancer, lung adenocarcinoma, lung squamous cell carcinoma, lung small cell cancer, renal carcinoma, and intrahepatic biliary cancer. In some embodiments, the methods comprise delivering the CAR T cells (e.g., anti-Ptk7 CAR T cells) of the present disclosure to a subject having cancer (e.g., solid tumors) including, pancreatic cancer, gastric cancer, ovarian cancer, cervical cancer, breast cancer, prostate cancer, testicular cancer, thyroid cancer, nasopharyngeal cancer, non-small cell lung (NSCLC), glioblastoma, and/or melanoma. In some embodiments, the methods comprise delivering the CAR T cells (e.g., anti-PTK7 CAR T cells) of the present disclosure to a subject having a leukemia or a lymphoma, e.g., leukemia or lymphomas of T cells, B cell, NK cell, dendritic cells. Non-limiting examples of leukemias include acute lymphoblastic leukemia (ALL), acute myeloid leukemia (AML), chronic lymphocytic leukemia (CLL) and chronic myeloid leukemia (CML).

The step of administering may include the placement (e.g., transplantation) of cells, e.g., engineered T cells, into a subject, by a method or route that results in at least partial localization of the introduced cells at a desired site, such as a tumor, such that a desired effect(s) is produced. Engineered T cells can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the subject, i.e., long-term engraftment. For example, in some aspects described herein, an effective amount of engineered T cells is administered via a systemic route of administration, such as an intraperitoneal or intravenous route.

A subject may be any subject for whom diagnosis, treatment, or therapy is desired. In some embodiments, the subject is a mammal. In some embodiments, the subject is a human.

A donor is an individual who is not the subject being treated. A donor is an individual who is not the patient. In some embodiments, a donor is an individual who does not have or is not suspected of having the cancer being treated. In some embodiments, multiple donors, e.g., two or more donors, are used.

In some embodiments, an engineered T cell population being administered according to the methods described herein comprises allogeneic T cells obtained from one or more donors. Allogeneic refers to a cell, cell population, or biological samples comprising cells, obtained from one or more different donors of the same species, where the genes at one or more loci are not identical to the recipient. For example, an engineered T cell population, being administered to a subject can be derived from one or more unrelated donors, or from one or more non-identical siblings. In some embodiments, syngeneic cell populations may be used, such as those obtained from genetically identical donors, (e.g., identical twins). In some embodiments, the cells are autologous cells; that is, the engineered T cells are obtained or isolated from a subject and administered to the same subject, i.e., the donor and recipient are the same.

In some embodiments, an engineered T cell population being administered according to the methods described herein does not induce toxicity in the subject, e.g., the engineered T cells do not induce toxicity in non-cancer cells. In some embodiments, an engineered T cell population being administered does not trigger complement mediated lysis, or does not stimulate antibody-dependent cell mediated cytotoxicity (ADCC).

An effective amount refers to the amount of a population of engineered T cells needed to prevent or alleviate at least one or more signs or symptoms of a medical condition (e.g., cancer), and relates to a sufficient amount of a composition to provide the desired effect, e.g., to treat a subject having a medical condition. An effective amount also includes an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate effective amount can be determined by one of ordinary skill in the art using routine experimentation.

For use in the various aspects described herein, an effective amount of cells (e.g., engineered T cells) comprises at least $10^2$ cells, at least $5 \times 10^2$ cells, at least $10^3$ cells, at least $5 \times 10^3$ cells, at least $10^4$ cells, at least $5 \times 10^4$ cells, at least $10^5$ cells, at least $2 \times 10^5$ cells, at least $3 \times 10^5$ cells, at least $4 \times 10^5$ cells, at least $5 \times 10^5$ cells, at least $6 \times 10^5$ cells, at least $7 \times 10^5$ cells, at least $8 \times 10^5$ cells, at least $9 \times 10^5$ cells, at least $1 \times 10^6$ cells, at least $2 \times 10^6$ cells, at least $3 \times 10^6$ cells, at least $4 \times 10^6$ cells, at least $5 \times 10^6$ cells, at least $6 \times 10^6$ cells, at least $7 \times 10^6$ cells, at least $8 \times 10^6$ cells, at least $9 \times 10^6$ cells, or multiples thereof. The cells are derived from one or more donors, or are obtained from an autologous source. In some examples described herein, the cells are expanded in culture prior to administration to a subject in need thereof.

Modes of administration include injection, infusion, instillation, or ingestion. Injection includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the route is intravenous.

In some embodiments, engineered T cells are administered systemically, which refers to the administration of a population of cells other than directly into a target site, tissue, or organ, such that it enters, instead, the subject's circulatory system and, thus, is subject to metabolism and other like processes.

The efficacy of a treatment comprising a composition for the treatment of a medical condition can be determined by the skilled clinician. A treatment is considered "effective treatment," if any one or all of the signs or symptoms of, as but one example, levels of functional target are altered in a beneficial manner (e.g., increased by at least 10%), or other clinically accepted symptoms or markers of disease (e.g., cancer) are improved or ameliorated. Efficacy can also be measured by failure of a subject to worsen as assessed by hospitalization or need for medical interventions (e.g., progression of the disease is halted or at least slowed). Methods of measuring these indicators are known to those of skill in the art and/or described herein. Treatment includes any treatment of a disease in subject and includes: (1) inhibiting the disease, e.g., arresting, or slowing the progression of symptoms; or (2) relieving the disease, e.g., causing regression of symptoms; and (3) preventing or reducing the likelihood of the development of symptoms.

The present disclosure is exemplified by the following embodiments:

Embodiment 1. An engineered T cell comprising a nucleic acid encoding a chimeric antigen receptor (CAR), wherein the CAR comprises an ectodomain that binds specifically to PTK7.

Embodiment 2. The engineered T cell of embodiment 1 further comprising a disrupted T cell receptor alpha chain constant region (TRAC) gene.

Embodiment 3. The engineered T cell of embodiment 2, wherein the nucleic acid encoding the CAR is inserted into the disrupted TRAC gene.

Embodiment 4. The engineered T cell of any one of embodiments 1-3 further comprising a disrupted beta-2-microglobulin (β2M) gene.

Embodiment 5. The engineered T cell of any one of embodiments 1-4, wherein the ectodomain of the CAR comprises an anti-PTK7 antibody.

Embodiment 6. The engineered T cell of embodiment 5, wherein the anti-PTK7 antibody is an anti-PTK7 single-chain variable fragment (scFv).

Embodiment 7. The engineered T cell of embodiment 6, wherein the anti-PTK7 scFv comprises the same heavy chain variable domain (VH) complementarity determining regions (CDRs) and the same light chain variable domain (VL) CDRs as a reference antibody, wherein the reference antibody comprises (i) a VH set forth as SEQ ID NO: 55 and a VL set forth as SEQ ID NO: 56, (ii) VH set forth as SEQ ID NO: 69 and a VL set forth as SEQ ID NO: 70, (iii) a VH set forth as SEQ ID NO: 76 and a VL set forth as SEQ ID NO: 77, or (iv) a VH set forth as SEQ ID NO: 83 and a VL set forth as SEQ ID NO: 84.

Embodiment 8. The engineered T cell of embodiment 7, wherein the anti-PTK7 scFv comprises the same VH and VL chains as the reference antibody.

Embodiment 9. The engineered T cell of embodiment 7, wherein the anti-PTK7 scFv comprises the amino acid sequence of any one of SEQ ID NOs: 54, 68, 75, or 82.

Embodiment 10. The engineered T cell of any one of embodiments 1-9, wherein the CAR comprises a CD28 co-stimulatory domain or a 41 BB co-stimulatory domain.

Embodiment 11. The engineered T cell of embodiment 10, wherein the CAR further comprises a CD3 cytoplasmic signaling domain.

Embodiment 12. The engineered T cell of any one of embodiments 3-11, wherein the TRAC gene comprises the nucleotide sequence encoding the LHA and/or RHA within any one of SEQ ID NOs: 63, 64, 71, 78, or 91 or the nucleotide sequence of SEQ ID NO: 92 or 100, and/or wherein the CAR is encoded by the nucleotide sequence of any one of SEQ ID NOs: 49, 51, 65, 72, 79, or 112.

Embodiment 13. The engineered T cell of any one of embodiments 4-12, wherein the disrupted β2M gene comprises at least one nucleotide sequence selected from any one of SEQ ID NOs: 9-14.

Embodiment 14. A population of the engineered T cell of any one of embodiments 1-13, wherein at least 25% or at least 50% of engineered T cells of the population express the CAR.

Embodiment 15. The population of embodiment 14, wherein at least 70% of engineered T cells of the population express the CAR.

Embodiment 16. The population of embodiments 14 or 15, wherein at least 25% of engineered T cells of the population express the CAR following at least 7 or at least 14 days of in vitro proliferation.

Embodiment 17. The population of any one of embodiments 14-16, wherein at least 50% of engineered T cells of the population do not express a detectable level of T cell receptor (TCR) protein.

Embodiment 18. The population of embodiment 17, wherein at least 90% of engineered T cells of the population do not express a detectable level of TCR protein.

Embodiment 19. The population of any one of embodiments 14-18, wherein at least 50% of engineered T cells of the population do not express a detectable level of β2M protein.

Embodiment 20. The population of embodiment 19, wherein at least 70% of engineered T cells of the population do not express a detectable level of β2M protein.

Embodiment 21. The population of any one of embodiments 14-20, wherein engineered T cells of the population, when co-cultured in vitro with a population of cancer cells that express PTK7, induce cell lysis of at least 10%, at least 25%, or at least 50% of the cancer cells of the population.

Embodiment 22. The population of embodiment 21, wherein engineered T cells of the population, when co-cultured in vitro with a population of cancer cells that express PTK7, induce cell lysis of at least 70%, at least 80%, or at least 90% of the population of cancer cells.

Embodiment 23. The population of embodiments 21 or 22, wherein engineered T cells of the population, when co-cultured in vitro with a population of cancer cells, secrete IFNγ.

Embodiment 24. The population of any one of embodiments 21-23, wherein the ratio of engineered T cells to cancer cells is 1:1 to 2:1.

Embodiment 25. The population of any one of embodiments 21-24, wherein the cancer cells comprise sarcoma cells.

Embodiment 26. The population of any one of embodiments 21-24, wherein the cancer cells comprise breast cancer cells, ovarian cancer cells, small cell lung cancer cells, and/or colon cancer cells.

Embodiment 27. The population of any one of embodiments 14-27, when administered in vivo to a subject, does not induce toxicity in the subject.

Embodiment 29. A method comprising administering the population of engineered T cells any one of embodiments 14-28 to a subject.

Embodiment 30. The method of embodiment 29, wherein the subject is a human subject.

Embodiment 31. The method of embodiment 30, wherein the subject has a cancer.

Embodiment 32. The method of embodiment 31, wherein the cancer is selected from the group consisting of: pancreatic cancer, gastric cancer, ovarian cancer, uterine cancer, breast cancer, prostate cancer, testicular cancer, thyroid cancer, nasopharyngeal cancer, non-small cell lung (NSCLC), glioblastoma, neuronal, soft tissue sarcomas, leukemia, lymphoma, melanoma, colon cancer, colon adenocarcinoma, brain glioblastoma, hepatocellular carcinoma, liver hepatocholangiocarcinoma, osteosarcoma, gastric cancer, esophagus squamous cell carcinoma, advanced stage pancreas cancer, lung adenocarcinoma, lung squamous cell carcinoma, lung small cell cancer, renal carcinoma, and intrahepatic biliary cancer.

Embodiment 33. The method of embodiments 31 or 32, wherein the cancer comprises cancer cells expressing PTK7.

Embodiment 34. A method for producing an engineered T cell, the method comprising (a) delivering to a T cell a RNA-guided nuclease, a gRNA targeting a TRAC gene, and a vector comprising a donor template that comprises a nucleic acid encoding a CAR that comprise an ectodomain that binds specifically to PTK7; and (b) producing an engineered T cell having a disrupted TRAC gene and expressing the CAR.

Embodiment 35. The method of embodiment 34, wherein the gRNA targeting the TRAC gene comprises the nucleotide sequence of SEQ ID NO: 18 or 19, or targets the nucleotide sequence of SEQ ID NO: 40.

Embodiment 36. The method of embodiments 34 or 35, wherein the nucleic acid encoding the CAR is flanked by left and right homology arms to the TRAC gene.

Embodiment 37. The method of any one of embodiments 34-36 further comprising delivering to the T cell a gRNA targeting the β2M gene.

Embodiment 38. The method of embodiment 37, wherein the gRNA targeting the β2M gene comprises the nucleotide sequence of SEQ ID NO: 20 or 21, or targets the nucleotide sequence of SEQ ID NO: 41.

Embodiment 39. The method of any one of embodiments 34-38, wherein the RNA-guided nuclease is a Cas9 nuclease, optionally a *S. pyogenes* Cas9 nuclease.

Embodiment 40. The method of any one of embodiments 34-39, wherein the ectodomain of the CAR is an anti-PTK7 antibody.

Embodiment 41. The method of embodiment 40, wherein the anti-PTK7 antibody is an anti-PTK7 single-chain variable fragment (scFv).

Embodiment 42. The method of embodiment 41, wherein the anti-PTK7 scFv comprises the same heavy chain variable domain (VH) complementarity determining regions (CDRs) and the same light chain variable domain (VL) CDRs as a reference antibody, wherein the reference antibody comprises (i) a VH set forth as SEQ ID NO: 55 and VL set forth as SEQ ID NO: 56, (ii) a VH set forth as SEQ ID NO: 69 and a VL set forth as SEQ ID NO: 70, (iii) a VH set forth as SEQ ID NO: 76 and a VL set forth as SEQ ID NO: 77, or (iv) a VH set forth as SEQ ID NO: 83 and a VL set forth as SEQ ID NO: 84.

Embodiment 43. The method of embodiment 42, wherein the anti-PTK7 scFv comprises the same VH and VL chains as the reference antibody.

Embodiment 44. The method of embodiment 42, wherein the anti-PTK7 scFv comprises the amino acid sequence of any one of SEQ ID NOs: 54, 68, 75, or 82.

Embodiment 45. The method of any one of embodiments 34-44, wherein the CAR comprises a CD28 co-stimulatory domain or a 41 BB co-stimulatory domain.

Embodiment 46. The method of embodiment 45, wherein the CAR further comprises a CD3 cytoplasmic signaling domain.

Embodiment 47. The method of any one of embodiments 34-46, wherein the donor template comprises the nucleotide sequence of any one of SEQ ID NOs: 63, 64, 71, 78, or 91.

Embodiment 48. The method of any one of embodiments 34-47, wherein the CAR is encoded by a nucleotide sequence of any one of SEQ ID NOs: 49, 51, 65, 72, 79, or 112.

The present disclosure is further exemplified by the following embodiments:

Embodiment A1. An engineered T cell comprising a nucleic acid encoding a chimeric antigen receptor (CAR), wherein the CAR comprises an ectodomain that binds specifically to PTK7.

Embodiment A2. The engineered T cell of embodiment A1 further comprising a disrupted T cell receptor alpha chain constant region (TRAC) gene.

Embodiment A3. The engineered T cell of embodiment A1 or A2 further comprising a disrupted beta-2-microglobulin (β2M) gene.

Embodiment A4. The engineered T cell of any one of embodiments A1-A3, wherein the ectodomain of the CAR comprises an anti-PTK7 antibody.

Embodiment A5. The engineered T cell of embodiment A4, wherein the anti-PTK7 antibody is an anti-PTK7 single-chain variable fragment (scFv).

Embodiment A6. The engineered T cell of embodiment A5, wherein the anti-PTK7 scFv comprises the same heavy chain variable domain (VH) complementarity determining regions (CDRs) and the same light chain variable domain (VL) CDRs as a reference antibody, wherein the reference antibody comprises (i) a VH set forth as SEQ ID NO: 55 and a VL set forth as SEQ ID NO: 56, (ii) a VH set forth as SEQ ID NO: 69 and a VL set forth as SEQ ID NO: 70, (iii) a VH set forth as SEQ ID NO: 76 and a VL set forth as SEQ ID NO: 77, or (iv) a VH set forth as SEQ ID NO: 83 and a VL set forth as SEQ ID NO: 84.

Embodiment A7. The engineered T cell of embodiment A6, wherein the anti-PTK7 scFv comprises the same VH and VL chains as the reference antibody.

Embodiment A8. The engineered T cell of embodiment A6, wherein the anti-PTK7 scFv comprises the amino acid sequence of any one of SEQ ID NOs: 54, 68, 75, or 82.

Embodiment A9. The engineered T cell of any one of embodiments A1-A8, wherein the CAR further comprises a CD28 co-stimulatory domain or a 41 BB co-stimulatory domain.

Embodiment A10. The engineered T cell of embodiment A9, wherein the CAR further comprises a CD3 cytoplasmic signaling domain.

Embodiment A11. The engineered T cell of any one of embodiments A1-A10, wherein the CAR is encoded by the nucleotide sequence of any one of SEQ ID NOs: 49, 51, 65, 72, 79, or 112 or a nucleotide sequence comprising a nucleic acid sequence that is at least 90% identical to SEQ ID NOs: 49, 51, 65, 72, 79, or 112.

Embodiment A12. The engineered T cell of any one of embodiments A1-A11, wherein the nucleic acid encoding the CAR is inserted into the disrupted TRAC gene.

Embodiment A13. The engineered T cell of any one of embodiments A2-A12, wherein the disrupted TRAC gene comprises the nucleotide sequence encoding the LHA and/or RHA within any one of SEQ ID NOs: 63, 64, 71, 78, or 91, the nucleotide sequence of SEQ ID NO: 92 or 100, and/or the nucleotide sequence of any one of SEQ ID NOs: 63, 64, 71, 78, or 91.

Embodiment A14. The engineered T cell of any one of embodiments A1-A13, wherein the disrupted β2M gene comprises at least one nucleotide sequence selected from any one of SEQ ID NOs: 9-14.

Embodiment A15. An engineered T cell comprising: (i) a disrupted TRAC gene; (ii) a disrupted β2M gene; and (iii) a nucleic acid encoding a CAR comprising an anti-PTK7 antigen-binding fragment.

Embodiment A16. The engineered T cell of embodiment A15, wherein the CAR comprises (a) an ectodomain that comprises an anti-PTK7 antigen-binding fragment, (b) a CD8 transmembrane domain, and (c) an endodomain that comprises a CD28 co-stimulatory domain and a CD3 cytoplasmic signaling domain.

Embodiment A17. The engineered T cell of embodiment A15 or A16, wherein the disrupted TRAC gene comprises the nucleic acid encoding the CAR.

Embodiment A18. An engineered T cell comprising: (i) a disrupted TRAC gene, wherein the disrupted TRAC gene comprises a nucleic acid encoding a CAR comprising (a) an ectodomain that comprises an anti-PTK7 antigen-binding fragment, (b) a CD8 transmembrane domain, and (c) an endodomain that comprises a CD28 co-stimulatory domain and a CD3ζ cytoplasmic signaling domain; and (ii) a disrupted 82M gene.

Embodiment A19. An engineered T cell comprising: (i) a disrupted TRAC gene, wherein the disrupted TRAC gene comprises a nucleic acid encoding a CAR comprising an amino acid sequence of any one of SEQ ID NOs: 50, 52, 66, 73, or 80; and (ii) a disrupted β2M gene.

Embodiment A20. An engineered T cell comprising: (i) a disrupted TRAC gene, wherein the disrupted TRAC gene comprises a nucleic acid encoding a CAR, wherein the nucleic acid sequence is at least 90% identical to SEQ ID NOs: 49, 51, 65, 72, 79, or 112 and encodes a CAR comprising an amino acid sequence of SEQ ID NOs: 50, 52, 66, 73, or 80; and (ii) a disrupted 82M gene.

Embodiment A21. The engineered T cell of any one of embodiments A1-A20, wherein the T cell is a human T cell.

Embodiment A22. A population of cells comprising the engineered T cell of any one of embodiments A1-A21, wherein at least 25% or at least 50% of engineered T cells of the population express the CAR.

Embodiment A23. The population of embodiment A22, wherein at least 70% of engineered T cells of the population express the CAR.

Embodiment A24. The population of embodiment A22, wherein at least 25% of engineered T cells of the population express the CAR following at least 7 days or at least 14 days of in vitro proliferation.

Embodiment A25. The population of any one of embodiments A22-A24, wherein at least 50% of engineered T cells of the population do not express a detectable level of T cell receptor (TCR) protein.

Embodiment A26. The population of embodiment A25, wherein at least 90% of engineered T cells of the population do not express a detectable level of TCR protein.

Embodiment A27. The population of any one of embodiments A22-A26, wherein at least 50% of engineered T cells of the population do not express a detectable level of β2M protein.

Embodiment A28. The population of embodiment A27, wherein at least 70% of engineered T cells of the population do not express a detectable level of β2M protein.

Embodiment A29. The population of any one of embodiments A22-A28, wherein engineered T cells of the population, when co-cultured in vitro with a population of cancer cells that express PTK7, induce cell lysis of at least 10%, at least 25%, or at least 50% of the cancer cells of the population.

Embodiment A30. The population of embodiment A29, wherein engineered T cells of the population, when co-cultured in vitro with a population of cancer cells that express PTK7, induce cell lysis of at least 70%, at least 80%, or at least 90% of the population of cancer cells.

Embodiment A31. The population of embodiment A29 or A30, wherein engineered T cells of the population, when co-cultured in vitro with a population of cancer cells, secrete IFNγ.

Embodiment A32. The population of any one of embodiments A29-A31, wherein the ratio of engineered T cells to cancer cells is 1:1 to 2:1.

Embodiment A33. The population of any one of embodiments A29-A32, wherein the cancer cells comprise sarcoma cells.

Embodiment A34. The population of any one of embodiments A29-3A2, wherein the cancer cells comprise breast cancer cells, ovarian cancer cells, small cell lung cancer cells, and/or colon cancer cells.

Embodiment A35. The population of any one of embodiments A22-A34, when administered in vivo to a subject, does not induce toxicity in the subject.

Embodiment A36. A population of cells comprising engineered T cells, wherein the engineered T cells comprise: (i) a disrupted TRAC gene; (ii) a disrupted β2M gene; and (iii) a nucleic acid encoding a CAR comprising an anti-PTK7 antigen-binding fragment.

Embodiment A37. The population of cells of embodiment A36, wherein the CAR comprises (a) an ectodomain that comprises an anti-PTK7 antigen-binding fragment, (b) a CD8 transmembrane domain, and (c) an endodomain that comprises a CD28 co-stimulatory domain and a CD3 cytoplasmic signaling domain.

Embodiment A38. The population of cells of embodiment A36 or A37, wherein the disrupted TRAC gene comprises the nucleic acid encoding the CAR.

Embodiment A39. A population of cells comprising engineered T cells, wherein the engineered T cells comprise: (i) a disrupted TRAC gene, wherein the disrupted TRAC gene comprises a nucleic acid encoding a CAR comprising (a) an ectodomain that comprises an anti-PTK7 antigen-binding fragment, (b) a CD8 transmembrane domain, and (c) an endodomain that comprises a CD28 co-stimulatory domain and a CD3 cytoplasmic signaling domain; and (ii) a disrupted 82M gene.

Embodiment A40. A population of cells comprising engineered T cells, wherein the engineered T cells comprise: (i) a disrupted TRAC gene, wherein the disrupted TRAC gene comprises a nucleic acid encoding a CAR, wherein the nucleic acid sequence is at least 90% identical to SEQ ID NOs: 49, 51, 65, 72, 79, or 112 and encodes the CAR of SEQ ID NOs: 50, 52, 66, 73, or 80; and (ii) a disrupted 82M gene.

Embodiment A41. A method comprising administering the population of engineered T cells any one of embodiments A22-A40 to a subject.

Embodiment A42. The method of embodiment A41, wherein the subject is a human subject.

Embodiment A43. The method of embodiment A42, wherein the subject has a cancer.

Embodiment A44. The method of embodiment A43, wherein the cancer is selected from the group consisting of: pancreatic cancer, gastric cancer, ovarian cancer, uterine cancer, breast cancer, prostate cancer, testicular cancer, thyroid cancer, nasopharyngeal cancer, non-small cell lung (NSCLC), glioblastoma, neuronal, soft tissue sarcomas, leukemia, lymphoma, melanoma, colon cancer, colon adenocarcinoma, brain glioblastoma, hepatocellular carcinoma, liver hepatocholangiocarcinoma, osteosarcoma, gastric cancer, esophagus squamous cell carcinoma, advanced stage pancreas cancer, lung adenocarcinoma, lung squamous cell carcinoma, lung small cell cancer, renal carcinoma, and intrahepatic biliary cancer.

Embodiment A45. The method of embodiment A43 or A44, wherein the cancer comprises cancer cells expressing PTK7.

Embodiment A46. A method for producing an engineered T cell, the method comprising (a) delivering to a T cell (i) a RNA-guided nuclease, (ii) a gRNA targeting a TRAC gene, and (iii) a vector comprising a donor template that comprises a nucleic acid encoding a CAR that comprise an ectodomain that binds specifically to PTK7; and (b) producing an engineered T cell having a disrupted TRAC gene and expressing the CAR.

Embodiment A47. The method of embodiment A46, wherein the gRNA targeting the TRAC gene comprises the nucleotide sequence of SEQ ID NO: 18 or 19, or targets the nucleotide sequence of SEQ ID NO: 40.

Embodiment A48. The method of embodiment A46 or A47 further comprising delivering to the T cell a gRNA targeting the β2M gene.

Embodiment A49. The method of embodiment A48, wherein the gRNA targeting the β2M gene comprises the nucleotide sequence of SEQ ID NO: 20 or 21, or targets the nucleotide sequence of SEQ ID NO: 41.

Embodiment A50. The method of any one of embodiments A46-A49, wherein the ectodomain of the CAR comprises an anti-PTK7 antibody.

Embodiment A51. The method of embodiment A50, wherein the anti-PTK7 antibody is an anti-PTK7 single-chain variable fragment (scFv).

Embodiment A52. The method of embodiment A51, wherein the anti-PTK7 scFv comprises the same heavy chain variable domain (VH) complementarity determining regions (CDRs) and the same light chain variable domain (VL) CDRs as a reference antibody, wherein the reference antibody comprises (i) a VH set forth as SEQ ID NO: 55 and VL set forth as SEQ ID NO: 56, (ii) a VH set forth as SEQ ID NO: 69 and a VL set forth as SEQ ID NO: 70, (iii) a VH set forth as SEQ ID NO: 76 and a VL set forth as SEQ ID NO: 77, or (iv) a VH set forth as SEQ ID NO: 83 and a VL set forth as SEQ ID NO: 84.

Embodiment A53. The method of embodiment A52, wherein the anti-PTK7 scFv comprises the same VH and VL chains as the reference antibody.

Embodiment A54. The method of embodiment A52, wherein the anti-PTK7 scFv comprises the amino acid sequence of any one of SEQ ID NOs: 54, 68, 75, or 82.

Embodiment A55. The method of any one of embodiments A46-A54, wherein the CAR further comprises a CD28 co-stimulatory domain or a 41 BB co-stimulatory domain.

Embodiment A56. The method of embodiment A55, wherein the CAR further comprises a CD3 cytoplasmic signaling domain.

Embodiment A57. The method of any one of embodiments A46-A56, wherein the CAR is encoded by a nucleotide sequence of any one of SEQ ID NOs: 49, 51, 65, 72, 79, or 112 or a nucleotide sequence comprising a nucleic acid sequence that is at least 90% identical to SEQ ID NOs: 49, 51, 65, 72, 79, or 112.

Embodiment A58. The method of any one of embodiments A46-A57, wherein the nucleic acid encoding the CAR is flanked by left and right homology arms to the TRAC gene.

Embodiment A59. The method of any one of embodiments A46-A58, wherein the donor template comprises the nucleotide sequence of any one of SEQ ID NOs: 63, 64, 71, 78, or 91.

Embodiment A60. The method of any one of embodiments A46-A59, wherein the RNA-guided nuclease is a Cas9 nuclease, optionally a S. pyogenes Cas9 nuclease.

Embodiment A61. An engineered T cell produced by the method of any one of embodiments A46-A60.

Embodiment A62. A population of cells comprising the engineered T cell of embodiment A61.

Embodiment A63. A method of treating cancer in a subject, comprising administering to the subject the population of cells of any one of embodiments A22-A40 or A62.

Embodiment A64. The method of embodiment A63, wherein the cancer is selected from the group consisting of: pancreatic cancer, gastric cancer, ovarian cancer, uterine cancer, breast cancer, prostate cancer, testicular cancer, thyroid cancer, nasopharyngeal cancer, non-small cell lung (NSCLC), glioblastoma, neuronal, soft tissue sarcomas, leukemia, lymphoma, melanoma, colon cancer, colon adenocarcinoma, brain glioblastoma, hepatocellular carcinoma, liver hepatocholangiocarcinoma, osteosarcoma, gastric cancer, esophagus squamous cell carcinoma, advanced stage pancreas cancer, lung adenocarcinoma, lung squamous cell carcinoma, lung small cell cancer, renal carcinoma, and intrahepatic biliary cancer.

Embodiment A65. The method of embodiments A63 or A64, wherein the cancer comprises cancer cells expressing PTK7.

EXAMPLES

Example 1. PTK7 Expression in Normal Human Tissues

PTK7 expression was evaluated on a frozen normal human tissue panel (FDA Standard, Biochain) using a custom recombinant monoclonal biotinylated antibody (CTX181 mAb, Creative Biolabs, 1 mg/ml, SEQ ID NO: 108 and SEQ ID NO: 109) specific to the PTK7 CAR construct or a biotinylated mouse isotype control (Novus, NBP2-21948). Slides were fixed with −20° C. acetone for 10 min at ambient temperature followed by a manual immunohistochemical staining at ambient temperature. Blocking to minimize non-specific staining was performed with Peroxidased 1, Avidin and Biotin and Background Sniper (BioCare Medical, PX968M, AB972L, BS966M) in sequential steps. Slides were stained with the biotinylated CTX181 primary monoclonal antibody (1:600) for 30 min followed by incubation with 4plus Streptavidin-HRP Label (BioCare Medical) reagent for 15 min each. Visualization of target antigen was visualized with DAB (brown color) substrate chromogen (Dako, K3468). Mayer's Hematoxylin (Dako, S3309) was used to counterstain the cell nuclei. FIG. 1 shows that PTK7 expression was not widespread in normal human tissues.

```
Sequences for CTX181 mAb:
>181_HC
                                  (SEQ ID NO: 108)
QVQLVESGGGVVQPGRSLRLSCAASGFTFSSYGMHWVRQAPGKGL

EWVAVIWDDGSNKYYVDSVKGRFTISRDNSKNTLYLQMNSLRAED
```

```
TAVYYCARDDYYGSGSFNSYYGTDVWGQGTTVTVSSASTKGPSVF

PLAPSSKSTSGGTAALGCLVKDYFPEPVTVSWNSGALTSGVHTFP

AVLQSSGLYSLSSVVTVPSSSLGTQTYICNVNHKPSNTKVDKKVE

PKSCDKTHTCPPCPAPELLGGPSVFLFPPKPKDTLMISRTPEVTC

VVVDVSHEDPEVKFNWYVDGVEVHNAKTKPREEQYNSTYRVVSVL

TVLHQDWLNGKEYKCKVSNKALPAPIEKTISKAKGQPREPQVYTL

PPSRDELTKNQVSLTCLVKGFYPSDIAVEWESNGQPENNYKTTPP

VLDSDGSFFLYSKLTVDKSRWQQGNVFSCSVMHEALHNHYTQKSL

SLSPGK

>181_LC
                              (SEQ ID NO: 109)
EIVLTQSPATLSLSPGERATLSCRASQSVSIYLAWYQQKPGQAPR

LLIYDASNRATGIPARFSGSGSGTDFTLTISSLEPEDFAVYYCQQ

RSNWPPFTFGPGTKVDIKRTVAAPSVFIFPPSDEQLKSGTASVVC

LLNNFYPREAKVQWKVDNALQSGNSQESVTEQDSKDSTYSLSSTL

TLSKADYEKHKVYACEVTHQGLSSPVTKSFNRGEC
```

Example 2. PTK7 Expression in Diseased Human Tissues

Figure 2A:
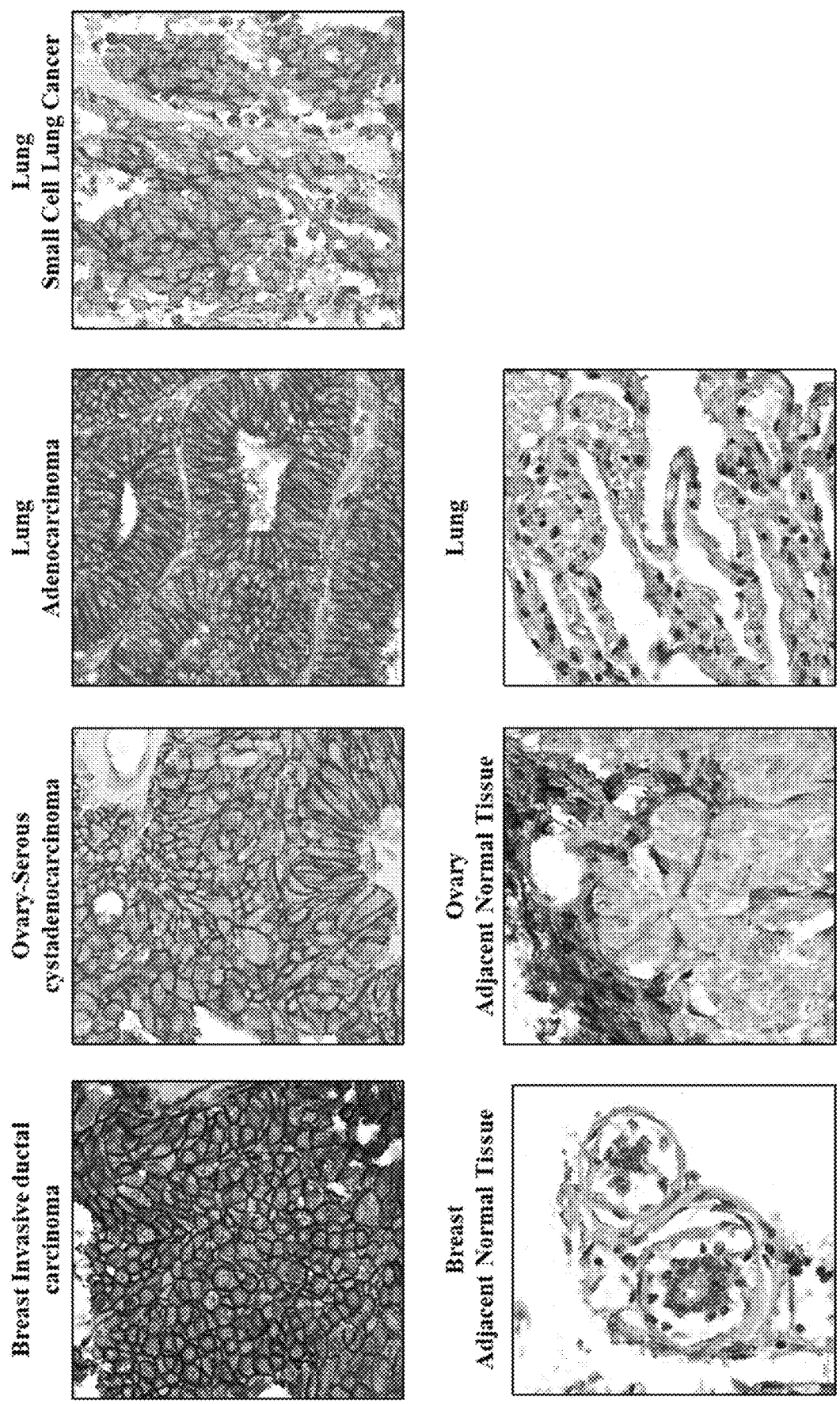
FIGS. 2A and 2B show PTK7 expression in human diseased and normal tissues.
Figure 2B:
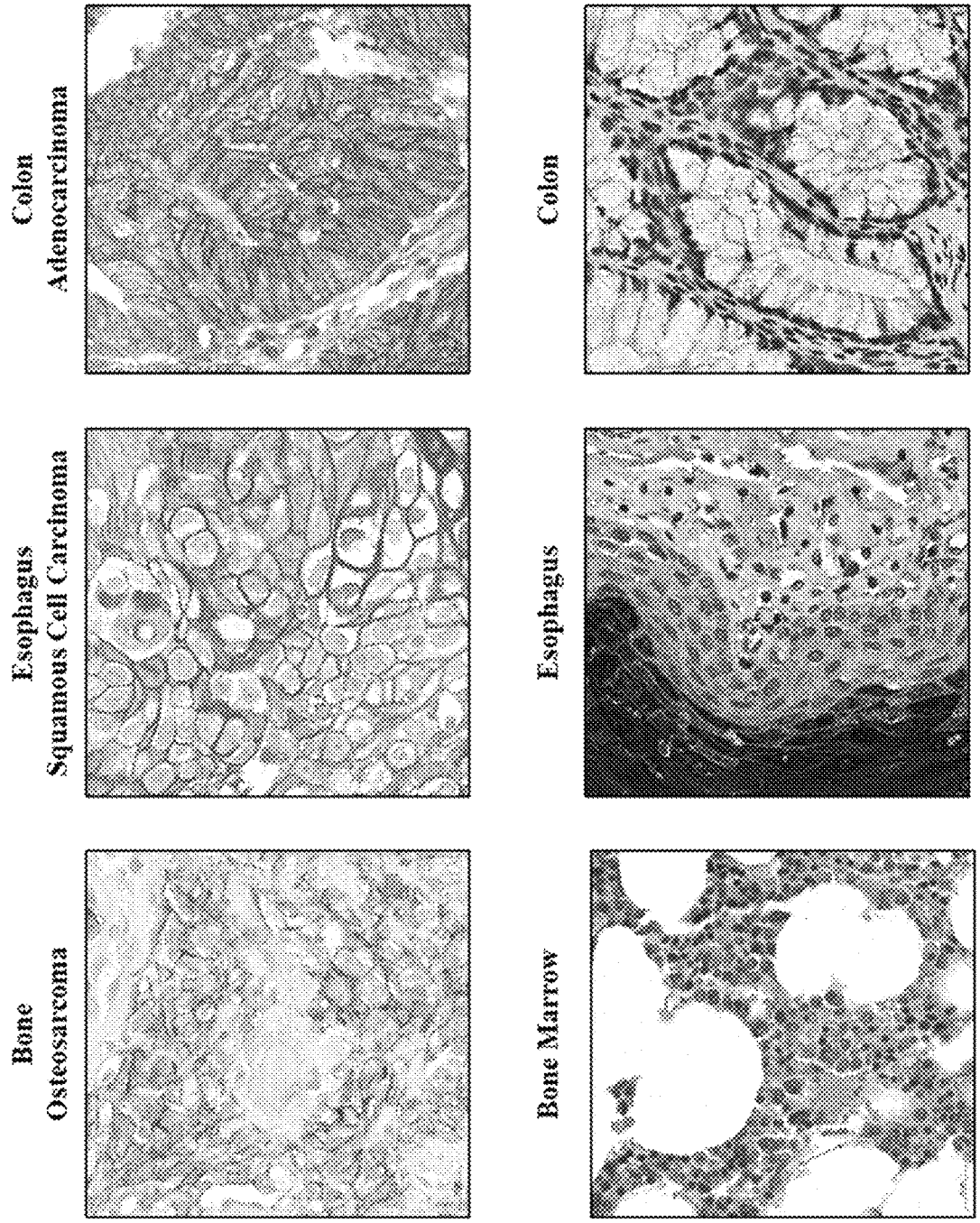
Figure 3:
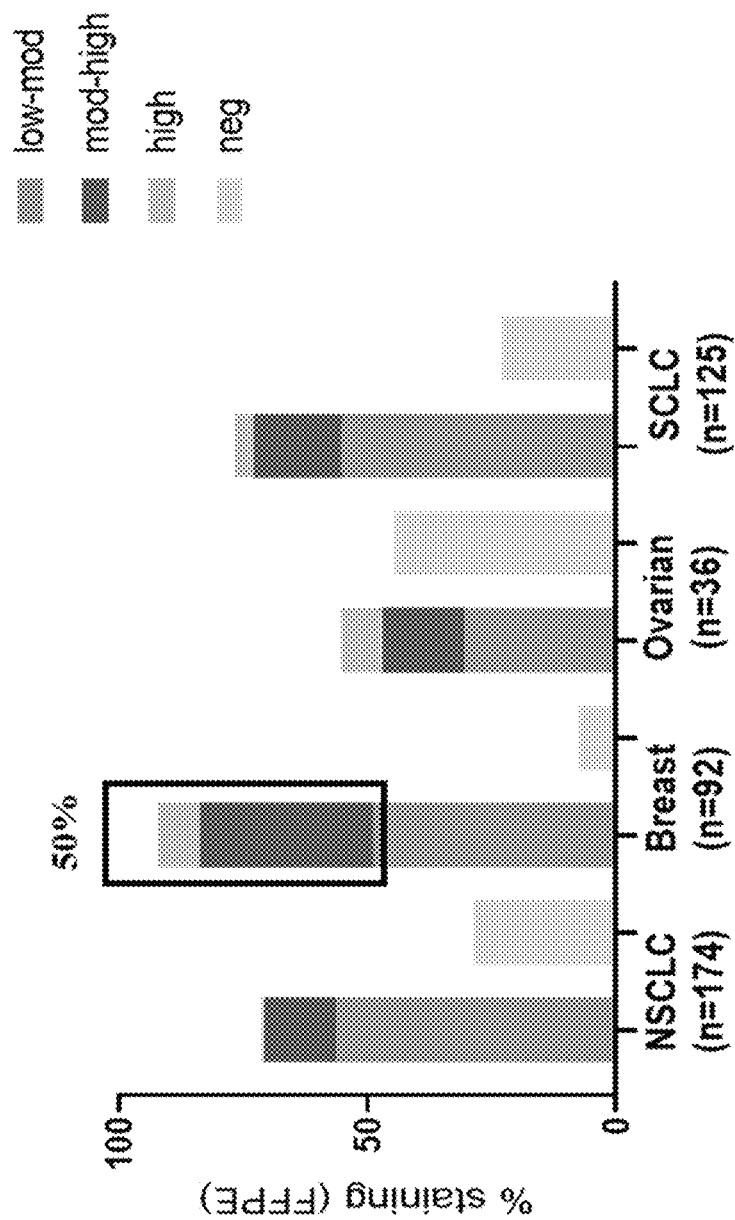
FIG. 3 shows PTK7 patient prevalence by immunohistochemistry (IHC) in solid tumors.

PTK7 expression was evaluated on formalin-fixed, paraffine-embedded (FFPE) diseased and normal patient tumor micro arrays using a mouse monoclonal anti-human PTK7 antibody, clone 4F9 (EMD Millipore, MABN721) (FIGS. 2A and 2B). Table 6 lists the FFPE tissue microarrays (TMA) used from US Biomax, Inc. FFPE sections were baked for 30 min at 60° C., deparaffinized and rehydrated. Antigen retrieval was performed for 40 min at 95° C. in 1× Reveal Decloaker solution using a Decloaker chamber (Bio-Care Medical). The remaining steps were performed at ambient temperature. Blocking to minimize non-specific staining was performed with Peroxidased 1 (BioCare Medical, PX968M) and Background Sniper (BioCare Medical, BS966M). Slides were stained for 60 min with the primary monoclonal anti-PTK7 antibody or mouse IgG isotype control (Novus Biologicals, LLC), washed and then stained for 30 min, with the secondary EnVision goat anti-mouse horseradish peroxidase antibody (Dako, K400111-2). Visualization of target antigen was visualized with DAB (brown color) substrate chromogen (Dako, K3468). Mayer's Hematoxylin (Dako, S3309) was used to counterstain the cell nuclei. Slides were scanned with the Pannoramic™ MIDI II scanner (3DHistech, ThermoFisher Scientific) and scored using semi-quantitative scoring system evaluating both the intensity of staining (1+-3+, where 1+ represents low antigen expression) as well as the percentage of the section stained (1-100%). Results were tabulated to establish patient prevalence summary data (FIG. 3). PTK7 was shown to be expressed in a broad range of solid tumor cancers.

TABLE 6

| Tissue | FFPE TMA (US Biomax, Inc. Name/Number) |
|---|---|
| Brain glioblastoma | GL806f |
| Hepatocellular carcinoma | LV631 |
| Liver hepatocholangiocarcinoma | LV642 |
| Osteosarcoma | OS804c |
| Gastric cancer | ST483e |
| Ovarian Cancer | OVC962 |
| Esophagus squamous cell carcinoma | HEso-Squ127Lym-01 |
| Advanced stage pancreas cancer | PA1921a |
| Lung adenocarcinoma | BCS04017b |
| Lung squamous cell carcinoma | HLug-Squ090Lym-01 |
| Lung small cell cancer | BS04116 |
| Intrahepatic biliary cancer | HIBD-Ade100PG-01 |

Example 3. Human/Mouse Cross Reactivity of Anti-PTK7 CTX181

Figure 4:
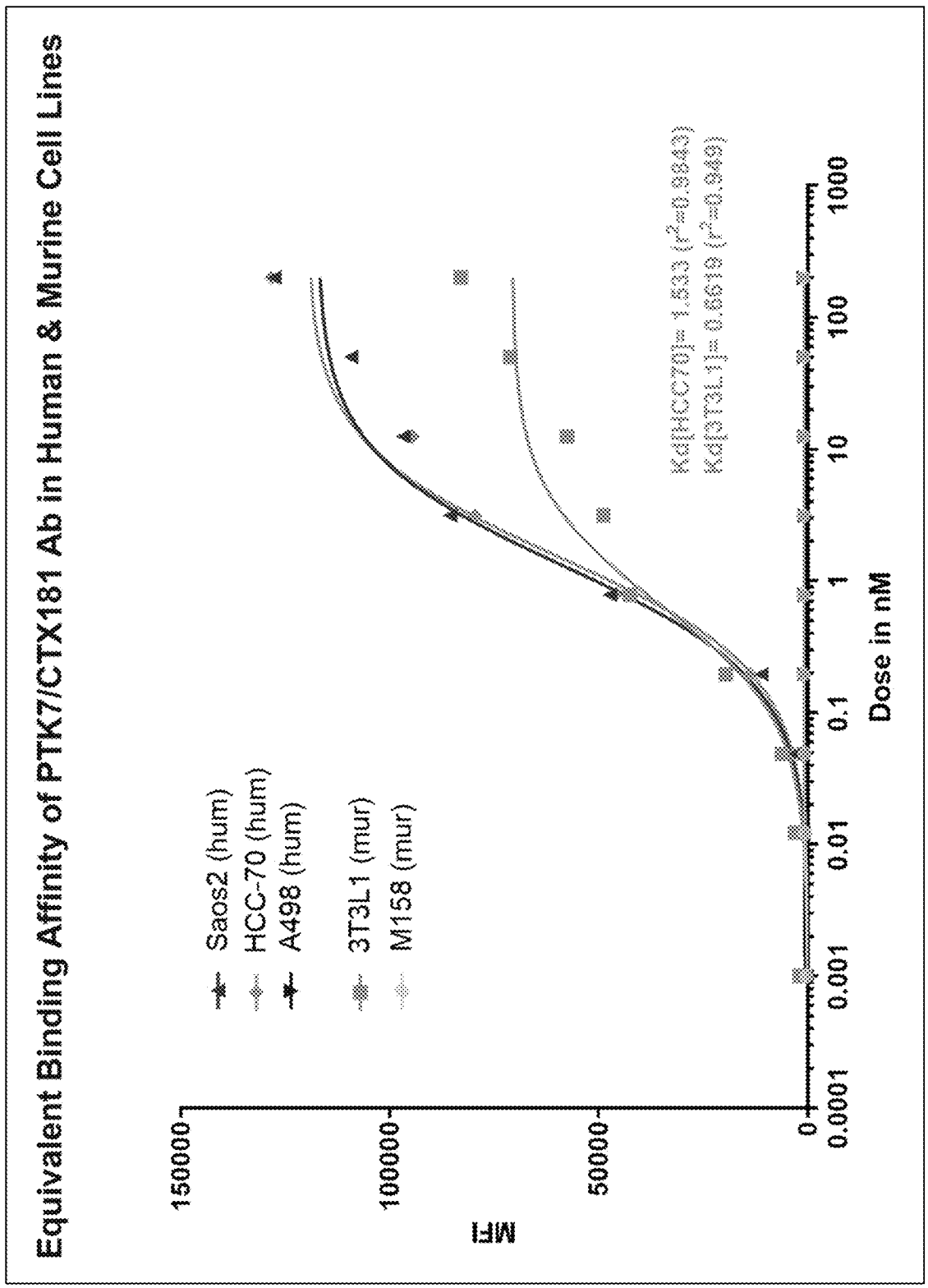
FIG. 4 shows binding affinity of PTK7/CTX181 Ab in human and murine cell lines.

To evaluate the species cross reactivity of the custom CTX181 antibody, its binding affinity was assessed in murine 3T3L1 fibroblast and murine M158 breast cancer cell lines and compared to its binding affinity in human Saos2 (osteosarcoma), A498 (renal carcinoma) and HCC70 (breast cancer) cell lines. For each cell line, a dose titration binding assay (200 nM-0.0032 nM final CTX181 antibody) was run on $2 \times 10^6$ cells at each concentration. Cells were stained 30 min on ice with CTX181 antibody, followed by washing and 15 min stain at RT with secondary APC fluorophore conjugated human IgG-Fc antibody. Cells were assessed for staining on a NovoCyte® flow cytometer (Acea Biosciences). FIG. 4 shows equivalent binding affinity for CTX181 antibody in murine and human cell lines.

Example 4. PTK7 Expression in Normal Human and Mouse Tissues

Figure 5A:
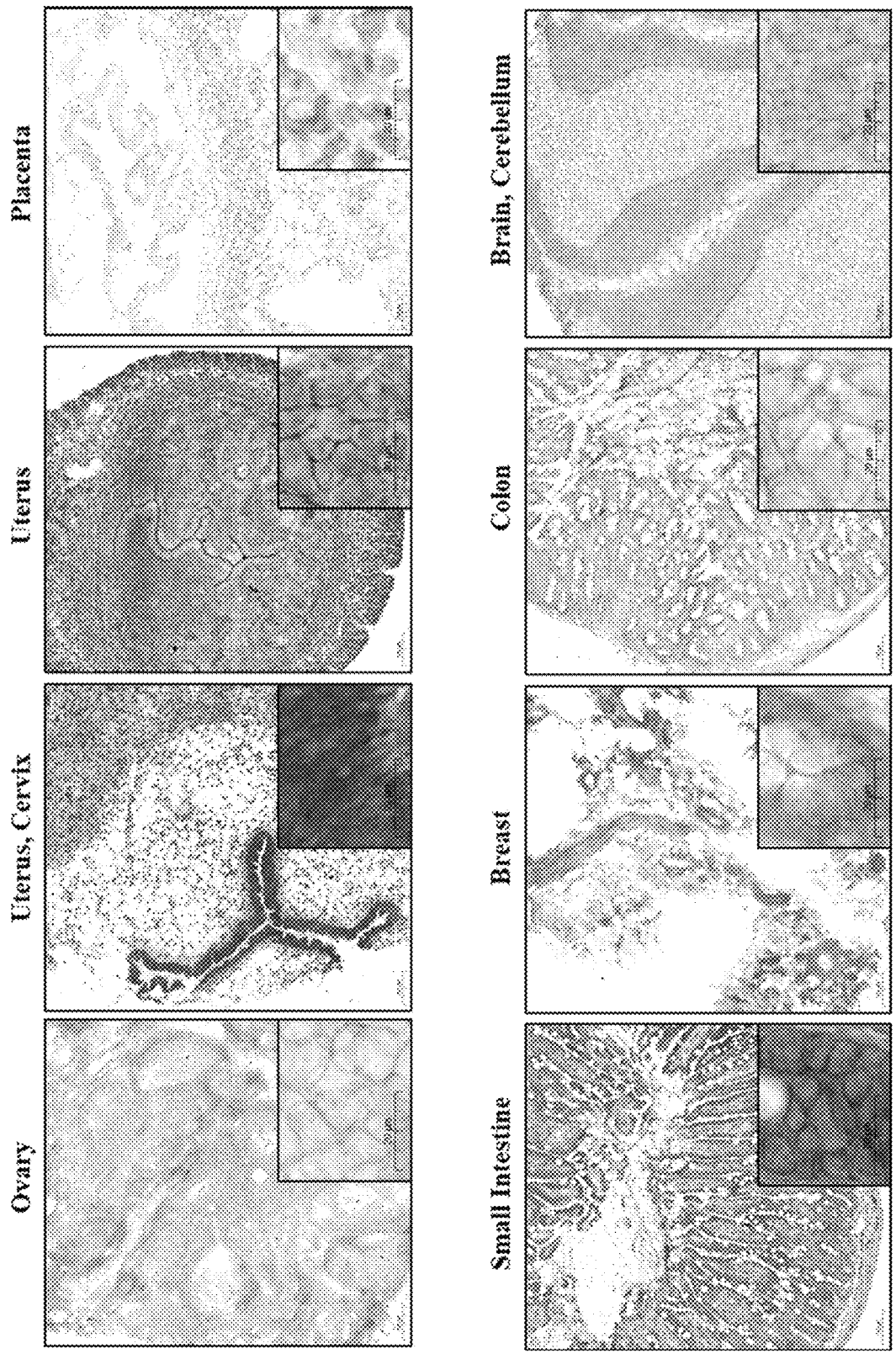
FIGS. 5A and 5B show PTK7 expression in frozen normal tissue panels (FDA standard) from mouse (FIG. 5A) and human (FIG. 5B).
Figure 5B:
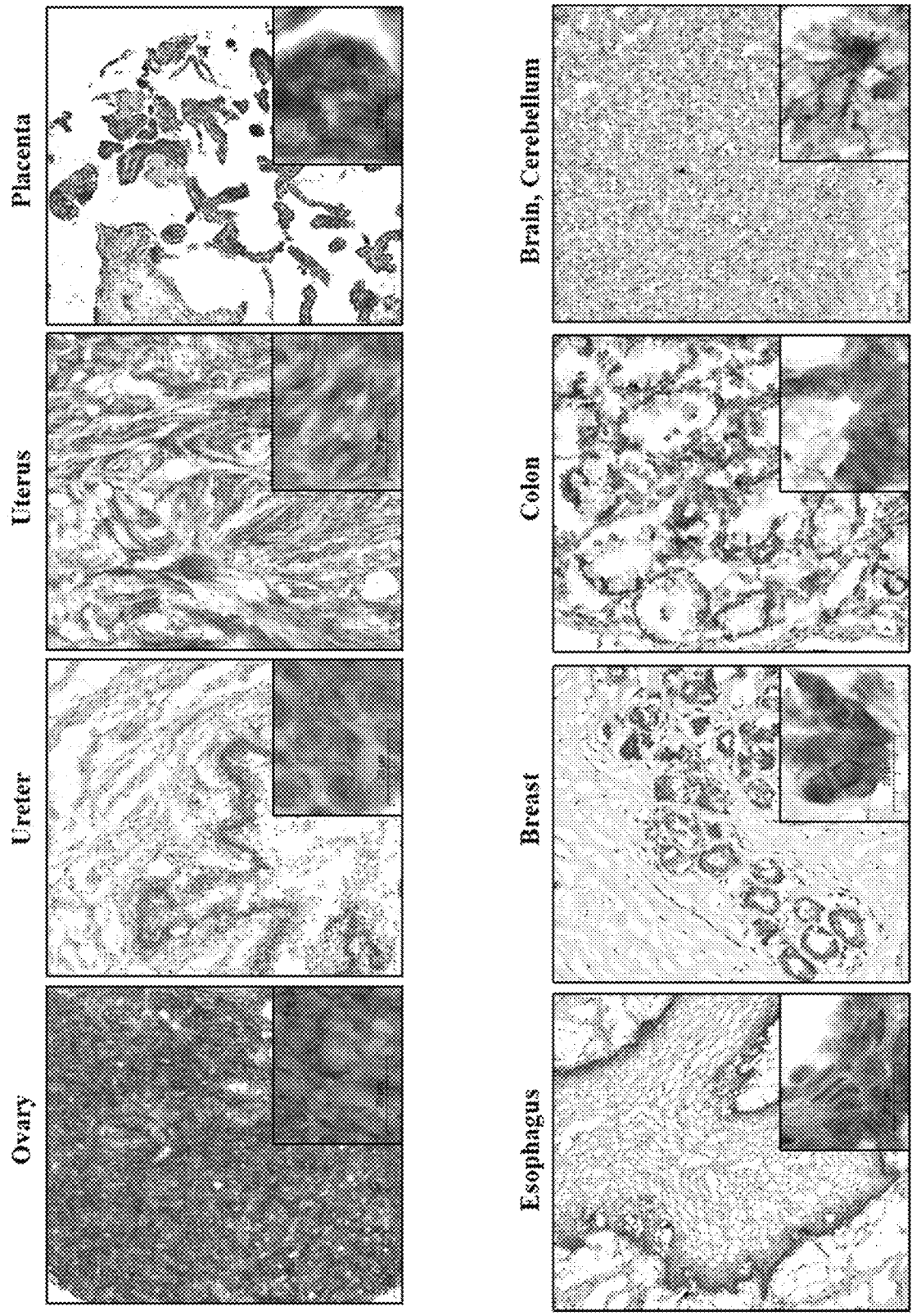
Figure 6:
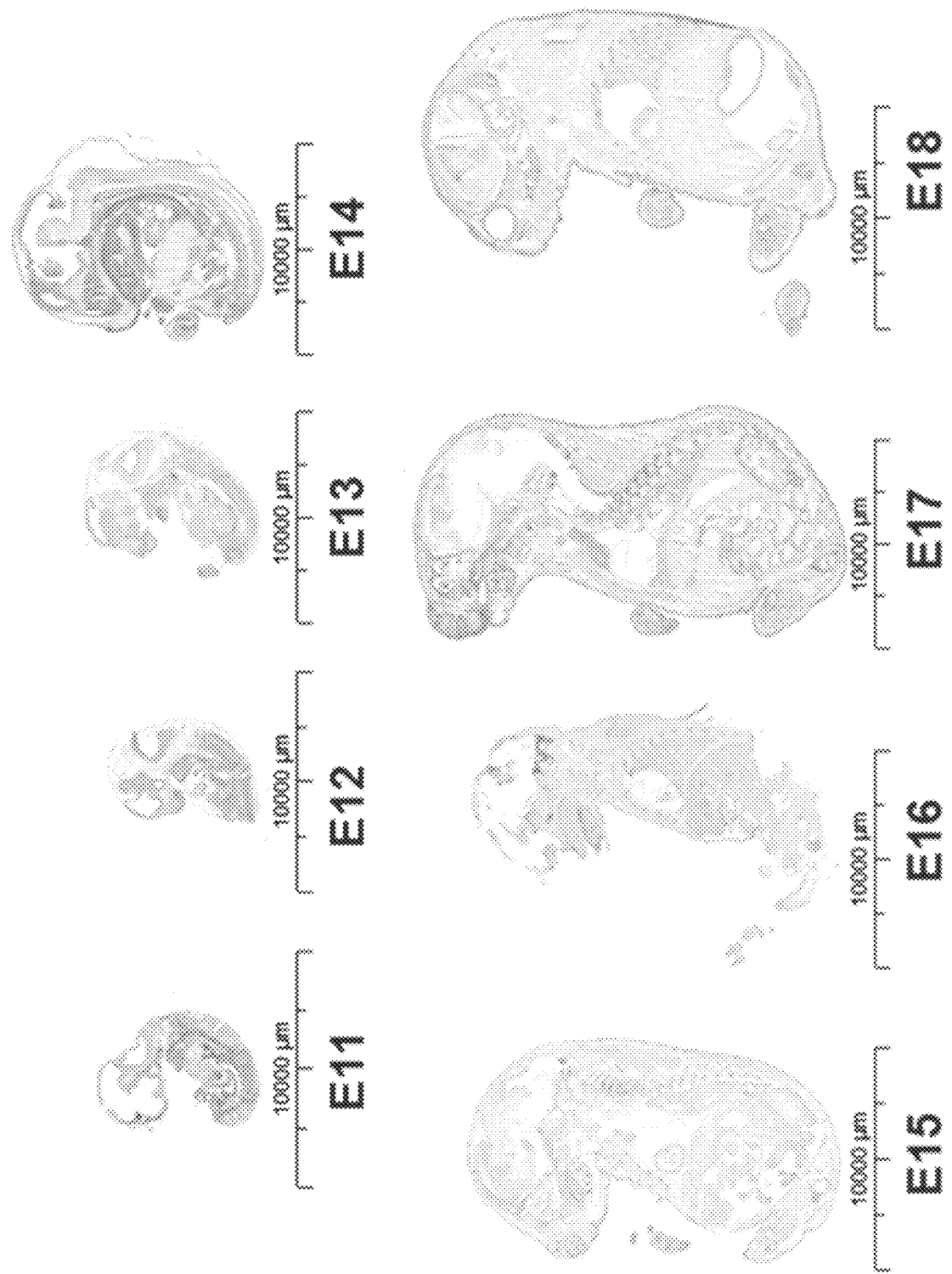
FIG. 6 shows PTK7 expression in frozen murine embryonic development array.

PTK7 expression was evaluated on a frozen normal mouse tissue panel (FDA Standard, Biochain; FIGS. 5A and 5B) as well as a frozen murine embryonic development array (Zyagen; FIG. 6) using CTX181, specific to the PTK7 CAR construct, or a biotinylated mouse isotype control (Novus, NBP2-21948). Slides were fixed with −20° C. acetone for 10 min at ambient temperature followed by a manual immunohistochemical staining at ambient temperature. Blocking to minimize non-specific staining was performed with Peroxidased 1, Avidin and Biotin and Background Sniper (BioCare Medical, PX968M, AB972L, BS966M) in sequential steps. Slides were stained with the biotinylated CTX181 primary monoclonal antibody (1:300 for human; 1:600 for murine) for 30 min followed by incubation with 4plus Streptavidin-HRP Label (BioCare Medical) reagent for 15 min each. Visualization of target antigen was visualized with DAB (brown color) substrate chromogen (Dako, K3468). Mayer's Hematoxylin (Dako, S3309) was used to counterstain the cell nuclei.

Example 5. Generation of TRAC⁻/β2M⁻/Anti-PTK7 CAR⁺ T Cells

Figure 8:
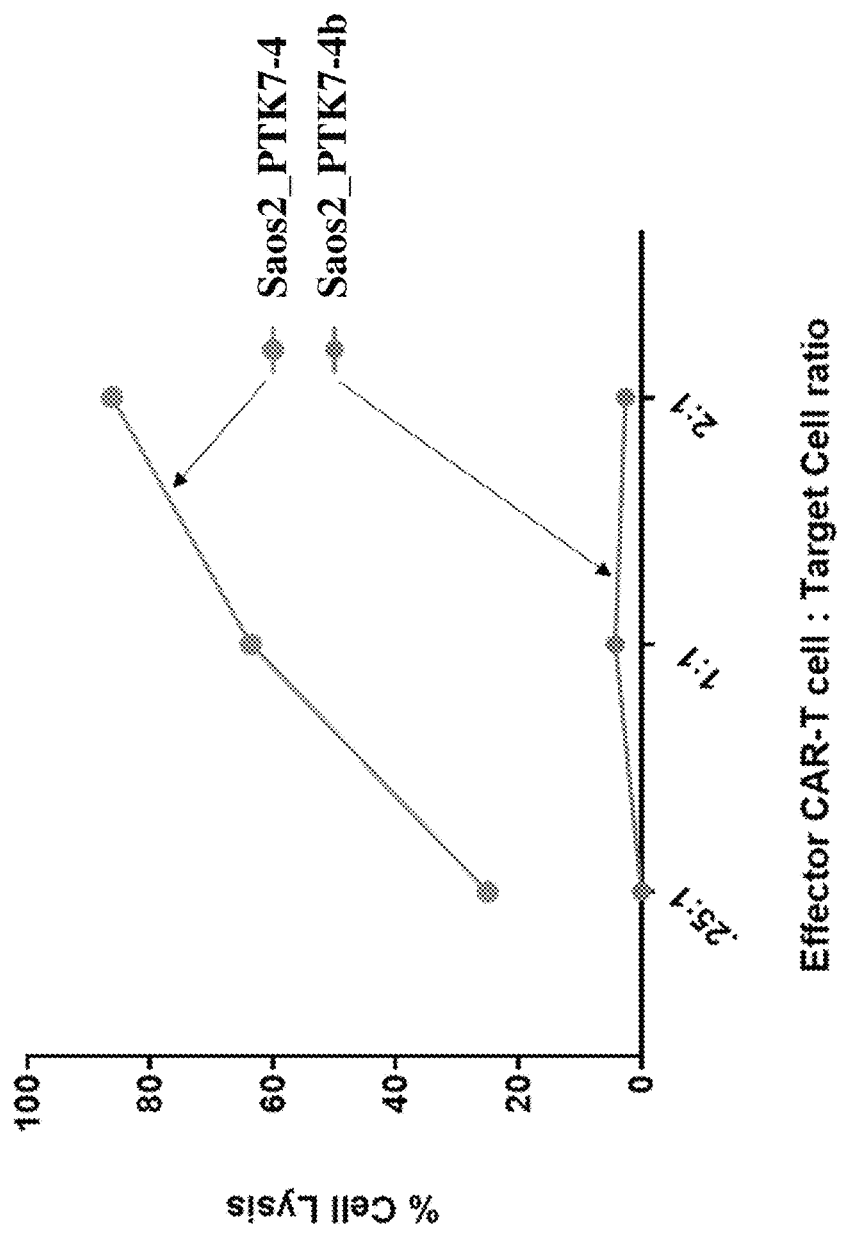
FIG. 8 includes a graph showing that the PTK7 CAR T cell with CD28 co-stimulatory domain (PTK7-4) was more efficacious than the PTK7 CAR T cell with 4-1 BB co-stimulatory domain (PTK7-4b).

This example describes the production of allogeneic human T cells that lack expression of the T cell receptor (TCR) gene (gene edited in the TCR Alpha Constant (TRAC) region), the β2-microglobulin (β2M) gene, and that express a chimeric antigen receptor (CAR) targeting protein tyrosine kinase 7 (PTK7) and PTK7+ cancers. Four unique anti-PTK7 CARs (PTK7-4, PTK7-7, PTK7-13, and PTK7-17) comprising CD28 co-stimulatory domains were sepa-rately expressed in TRAC$^-$/β2M$^-$ T cells for experimentation and evaluation. The PTK7-4 was also generated with a 41 BB co-stimulatory domain in place of CD28 (PTK7-4b). Table 7 lists the PTK7 CAR structures. Table 11 lists the PTK7 CAR component sequences. Table 12 lists the donor components.

the orientation of the VH and VL sequence, however, PTK7-7 only expressed in <50% of the viable cell population. The PTK7 CAR T cell with the CD28 co-stimulatory domain (PTK7-4) was more efficacious than the 4-1 BB co-stimulatory domain (PTK7-4b) (FIG. 8).

TABLE 8

| Antibody | Clone | Fluor | Catalogue # | Dilution |
| --- | --- | --- | --- | --- |
| TCRαβ | BW242/412 | PE | 130-099-661 (Miltenyi) | 1:100 |
| β2M | 2M2 | FITC | 316304 (Biolegend) | 1:100 |
| IgG, F(ab')$_2$ fragment specific | polyclonal | Biotinylated; Detected with SA-APC | 109-006-097 (Jackson Immuno-research) | 1:20 |
| Streptavidin-APC (SA-APC) | N/A | APC | 17-4317-82 (eBioscience through ThermoFisher) | 1:100 |

TABLE 7

| CAR | CAR structure | SEQ ID NO: |
| --- | --- | --- |
| PTK7-4 | CD8[signal peptide]-VH-linker-VL-CD8[tm]-CD28[co-stimulatory domain]-CD3ζ | 50 |
| PTK7-4b | CD8[signal peptide]-VH-linker-VL-CD8[tm]-41 BB[co-stimulatory domain]-CD3 ζ | 52 |
| PTK7-7 | CD8[signal peptide]-VL-linker-VH-CD8[tm]-CD28[co-stimulatory domain]-CD3 ζ | 66 |
| PTK7-13 | CD8[signal peptide]-VL-linker-VH-CD8[tm]-CD28[co-stimulatory domain]-CD3 ζ | 73 |
| PTK7-17 | CD8[signal peptide]-VH-linker-VL-CD8[tm]-CD28[co-stimulatory domain]-CD3 ζ | 80 |

Activated primary human T cells were electroporated with Cas9:gRNA RNP complexes and adeno-associated adenoviral vectors (AAVs) to generate TRAC$^-$/β2M$^-$/anti-PTK7 CAR$^+$ T cells. Recombinant AAV serotype 6 (AAV6) comprising one of the nucleotide sequences encoding an anti-PTK7 CAR (SEQ ID NOs: 49, 51, 65, 72, 79, or 112) were delivered with Cas9:sgRNA RNPs (1 μM Cas9, 5 μM gRNA) to activated allogeneic human T cells. The following sgRNAs were used: TRAC (SEQ ID NO: 28) and β2M (SEQ ID NO: 30). The unmodified versions (or other modified versions) of the gRNAs may also be used (e.g., SEQ ID NO: 18 or SEQ ID NO: 20). See also Table 4.

Figure 7:
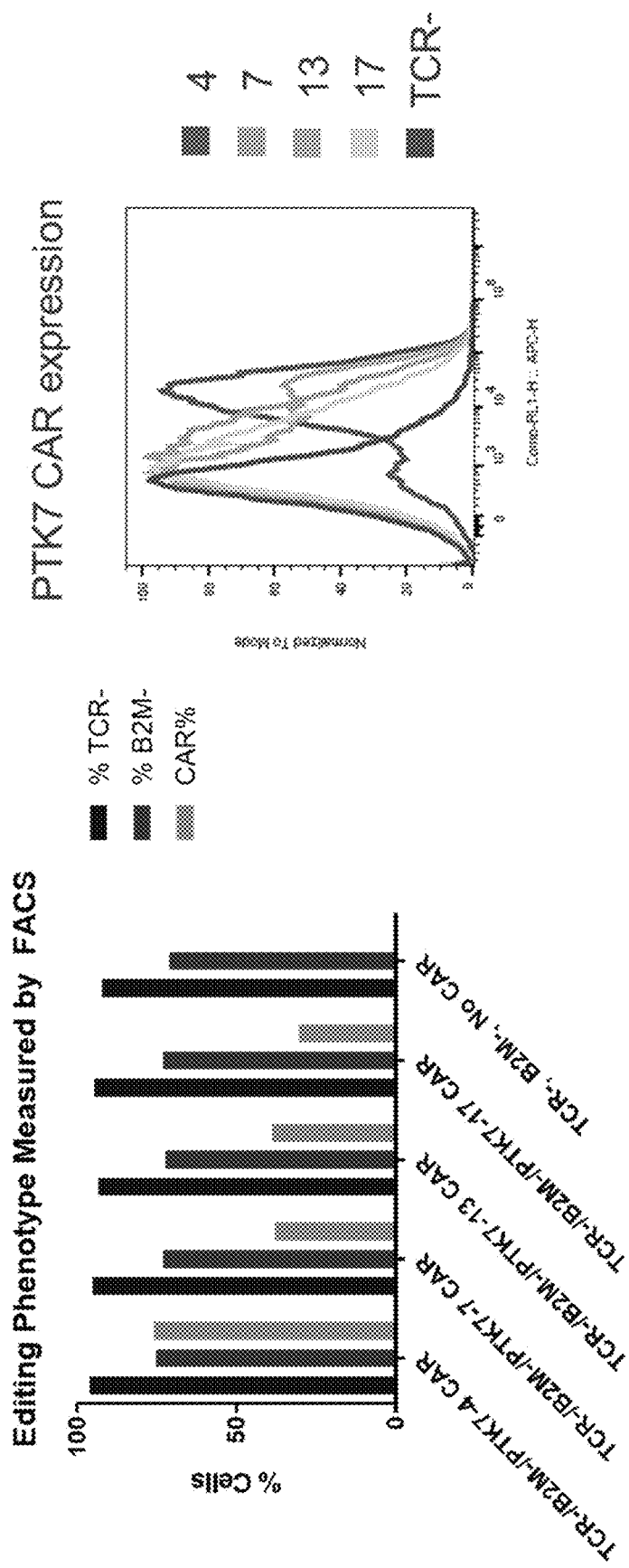
FIG. 7 includes graphs showing highly efficient multiple gene editing in TRAC⁻/β2M⁻/anti-PTK7 CAR⁺ T cells. Editing phenotypes as measured by FACS (left graph) and anti-PTK7 CAR⁺ expression as measured by immunohistochemistry (right graph) are shown for four different anti-PTK7 CAR⁺ constructs (PTK7-4, PTK7-7, PTK7-13, and PTK7-17).
Figure 9A:
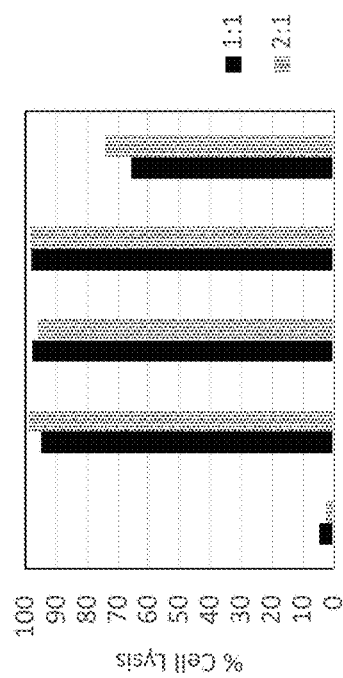
FIGS. 9A-9C include graphs showing cell-killing effects of TRAC⁻/β2M⁻/anti-PTK7 CAR⁺ T cells against adherent sarcoma cell lines A-204 (FIG. 9A) and Saos-2 (FIG. 9B) and the breast cancer cell line MCF7 (FIG. 9C). Cell ratios (CAR T cell:target cancer cell) of 2:1 and 1:1 were used.
Figure 9B:
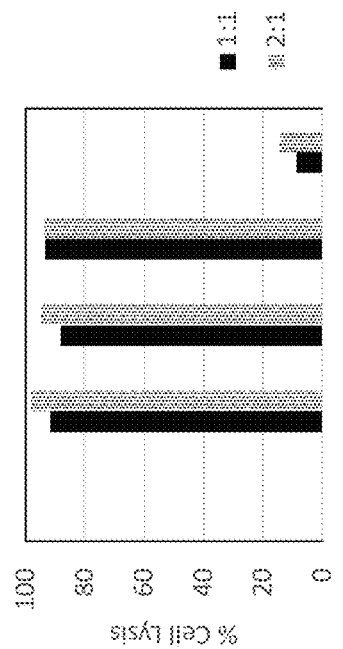
Figure 9C:
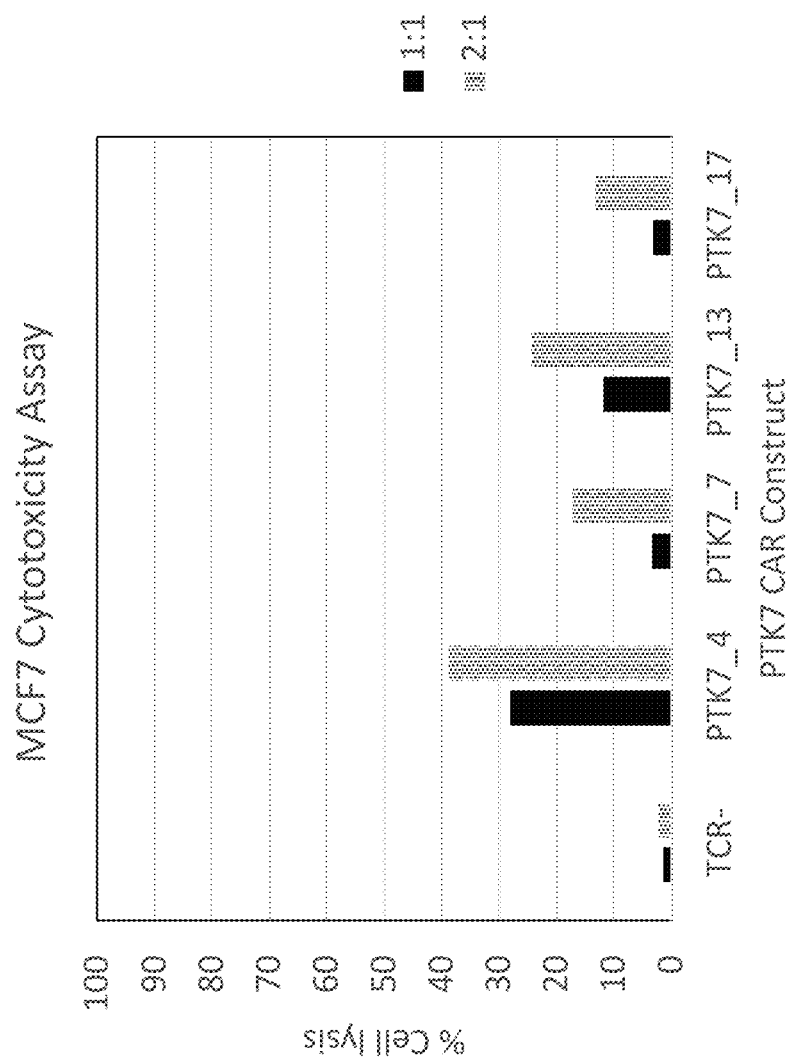

About one (1) week post electroporation, cells were processed for flow cytometry to assess TRAC, β2M, and anti-PTK7 CAR expression levels at the cell surface of the edited cell population (FIG. 7). Table 8 list the antibodies that were used. For all anti-PTK7 CAR T cells and TRAC$^-$/β2M$^-$ control cells, >90% of viable cells lacked expression of TCR and >60% lacked expression of β2M. The cells treated with the construct encoding the PTK7-4 CAR had the highest percentage of viable cells expressing an anti-PTK7 CAR$^+$ (>70%). The orientation of the VH and VL sequences in the scFV appear to effects expression of the CAR. The PTK7-4 CAR differs from the PTK7-7 CAR in Cell Kill Assay. A cell killing (cytotoxicity) assay was then used to assess the ability of the TRAC$^-$/β2M$^-$/anti-PTK7 CAR$^+$ T cells to cause cellular lysis in adherent sarcoma cell lines that express PTK7 (A-204 and Saos-2) and a breast cancer cell line that expresses PTK7 (MCF7). Adherent cells were seeded in 96-well plates at 50,000 cells per well and left overnight at 37° C. During the following day, T cells were added to the wells containing target cells at ratios of 2:1 or 1:1 T cell:target cell. TRAC$^-$/β2M$^-$ T cells were used as a negative control. After approximately 20 hours, T cells were removed from the culture by aspiration and 100 μL Cell titer-Glo (Promega) was added to each well of the plate to assess the number of remaining viable cells. The amount of light emitted from each well was then quantified using a plate reader. The anti-PTK7 CAR T cells, particularly those expressing the PTK7-4, PTK7-7 and PTK7-13 constructs, exhibited potent cytotoxicity towards A-204 (FIG. 9A) and Saos (FIG. 9B) cell lines. Further, the anti-PTK7 CAR T cells expressing the PTK7-4 CAR showed the highest cytotoxic activity towards the MCF7 cell line (FIG. 9C), which is known to have lower PTK7 mRNA expression than the tested sarcoma cell lines.

Figure 10A:
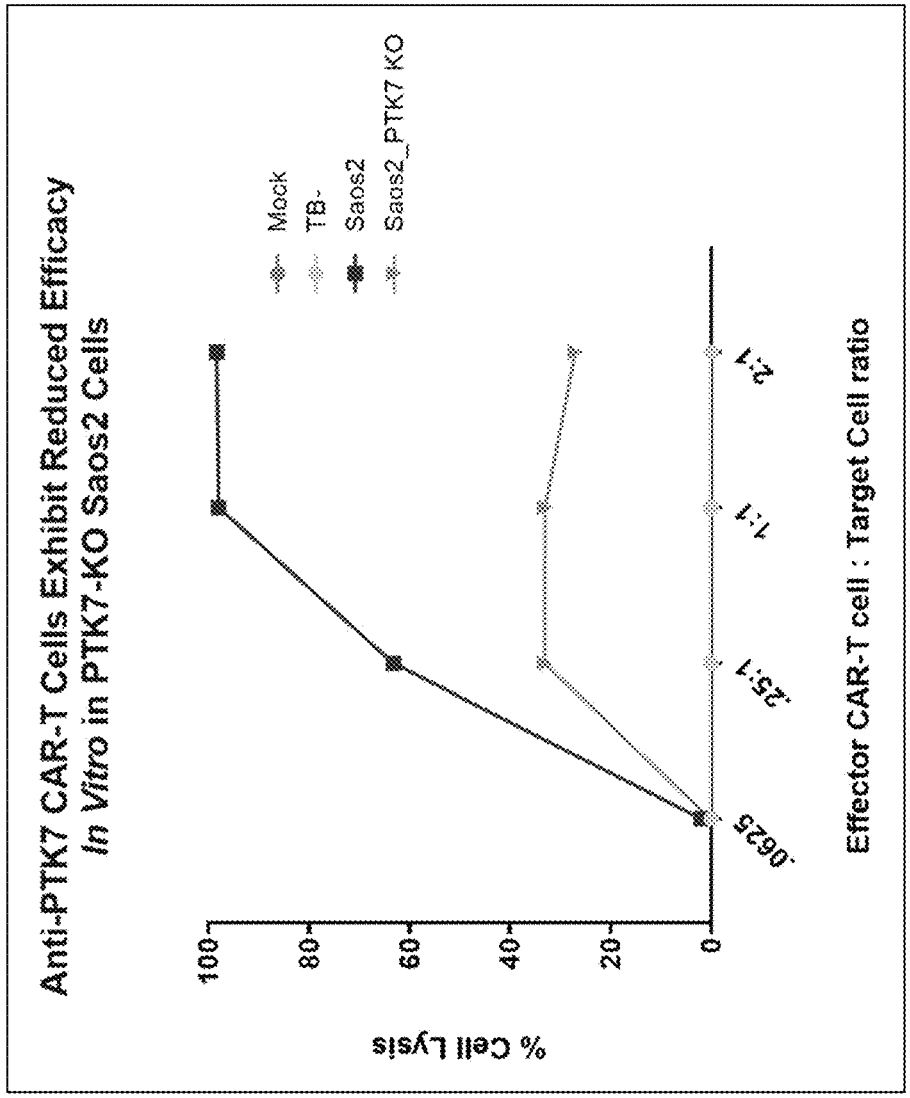
FIGS. 10A-10C show PTK7 CAR T cell specificity in PTK7-KO Saos2 cells (FIG. 10A) and PTK7 overexpressing A498 cells (FIG. 10B).
Figure 10C:
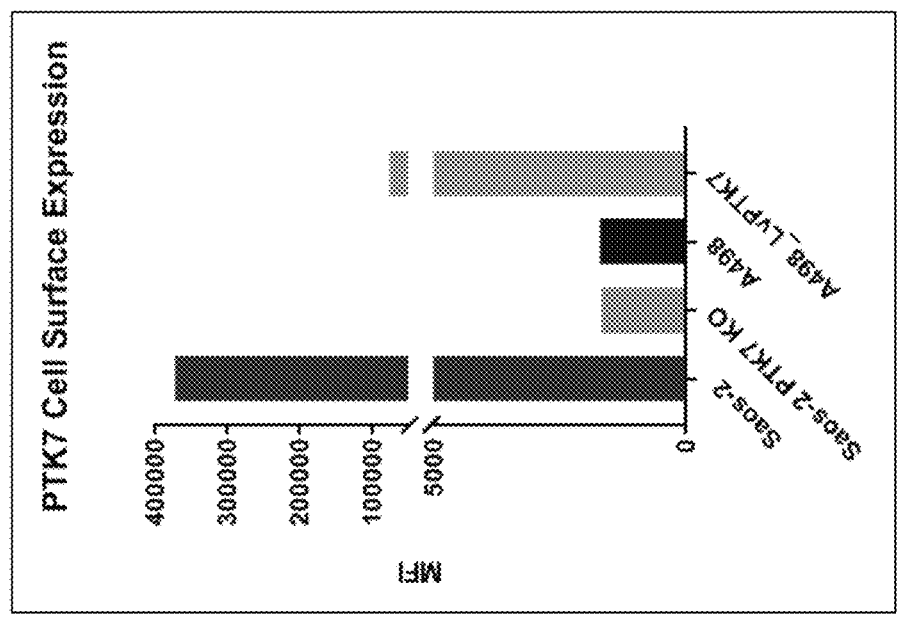
Figure 10B:
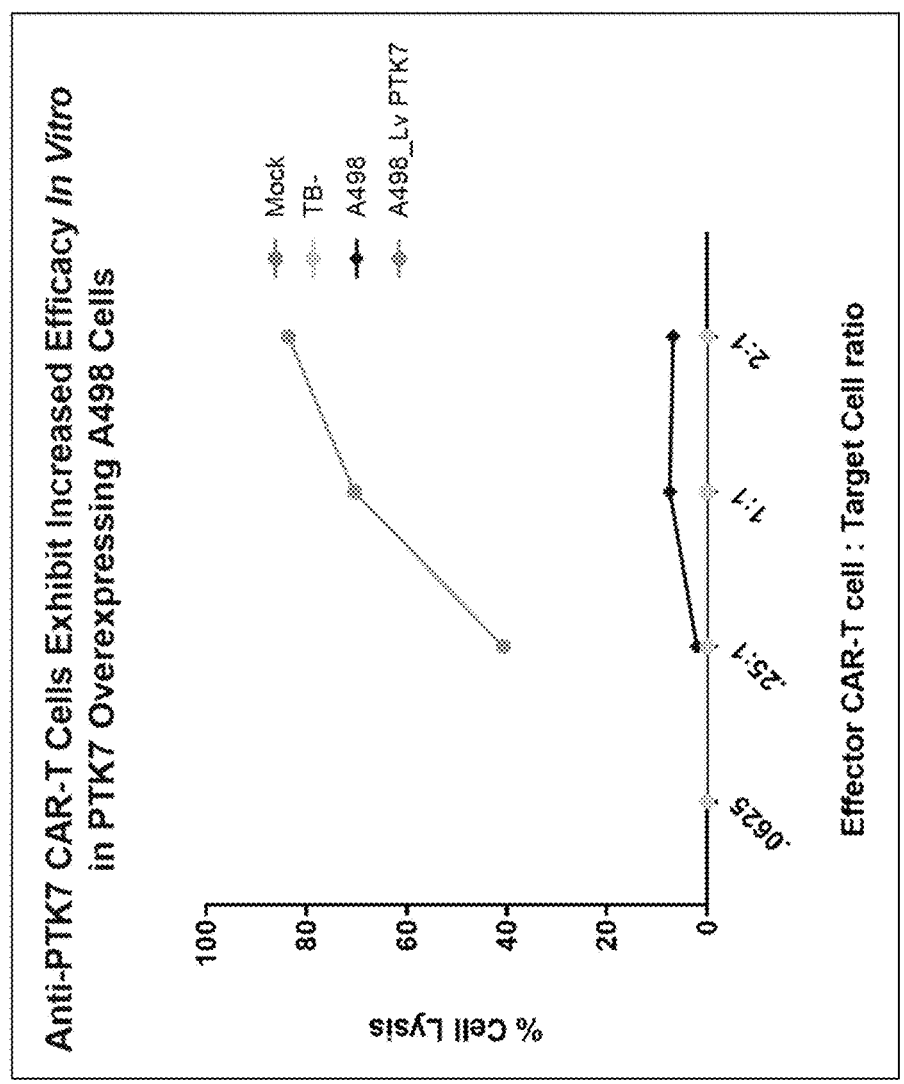

The cell specificity of the PTK7-4 CAR T cells was exemplified using PTK7 knock-out (KO) Saos2 cells (FIG. 10A) and PTK7 overexpressing A498 cells (FIG. 10B). PTK7 KO Saos-2 cells were generated via electroporation of ribonucleoprotein particle (RNP) complexes (1 μM Cas9 and 5 μM PTK7 gRNA (SEQ ID NO: 111; see Table 9)) according to established methods. Cells were analyzed for loss of PTK7 cell surface expression by flow cytometry using the CTX181 mAb (FIG. 10C) and subsequently expanded. Flow cytometry analysis showed that protein expression was reduced by 88.6% indicating highly efficient gene editing. In vitro efficacy of PTK7 KO Saos-2 cells was evaluated in a cell cytotoxicity assay compared to Saos-2 WT cells. FIG. 10A show a decrease in efficacy of Saos2 PTK7 KO cells to be lysed by PTK7 CAR T cells, indicating the CAR T-cells were specific to PTK7 expressing target cells.

TABLE 9

PTK7 gRNA Sequence

| Name | Unmodified Sequence (gRNA Spacer Sequence underlined) (SEQ ID NO: 110) | Modified Sequence (SEQ ID NO: 111) |
| --- | --- | --- |
| PTK7_T11 | CCGCCGCGAUGGGAGCUGCGg uuuuagagcuagaaauagcaa | C*C*G*CCGCGAUGGGA GCUGCGguuuuagagcu |

TABLE 9-continued

PTK7 gRNA Sequence

| Name | Unmodified Sequence (gRNA Spacer Sequence underlined) (SEQ ID NO: 110) | Modified Sequence (SEQ ID NO: 111) |
|---|---|---|
| | guuaaaauaaggcuaguccgu uaucaacuugaaaaaguggca ccgagucggugcUUUU | agaaauagcaaguuaaa auaaggcuaguccguua ucaacuugaaaaagugg caccgagucggugcU\*U\*U\*U |

\*: 2'-O-methyl phosphorothioate residue

PTK7 overexpressing A498 cells were generated as follows: A498 renal cell carcinoma cells were plated at 60-70% confluency in MEM1α+10% FBS media supplemented with 10 μg/ml polybrene. Based on the desired multiplicity of infection (MOI), A498 cells were transduced the next day with a lentivirus expressing humPTK7 cDNA (LPP-A6381-Lv225-200, GeneCopoeia, Rockville, MD). Following 24-48 hrs lentivirus infection, fresh media was replaced containing 4 μg/ml puromycin selection. Puromycin treatment was continued for 5-7 days post transduction until all non-transduced cells were eliminated from the culture. Expression of the humPTK7cDNA lentiviral construct was assessed by flow cytometry (FIG. 10C) using CTX181 mAb. In vitro efficacy of humPTK7 cDNA expressing A498 cells was evaluated in a cell cytotoxicity assay compared to A498 WT cells. FIG. 10B shows an increase in efficacy of PTK7 CAR T cells to lyse humPTK7 cDNA expressing A498 cells as compared to A498 WT cells, indicating the PTK7 CAR T-cells were specific to PTK7 antigen expressing target cells.

Example 6. In Vitro Potency of PTK7 CAR T Cells in Solid Tumor Cell Lines

Figure 11A:
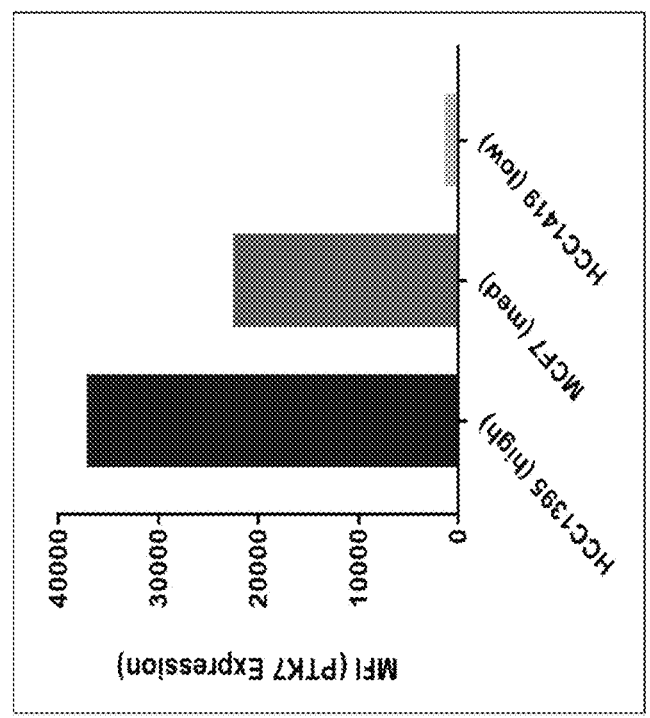
FIGS. 11A-11C show that in vitro potency of PTK7 CAR T cells trended with expression pattern in solid tumor cell lines: breast cancer (FIG. 11A), pancreatic cancer (FIG. 11B), and lung (NSCLC) cancer (FIG. 11C).
Figure 11A:
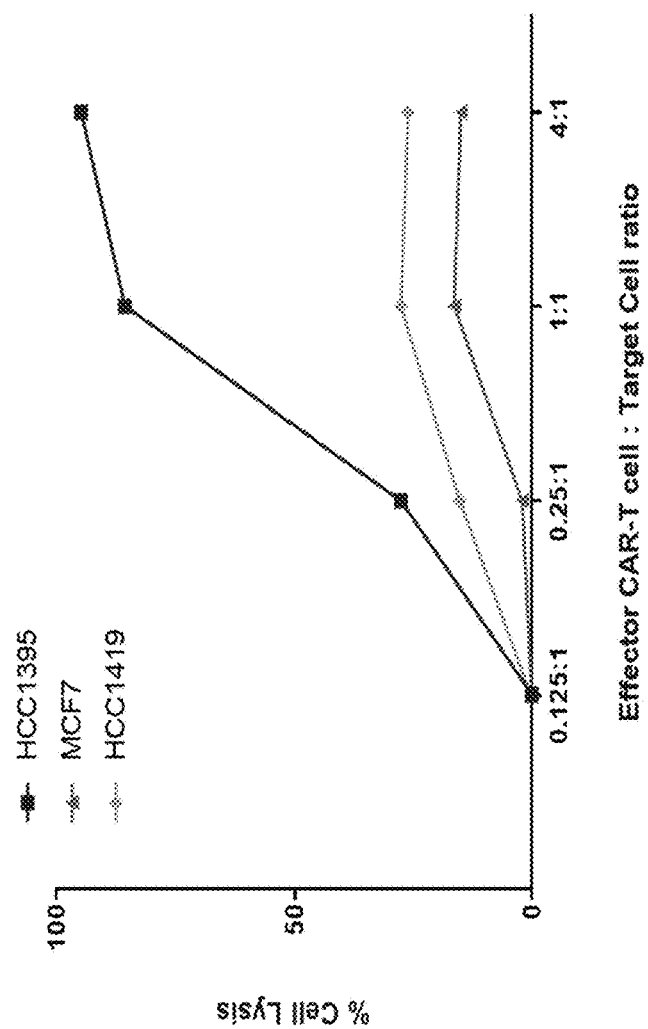
Figure 11B:
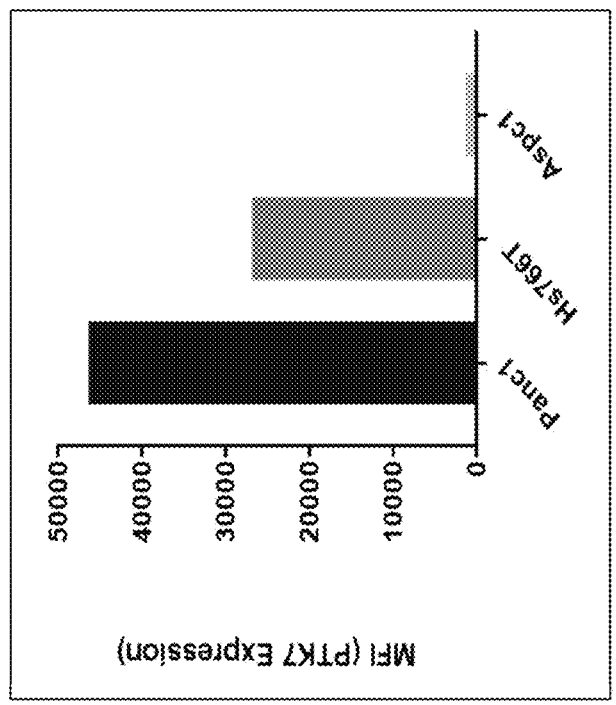
Figure 11B:
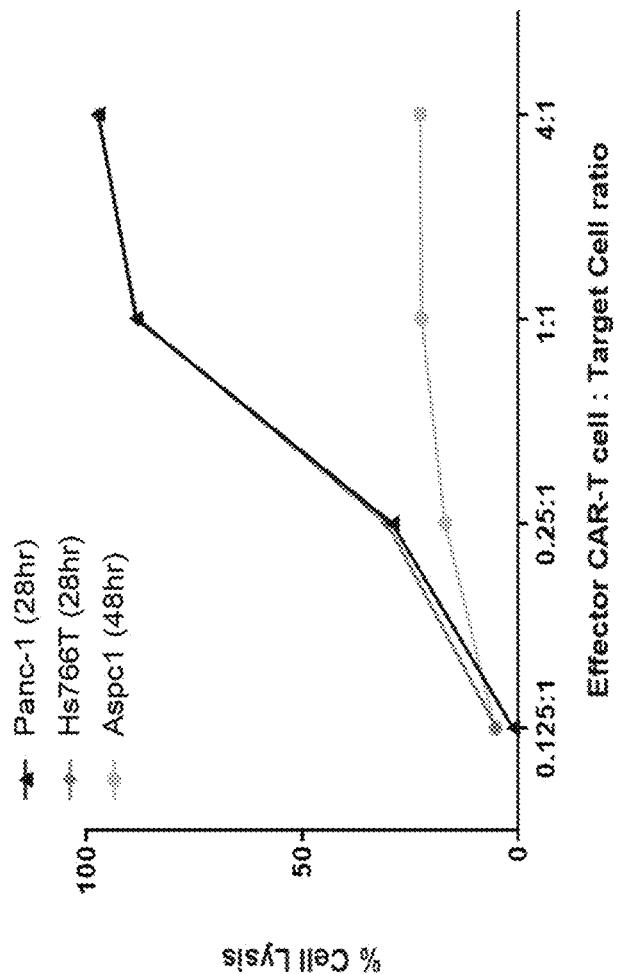
Figure 11C:
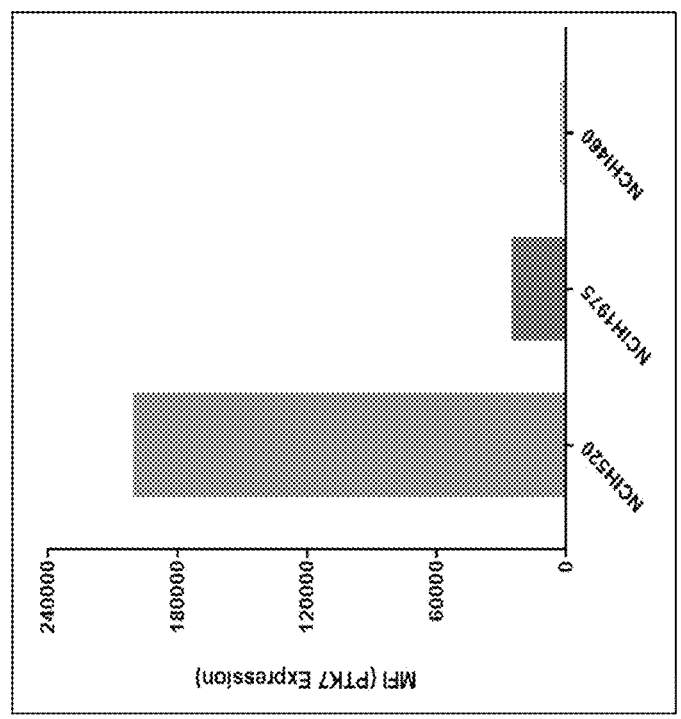
Figure 11C:
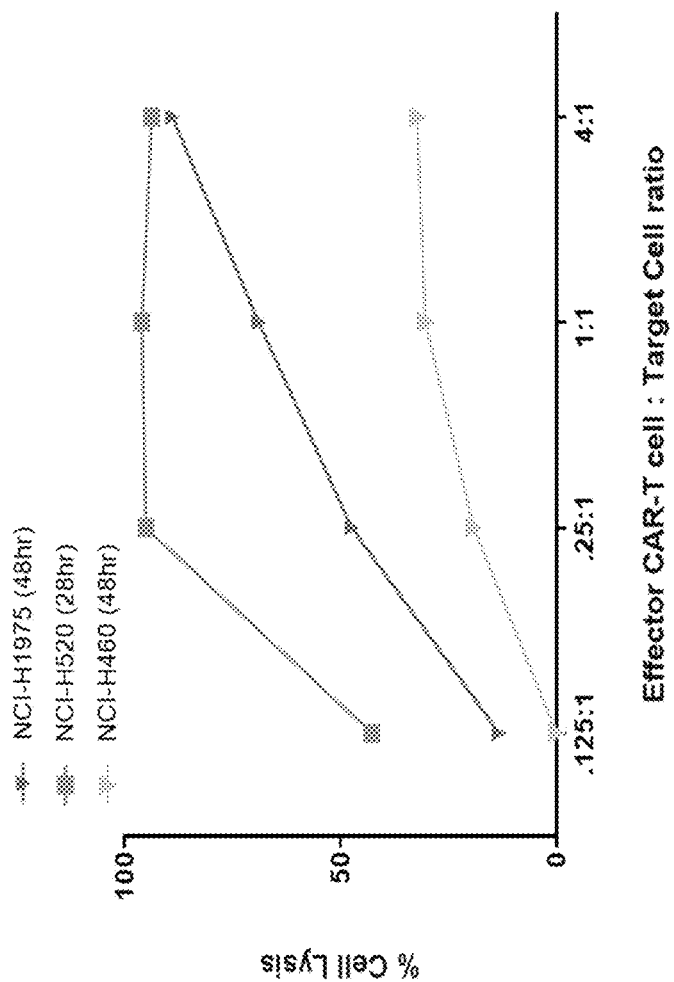

Cell Kill Assay. To examine the efficacy in additional tumor cell lines, high, med, low PTK7 expressing cell lines for breast, pancreatic and NSCL cancers were selected from the Broad Cancer Cell Line database. A cell killing (cytotoxicity) assay was used to assess the ability of the TRAC$^-$/β2M$^-$/anti-PTK7 CAR$^+$ T cells to cause cellular lysis in an adherent sarcoma cell line that expresses PTK7 (Saos-2), breast cancer cell lines that expresses PTK7 to varying degrees (HCC1395, MCF7, HCC1419), pancreatic cell lines that express PTK7 to varying degrees (Panc-1, Hs766T, Aspc1) and non-small cell lung cancer cell lines that express PTK7 to varying degrees (NCI-H1975, NCI-H520, NCI-H460). Adherent cells were seeded in 96-well plates at 50,000 cells per well and left overnight at 37° C. During the following day, T cells were added to the wells containing target cells at ratios of 0.125:1, 0.25:1, 1:1 or 4:1 effector T cell:target cell. TRAC$^-$/β2M$^-$T cells were used as a negative control. After approximately 24 hours, T cells were removed from the culture by aspiration and 100 μL CellTiter-Glo® (Promega) was added to each well of the plate to assess the number of remaining viable cells. The amount of light emitted from each well was then quantified using a plate reader. PTK7 protein expression was assessed by staining target cells for 30 min on ice with the CTX181 antibody, followed by washing and a 15 min stain at RT with secondary APC fluorophore conjugated human IgG-Fc antibody. Target cells were assessed for staining on a Novocyte® flow cytometer (Acea Biosciences). FIGS. 11A-11C show that the anti-PTK7 CAR T cells exhibited cytotoxicity towards all cell lines tested and their in vitro potency trended with the level of PTK7 expression in these tumor cell lines.

Functional activity of PTK7 CAR T cells was further assessed using cytokine release assays for Interferon gamma (IFNγ) and Interleukin-2 (IL2). T cells of all tested genotypes were incubated with target cells for 24 hours at cellular ratios indicated above. After 24 hours, supernatant media surrounding a cellular sample was collected and the levels of IFNγ and IL2 were measured using an ELISA (RD Systems) following the manufacturer's instructions. PTK7 CAR T cells secreted IFNγ and IL2 in the presence of PTK7 expressing cancer cell lines (Saos2, HCC1395, MCF7, Panc1, Hs766T, NCI-H520 and NCI-H1975) when used at a 4:1 or 1:1 T cell:target cell ratio. The control cells (TCR$^-$/β2M$^-$ (No AAV) and non-edited (no RNP)) showed no specific IFNγ or IL2 secretory response in the presence of any of the cancer cell lines listed. Collectively, these functional assays demonstrated that anti-PTK7 CAR T cells were cytotoxic towards and secreted IFNγ and IL2 in the presence of cells that were expressing PTK7.

Example 7. Functional Capabilities of Anti-PTK7 CAR T Cells

Figure 12:
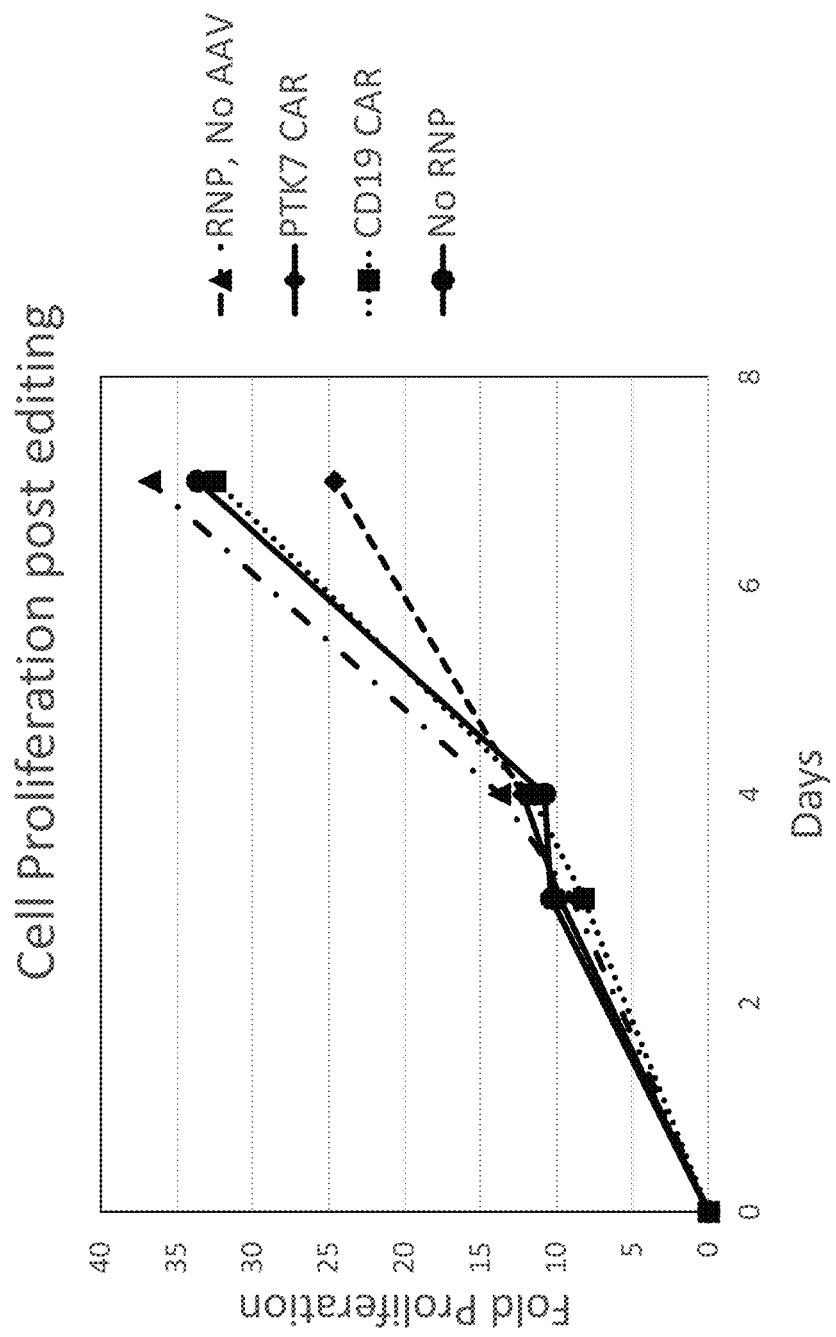
FIG. 12 includes a graph showing cell proliferation of TRAC$^-$/β2M$^-$/anti-PTK7 CAR$^+$ T cells following gene editing, compared to controls.
Figure 13A:
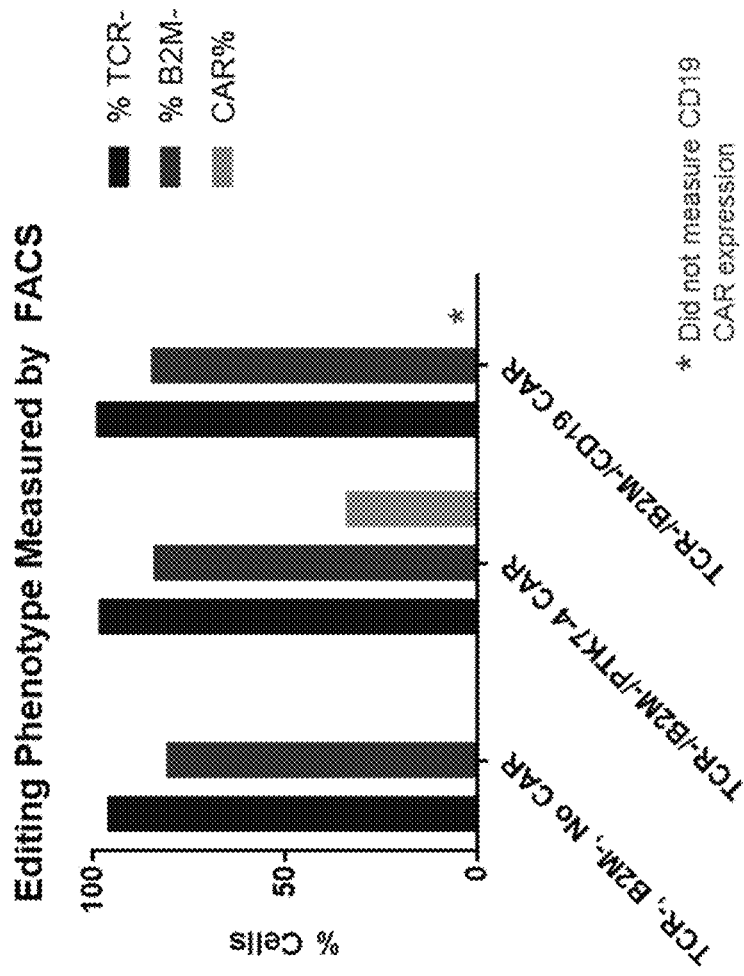
FIGS. 13A-13B include graphs showing persistence of multiple gene editing in T cells. Editing phenotypes as measured by FACS remained consistent from Day 7 (FIG. 13A) to Day 14 (FIG. 13B) post-editing.
Figure 13B:
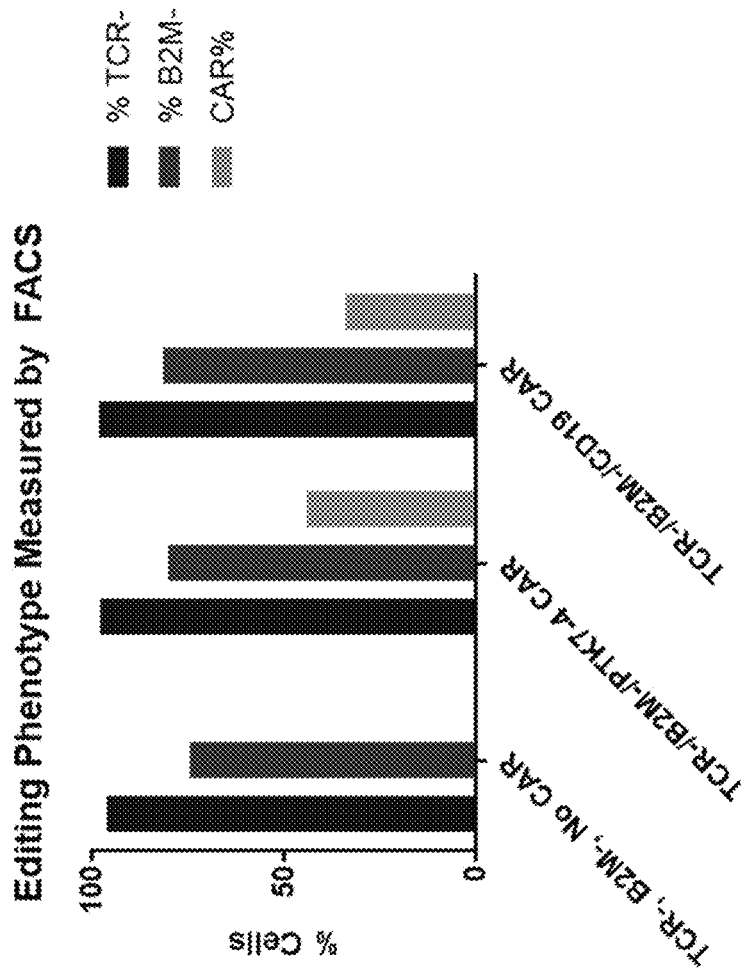
Figure 13C:
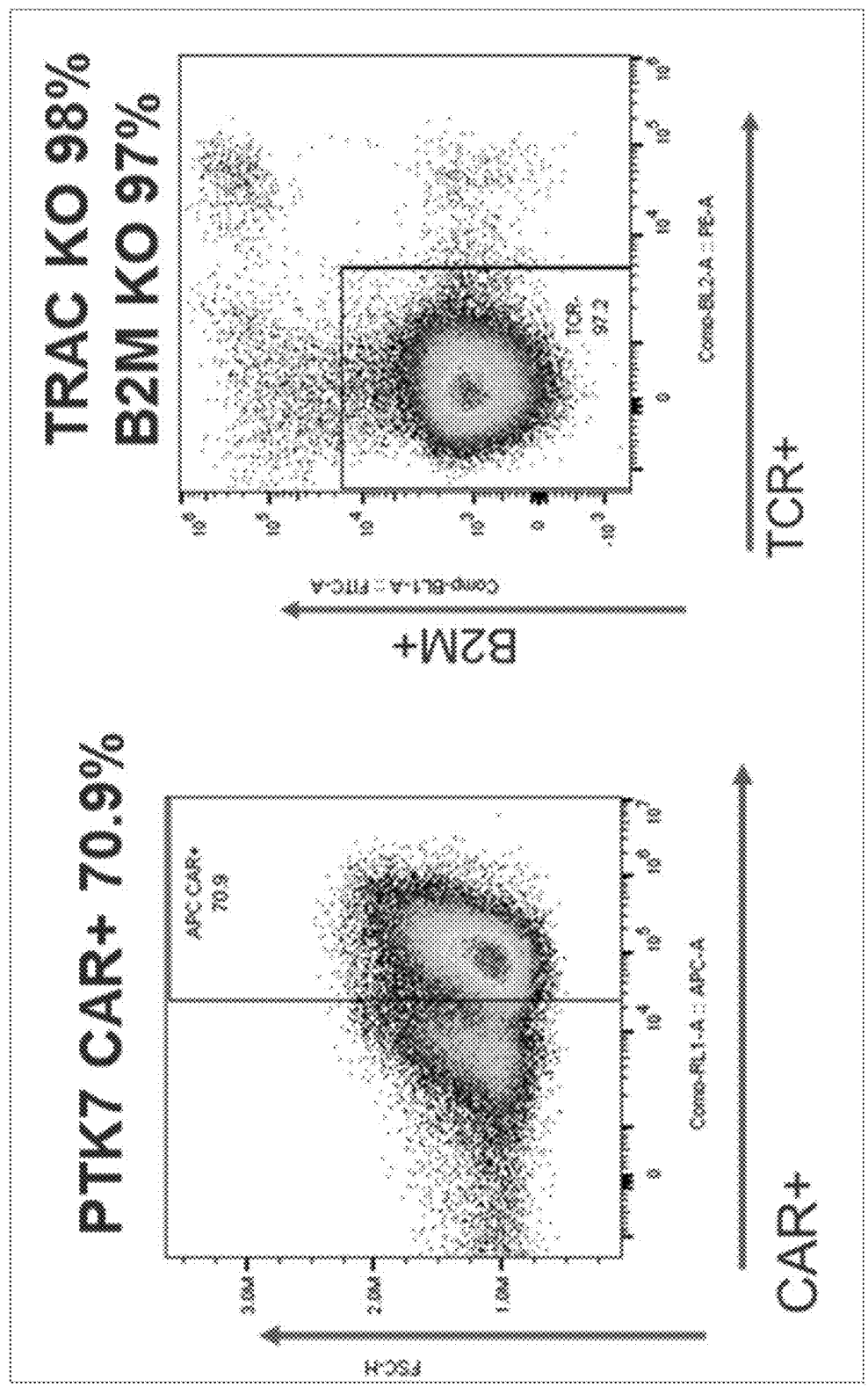
FIGS. 13C-13D show editing phenotype of PTK7-4 CAR-T cells measured by FACS on Day 7 post-editing presented as FACS plot (FIG. 13C) and graph (FIG. 13D).
Figure 13D:
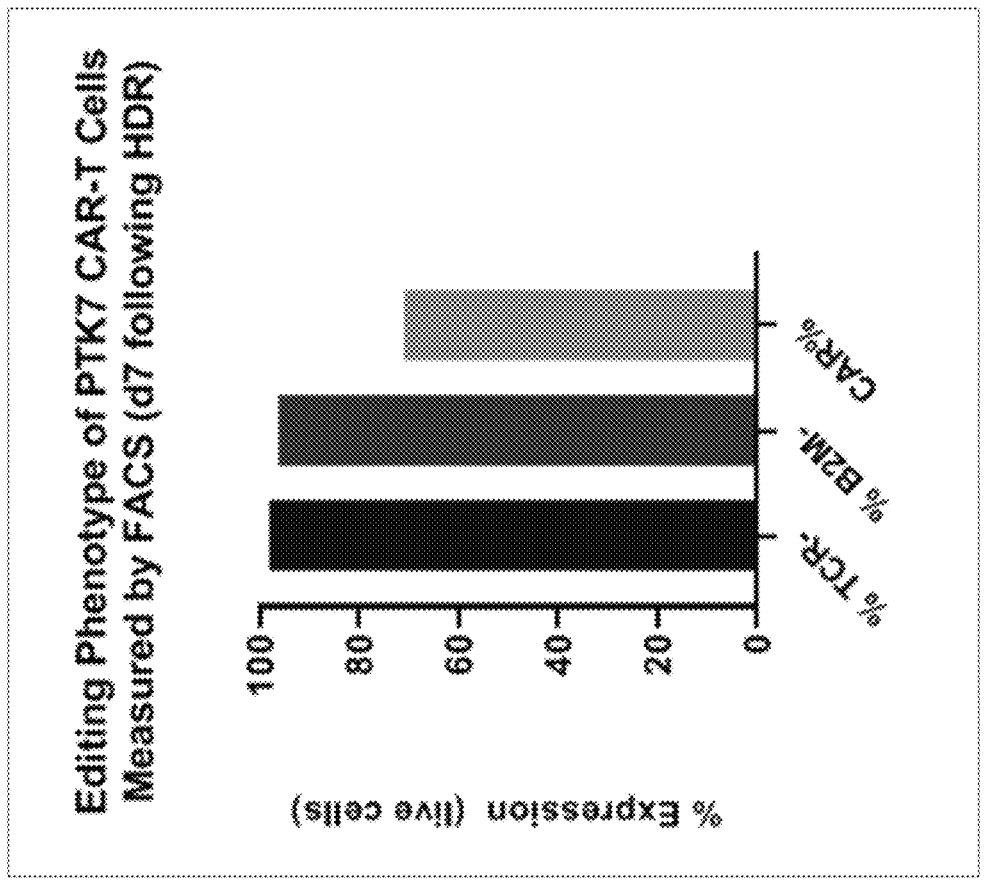
Figure 14A:
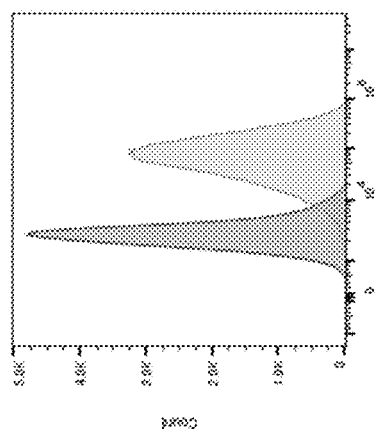
FIGS. 14A-14F include graphs showing that TRAC$^-$/β2M$^-$/anti-PTK7 CAR$^+$ T cells are more effective at cell killing and secrete higher levels of IFNγ than TRAC$^-$/β2M$^-$/anti-CD19 CAR$^+$ T cells when contacted with MCF7 (FIGS. 14A-14C) and Saos-2 (FIGS. 14D-14F) cells.
Figure 14B:
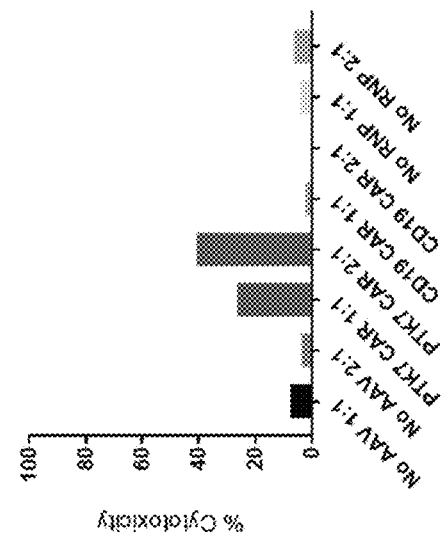
Figure 14C:
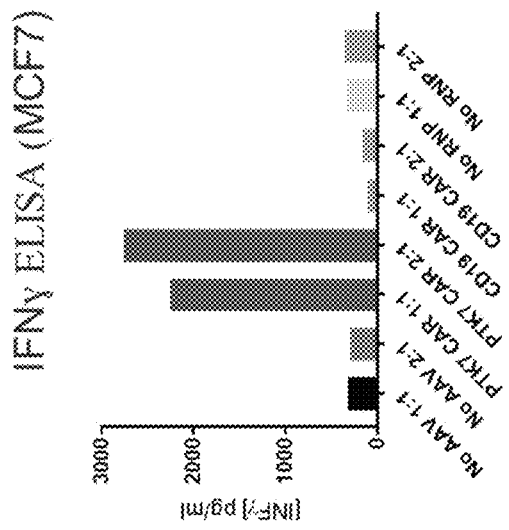
Figure 14D:
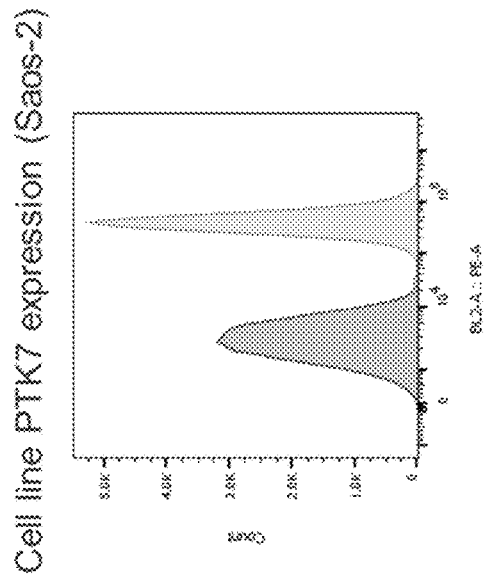

TRAC$^-$/β2M$^-$/anti-PTK7-4 CAR$^+$ T cells (also referred to as PTK7-4 CAR T cells) were generated as described in Example 5. Populations of TRAC$^-$/β2M$^-$/anti-CD19 CAR$^+$ T cells and TRAC$^-$/β2M$^-$ T cells were similarly generated for use as controls. Following preparation of the edited T cells by transfection, the ability of all edited cell types, and non-edited T cells, to proliferate over the course of 7 days was tested. 5×10$^6$ cells were plated for each genotype of T cells. Notably, as shown in FIG. 12, TRAC$^-$/β2M$^-$/anti-PTK7-4 CAR$^+$ T cells were able to proliferate at rates and levels comparable to all control experiments. After 7 days of cellular proliferation, a sample of each genotype to be injected into mouse models were frozen in cyrostor10 and stored in liquid nitrogen. The remaining cells of each genotype were allowed to continue to proliferate until day 14 post-editing. Notably, as shown in FIGS. 13A-13B, the percentage of viable cells with genetic editing of TCR, β2M, and CAR remained consistent from Day 7 to Day 14 post-editing. FIGS. 13C-13D show that in subsequent experiments, 70.9% of the cells expressed the PTK7-4 CAR construct while 98% of the cells had the TRAC KO and 97% of the cells had the β2M KO. The expression of anti-CD19 CAR was detected using a biotinylated polyclonal anti-mouse FAB primary followed by a streptavidin-APC conjugate; the expression of anti-PTK7 CAR was detected using an anti-PTK7 antibody-PE conjugate (Miltenyi cat #: 130-091-364) (FIGS. 14A and 14D).

Figure 14E:
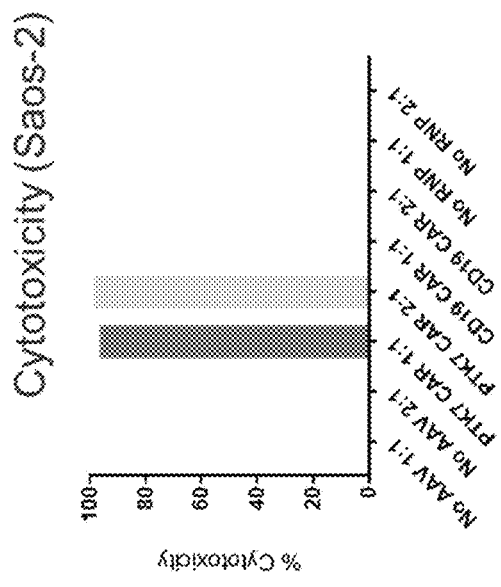

The functional activity of the PTK7-4 CAR T cells was verified using an adherent cytotoxicity assay as described in Example 5. PTK7-4 CAR T cells (PTK7 CAR) were capable of causing cytotoxicity of PTK7 expressing Saos-2 and MCF7 cells when used at a 1:1 or 2:1 T cell:target cell ratio. The control cells (TCR$^-$/β2M$^-$ (No AAV); TCR$^-$/β2M$^-$/anti-CD19 CAR(CD19 CAR); and non-edited(no RNP)) showed no specific cytotoxicity against either Saos-2 or MCF7 cells (FIGS. 14B and 14E).

Figure 14F:
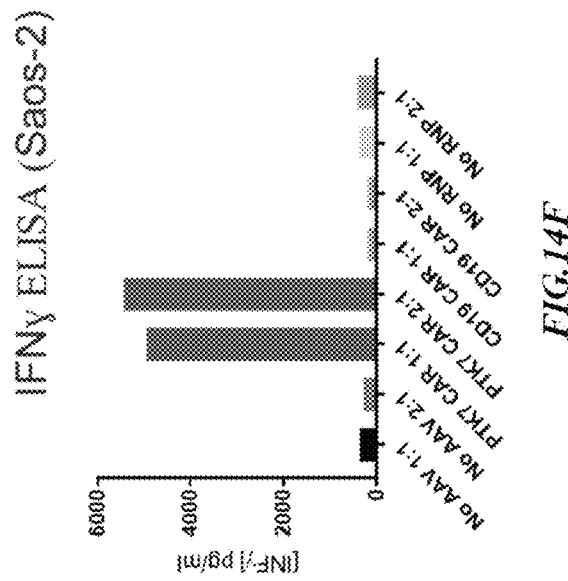

Functional activity of PTK7-4 CAR T cells was further assessed using a cytokine (Interferon gamma/IFNγ) release assay. T cells of all tested genotypes were incubated with target cells (Saos-2 and MCF7 cells) for 24 hours at cellular ratios of 1:1 and 2:1. After 24 hours, supernatant media surrounding a cellular sample was collected and the levels of IFNγ were measured using an ELISA (RD Systems) following the manufacturer's instructions PTK7-4 CAR T cells (PTK7 CAR) secreted IFNγ in the presence of PTK7 expressing Saos-2 and MCF7 cells when used at a 1:1 or 2:1 T cell:target cell ratio. The control cells (TCR−/β2M− (No AAV); TCR−/β2M−/anti-CD19 CAR+ (CD19 CAR); and non-edited(no RNP)) showed no specific IFNγ secretory response in the presence of either Saos-2 or MCF7 cells (FIGS. 14C and 14F).

Collectively, these functional assays demonstrated that anti-PTK7 CAR T cells were cytotoxic towards and secreted IFNγ in the presence of cells that are expressing PTK7.

Example 8. In Vitro Cytotoxicity Assay

Figure 15:
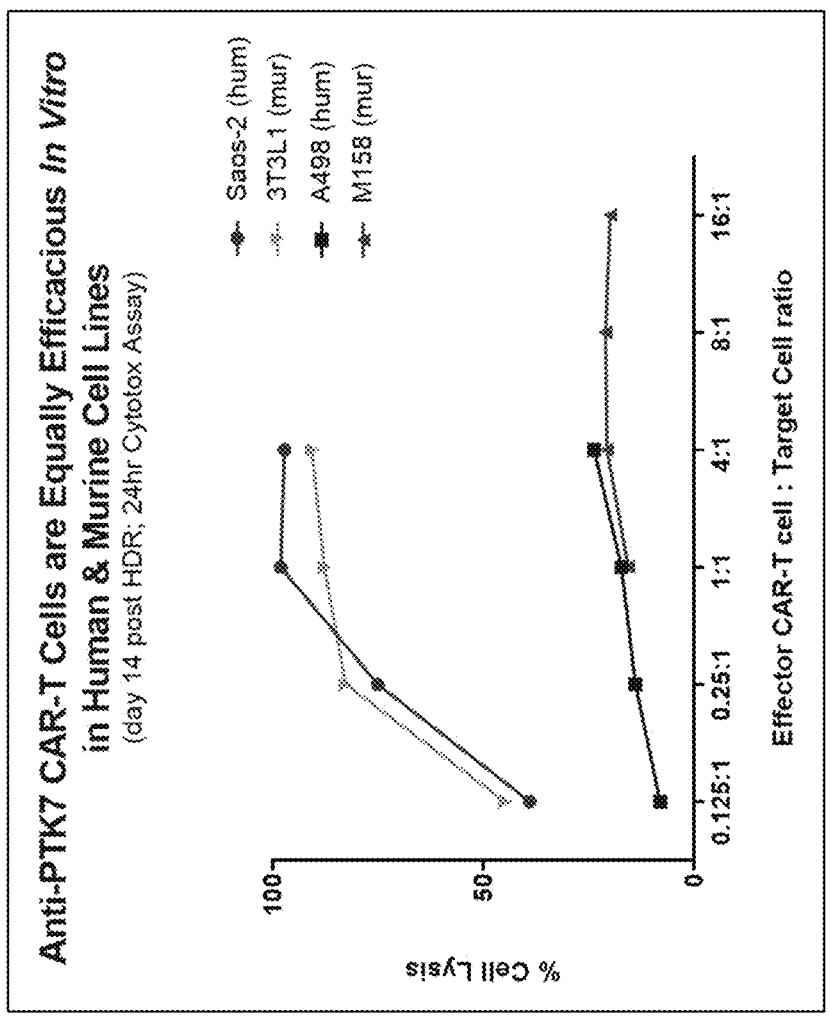
FIG. 15 shows that anti-PTK7 CAR T cells were equally efficacious in vitro in human and murine cell lines.

To evaluate the efficacy in vitro of anti-PTK7 CAR T cells against murine cells, 3T3L1 fibroblast and M158 breast cancer cells, a 24 hour cytotoxicity assay was performed. Results were compared to efficacy of anti-PTK7 CAR T cells to lyse human Saos2 osteosarcoma and human A498 renal cell carcinoma cell lines. Adherent cells were seeded in 96-well plates at 50,000 cells per well and left overnight at 37° C. During the following day, T cells were added to the wells containing target cells at ratios of 0.125:1, 0.25:1, 1:1 or 4:1 effector T cell:target cell. TRAC−/β2M− T cells were used as a negative control. After approximately 24 hours, T cells were removed from the culture by aspiration and 100 µL CellTiter-Glo® (Promega) was added to each well of the plate to assess the number of remaining viable cells. The amount of light emitted from each well was then quantified using a plate reader. The anti-PTK7 CAR T cells exhibited cytotoxicity equally well towards human Saos2 and murine 3T3L1 cell lines (FIG. 15). Conversely, human A498 and murine M158 cells did not lyse in the presence of anti-PTK7 CAR T cells since PTK7 expression levels are low in these 2 cell lines.

Example 9. Tolerability of Anti-PTK7 CAR T Cells in Mouse Models

The ability of NOG mice to tolerate treatment via injection with TRAC−/β2M−/anti-PTK7-4 CAR+ T cells was tested. Two NOG mice were dosed with 10 million TRAC−/β2M−/anti-PTK7-4 CAR T cells (generated as previously described above); two additional mice were dosed with 10 million anti-CD19 CAR T cells. All CAR T cells were administered via tail vein injection.

Figure 16:
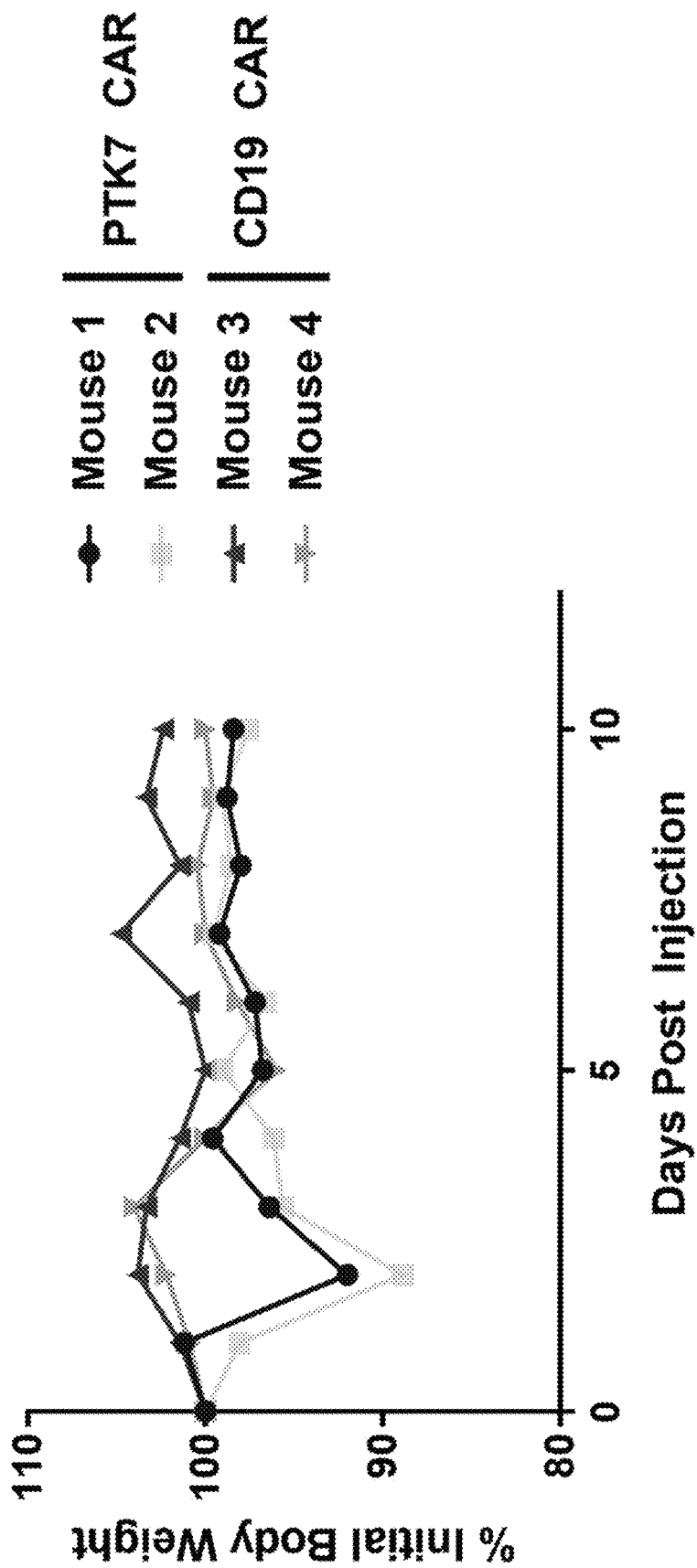
FIG. 16 includes a graph showing that mice treated with TRAC$^-$/β2M$^-$/anti-PTK7 CAR$^+$ T cells showed minimal body weight loss for up to 10 days following treatment/injection.

Mice were weighed daily and monitored for distress or moribundity. Mice treated with anti-PTK7 CAR T cells showed minimal weight loss similar to mice treated with anti-CD19 CAR T cells (FIG. 16). Following a period of ten days post injection, the animals were sacrificed, and spleens and blood samples were analyzed for the presence of human T cells (human CD45+ cells). In both the spleen and blood, mice treated with anti-PTK7 CAR T had higher levels of edited CAR T cells (huCD45+ cells) than in mice treated with anti-CD19 CAR T cells (Table 10), suggesting that the anti-PTK7 CAR T cells will expand in the presence of the mouse antigen.

TABLE 10

Percent humanCD45+ cells ((huCD45+/muCD45+)*100) in PTK7 and CD19 CAR T cell treated mice

| | PTK7 | | CD19 | |
|---|---|---|---|---|
| | Mouse 1 | Mouse 2 | Mouse 1 | Mouse 2 |
| Spleen | 8.56 | 10.01 | 0.58 | 0.82 |
| Blood | 18.47 | 15.13 | 0.42 | 0.93 |

Collectively, the transient body weight loss and higher levels of CAR T cells in the anti-PTK7 CAR treated mice suggested that the anti-PTK7 CAR recognized an antigen in the mouse, which resulted in CAR T cell proliferation. A general lack of significant toxicities was surprising and indicates that the known on-target/off-tissue toxicities associated with targeting PTK7 are tolerable in mice and may further be tolerable in humans.

Example 10. In Vivo Efficacy of Anti-PTK7 CAR-T Cells in Xenograft Mouse Models

Figure 17:
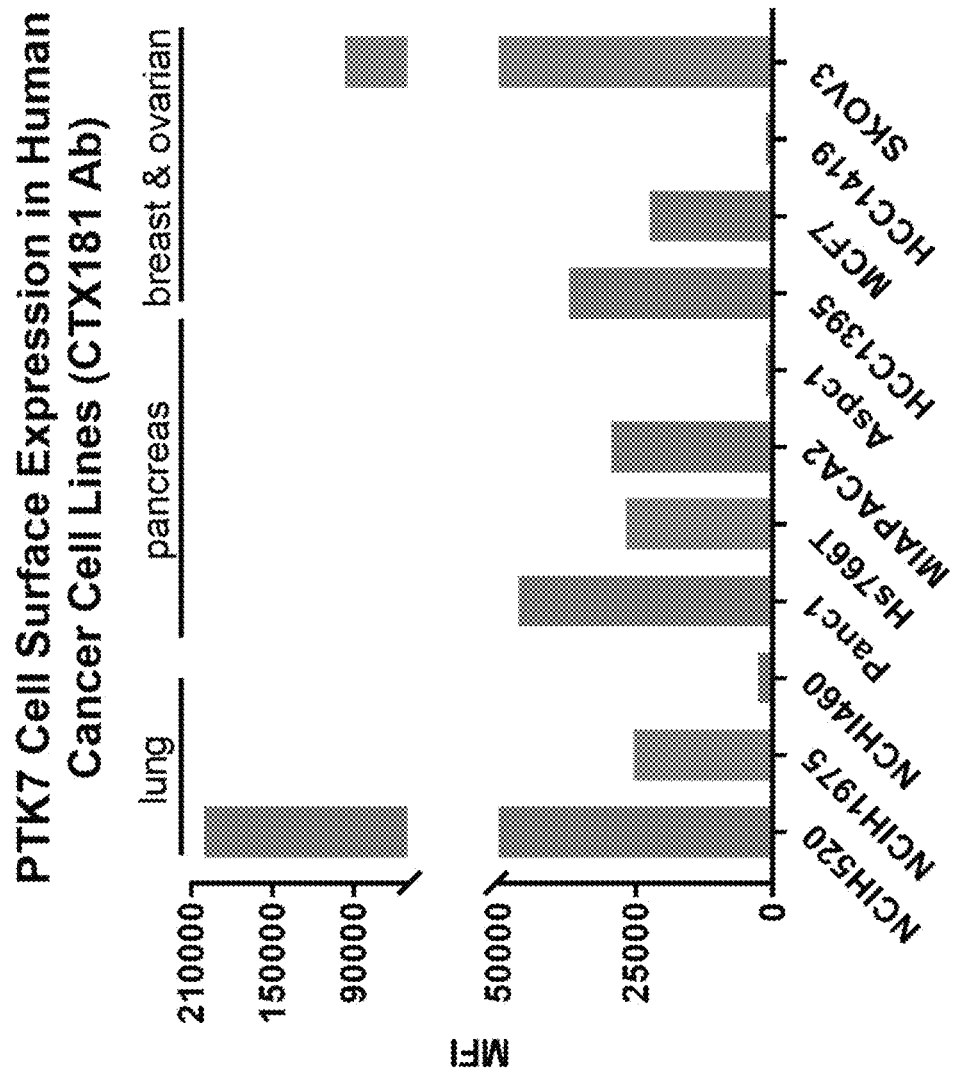
FIG. 17 shows PTK7 cell surface expression levels in human cancer cell lines.
Figure 18A:
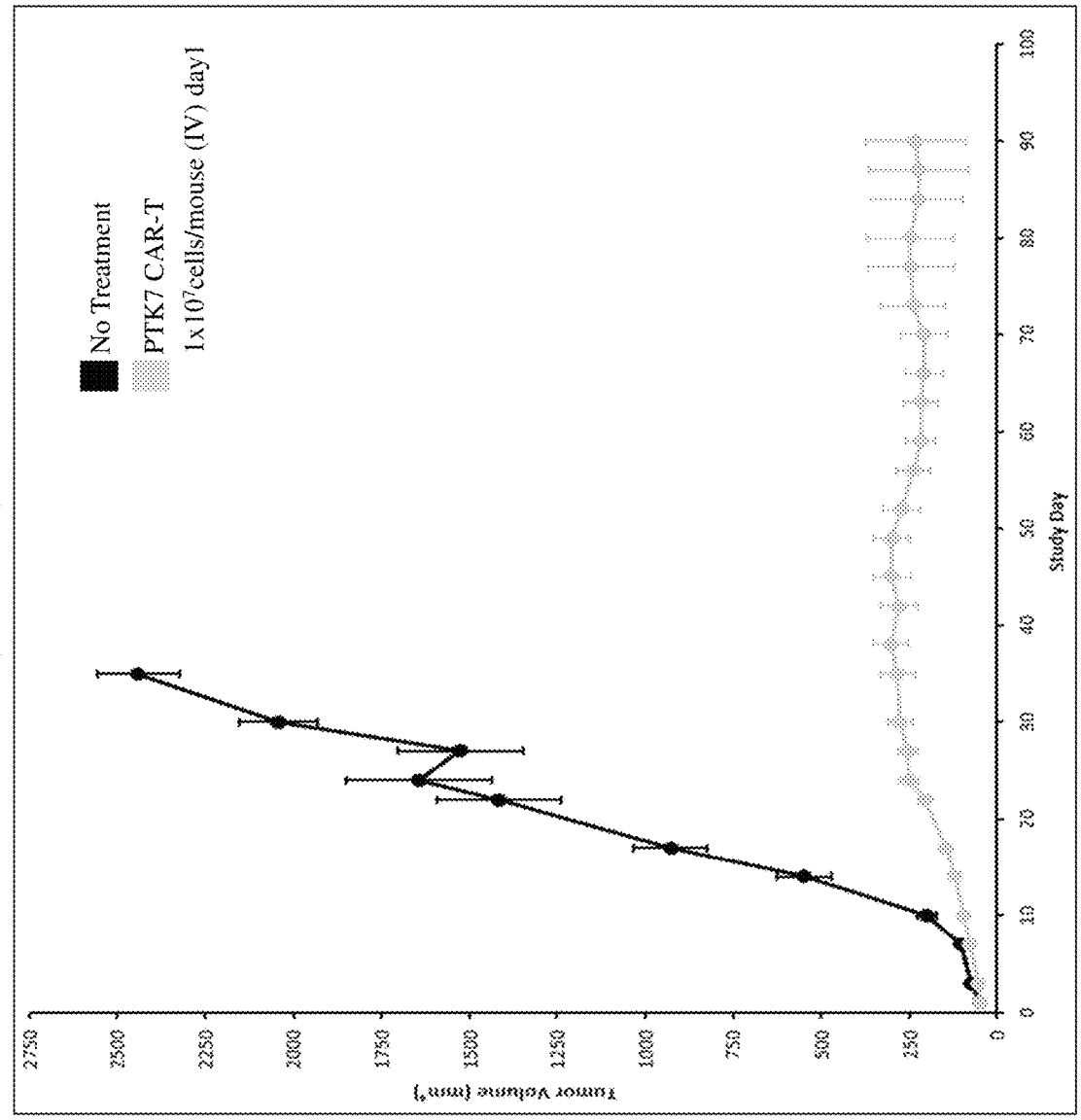
FIGS. 18A-18C show the efficacy of anti-PTK7 CAR T cells in various in vivo xenograft models.
Figure 18B:
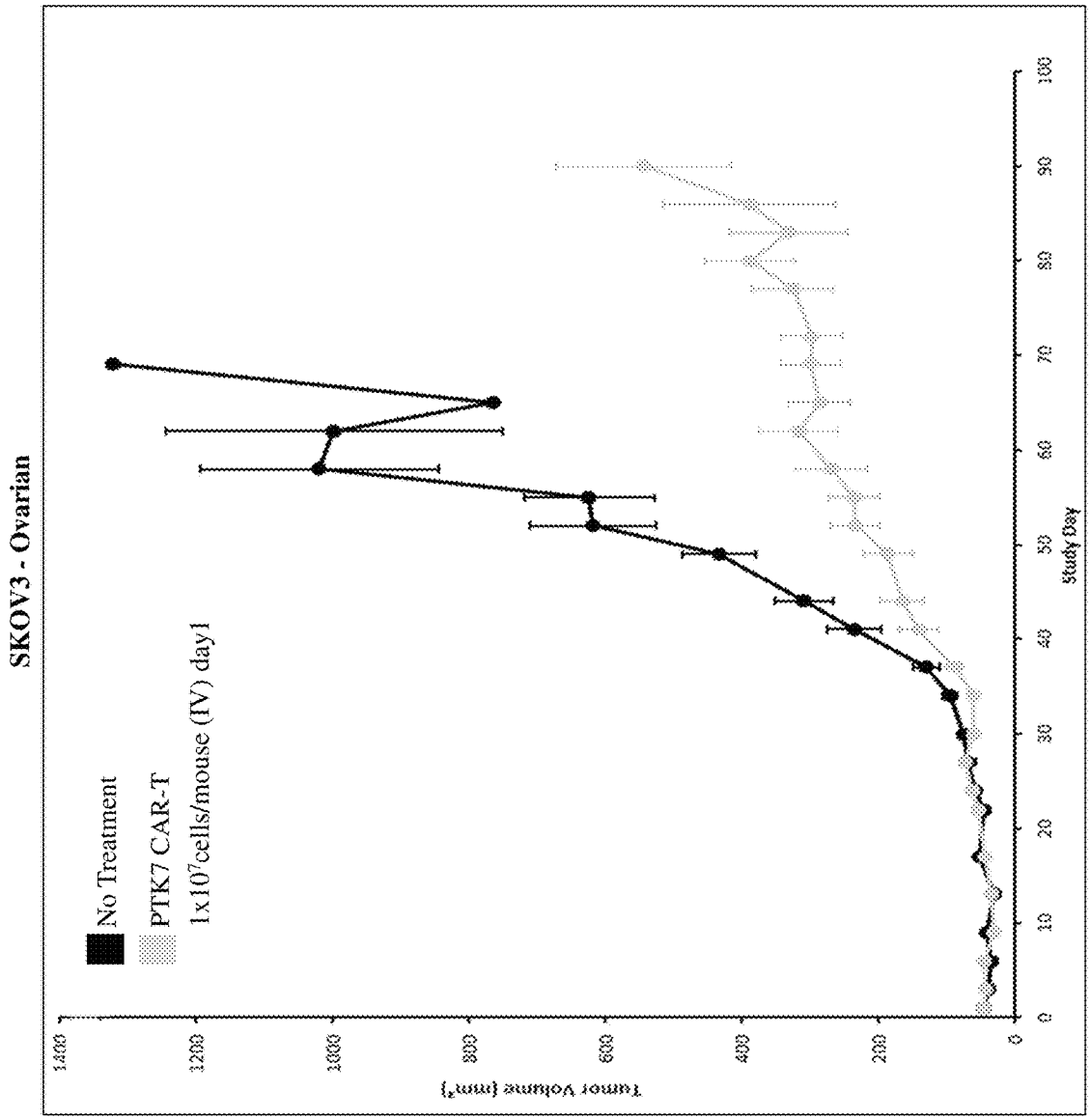
Figure 18C:
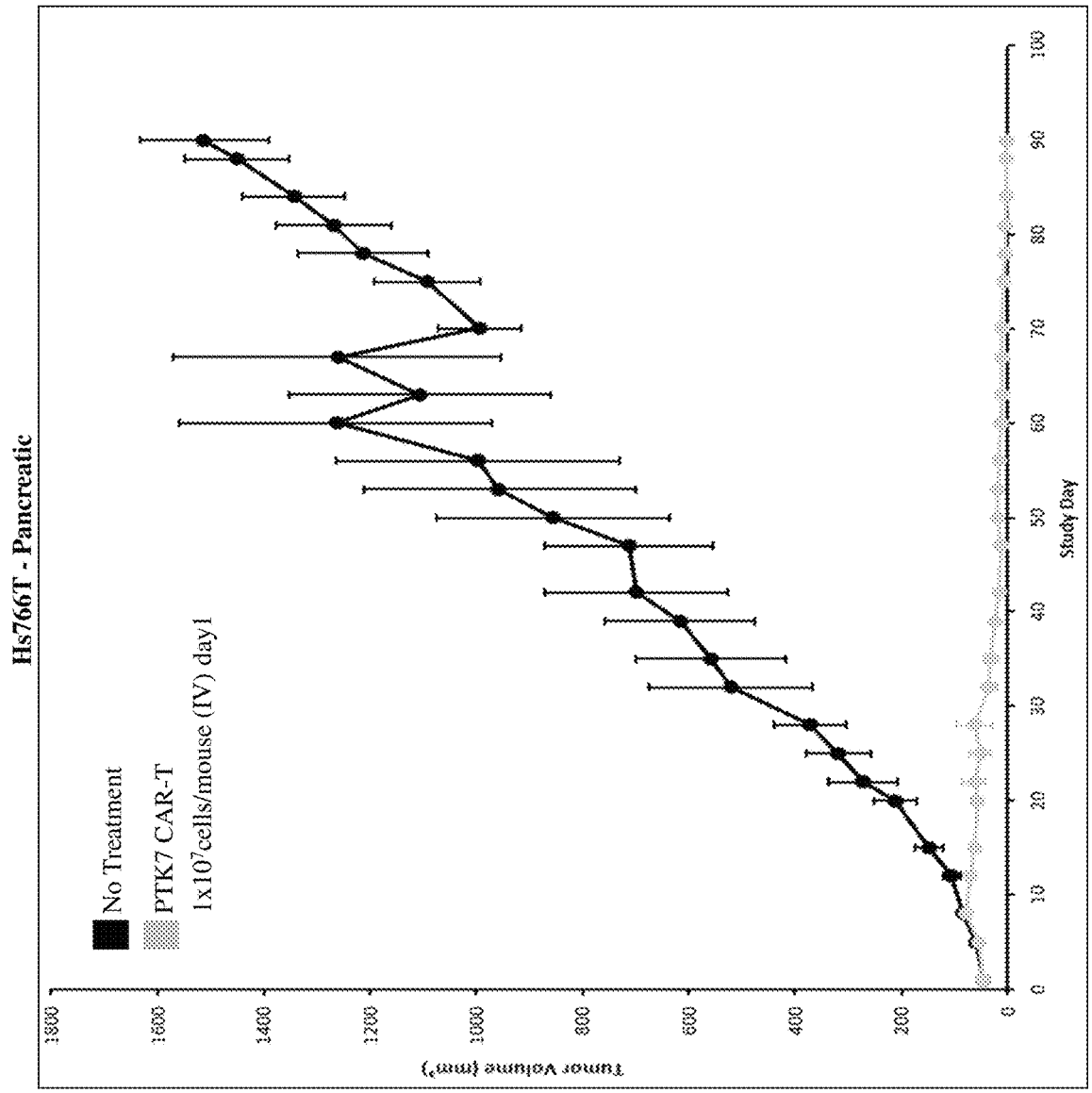

The efficacy of anti-PTK7 CAR-T cells was tested in vivo in SKOV-3 human ovarian, NCI-H1975 human non-small cell lung cancer and human pancreatic Hs766T tumor xenograft mouse models. FIG. 17 shows the PTK7 cell surface expression levels in human cancer cell lines using the CTX181 Ab. For each xenograft model, 5 female (5-8 weeks) NOG mice were dosed single time point IV, single dose ($5 \times 10^7$ cells/ml) TRAC−/β2M−/anti-PTK7 CAR T cells (generated as previously described above). Body weight (2× weekly) and tumor volume were the endpoints measured throughout course of the study. Mice were dosed with anti-PTK7 CAR T cells when tumors (cell lines injected subcutaneous into right flank) reached 50 mm. Studies were terminated when tumors reached endpoint size (1000 mm for SKOV3 (ovarian), 2000 mm for NCI-H1975 (NSCLC) and Hs766T (pancreatic)) or 90 days, whichever occurred first. Mice were housed and monitored under pathogen free conditions and IACUC standards. Anti-PTK7 CAR-T cells were efficacious in all three xenograft models (NCI-H1975 non-small cell lung cancer xenograft model (FIG. 18A), SKOV3 ovarian cancer xenograft model (FIG. 18B), and Hs766T pancreatic cancer xenograft model (FIG. 18C)).

Example 11. In Vivo Efficacy of Anti-PTK7 CAR-T Cells in Xenograft Mouse Models

Figure 19A:
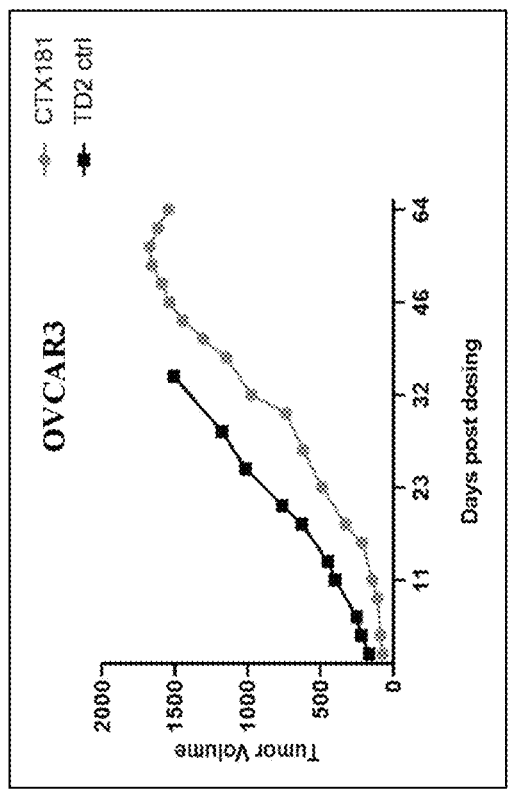
FIGS. 19A-19C show blinded follow-on in vivo studies to assess PTK7 CAR T cell efficacy in ovarian (FIG. 19A), colon and SCLC (FIG. 19B), and breast (FIG. 19C) cancer types.
Figure 19A:
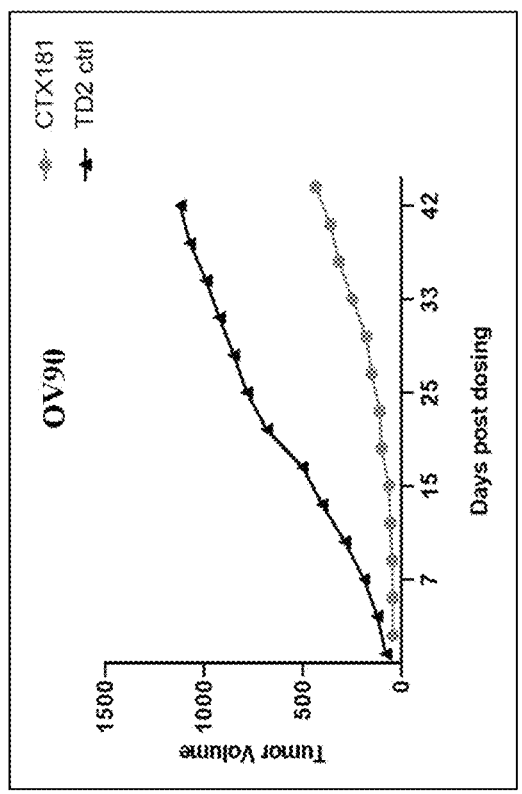
Figure 19A:
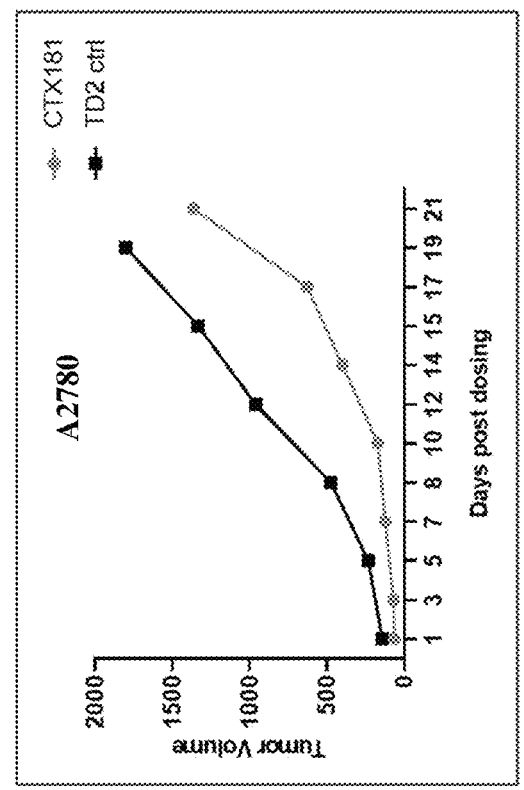
Figure 19B:
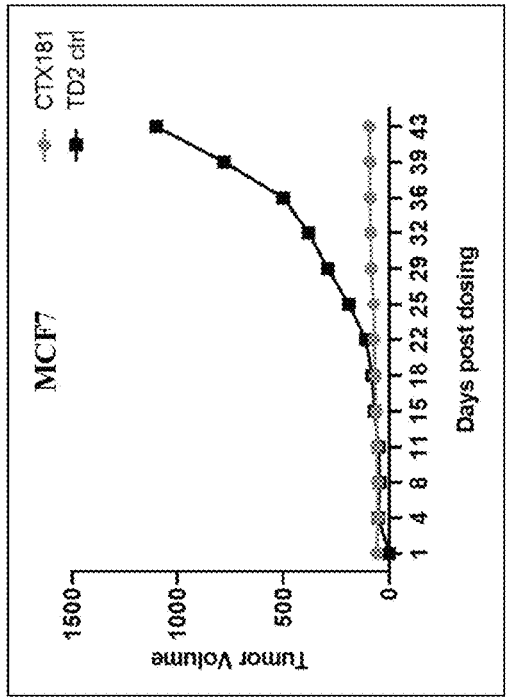
Figure 19B:
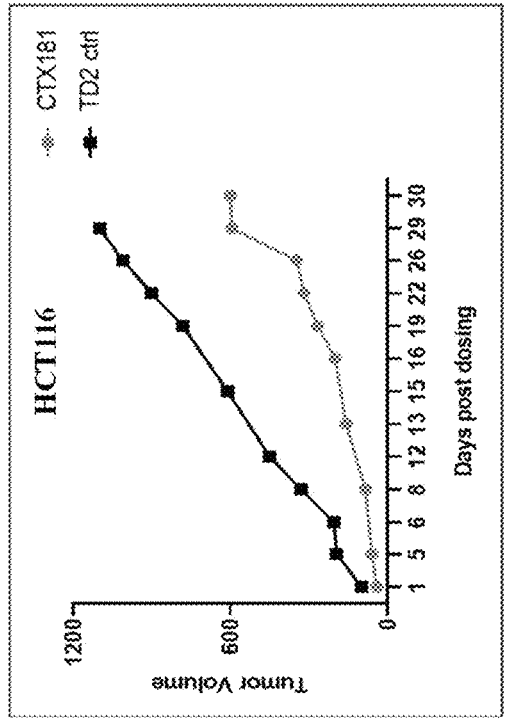
Figure 19C:
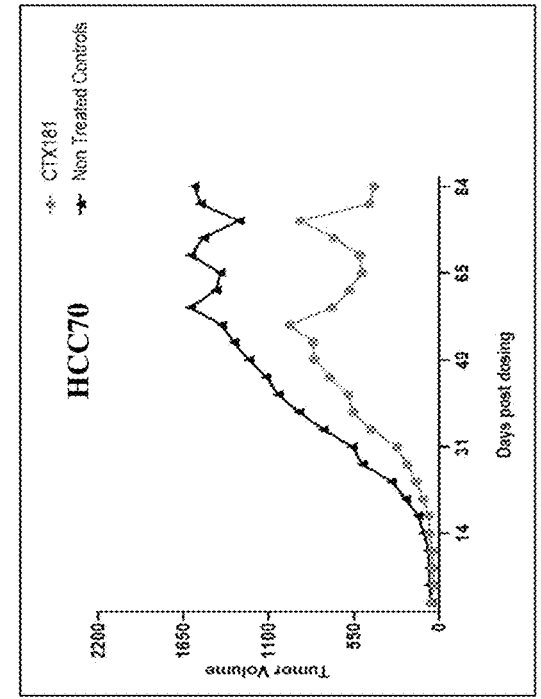
Figure 19C:
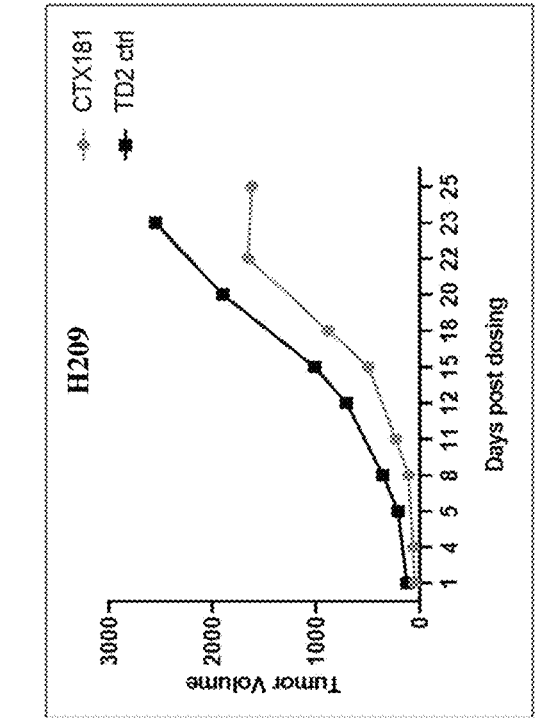
Figure 20:
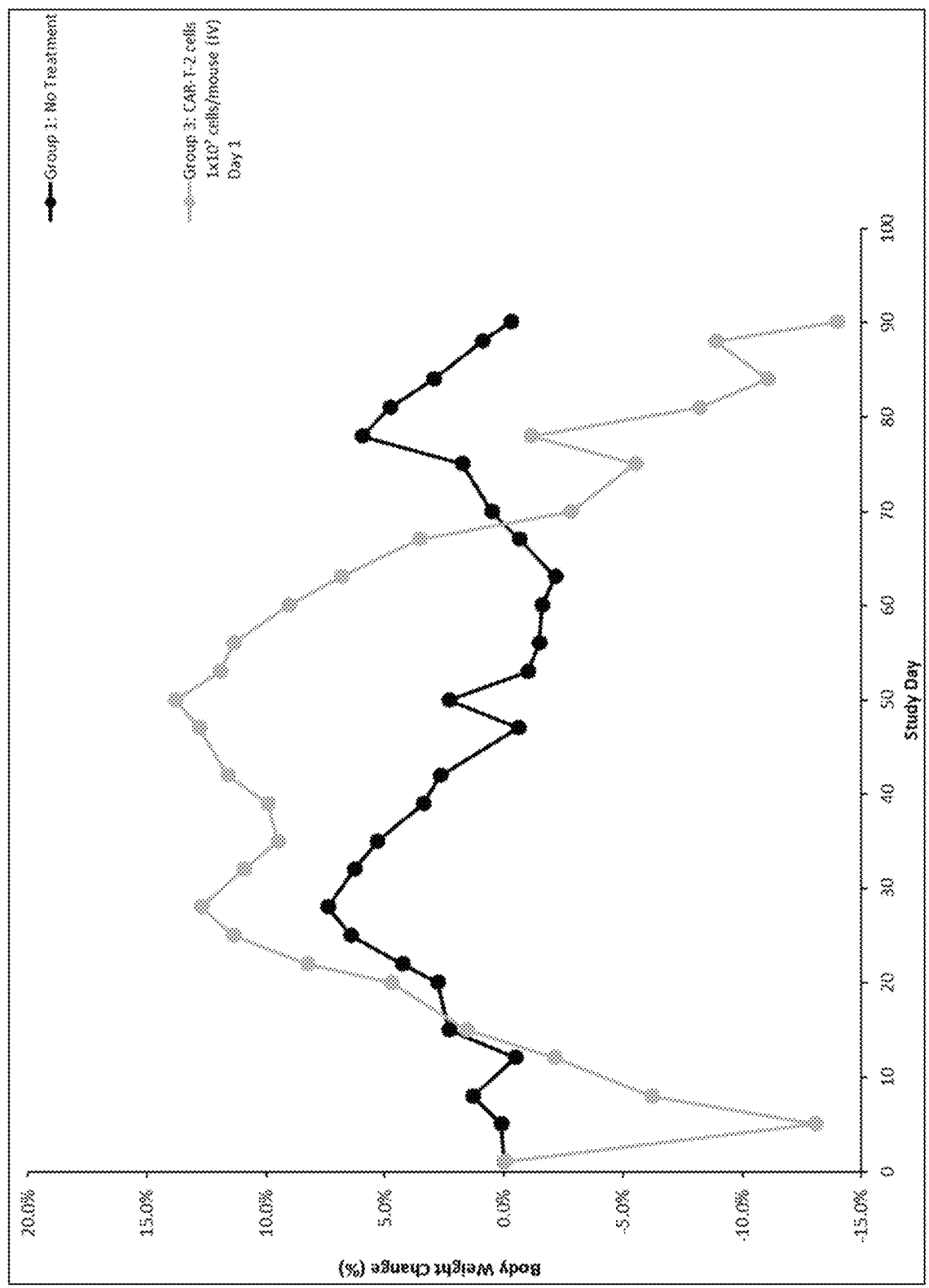
FIG. 20 shows the effect of PTK7 CAR T cell treatment on body weight in Hs-766T pancreatic tumor xenograft mouse model.

The efficacy of anti-PTK7 CAR-T cells was tested in vivo in OV90, OVCAR3, A2780 human ovarian, MCF7, HCC70 human breast, HCT116 human colon and H209 human small cell lung cancer tumor xenograft mouse models. For each xenograft model, 5 female (5-8 weeks) NOG mice were dosed single time point IV, single dose ($5 \times 10^7$ cells/ml) TRAC−/β2M−/anti-PTK7 CAR T cells (generated as previously described above). Body weight (2× weekly) and tumor volume were the endpoints measured throughout course of the study. Mice were dosed with anti-PTK7 CAR-T cells when tumors (cell lines injected subcutaneous into right flank) reached 50 mm. Studies were terminated when tumors reached endpoint size (2000 mm) or 90 days, whichever occurred first. Mice were housed and monitored under pathogen free conditions and IACUC standards. FIG. 19A shows the efficacy of anti-PTK7 CAR T cells against OV90 ovarian tumor xenograft model. FIG. 19B shows the efficacy of anti-PTK7 CAR T cells against HCT116 colon tumor xenograft model. FIG. 19C shows that anti-PTK7 CAR T cells were particularly efficacious in MCF7 tumor xenograft models. FIG. 20 shows the percent body weight change of Hs-766T pancreatic tumor xenograft model treated with PTK7 CAR T cells. Equivalent percent body weight changes were observed in all xenograft studies measured. Latent toxicity showed variability in xenograft models.

TABLE 11

CAR Components
CAR Structure:
CD8[signal peptide]-anti-Pkt7[scFV]-CD8[tm]-
CD28[co-stimulatory domain]-CD3ζ; or
CD8[signal peptide]-anti-Pkt7[scFV]-CD8[tm]-
41BB[co-stimulatory domain]-CD3ζ

| Name | Sequence | SEQ ID NO: |
|---|---|---|
| PTK7-4 | | |
| PKT7-4 CAR CD28 co-stim | ATGGCGCTGCCGGTGACCGCGCTGCTGCTGCCGCTGGCGCTGCTGCTGC ATGCGGCGCGCCCGCAGGTGCAGCTGGTGGAAAGCGGCGGCGGCGTGG TGCAGCCGGGCCGCAGCCTGCGCCTGAGCTGCGCGGCGAGCGGCTTTA CCTTTAGCAGCTATGGCATGCATTGGGTGCGCCAGGCGCCGGGCAAAGG CCTGGAATGGGTGGCCGTGATTTGGGATGATGGCAGCAACAAATATTATG TGGATAGCGTGAAAGGCCGCTTTACCATTAGCCGCGATAACAGCAAAAAC ACCCTGTATCTGCAGATGAACAGCCTGCGCGCGGAAGATACCGCGGTGT ATTATTGCGCGCGCGATGATTATTATGGCAGCGGCAGCTTTAACAGCTATT ATGGCACCGATGTGTGGGGCCAGGGCACCACCGTGACCGTGAGCAGCG GCGGCGGCGGCAGCGGCGGCGGCGGCAGCGGCGGCGGCGGCAGCGAA ATTGTGCTGACCCAGAGCCCGGCGACCCTGAGCCTGAGCCCGGGCGAAC GCGCGACCCTGAGCTGCCGCGCGAGCCAGAGCGTGAGCATTTATCTGGC GTGGTATCAGCAGAAACCGGGCCAGGCGCCCGCGCCTGCTGATTTATGAT GCGAGCAACCGCGCGACCGGCATTCCGGCGCGCTTTAGCGGCAGCGGC AGCGGCACCGATTTTACCCTGACCATTAGCAGCCTGGAACCGGAAGATTT TGCGGTGTATTATTGCCAGCAGCGCAGCAACTGGCCGCCGTTTACCTTTG GCCCGGGCACCAAAGTGGATATTAAAAGCGCGGCGGCGTTTGTGCCGGT GTTTCTGCCGGCGAAACCGACCACCACCCCGGCGCCGCGCCCGGCCGAC CCCGGCGCCGACCATTGCGAGCCAGCCGCTGAGCCTGCGCCCGGAAGC GTGCCGCCCGGCGGCGGGCGGCGCGGTGCATACCCGCGGCCTGGATTT TGCGTGCGATATTTATATTTGGGCGCCGCTGGCGGGCACCTGCGGCGTG CTGCTGCTGAGCCTGGTGATTACCCTGTATTGCAACCATCGCAACCGCAG CAAACGCAGCCGCCTGCTGCATAGCGATTATATGAACATGACCCCGCGCC GCCCGGGCCCGACCCGCAAACATTATCAGCCGTATGCGCCGCCGCGCGA TTTTGCGGCGTATCGCAGCCGCGTGAAATTTAGCCGCAGCGCGGATGCG CCGGCGTATCAGCAGGGCCAGAACCAGCTGTATAACGAACTGAACCTGG GCCGCCGCGAAGAATATGATGTGCTGGATAAACGCCGCGGCCGCGATCC GGAAATGGGCGGCAAACCGCGCCGCAAAAACCCGCAGGAAGGCCTGTAT AACGAACTGCAGAAAGATAAAATGGCGGAAGCGTATAGCGAAATTGGCAT GAAAGGCGAACGCCGCCGCGGCAAAGGCCATGATGGCCTGTATCAGGGC CTGAGCACCGCGACCAAAGATACCTATGATGCGCTGCATATGCAGGCGCT GCCGCCGCGC | 49 |
| PKT7-4 CAR CD28 co-stim | ATGGCGCTTCCGGTGACAGCACTGCTCCTCCCCTTGGCGCTGTTGCTCCA CGCAGCAAGGCCGCAGGTGCAGCTGGTGGAGAGCGGCGGAGGAGTGGT GCAACCCGGAAGGTCCCTGAGGCTCTCCTGTGCCGCCAGCGGCTTCACC TTCTCCAGCTACGGTATGCACTGGGTGAGACAAGCCCCCGGAAAGGGCCT CGAGTGGGTGGCCGTGATCTGGGATGATGGCTCCAACAAGTACTACGTG GACAGCGTCAAGGGCAGATTCACCATCAGCAGGGACAACAGCAAGAACAC CCTGTACCTGCAGATGAACTCCCTGAGAGCCGAAGACACCGCCGTGTACT ATTGTGCCAGGGACGACTACTATGGCTCCGGCTCCTTCAATAGCTACTATG GCACCGACGTGTGGGGCCAGGGCACCACAGTGACAGTGAGCAGCGGCG GAGGAGGATCCGGAGGAGGAGGAAGCGGAGGAGGAGGAAGCGAGATCG TGCTGACACAGTCCCCCGCTACCCTGAGCCTGAGCCCCGGCGAGAGAGC TACCCTGAGCTGCAGAGCCAGCCAGAGCGTCTCCATCTACCTGGCCTGGT ACCAGCAGAAGCCTGGCCAGGCCCCTAGACTGCTGATCTACGACGCCAG CAACAGGGCCACCGGCATTCCTGCCAGATTCAGCGGCTCCGGCTCCGGC ACCGATTTCACACTGACCATCAGCTCCCTGGAGCCTGAGGACTTCGCCGT GTATTACTGCCAGCAGAGGAGCAACTGGCCCCCCTTTACCTTCGGCCCCG GCACCAAGGTCGACATCAAGAGTGCTGCTGCCTTTGTCCCGGTATTTCTC CCAGCCAAACCGACCACGACTCCCGCCCCGCGCCCTCCGACACCCGCTC CCACCATCGCCTCTCAACCTCTTAGTCTTCGCCCCGAGGCATGCCGACCC GCCGCCGGGGGTGCTGTTCATACGAGGGGCTTGGACTTCGCTTGTGATAT TTACATTTGGGCTCCGTTGGCGGGTACGTGCGGCGTCCTTTTGTTGTCAC TCGTTATTACTTTGTATTGTAATCACAGGAATCGCTCAAAGCGGAGTAGGT TGTTGCATTCCGATTACATGAATATGACTCCTCGCCGGCCTGGGCCGACA AGAAAACATTACCAACCCTATGCCCCCCACGAGACTTCGCTGCGTACAG GTCCCGAGTGAAGTTTTCCCGAAGCGCAGACGCTCCGGCATATCAGCAAG GACAGAATCAGCTGTATAACGAACTGAATTTGGGACGCCGCGAGGAGTAT GACGTGCTTGATAAACGCCGGGGAGAGACCCGGAAATGGGGGGTAAAC CCCGAAGAAAGAATCCCCAAGAAGGACTCTACAATGAACTCCAGAAGGAT AAGATGGCGGAGGCCTACTCAGAAATAGGTATGAAGGGCAACGACGAC | 112 |

TABLE 11-continued

CAR Components
CAR Structure:
CD8[signal peptide]-anti-Pkt7[scFV]-CD8[tm]-
CD28[co-stimulatory domain]-CD3ζ; or
CD8[signal peptide]-anti-Pkt7[scFV]-CD8[tm]-
41BB[co-stimulatory domain]-CD3ζ

| Name | Sequence | SEQ ID NO: |
|---|---|---|
|  | GGGGAAAAGGTCACGATGGCCTCTACCAAGGGTTGAGTACGGCAACCAAA GATACGTACGATGCACTGCATATGCAGGCCCTGCCTCCCAGA |  |
| PKT7-4 CAR CD28 co-stim | MALPVTALLLPLALLLHAARPQVQLVESGGGVVQPGRSLRLSCAASGFTFSS YGMHWVRQAPGKGLEWVAVIWDDGSNKYYVDSVKGRFTISRDNSKNTLYLQ MNSLRAEDTAVYYCARDDYYGSGSFNSYYGTDVWGQGTTVTVSSGGGGSG GGGSGGGGSEIVLTQSPATLSLSPGERATLSCRASQSVSIYLAWYQQKPGQA PRLLIYDASNRATGIPARFSGSGSGTDFTLTISSLEPEDFAVYYCQQRSNWPP FTFGPGTKVDIKSAAAFVPVFLPAKPTTTPAPRPPTPAPTIASQPLSLRPEACR PAAGGAVHTRGLDFACDIYIWAPLAGTCGVLLLSLVITLYCNHRNRSKRSRLL HSDYMNMTPRRPGPTRKHYQPYAPPRDFAAYRSRVKFSRSADAPAYQQGQ NQLYNELNLGRREEYDVLDKRRGRDPEMGGKPRRKNPQEGLYNELQKDKM AEAYSEIGMKGERRRGKGHDGLYQGLSTATKDTYDALHMQALPPR | 50 |
| PKT7-4b CAR 41BB co-stim | ATGGCGCTGCCGGTGACCGCGCTGCTGCTGCCGCTGGCGCTGCTGCTGC ATGCGGCGCGCCCGCAGGTGCAGCTGGTGGAAAGCGGCGGCGGCGTGG TGCAGCCGGGCCGCAGCCTGCGCCTGAGCTGCGCGGCGAGCGGCTTTA CCTTTAGCAGCTATGGCATGCATTGGGTGCGCCAGGCGCCGGGCAAAGG CCTGGAATGGGTGGCGGTGATTTGGGATGATGGCAGCAACAAATATTATG TGGATAGCGTGAAAGGCCGCTTTACCATTAGCCGCGATAACAGCAAAAAC ACCCTGTATCTGCAGATGAACAGCCTGCGCGCGGAAGATACCGCGGTGT ATTATTGCGCGCGCGATGATTATTATGGCAGCGGCAGCTTTAACAGCTATT ATGGCACCGATGTGTGGGGCCAGGGCACCACCGTGACCGTGAGCAGCG GCGGCGGCGGCAGCGGCGGCGGCGGCAGCGGCGGCGGCGGCAGCGAA ATTGTGCTGACCCAGAGCCCGGCGACCCTGAGCCTGAGCCCGGGCGAAC GCGCGACCCTGAGCTGCCGCGCGAGCCAGAGCGTGAGCATTTATCTGGC GTGGTATCAGCAGAAACCGGGCCAGGCGCCGCGCCTGCTGATTTATGAT GCGAGCAACCGCGCGACCGGCATTCCGGCGCGCTTTAGCGGCAGCGGC AGCGGCACCGATTTTACCCTGACCATTAGCAGCCTGGAACCGGAAGATTT TGCGGTGTATTATTGCCAGCAGCGCAGCAACTGGCCGCCGTTTACCTTTG GCCCGGGCACCAAAGTGGATATTAAAAGCGCGGCGGCGTTTGTGCCGGT GTTTCTGCCGGCGAAACCGACCACCACCCCGGCGCCGCGCCCGCCGAC CCCGGCGCCGACCATTGCGAGCCAGCCGCTGAGCCTGCGCCCGGAAGC GTGCCGCCCGGCGGCGGGCGGCGCGGTGCATACCCGCGGCCTGGATTT TGCGTGCGATATTTATATTTGGGCGCCGCTGGCGGGCACCTGCGGCGTG CTGCTGCTGAGCCTGGTGATTACCCTGTATTGCAACCATCGCAACCGCAA ACGCGGCCGCAAAAAACTGCTGTATATTTTTAAACAGCCGTTTATGCGCCC GGTGCAGACCACCCAGGAAGAAGATGGCTGCAGCTGCCGCTTTCCGGAA GAAGAAGAAGGCGGCTGCGAACTGCGCGTGAAATTTAGCCGCAGCGCGG ATGCGCCGGCGTATCAGCAGGGCCAGAACCAGCTGTATAACGAACTGAA CCTGGGCCGCCGCGAAGAATATGATGTGCTGGATAAACGCCGCGGCCGC GATCCGGAAATGGGCGGCAAACCGCGCCGCAAAAACCCGCAGGAAGGC CTGTATAACGAACTGCAGAAAGATAAAATGGCGGAAGCGTATAGCGAAAT TGGCATGAAAGGCGAACGCCGCCGCGGCAAAGGCCATGATGGCCTGTAT CAGGGCCTGAGCACCGCGACCAAAGATACCTATGATGCGCTGCATATGCA GGCGCTGCCGCCGCGC | 51 |
| PKT7-4b CAR 41BB co-stim | MALPVTALLLPLALLLHAARPQVQLVESGGGVVQPGRSLRLSCAASGFTFSS YGMHWVRQAPGKGLEWVAVIWDDGSNKYYVDSVKGRFTISRDNSKNTLYLQ MNSLRAEDTAVYYCARDDYYGSGSFNSYYGTDVWGQGTTVTVSSGGGGSG GGGSGGGGSEIVLTQSPATLSLSPGERATLSCRASQSVSIYLAWYQQKPGQA PRLLIYDASNRATGIPARFSGSGSGTDFTLTISSLEPEDFAVYYCQQRSNWPP FTFGPGTKVDIKSAAAFVPVFLPAKPTTTPAPRPPTPAPTIASQPLSLRPEACR PAAGGAVHTRGLDFACDIYIWAPLAGTCGVLLLSLVITLYCNHRNRKRGRKKL LYIFKQPFMRPVQTTQEEDGCSCRFPEEEEGGCELRVKFSRSADAPAYQQG QNQLYNELNLGRREEYDVLDKRRGRDPEMGGKPRRKNPQEGLYNELQKDK MAEAYSEIGMKGERRRGKGHDGLYQGLSTATKDTYDALHMQALPPR | 52 |
| PTK7-4 scFv | CAGGTGCAGCTGGTGGAAAGCGGCGGCGGCGTGGTGCAGCCGGGCCGC AGCCTGCGCCTGAGCTGCGCGGCGAGCGGCTTTACCTTTAGCAGCTATG GCATGCATTGGGTGCGCCAGGCGCCGGGCAAAGGCCTGGAATGGGTGG CGGTGATTTGGGATGATGGCAGCAACAAATATTATGTGGATAGCGTGAAA GGCCGCTTTACCATTAGCCGCGATAACAGCAAAAACACCCTGTATCTGCA GATGAACAGCCTGCGCGCGGAAGATACCGCGGTGTATTATTGCGCGCGC GATGATTATTATGGCAGCGGCAGCTTTAACAGCTATTATGGCACCGATGTG TGGGGCCAGGGCACCACCGTGACCGTGAGCAGCGGCGGCGGCGGCAGC GGCGGCGGCGGCAGCGGCGGCGGCGGCAGCGAAATTGTGCTGACCCAG AGCCCGGCGACCCTGAGCCTGAGCCCGGGCGAACGCGCGACCCTGAGC TGCCGCGCGAGCCAGAGCGTGAGCATTTATCTGGCGTGGTATCAGCAGA AACCGGGCCAGGCGCCGCGCCTGCTGATTTATGATGCGAGCAACCGCGC | 53 |

TABLE 11-continued

CAR Components
CAR Structure:
CD8[signal peptide]-anti-Pkt7[scFV]-CD8[tm]-
CD28[co-stimulatory domain]-CD3ζ; or
CD8[signal peptide]-anti-Pkt7[scFV]-CD8[tm]-
41BB[co-stimulatory domain]-CD3ζ

| Name | Sequence | SEQ ID NO: |
|---|---|---|
| | GACCGGCATTCCGGCGCGCTTTAGCGGCAGCGGCAGCGGCACCGATTTT<br>ACCCTGACCATTAGCAGCCTGGAACCGGAAGATTTTGCGGTGTATTATTG<br>CCAGCAGCGCAGCAACTGGCCGCCGTTTACCTTTGGCCCGGGCACCAAA<br>GTGGATATTAAA | |
| PTK7-4 scFv | CAGGTGCAGCTGGTGGAAAGCGGCGGCGGCGTGGTGCAGCCGGGCCGC<br>AGCCTGCGCCTGAGCTGCGCGGCGAGCGGCTTTACCTTTAGCAGCTATG<br>GCATGCATTGGGTGCGCCAGGCGCCGGGCAAAGGCCTGGAATGGGTGG<br>CGGTGATTTGGGATGATGGCAGCAACAAATATTATGTGGATAGCGTGAAA<br>GGCCGCTTTACCATTAGCCGCGATAACAGCAAAAACACCCTGTATCTGCA<br>GATGAACAGCCTGCGCGCGGAAGATACCGCGGTGTATTATTGCGCGCGC<br>GATGATTATTATGGCAGCGGCAGCTTTAACAGCTATTATGGCACCGATGTG<br>TGGGGCCAGGGCACCACCGTGACCGTGAGCAGCGGCGGCGGCGGCAGC<br>GGCGGCGGCGGCAGCGGCGGCGGCGGCAGCGAAATTGTGCTGACCCAG<br>AGCCCGGCGACCCTGAGCCTGAGCCCGGGCGAACGCGCGACCCTGAGC<br>TGCCGCGCGAGCCAGAGCGTGAGCATTTATCTGGCGTGGTATCAGCAGAA<br>ACCGGGCCAGGCGCCGCGCCTGCTGATTTATGATGCGAGCAACCGCGCG<br>ACCGGCATTCCGGCGCGCTTTAGCGGCAGCGGCAGCGGCACCGATTTTA<br>CCCTGACCATTAGCAGCCTGGAACCGGAAGATTTTGCGGTGTATTATTGC<br>CAGCAGCGCAGCAACTGGCCGCCGTTTACCTTTGGCCCGGGCACCAAAG<br>TGGATATTAAA | 113 |
| PTK7-4 scFv (linker underlined) | QVQLVESGGGVVQPGRSLRLSCAASGFTFSSYGMHWVRQAPGKGLEWVAV<br>IWDDGSNKYYVDSVKGRFTISRDNSKNTLYLQMNSLRAEDTAVYYCARDDYY<br>GSGSFNSYYGTDVWGQGTTVTVSS<u>GGGGSGGGGSGGGGS</u>EIVLTQSPATL<br>SLSPGERATLSCRASQSVSIYLAWYQQKPGQAPRLLIYDASNRATGIPARFSG<br>SGSGTDFTLTISSLEPEDFAVYYCQQRSNWPPFTFGPGTKVDIK | 54 |
| PTK7-4 scFv VH CDRs- in bold | QVQLVESGGGVVQPGRSLRLSCAASGFTFSSYGMHWVRQAPGKGLEWVAV<br>IWDDGSNKYYVDSVKGRFTISRDNSKNTLYLQMNSLRAEDTAVYYCARDDYY<br>GSGSFNSYYGTDVWGQGTTVTVSS | 55 |
| PTK7-4 scFv VL CDRs- in bold | EIVLTQSPATLSLSPGERATLSCRASQSVSIYLAWYQQKPGQAPRLLIYDASN<br>RATGIPARFSGSGSGTDFTLTISSLEPEDFAVYYCQQRSNWPPFTFGPGTKV<br>DIK | 56 |
| PTK7-4 VH CDR1 | SYGMH | 57 |
| PTK7-4 VH CDR2 | VIWDDGSNKYYVDSVKG | 58 |
| PTK7-4 VH CDR3 | DDYYGSGSFNSYYGTDV | 59 |
| PTK7-4 VL CDR1 | RASQSVSIYLA | 60 |
| PTK7-4 VL CDR2 | DASNRAT | 61 |
| PTK7-4 VL CDR3 | QQRSNWPPFT | 62 |
| PTK7-4 Donor LHA to RHA | GAGATGTAAGGAGCTGCTGTGACTTGCTCAAGGCCTTATATCGAGTAAAC<br>GGTAGTGCTGGGGCTTAGACGCAGGTGTTCTGATTTATAGTTCAAAACCT<br>CTATCAATGAGAGAGCAATCTCCTGGTAATGTGATAGATTTCCCAACTTAA<br>TGCCAACATACCATAAACCTCCCATTCTGCTAATGCCCAGCTAAGTTGGG<br>GAGACCACTCCAGATTCCAAGATGTACAGTTTGCTTTGCTGGGCCTTTTTC<br>CCATGCCTGCCTTTACTCTGCCAGAGTTATATTGCTGGGGTTTTGAAGAAG<br>ATCCTATTAAATAAAAGAATAAGCAGTATTATTAAGTAGCCCTGCATTTCAG<br>GTTTCCTTGAGTGGCAGGCCAGGCCTGGCCGTGAACGTTCACTGAAATCA<br>TGGCCTCTTGGCCAAGATTGATAGCTTGTGCCTGTCCCTGAGTCCAGTC<br>CATCACGAGCAGCTGGTTTCTAAGATGCTATTTCCCGTATAAAGCATGAGA<br>CCGTGACTTGCCAGCCCCACAGAGCCCGCCCTTGTCCATCACTGGCATC<br>TGGACTCCAGCCTGGGTTGGGGCAAAGAGGGAAATGAGATCATGTCCTAA<br>CCCTGATCCTCTTGTCCCACAGATATCCAGAACCCTGACCCTGCCGTGTA<br>CCAGCTGAGAGACTCTAAATCAGTGACAAGTCTGTCTGCCTATTCACCG<br>ATTTTGATTCTCAAACAAATGTGTCACAAAGTAAGGATTCTGATGTGTATAT<br>CACAGACAAAACTGTGCTAGACATGAGGTCTATGGACTTCAGGCTCCGGT | 63 |

TABLE 11-continued

CAR Components
CAR Structure:
CD8[signal peptide]-anti-Pkt7[scFV]-CD8[tm]-
CD28[co-stimulatory domain]-CD3ζ; or
CD8[signal peptide]-anti-Pkt7[scFV]-CD8[tm]-
41BB[co-stimulatory domain]-CD3ζ

| Name | Sequence | SEQ ID NO: |
|---|---|---|
| | GCCCGTCAGTGGGCAGAGCGCACATCGCCCACAGTCCCCGAGAAGTTGG<br>GGGGAGGGGTCGGCAATTGAACCGGTGCCTAGAGAAGGTGGCGCGGGG<br>TAAACTGGGAAAGTGATGTCGTGTACTGGCTCCGCCTTTTTCCCGAGGGT<br>GGGGGAGAACCGTATATAAGTGCAGTAGTCGCCGTGAACGTTCTTTTTCG<br>CAACGGGTTTGCCGCCAGAACACAGGTAAGTGCCGTGTGTGGTTCCCGC<br>GGGCCTGGCCTCTTTACGGGTTATGGCCCTTGCGTGCCTTGAATTACTTC<br>CACTGGCTGCAGTACGTGATTCTTGATCCCGAGCTTCGGGTTGGAAGTGG<br>GTGGGAGAGTTCGAGGCCTTGCGCTTAAGGAGCCCCTTCGCCTCGTGCT<br>TGAGTTGAGGCCTGGCCTGGGCGCTGGGGCCGCCGCGTGCGAATCTGG<br>TGGCACCTTCGCGCCTGTCTCGCTGCTTTCGATAAGTCTCTAGCCATTTAA<br>AATTTTTGATGACCTGCTGCGACGCTTTTTTTCTGGCAAGATAGTCTTGTAA<br>ATGCGGGCCAAGATCTGCACACTGGTATTTCGGTTTTTGGGGCCGCGGG<br>CGGCGACGGGCCCGTGCGTCCCAGCGCACATGTTCGGCGAGGCGGGG<br>CCTGCGAGCGCGGCCACCGAGAATCGGACGGGGGTAGTCTCAAGCTGG<br>CCGGCCTGCTCTGGTGCCTGGCCTCGCCGCCGTGTATCGCCCCGCCT<br>TGGGCGGCAAGGCTGGCCGGTCGGCACCAGTTGCGTGAGCGGAAAGA<br>TGGCCGCTTCCCGGCCCTGCTGCAGGGAGCTCAAAATGGAGACGCGGC<br>GCTCGGGAGAGCGGGCGGGTGAGTCACCCACACAAAGGAAAAGGGCCTT<br>TCCGTCCTCAGCCGTCGCTTCATGTGACTCCACGGAGTACCGGGCGCCG<br>TCCAGGCACCTCGATTAGTTCTCGAGCTTTTGGAGTACGTCGTCTTTAGGT<br>TGGGGGGAGGGGTTTTATGCGATGGAGTTTCCCCACACTGAGTGGGTGG<br>AGACTGAAGTTAGGCCAGCTTGGCACTTGATGTAATTCTCCTTGGAATTTG<br>CCCTTTTTGAGTTTGGATCTTGGTTCATTCTCAAGCCTCAGACAGTGGTTC<br>AAAGTTTTTTTCTTCCATTTCAGGTGTCGTGACCACCATGGCGCTTCCGGT<br>GACAGCACTGCTCCTCCCCTTGGCGCTGTTGCTCCACGCAGCAAGGCCG<br>CAGGTGCAGCTGGTGGAGAGCGGCGGAGGAGTGGTGCAACCCGGAAGG<br>TCCCTGAGGCTCTCCTGTGCCGCCAGCGGCTTCACCTTCTCCAGCTACGG<br>TATGCACTGGGTGAGACAAGCCCCCGGAAAGGGCCTCGAGTGGGTGGCC<br>GTGATCTGGGATGATGGCTCCAACAAGTACTACGTGGACAGCGTCAAGGG<br>CAGATTCACCATCAGCAGGGACAACAGCAAGAACACCCTGTACCTGCAGA<br>TGAACTCCCTGAGAGCCAAGACACCGCCGTGTACTATTGTGCCAGGGAC<br>GACTACTATGGCTCCGGCTCCTTCAATAGCTACTATGGCACCGACGTGTG<br>GGGCCAGGGCACCACAGTGACAGTGAGCAGCGGCGGAGGAGGATCCGG<br>AGGAGGAGGAAGCGGAGGAGGAGGAAGCGAGATCGTGCTGACACAGTC<br>CCCCGCTACCCTGAGCCTGAGCCCCGGCGAGAGAGCTACCCTGAGCTGC<br>AGAGCCAGCCAGAGCGTCTCCATCTACCTGGCCTGGTACCAGCAGAAGC<br>CTGGCCAGGCCCCTAGACTGCTGATCTACGACGCCAGCAACAGGGCCAC<br>CGGCATTCCTGCCAGATTCAGCGGCTCCGGCTCCGGCACCGATTTCACAC<br>TGACCATCAGCTCCCTGGAGCCTGAGGACTTCGCCGTGTATTACTGCCAG<br>CAGAGGAGCAACTGGCCCCCCCTTTACCTTCGGCCCCGGCACCAAGGTCG<br>ACATCAAGAGTGCTGCTGCCTTTGTCCCGGTATTTCTCCCAGCCAAACCG<br>ACCACGACTCCCGCCCCGCGCCCTCCGACACCCGCTCCCACCATCGCCT<br>CTCAACCTCTTAGTCTTCGCCCCGAGGCATGCCGACCCGCCGCCGGGGG<br>TGCTGTTCATACGAGGGGCTTGGACTTCGCTTGTGATATTTACATTTGGGC<br>TCCGTTGGCGGGTACGTGCGGCGTCCTTTTGTTGTCACTCGTTATTACTTT<br>GTATTGTAATCACAGGAATCGCTCAAAGCGGAGTAGGTTGTTGCATTCCG<br>ATTACATGAATATGACTCCTCGCCGGCCTGGGCCGACAAGAAAACATTAC<br>CAACCCTATGCCCCCCACGAGACTTCGCTGCGTACAGGTCCCGAGTGAA<br>GTTTTCCCGAAGCGCAGACGCTCCGGCATATCAGCAAGGACAGAATCAGC<br>TGTATAACGAACTGAATTTGGGACGCCGCGAGGAGTATGACGTGCTTGAT<br>AAACGCCGGGGAGAGACCCGGAAATGGGGGTAAACCCCGAAGAAAG<br>AATCCCCAAGAAGGACTCTACAATGAACTCCAGAAGGATAAGATGGCGGA<br>GGCCTACTCAGAAATAGGTATGAAGGGCGAACGACGACGGGGAAAAGGT<br>CACGATGGCCTCTACCAAGGGTTGAGTACGGCAACCAAAGATACGTACGA<br>TGCACTGCATATGCAGGCCCTGCCTCCCAGATAATAATAAAATCGCTATCC<br>ATCGAAGATGGATGTGTGTTGGTTTTTGTGTGTGGAGCAACAAATCTGAC<br>TTTGCATGTGCAAACGCCTTCAACAACAGCATTATTCCAGAAGACACCTTC<br>TTCCCCAGCCCAGGTAAGGGCAGCTTTGGTGCCTTCGCAGGCTGTTTCCT<br>TGCTTCAGGAATGGCCAGGTTCTGCCCAGAGCTCTGGTCAATGATGTCTA<br>AAACTCCTCTGATTGGTGGTCTCGGCCTTATCCATTGCCACCAAAACCCTC<br>TTTTTACTAAGAAACAGTGAGCCTTGTTCTGGCAGTCCAGAGATGACACG<br>GGAAAAAAGCAGATGAAGAGAAGGTGGCAGGAGAGGGCACGTGGCCCA<br>GCCTCAGTCTCTCCAACTGAGTTCCTGCCTGCCTGCCTTTGCTCAGACTG<br>TTTGCCCCTTACTGCTCTTCTAGGCCTCATTCTAAGCCCCTTCTCCAAGTT<br>GCCTCTCCTTATTTCTCCCTGTCTGCCAAAAAATCTTTCCCAGCTCACTAA<br>GTCAGTCTCACGCAGTCACTCATTAACCCACCAATCACTGATTGTGCCGG<br>CACATGAATGCACCAGGTGTTGAAGTGGAGGAATTAAAAAGTCAGATGAG<br>GGGTGTGCCCAGAGGAAGCACCATTCTAGTTGGGGGAGCCCATCTGTCA<br>GCTGGGAAAGTCCAAATAACTTCAGATTGGAATGTGTTTTAACTCAGGGT<br>TGAGAAAACAGCTACCTTCAGGACAAAAGTCAGGGAAGGGCTCTCTGAAG | |

TABLE 11-continued

CAR Components
CAR Structure:
CD8[signal peptide]-anti-Pkt7[scFV]-CD8[tm]-
CD28[co-stimulatory domain]-CD3ζ; or
CD8[signal peptide]-anti-Pkt7[scFV]-CD8[tm]-
41BB[co-stimulatory domain]-CD3ζ

| Name | Sequence | SEQ ID NO: |
|---|---|---|
| | AAATGCTACTTGAAGATACCAGCCCTACCAAGGGCAGGGAGAGGACCCTA TAGAGGCCTGGGACAGGAGCTCAATGAGAAAGG | |
| PTK7-4b Donor LHA to RHA | GAGATGTAAGGAGCTGCTGTGACTTGCTCAAGGCCTTATATCGAGTAAAC GGTAGTGCTGGGGCTTAGACGCAGGTGTTCTGATTTATAGTTCAAAACCT CTATCAATGAGAGAGCAATCTCCTGGTAATGTGATAGATTTCCCAACTTAA TGCCAACATACCATAAACCTCCCATTCTGCTAATGCCCAGCCTAAGTTGGG GAGACCACTCCAGATTCCAAGATGTACAGTTTGCTTTGCTGGGCCTTTTTC CCATGCCTGCCTTTACTCTGCCAGAGTTATATTGCTGGGGTTTTGAAGAAG ATCCTATTAAATAAAAGAATAAGCAGTATTATTAAGTAGCCCTGCATTTCAG GTTTCCTTGAGTGGCAGGCCAGGCCTGGCCGTGAACGTTCACTGAAATCA TGGCCTCTTGGCCAAGATTGATAGCTTGTGCCTGTCCCTGAGTCCCAGTC CATCACGAGCAGCTGGTTTCTAAGATGCTATTTCCCGTATAAAGCATGAGA CCGTGACTTGCCAGCCCCACAGAGCCCCGCCCTTGTCCATCACTGGCATC TGGACTCCAGCCTGGGTTGGGGCAAAGAGGGAAATGAGATCATGTCCTAA CCCTGATCCTCTTGTCCCACAGATATCCAGAACCCTGACCCTGCCGTGTA CCAGCTGAGAGACTCTAAATCCAGTGACAAGTCTGTCTGCCTATTCACCG ATTTTGATTCTCAAACAAATGTGTCACAAAGTAAGGATTCTGATGTGTATAT CACAGACAAAACTGTGCTAGACATGAGGTCTATGGACTTCAGGCTCCGGT GCCCGTCAGTGGGCAGAGCGCACATCGCCCACAGTCCCGAGAAGTTGG GGGGAGGGGTCGGCAATTGAACCGGTGCCTAGAGAAGGTGGCGCGGGG TAAACTGGGAAAGTGATGTCGTGTACTGGCTCCGCCTTTTTCCCGAGGGT GGGGGAGAACCGTATATAAGTGCAGTAGTCGCCGTGAACGTTCTTTTTCG CAACGGGTTTGCCGCCAGAACACAGGTAAGTGCCGTGTGTGGTTCCCGC GGGCCTGGCCTCTTTACGGGTTATGGCCCTTGCGTGCCTTGAATTACTTC CACTGGCTGCAGTACGTGATTCTTGATCCCGAGCTTCGGGTTGGAAGTGG GTGGGAGAGTTCGAGGCCTTGCGCTTAAGGAGCCCCTTCGCCTCGTGCT TGAGTTGAGGCCTGGCCTGGGCGCTGGGGCCGCCGCGTGCGAATCTGG TGGCACCTTCGCGCCTGTCTCGCTGCTTTCGATAAGTCTCTAGCCATTTAA AATTTTTGATGACCTGCTGCGACGCTTTTTTTCTGGCAAGATAGTCTTGTAA ATGCGGGCCAAGATCTGCACACTGGTATTTCGGTTTTTGGGGCCGCGGG CGGCGACGGGGCCCGTGCGTCCCAGCGCACATGTTCGGCGAGGCGGGG CCTGCGAGCGCGGCCACCGAGAATCGGACGGGGGTAGTCTCAAGCTGG CCGGCCTGCTCTGGTGCCTGGCCTCGCGCCGCCGTGTATCGCCCCGCCC TGGGCGGCAAGGCTGGCCCGGTCGGCACCAGTTGCGTGAGCGGAAAGA TGGCCGCTTCCCGGCCCTGCTGCAGGGAGCTCAAAATGGAGGACGCGGC GCTCGGGAGAGCGGGCGGGTGAGTCACCCACACAAAGGAAAAGGGCCTT TCCGTCCTCAGCCGTCGCTTCATGTGACTCCACGGAGTACCGGGCGCCG TCCAGGCACCTCGATTAGTTCTCGAGCTTTTGGAGTACGTCGTCTTTAGGT TGGGGGGAGGGGTTTTATGCGATGGAGTTTCCCCACACTGAGTGGGTGG AGACTGAAGTTAGGCCAGCTTGGCACTTGATGTAATTCTCCTTGGAATTTG CCCTTTTTGAGTTTGGATCTTGGTTCATTCTCAAGCCTCAGACAGTGGTTC AAAGTTTTTTTCTTCCATTTCAGGTGTCGTGACCACCATGGCGCTTCCGGT GACAGCACTGCTCCTCCCCTTGGCGCTGTTGCTCCACGCAGCAAGGCCG CAGGTGCAGCTGGTGGAGAGCGGCGGAGGAGTGGTGCAACCCGGAAGG TCCCTGAGGCTCTCCTGTGCCGCCAGCGGCTTCACCTTCTCCAGCTACGG TATGCACTGGGTGAGACAAGCCCCCGGAAAGGGCCTCGAGTGGGTGGCC GTGATCTGGGATGATGGCTCCAACAAGTACTACGTGGACAGCGTCAAGGG CAGATTCACCATCAGCAGGGACAACAGCAAGAACACCCTGTACCTGCAGA TGAACTCCCTGAGAGCCGAAGACACCGCCGTGTACTATTGTGCCAGGGAC GACTACTATGGCTCCGGCTCCTTCAATAGCTACTATGGCACCGACGTGTG GGGCCAGGGCACCACAGTGACAGTGAGCAGCGGCGGAGGAGGATCCGG AGGAGGAGGAAGCGGAGGAGGAGGAAGCGAGATCGTGCTGACACAGTC CCCCGCTACCCTGAGCCTGAGCCCCGGCGAGAGAGCTACCCTGAGCTGC AGAGCCAGCCAGAGCGTCTCCATCTACCTGGCCTGGTACCAGCAGAAGC CTGGCCAGGCCCCTAGACTGCTGATCTACGACGCCAGCAACAGGGCCAC CGGCATTCCTGCCAGATTCAGCGGCTCCGGCTCCGGCACCGATTTCACAC TGACCATCAGCTCCCTGGAGCCTGAGGACTTCGCCGTGTATTACTGCCAG CAGAGGAGCAACTGGCCCCCCTTTACCTTCGGCCCCGGCACCAAGGTCG ACATCAAGAGTGCTGCTGCCTTTGTCCCGGTATTCTCCCAGCCAAACCG ACCACGACTCCCGCCCCGCGCCCTCCGACACCCGCTCCCACCATCGCCT CTCAACCTCTTAGTCTTCGCCCCGAGGCATGCCGACCCGCCGCGGGGG TGCTGTTCATACGAGGGGCTTGGACTTCGCTTGTGATATTTACATTTGGGC TCCGTTGGCGGGTACGTGCGGCGTCCTTTTGTTGTCACTCGTTATTACTTT GTATTGTAATCACAGGAATCGCAAACGGGGCAGAAAGAAACTCCTGTATA TATTCAAACAACCATTTATGAGACCAGTACAAACTACTCAAGAGGAAGATG GCTGTAGCTGCCGATTTCCAGAAGAAGAAGAAGGAGGATGTGAACTGCGA GTGAAGTTTTCCCGAAGCGCAGAGCTCCGGCATATCAGCAAGGACAGAA TCAGCTGTATAACGAACTGAATTTGGGACGCCGCGAGGAGTATGACGTGC TTGATAAACGCCGGGGAGAGACCCGGAAATGGGGGGTAAACCCCGAAG | 64 |

TABLE 11-continued

CAR Components
CAR Structure:
CD8[signal peptide]-anti-Pkt7[scFV]-CD8[tm]-
CD28[co-stimulatory domain]-CD3ζ; or
CD8[signal peptide]-anti-Pkt7[scFV]-CD8[tm]-
41BB[co-stimulatory domain]-CD3ζ

| Name | Sequence | SEQ ID NO: |
|---|---|---|
| | AAAGAATCCCCAAGAAGGACTCTACAATGAACTCCAGAAGGATAAGATGG<br>CGGAGGCCTACTCAGAAATAGGTATGAAGGGCGAACGACGACGGGGAAA<br>AGGTCACGATGGCCTCTACCAAGGGGTTGAGTACGGCAACCAAAGATACGT<br>ACGATGCACTGCATATGCAGGCCCTGCCTCCCAGATAATAATAAAATCGCT<br>ATCCATCGAAGATGGATGTGTGTTGGTTTTTTGTGTGTGGAGCAACAAATC<br>TGACTTTGCATGTGCAAACGCCTTCAACAACAGCATTATTCCAGAAGACAC<br>CTTCTTCCCCAGCCCAGGTAAGGGCAGCTTTGGTGCCTTCGCAGGCTGTT<br>TCCTTGCTTCAGGAATGGCCAGGTTCTGCCCAGAGCTCTGGTCAATGATG<br>TCTAAAACTCCTCTGATTGGTGGTCTCGGCCTTATCCATTGCCACCAAAAC<br>CCTCTTTTTACTAAGAAACAGTGAGCCTTGTTCTGGCAGTCCAGAGAATGA<br>CACGGGAAAAAAGCAGATGAAGAGAAGGTGGCAGGAGAGGGCACGTGG<br>CCCAGCCTCAGTCTCTCCAACTGAGTTCCTGCCTGCCTGCCTTTGCTCAG<br>ACTGTTTGCCCCTTACTGCTCTTCTAGGCCTCATTCTAAGCCCCTTCTCCA<br>AGTTGCCTCTCCTTATTTCTCCCTGTCTGCCAAAAAATCTTTCCCAGCTCA<br>CTAAGTCAGTCTCACGCAGTCACTCATTAACCCACCAATCACTGATTGTGC<br>CGGCACATGAATGCACCAGGTGTTGAAGTGGAGGAATTAAAAAGTCAGAT<br>GAGGGGTGTGCCCAGAGGAAGCACCATTCTAGTTGGGGGAGCCCATCTG<br>TCAGCTGGGAAAAGTCCAAATAACTTCAGATTGGAATGTGTTTTAACTCAG<br>GGTTGAGAAAACAGCTACCTTCAGGACAAAAGTCAGGGAAGGGCTCTCTG<br>AAGAAATGCTACTTGAAGATACCAGCCCTACCAAGGGCAGGGAGAGGAC<br>CCTATAGAGGCCTGGGACAGGAGCTCAATGAGAAAGG | |

PTK7-7

| PKT7-7 CAR | ATGGCGCTGCCGGTGACCGCGCTGCTGCTGCCGCTGGCGCTGCTGCTGC<br>ATGCGGCGCGCCCGGAAATTGTGCTGACCCAGAGCCCGGCGACCCTGAG<br>CCTGAGCCCGGGCGAACGCGCGACCCTGAGCTGCCGCGCGAGCCAGAG<br>CGTGAGCATTTATCTGGCGTGGTATCAGCAGAAACCGGGCCAGGCGCCG<br>CGCCTGCTGATTTATGATGCGAGCAACCGCGCGACCGGCATTCCGGCGC<br>GCTTTAGCGGCAGCGGCAGCGGCACCGATTTTACCCTGACCATTAGCAGC<br>CTGGAACCGGAAGATTTTGCGGTGTATTATTGCCAGCAGCGCAGCAACTG<br>GCCGCCGTTTACCTTTGGCCCGGGCACCAAAGTGGATATTAAAGGCGGC<br>GGCGGCAGCGGCGGCGGCGGCAGCGGCGGCGGCGGCAGCCAGGTGCA<br>GCTGGTGGAAAGCGGCGGCGGCGTGGTGCAGCCGGGCCGCAGCCTGCG<br>CCTGAGCTGCGCGGCGAGCGGCTTTACCTTTAGCAGCTATGGCATGCATT<br>GGGTGCGCCAGGCGCCGGGCAAAGGCCTGGAATGGGTGGCGGTGATTT<br>GGGATGATGGCAGCAACAAATATTATGTGGATAGCGTGAAAGGCCGCTTT<br>ACCATTAGCCGCGATAACAGCAAAAACACCCTGTATCTGCAGATGAACAG<br>CCTGCGCGCGGAAGATACCGCGGTGTATTATTGCGCGCGCGATGATTATT<br>ATGGCAGCGGCAGCTTTAACAGCTATTATGGCACCGATGTGTGGGGCCAG<br>GGCACCACCGTGACCGTGAGCAGCGCGGCGGCGTTTGTGCCGGTGTTTC<br>TGCCGGCGAAACCGACCACCACCCCGGCGCCGCGCCCGCCGACCCCGG<br>CGCCGACCATTGCGAGCCAGCCGCTGAGCCTGCGCCCGGAAGCGTGCC<br>GCCCGGCGGCGGGCGGCGCGGTGCATACCCGCGGCCTGGATTTTGCGT<br>GCGATATTTATATTTGGGCGCCGCTGGCGGGCACCTGCGGCGTGCTGCT<br>GCTGAGCCTGGTGATTACCCTGTATTGCAACCATCGCAACCGCAGCAAAC<br>GCAGCCGCCTGCTGCATAGCGATTATATGAACATGACCCCGCGCCGCCC<br>GGGCCCGACCCGCAAACATTATCAGCCGTATGCGCCGCCGCGCGATTTT<br>GCGGCGTATCGCAGCCGCGTGAAATTTAGCCGCAGCGCGGATGCGCCGG<br>CGTATCAGCAGGGCCAGAACCAGCTGTATAACGAACTGAACCTGGGCCG<br>CCGCGAAGAATATGATGTGCTGGATAAAGCCGCGGCCGCGATCCGGAA<br>ATGGGCGGCAAACCGCGCCGCAAAAACCCGCAGGAAGGCCTGTATAACG<br>AACTGCAGAAAGATAAAATGGCGGAAGCGTATAGCGAAATTGGCATGAAA<br>GGCGAACGCCGCCGCGGCAAAGGCCATGATGGCCTGTATCAGGGCCTGA<br>GCACCGCGACCAAAGATACCTATGATGCGCTGCATATGCAGGCGCTGCC<br>GCCGCGC | 65 |
| PKT7-7 CAR | MALPVTALLLPLALLLHAARPEIVLTQSPATLSLSPGERATLSCRASQSVSIYLA<br>WYQQKPGQAPRLLIYDASNRATGIPARFSGSGSGTDFTLTISSLEPEDFAVYY<br>CQQRSNWPPFTFGPGTKVDIKGGGGSGGGGSGGGGSQVQLVESGGGVVQ<br>PGRSLRLSCAASGFTFSSYGMHWVRQAPGKGLEWVAVIWDDGSNKYYVDS<br>VKGRFTISRDNSKNTLYLQMNSLRAEDTAVYYCARDDYYGSGSFNSYYGTDV<br>WGQGTTVTVSSAAAFVPVFLPAKPTTTPAPRPPTPAPTIASQPLSLRPEACRP<br>AAGGAVHTRGLDFACDIYIWAPLAGTCGVLLLSLVITLYCNHRNRSKRSRLLH<br>SDYMNMTPRRPGPTRKHYQPYAPPRDFAAYRSRVKFSRSADAPAYQQGQN<br>QLYNELNLGRREEYDVLDKRRGRDPEMGGKPRRKNPQEGLYNELQKDKMA<br>EAYSEIGMKGERRRGKGHDGLYQGLSTATKDTYDALHMQALPPR | 66 |
| PTK7-7 scFv | GAAATTGTGCTGACCCAGAGCCCGGCGACCCTGAGCCTGAGCCCGGGCG<br>AACGCGCGACCCTGAGCTGCCGCGCGAGCCAGAGCGTGAGCATTTATCT | 67 |

TABLE 11-continued

CAR Components
CAR Structure:
CD8[signal peptide]-anti-Pkt7[scFV]-CD8[tm]-
CD28[co-stimulatory domain]-CD3ζ; or
CD8[signal peptide]-anti-Pkt7[scFV]-CD8[tm]-
41BB[co-stimulatory domain]-CD3ζ

| Name | Sequence | SEQ ID NO: |
|---|---|---|
| | GGCGTGGTATCAGCAGAAACCGGGCCAGGCGCCGCGCCTGCTGATTTAT<br>GATGCGAGCAACCGCGCGACCGGCATTCCGGCGCGCTTTAGCGGCAGC<br>GGCAGCGGCACCGATTTTACCCTGACCATTAGCAGCCTGGAACCGGAAG<br>ATTTTGCGGTGTATTATTGCCAGCAGCGCAGCAACTGGCCGCCGTTTACC<br>TTTGGCCCGGGCACCAAAGTGGATATTAAAGGCGGCGGCGGCAGCGGCG<br>GCGGCGGCAGCGGCGGCGGCGGCAGCCAGGTGCAGCTGGTGGAAAGC<br>GGCGGCGGCGTGGTGCAGCCGGGCCGCAGCCTGCGCCTGAGCTGCGCG<br>GCGAGCGGCTTTACCTTTAGCAGCTATGGCATGCATTGGGTGCGCCAGG<br>CGCCGGGCAAAGGCCTGGAATGGGTGGCCGTGATTTGGGATGATGGCAG<br>CAACAAATATTATGTGGATAGCGTGAAAGGCCGCTTTACCATTAGCCGCG<br>ATAACAGCAAAAACACCCTGTATCTGCAGATGAACAGCCTGCGCGCGGAA<br>GATACCGCGGTGTATTATTGCGCGCGCGATGATTATTATGGCAGCGGCAG<br>CTTTAACAGCTATTATGGCACCGATGTGTGGGGCCAGGGCACCACCGTGA<br>CCGTGAGCAGC | |
| PTK7-7 scFv (linker underlined) | EIVLTQSPATLSLSPGERATLSCRASQSVSIYLAWYQQKPGQAPRLLIYDASN<br>RATGIPARFSGSGSGTDFTLTISSLEPEDFAVYYCQQRSNWPPFTFGPGTKV<br>DIK<u>GGGGSGGGGSGGGGS</u>QVQLVESGGGVVQPGRSLRLSCAASGFTFSSY<br>GMHWVRQAPGKGLEWVAVIWDDGSNKYYVDSVKGRFTISRDNSKNTLYLQ<br>MNSLRAEDTAVYYCARDDYYGSGSFNSYYGTDVWGQGTTVTVSS | 68 |
| PTK7-7 scFv VH | QVQLVESGGGVVQPGRSLRLSCAASGFTFSSYGMHWVRQAPGKGLEWVAV<br>IWDDGSNKYYVDSVKGRFTISRDNSKNTLYLQMNSLRAEDTAVYYCARDDYY<br>GSGSFNSYYGTDVWGQGTTVTVSS | 69 |
| PTK7-7 scFv VL | EIVLTQSPATLSLSPGERATLSCRASQSVSIYLAWYQQKPGQAPRLLIYDASN<br>RATGIPARFSGSGSGTDFTLTISSLEPEDFAVYYCQQRSNWPPFTFGPGTKV<br>DIK | 70 |
| PTK7-7 Donor LHA to RHA | GAGATGTAAGGAGCTGCTGTGACTTGCTCAAGGCCTTATATCGAGTAAAC<br>GGTAGTGCTGGGGCTTAGACGCAGGTGTTCTGATTTATAGTTCAAAACCT<br>CTATCAATGAGAGAGCAATCTCCTGGTAATGTGATAGATTTCCCAACTTAA<br>TGCCAACATACCATAAACCTCCCATTCTGCTAATGCCCAGCCTAAGTTGGG<br>GAGACCACTCCAGATTCCAAGATGTACAGTTTGCTTTGCTGGGCCTTTTTC<br>CCATGCCTGCCTTTACTCTGCCAGAGTTATATTGCTGGGGTTTTGAAGAAG<br>ATCCTATTAAATAAAAGAATAAGCAGTATTATTAAGTAGCCCTGCATTTCAG<br>GTTTCCTTGAGTGGCAGGCCAGGCCTGGCCGTGAACGTTCACTGAAATCA<br>TGGCCTCTTGGCCAAGATTGATAGCTTGTGCCTGTCCCTGAGTCCCAGTC<br>CATCACGAGCAGCTGGTTTCTAAGATGCTATTTCCCGTATAAAGCATGAGA<br>CCGTGACTTGCCAGCCCCACAGAGCCCCGCCCTTGTCCATCACTGGCATC<br>TGGACTCCAGCCTGGGTTGGGGCAAAGAGGGAAATGAGATCATGTCCTAA<br>CCCTGATCCTCTTGTCCCACAGATATCCAGAACCCTGACCCTGCCGTGTA<br>CCAGCTGAGAGACTCTAAATCCAGTGACAAGTCTGTCTGCCTATTCACCG<br>ATTTTGATTCTCAAACAAATGTGTCACAAAGTAAGGATTCTGATGTGTATAT<br>CACAGACAAAACTGTGCTAGACATGAGGTCTATGGACTTCAGGCTCCGGT<br>GCCCGTCAGTGGGCAGAGCGCACATCGCCCACAGTCCCCGAGAAGTTGG<br>GGGGAGGGGTCGGCAATTGAACCGGTGCCTAGAGAAGGTGGCGCGGGG<br>TAAACTGGGAAAGTGATGTCGTGTACTGGCTCCGCCTTTTTCCCGAGGGT<br>GGGGGAGAACCGTATATAAGTGCAGTAGTCGCCGTGAACGTTCTTTTTCG<br>CAACGGGTTTGCCGCCAGAACACAGGTAAGTGCCGTGTGTGGTTCCCGC<br>GGGCCTGGCCTCTTTACGGGTTATGGCCCTTGCGTGCCTTGAATTACTTC<br>CACTGGCTGCAGTACGTGATTCTTGATCCCGAGCTTCGGGTTGGAAGTGG<br>GTGGGAGAGTTCGAGGCCTTGCGCTTAAGGAGCCCCTTCGCCTCGTGCT<br>TGAGTTGAGGCCTGGCCTGGGCGCTGGGGCCGCCGCGTGCGAATCTGG<br>TGGCACCTTCGCGCCTGTCTCGCTGCTTTCGATAAGTCTCTAGCCATTTAA<br>AATTTTTGATGACCTGCTGCGACGCTTTTTTCTGGCAAGATAGTCTTGTAA<br>ATGCGGGCCAAGATCTGCACACTGGTATTTCGGTTTTTGGGGCCGCGGG<br>CGGCGACGGGCCCGTGCGTCCCAGCGCACATGTTCGGCGAGGCGGGG<br>CCTGCGAGCGCGGCCACCGAGAATCGGACGGGGGTAGTCTCAAGCTGG<br>CCGGCCTGCTCTGGTGCCTGGCCTCGCGCCGCCGTGTATCGCCCCGCCC<br>TGGGCGGCAAGGCTGGCCCGGTCGGCACCAGTTGCGTGAGCGGAAAGA<br>TGGCCGCTTCCCGGCCCTGCTGCAGGGAGCTCAAAATGGAGGACGCGGC<br>GCTCGGGAGAGCGGGCGGGTGAGTCACCCACACAAAGGAAAAGGGCCTT<br>TCCGTCCTCAGCCGTCGCTTCATGTGACTCCACGGAGTACCGGGCGCCG<br>TCCAGGCACCTCGATTAGTTCTCGAGCTTTTGGAGTACGTCGTCTTTAGGT<br>TGGGGGGAGGGGTTTTATGCGATGGAGTTTCCCCACACTGAGTGGGTG<br>AGACTGAAGTTAGGCCAGCTTGGCACTTGATGTAATTCTCCTTGGAATTTG<br>CCCTTTTTGAGTTTGGATCTTGGTTCATTCTCAAGCCTCAGACAGTGGTTC<br>AAAGTTTTTTTCTTCCATTTCAGGTGTCGTGACCACCATGGCGCTTCCGGT<br>GACAGCACTGCTCCTCCCCTTGGCGCTGTTGCTCCACGCAGCAAGGCCG | 71 |

TABLE 11-continued

CAR Components
CAR Structure:
CD8[signal peptide]-anti-Pkt7[scFV]-CD8[tm]-
CD28[co-stimulatory domain]-CD3ζ; or
CD8[signal peptide]-anti-Pkt7[scFV]-CD8[tm]-
41BB[co-stimulatory domain]-CD3ζ

| Name | Sequence | SEQ ID NO: |
|---|---|---|
| | GAGATCGTGCTGACCCAGAGCCCTGCCACACTGAGCCTGAGCCCCGGAG | |
| | AGAGGGCTACCCTGAGCTGCAGGGCCTCCCAGTCCGTGAGCATCTACCT | |
| | GGCCTGGTACCAGCAGAAACCTGGCCAGGCCCCCAGGCTGCTGATCTAC | |
| | GACGCCAGCAATAGGGCCACCGGAATCCCTGCCAGGTTTAGCGGCTCCG | |
| | GAAGCGGCACCGACTTCACCCTGACCATCTCCTCCCTGGAGCCCGAGGA | |
| | TTTCGCCGTGTACTACTGCCAGCAGAGGTCCAACTGGCCTCCCTTTACCT | |
| | TCGGCCCCGGCACCAAGGTGGATATTAAGGGCGGCGGCGGATCCGGAG | |
| | GAGGAGGCAGCGGAGGAGGAGGAAGCCAGGTGCAACTGGTGGAGTCCG | |
| | GCGGAGGCGTGGTGCAACCTGGCAGAAGCCTGAGGCTGAGCTGTGCCG | |
| | CCAGCGGCTTCACCTTCAGCAGCTACGGTATGCACTGGGTGAGGCAGGC | |
| | TCCCGGAAAGGGCCTGGAATGGGTGGCCGTGATCTGGGACGACGGCTCC | |
| | AACAAGTACTACGTGGACTCCGTGAAGGGCAGGTTCACCATCAGCAGGG | |
| | ACAACTCCAAGAACACACTGTACCTGCAGATGAACAGCCTGAGGGCCGA | |
| | GGATACCGCTGTGTATTACTGCGCCAGGGACGATTACTACGGCAGCGGCA | |
| | GCTTCAATTCCTACTACGGAACCGACGTCTGGGGCCAGGGAACCACCGT | |
| | GACCGTGAGCAGCAGTGCTGCTGCCTTTGTCCCGGTATTTCTCCCAGCCA | |
| | AACCGACCACGACTCCCGCCCCGCGCCCTCCGACACCCGCTCCCACCAT | |
| | CGCCTCTCAACCTCTTAGTCTTCGCCCCGAGGCATGCCGACCCGCCGCC | |
| | GGGGGTGCTGTTCATACGAGGGGCTTGGACTTCGCTTGTGATATTTACAT | |
| | TTGGGCTCCGTTGGCGGGTACGTGCGGCGTCCTTTTGTTGTCACTCGTTA | |
| | TTACTTTGTATTGTAATCACAGGAATCGCTCAAAGCGGAGTAGGTTGTTGC | |
| | ATTCCGATTACATGAATATGACTCCTCGCCGGCCTGGGCCGACAAGAAAA | |
| | CATTACCAACCCTATGCCCCCCACGAGACTTCGCTGCGTACAGGTCCCG | |
| | AGTGAAGTTTTCCCGAAGCGCAGACGCTCCGGCATATCAGCAAGGACAGA | |
| | ATCAGCTGTATAACGAACTGAATTTGGGACGCCGCGAGGAGTATGACGTG | |
| | CTTGATAAACGCCGGGGAGAGACCCGGAAATGGGGGGTAAACCCCGAA | |
| | GAAAGAATCCCCAAGAAGGACTCTACAATGAACTCCAGAAGGATAAGATG | |
| | GCGGAGGCCTACTCAGAAATAGGTATGAAGGGCGAACGACGACGGGGAA | |
| | AAGGTCACGATGGCCTCTACCAAGGGTTGAGTACGGCAACCAAAGATACG | |
| | TACGATGCACTGCATATGCAGGCCCTGCCTCCCAGATAATAATAAAATCGC | |
| | TATCCATCGAAGATGGATGTGTGTTGGTTTTTGTGTGTGGAGCAACAAAT | |
| | CTGACTTTGCATGTGCAAACGCCTTCAACAACAGCATTATTCCAGAAGACA | |
| | CCTTCTTCCCCAGCCCAGGTAAGGGCAGCTTTGGTGCCTTCGCAGGCTGT | |
| | TTCCTTGCTTCAGGAATGGCCAGGTTCTGCCCAGAGCTCTGGTCAATGAT | |
| | GTCTAAAACTCCTCTGATTGGTGGTCTCGGCCTTATCCATTGCCACCAAAA | |
| | CCCTCTTTTTACTAAGAAACAGTGAGCCTTGTTCTGGCAGTCCAGAGAATG | |
| | ACACGGGAAAAAAGCAGATGAAGAGAAGGTGGCAGGAGAGGGCACGTGG | |
| | CCCAGCCTCAGTCTCTCCAACTGAGTTCCTGCCTGCCTGCCTTTGCTCAG | |
| | ACTGTTTGCCCCTTACTGCTCTTCTAGGCCTCATTCTAAGCCCCTTCTCCA | |
| | AGTTGCCTCTCCTTATTTCTCCCTGTCTGCCAAAAAATCTTTCCCAGCTCA | |
| | CTAAGTCAGTCTCACGCAGTCACTCATTAACCCACCAATCACTGATTGTGC | |
| | CGGCACATGAATGCACCAGGTGTTGAAGTGGAGGAATTAAAAAGTCAGAT | |
| | GAGGGGTGTGCCCAGAGGAAGCACCATTCTAGTTGGGGGAGCCCATCTG | |
| | TCAGCTGGGAAAAGTCCAAATAACTTCAGATTGGAATGTGTTTTAACTCAG | |
| | GGTTGAGAAAACAGCTACCTTCAGGACAAAAGTCAGGGAAGGGCTCTCTG | |
| | AAGAAATGCTACTTGAAGATACCAGCCCTACCAAGGGCAGGGAGAGGAC | |
| | CCTATAGAGGCCTGGGACAGGAGCTCAATGAGAAAGG | |

PTK7-13

| PKT7-13 CAR | ATGGCGCTGCCGGTGACCGCGCTGCTGCTGCCGCTGGCGCTGCTGCTGC | 72 |
|---|---|---|
| | ATGCGGCGCGCCCGGAAATTGTGCTGACCCAGAGCCCGGGCACCCTGAG | |
| | CCTGAGCCCGGGCGAACGCGCGACCCTGAGCTGCCGCGCGAGCCAGAG | |
| | CGTGAGCAGCAGCTATCTGGCGTGGTATCAGCAGAAACCGGGCCAGGCG | |
| | CCGCGCCTGCTGATTTATGGCGCGAGCAGCCGCGCGACCGGCATTCCGG | |
| | ATCGCTTTAGCGGCAGCGGCAGCGGCACCGATTTTACCCTGACCATTAGC | |
| | CGCCTGGAACCGGAAGATTTTGCGGTGTATTATTGCCAGCAGTATGGCAG | |
| | CAGCCCGATGTATACCTTTGGCCAGGGCACCAAACTGGAAATTAAAGGCG | |
| | GCGGCGGCAGCGGCGGCGGCGGCAGCGGCGGCGGCAGCGAAGTG | |
| | CAGCTGGTGCAGAGCGGCGGCGGCCTGGTGCATCCGGGCGGCAGCCTG | |
| | CGCCTGAGCTGCGCGGGCAGCGGCTTTACCTTTAGCACCTATCTGATGTA | |
| | TTGGGTGCGCCAGGCGCCGGGCAAAACCCTGGAATGGGTGAGCGCGATT | |
| | GGCAGCGGCGGCGATACCTATTATGCGGATAGCGTGAAAGGCCGCTTTA | |
| | CCATTAGCCGCGATAACGCGAAAAACAGCCTGTATCTGCAGATGAACAGC | |
| | CTGCGCGCGGAAGATATGGCGGTGTATTATTGCGCGCGCGCTGGGCT | |
| | ATTGGGGCCAGGGCACCCTGGTGACCGTGAGCAGCGCGGCGGCGTTTGT | |
| | GCCGGTGTTTCTGCCGGCGAAACCGACCACCACCCCGGCGCCGCGCCC | |
| | GCCGACCCCGGCGCCGACCATTGCGAGCCAGCCGCTGAGCCTGCGCCC | |
| | GGAAGCGTGCCGCCCGGCGGCGGGCGGCGCGGTGCATACCCGCGGCCT | |
| | GGATTTTGCGTGCGATATTTATATTTGGGCGCCGCTGGCGGGCACCTGCG | |

TABLE 11-continued

CAR Components
CAR Structure:
CD8[signal peptide]-anti-Pkt7[scFV]-CD8[tm]-
CD28[co-stimulatory domain]-CD3ζ; or
CD8[signal peptide]-anti-Pkt7[scFV]-CD8[tm]-
41BB[co-stimulatory domain]-CD3ζ

| Name | Sequence | SEQ ID NO: |
|---|---|---|
|  | GCGTGCTGCTGCTGAGCCTGGTGATTACCCTGTATTGCAACCATCGCAAC<br>CGCAGCAAACGCAGCCGCCTGCTGCATAGCGATTATATGAACATGACCCC<br>GCGCCGCCCGGGCCCGACCCGCAAACATTATCAGCCGTATGCGCCGCCG<br>CGCGATTTTGCGGCGTATCGCAGCCGCGTGAAATTTAGCCGCAGCGCGG<br>ATGCGCCGGCGTATCAGCAGGGCCAGAACCAGCTGTATAACGAACTGAA<br>CCTGGGCCGCCGCAAGAATATGATGTGCTGGATAAACGCCGCGGCCGC<br>GATCCGGAAATGGGCGGCAAACCGCCGCGCAAAAACCCGCAGGAAGGC<br>CTGTATAACGAACTGCAGAAAGATAAAATGGCGGAAGCGTATAGCGAAAT<br>TGGCATGAAAGGCGAACGCCGCCGCGGCAAAGGCCATGATGGCCTGTAT<br>CAGGGCCTGAGCACCGCGACCAAAGATACCTATGATGCGCTGCATATGCA<br>GGCGCTGCCGCCGCGC |  |
| PKT7-13 CAR | MALPVTALLLPLALLLHAARPEIVLTQSPGTLSLSPGERATLSCRASQSVSSSY<br>LAWYQQKPGQAPRLLIYGASSRATGIPDRFSGSGSGTDFTLTISRLEPEDFAV<br>YYCQQYGSSPMYTFGQGTKLEIKGGGGSGGGGSGGGGSEVQLVQSGGGL<br>VHPGGSLRLSCAGSGFTFSTYLMYWVRQAPGKTLEWVSAIGSGGDTYYADS<br>VKGRFTISRDNAKNSLYLQMNSLRAEDMAVYYCARGLGYWGQGTLVTVSSA<br>AAFVPVFLPAKTTTPAPRPPTPAPTIASQPLSLRPEACRPAAGGAVHTRGLD<br>FACDIYIWAPLAGTCGVLLLSLVITLYCNHRNRSKRSRLLHSDYMNMTPRRPG<br>PTRKHYQPYAPPRDFAAYRSRVKFSRSADAPAYQQGQNQLYNELNLGRREE<br>YDVLDKRRGRDPEMGGKPRRKNPQEGLYNELQKDKMAEAYSEIGMKGERR<br>RGKGHDGLYQGLSTATKDTYDALHMQALPPR | 73 |
| PTK7-13 scFv | GAAATTGTGCTGACCCAGAGCCCGGGCACCCTGAGCCTGAGCCCGGGCG<br>AACGCGCGACCCTGAGCTGCCGCGCGAGCCAGAGCGTGAGCAGCAGCT<br>ATCTGGCGTGGTATCAGCAGAAACCGGGCCAGGCGCCGCGCCTGCTGAT<br>TTATGGCGCGAGCAGCCGCGCGACCGGCATTCCGGATCGCTTTAGCGGC<br>AGCGGCAGCGGCACCGATTTTACCCTGACCATTAGCCGCCTGGAACCGG<br>AAGATTTTGCGGTGTATTATTGCCAGCAGTATGGCAGCAGCCCGATGTATA<br>CCTTTGGCCAGGGCACCAAACTGGAAATTAAAGGCGGCGGCGGCAGCGG<br>CGGCGGCGGCAGCGGCGGCGGCGGCAGCGAAGTGCAGCTGGTGCAGA<br>GCGGCGGCGGCCTGGTGCATCCGGGCGGCAGCCTGCGCCTGAGCTGCG<br>CGGGCAGCGGCTTTACCTTTAGCACCTATCTGATGTATTGGGTGCGCCAG<br>GCGCCGGGCAAAACCCTGGAATGGGTGAGCGCGATTGGCAGCGGCGGC<br>GATACCTATTATGCGGATAGCGTGAAAGGCCGCTTTACCATTAGCCGCGA<br>TAACGCGAAAAACAGCCTGTATCTGCAGATGAACAGCCTGCGCGCGGAA<br>GATATGGCGGTGTATTATTGCGCGCGCGGCCTGGGCTATTGGGGCCAGG<br>GCACCCTGGTGACCGTGAGCAGC | 74 |
| PTK7-13 scFv (linker underlined) | EIVLTQSPGTLSLSPGERATLSCRASQSVSSSYLAWYQQKPGQAPRLLIYGAS<br>SRATGIPDRFSGSGSGTDFTLTISRLEPEDFAVYYCQQYGSSPMYTFGQGTK<br>LEIKGGGGSGGGGSGGGGSEVQLVQSGGGLVHPGGSLRLSCAGSGFTFST<br>YLMYWVRQAPGKTLEWVSAIGSGGDTYYADSVKGRFTISRDNAKNSLYLQM<br>NSLRAEDMAVYYCARGLGYWGQGTLVTVSS | 75 |
| PTK7-13 scFv VH | EVQLVQSGGGLVHPGGSLRLSCAGSGFTFSTYLMYWVRQAPGKTLEWVSAI<br>GSGGDTYYADSVKGRFTISRDNAKNSLYLQMNSLRAEDMAVYYCARGLGYW<br>GQGTLVTVSS | 76 |
| PTK7-13 scFv VL | EIVLTQSPGTLSLSPGERATLSCRASQSVSSSYLAWYQQKPGQAPRLLIYGAS<br>SRATGIPDRFSGSGSGTDFTLTISRLEPEDFAVYYCQQYGSSPMYTFGQGTK<br>LEIK | 77 |
| PTK7-13 Donor LHA to RHA | GAGATGTAAGGAGCTGCTGTGACTTGCTCAAGGCCTTATATCGAGTAAAC<br>GGTAGTGCTGGGGCTTAGACGCAGGTGTTCTGATTTATAGTTCAAAACCT<br>CTATCAATGAGAGCAATCTCCTGGTAATGTGATAGATTTCCCAACTTAA<br>TGCCAACATACCATAAACCTCCCATTCTGCTAATGCCCAGCTAAGTTGGG<br>GAGACCACTCCAGATTCCAAGATGTACAGTTTGCTTTGCTGGGCCTTTTTC<br>CCATGCCTGCCTTTACTCTGCCAGAGTTATATTGCTGGGGTTTTGAAGAAG<br>ATCCTATTAAATAAAAGAATAAGCAGTATTATTAAGTAGCCCTGCATTTCAG<br>GTTTCCTTGAGTGGCAGGCCAGGCCTGGCCGTGAACGTTCACTGAAATCA<br>TGGCCTCTTGGCCAAGATTGATAGCTTGTGCCTGTCCCTGAGTCCCAGTC<br>CATCACGAGCAGCTGGTTTCTAAGATGCTATTTCCCGTATAAAGCATGAGA<br>CCGTGACTTGCCAGCCCCACAGAGCCCCGCCCTTGTCCATCACTGGCATC<br>TGGACTCCAGCTGGGTTGGGGCAAAGAGGGAAATGAGATCATGTCCTAA<br>CCCTGATCCTCTTGTCCCACAGATATCCAGAACCCTGACCCTGCCGTGTA<br>CCAGCTGAGAGACTCTAAATCCAGTGACAAGTCTGTCTGCCTATTCACCG<br>ATTTTGATTCTCAAACAAATGTGTCACAAAGTAAGGATTCTGATGTGTATAT<br>CACAGACAAAACTGTGCTAGACATGAGGTCTATGGACTTCAGGCTCCGGT<br>GCCCGTCAGTGGGCAGAGCGCACATCGCCCACAGTCCCCGAGAAGTTGG | 78 |

TABLE 11-continued

CAR Components
CAR Structure:
CD8[signal peptide]-anti-Pkt7[scFV]-CD8[tm]-
CD28[co-stimulatory domain]-CD3ζ; or
CD8[signal peptide]-anti-Pkt7[scFV]-CD8[tm]-
41BB[co-stimulatory domain]-CD3ζ

| Name | Sequence | SEQ ID NO: |
|---|---|---|
| | GGGGAGGGGTCGGCAATTGAACCGGTGCCTAGAGAAGGTGGCGCGGGG<br>TAAACTGGGAAAGTGATGTCGTGTACTGGCTCCGCCTTTTTCCCGAGGGT<br>GGGGGAGAACCGTATATAAGTGCAGTAGTCGCCGTGAACGTTCTTTTTCG<br>CAACGGGTTTGCCGCCAGAACACAGGTAAGTGCCGTGTGTGGTTCCCGC<br>GGGCCTGGCCTCTTTACGGGTTATGGCCCTTGCGTGCCTTGAATTACTTC<br>CACTGGCTGCAGTACGTGATTCTTGATCCCGAGCTTCGGGTTGGAAGTGG<br>GTGGGAGAGTTCGAGGCCTTGCGCTTAAGGAGCCCCTTCGCCTCGTGCT<br>TGAGTTGAGGCCTGGCCTGGGCGCTGGGGCCGCCGCGTGCGAATCTGG<br>TGGCACCTTCGCGCCTGTCTCGCTGCTTTCGATAAGTCTCTAGCCATTTAA<br>AATTTTTGATGACCTGCTGCGACGCTTTTTTCTGGCAAGATAGTCTTGTAA<br>ATGCGGGCCAAGATCTGCACACTGGTATTTCGGTTTTTGGGGCCGCGGG<br>CGGCGACGGGGCCCGTGCGTCCCAGCGCACATGTTCGGCGAGGCGGGG<br>CCTGCGAGCGCGGCCACCGAGAATCGGACGGGGGTAGTCTCAAGCTGG<br>CCGGCCTGCTCTGGTGCCTGGCCTCGCGCCGCCGTGTATCGCCCCGCCC<br>TGGGCGGCAAGGCTGGCCCGGTCGGCACCAGTTGCGTGAGCGGAAAGA<br>TGGCCGCTTCCCGGCCCTGCTGCAGGGAGCTCAAAATGGAGGACGCGGC<br>GCTCGGGAGAGCGGGCGGGTGAGTCACCCACACAAAGGAAAAGGGCCTT<br>TCCGTCCTCAGCCGTCGCTTCATGTGACTCCACGGAGTACCGGGCGCCG<br>TCCAGGCACCTCGATTAGTTCTCGAGCTTTTGGAGTACGTCGTCTTTAGGT<br>TGGGGGGAGGGGTTTTATGCGATGGAGTTTCCCCACACTGAGTGGGTGG<br>AGACTGAAGTTAGGCCAGCTTGGCACTTGATGTAATTCTCCTTGGAATTTG<br>CCCTTTTTGAGTTTGGATCTTGGTTCATTCTCAAGCCTCAGACAGTGGTTC<br>AAAGTTTTTTTCTTCCATTTCAGGTGTCGTGACCACCATGGCGCTTCCGGT<br>GACAGCACTGCTCCTCCCCTTGGCGCTGTTGCTCCACGCAGCAAGGCCG<br>GAGATCGTGCTGACCCAGAGCCCCGGAACACTGAGCCTGTCCCCCGGAG<br>AAAGAGCCACACTGTCCTGCAGGGCCAGCCAGAGCGTGAGCAGCTCCTA<br>CCTGGCCTGGTACCAGCAGAAGCCTGGACAGGCCCCCAGGCTGCTGATT<br>TACGGCGCCAGCAGCAGGGCCACCGGCATCCCCGACAGATTCAGCGGAT<br>CCGGCAGCGGCACCGACTTCACCCTGACCATCAGCAGGCTGGAGCCCGA<br>GGACTTCGCTGTGTACTACTGCCAGCAGTACGGCAGCAGCCCCATGTACA<br>CCTTCGGCCAGGGCACCAAGCTGGAGATCAAGGGAGGAGGAGGATCCG<br>GAGGAGGCGGAAGCGGAGGAGGAGGAAGCGAGGTGCAGCTGGTGCAGA<br>GCGGCGGAGGACTGGTGCATCCCGGAGGATCCCTGAGACTGAGCTGTGC<br>CGGCAGCGGATTCACATTCTCCACCTACCTGATGTACTGGGTGAGGCAGG<br>CCCCTGGCAAGACCCTGGAGTGGGTGTCCGCCATTGGCTCCGGCGGAGA<br>CACCTATTATGCCGACTCCGTCAAGGGCAGGTTCACCATCAGCAGAGACA<br>ACGCCAAGAACTCCCTGTACCTGCAGATGAACAGCCTGAGGGCCGAGGA<br>TATGGCTGTGTACTATTGCGCTAGGGGCCTGGGATACTGGGGCCAGGGA<br>ACCCTGGTGACCGTGAGCTCCAGTGCTGCTGCCTTTGTCCCGGTATTTCT<br>CCCAGCCAAACCGACCACGACTCCCGCCCCGCGCCCTCCGACACCCGCT<br>CCCACCATCGCCTCTCAACCTCTTAGTCTTCGCCCCGAGGCATGCCGACC<br>CGCCGCCGGGGGTGCTGTTCATACGAGGGGCTTGGACTTCGCTTGTGAT<br>ATTTACATTTGGGCTCCGTTGGCGGGTACGTGCGGCGTCCTTTTGTTGTC<br>ACTCGTTATTACTTTGTATTGTAATCACAGGAATCGCTCAAAGCGGAGTAG<br>GTTGTTGCATTCCGATTACATGAATATGACTCCTCGCCGGCCTGGGCCGA<br>CAAGAAAACATTACCAACCCTATGCCCCCCCACGAGACTTCGCTGCGTAC<br>AGGTCCCGAGTGAAGTTTTCCCGAAGCGCAGACGCTCCGGCATATCAGCA<br>AGGACAGAATCAGCTGTATAACGAACTGAATTTGGGACGCCGCGAGGAGT<br>ATGACGTGCTTGATAAACGCCGGGGAGAGACCCGGAAATGGGGGGTAA<br>ACCCCGAAGAAAGAATCCCCAAGAAGGACTCTACAATGAACTCCAGAAGG<br>ATAAGATGCGGAGGCCTACTCAGAAATAGGTATGAAGGGCGAACGACG<br>ACGGGGAAAAGGTCACGATGGCCTCTACCAAGGGTTGAGTACGGCAACC<br>AAAGATACGTACGATGCACTGCATATGCAGGCCCTGCCTCCCAGATAATA<br>ATAAAATCGCTATCCATCGAAGATGGATGTGTGTTGGTTTTTTGTGTGTGG<br>AGCAACAAATCTGACTTTGCATGTGCAAACGCCTTCAACAACAGCATTATT<br>CCAGAAGACACCTTCTTCCCCAGCCCAGGTAAGGGCAGCTTTGGTGCCTT<br>CGCAGGCTGTTTCCTTGCTTCAGGAATGGCCAGGTTCTGCCCAGAGCTCT<br>GGTCAATGATGTCTAAAACTCCTCTGATTGGTGGTCTCGGCCTTATCCATT<br>GCCACCAAAACCCTCTTTTTACTAAGAAACAGTGAGCCTTGTTCTGGCAGT<br>CCAGAGAATGACACGGAAAAAGCAGATGAAGAGAAGGTGGCAGGAGA<br>GGGCACGTGGCCCAGCCTCAGTCTCTCCAACTGAGTTCCTGCCTGCCTG<br>CCTTTGCTCAGACTGTTTGCCCCTTACTGCTCTTCTAGGCCTCATTCTAAG<br>CCCCTTCTCCAAGTTGCCTCTCCTTATTTCTCCCTGTCTGCCAAAAAATCTT<br>TCCCAGCTCACTAAGTCAGTCTCACGCAGTCACTCATTAACCCACCAATCA<br>CTGATTGTGCCGGCACATGAATGCACCAGGTGTTGAAGTGGAGGAATTAA<br>AAAGTCAGATGAGGGGTGTGCCCAGAGGAAGCACCATTCTAGTTGGGGG<br>AGCCCATCTGTCAGCTGGGAAAAGTCCAAATAACTTCAGATTGGAATGTGT<br>TTTAACTCAGGGTTGAGAAAACAGCTACCTTCAGGACAAAAGTCAGGGAA<br>GGGCTCTCTGAAGAAATGCTACTTGAAGATACCAGCCCTACCAAGGGCAG<br>GGAGAGGACCCTATAGAGGCCTGGACAGGAGCTCAATGAGAAAGG | |

TABLE 11-continued

CAR Components
CAR Structure:
CD8[signal peptide]-anti-Pkt7[scFV]-CD8[tm]-
CD28[co-stimulatory domain]-CD3ζ; or
CD8[signal peptide]-anti-Pkt7[scFV]-CD8[tm]-
41BB[co-stimulatory domain]-CD3ζ

| Name | Sequence | SEQ ID NO: |
|---|---|---|
| | PTK7-17 | |
| PKT7-17 CAR | ATGGCGCTGCCGGTGACCGCGCTGCTGCTGCCGCTGGCGCTGCTGCTGC<br>ATGCGGCGCGCCCGGAAGTGCAGCTGGTGCAGAGCGGCGGCGGCCTGG<br>TGCATCCGGGCGGCAGCCTGCGCCTGAGCTGCGCGGGCAGCGGCTTTA<br>CCTTTAGCACCTATCTGATGTATTGGGTGCGCCAGGCGCCGGGCAAAACC<br>CTGGAATGGGTGAGCGCGATTGGCAGCGGCGGCGATACCTATTATGCGG<br>ATAGCGTGAAAGGCCGCTTTACCATTAGCCGCGATAACGCGAAAAACAGC<br>CTGTATCTGCAGATGAACAGCCTGCGCGCGGAAGATATGGCGGTGTATTA<br>TTGCGCGCGCGGCCTGGGCTATTGGGGCCAGGGCACCCTGGTGACCGT<br>GAGCAGCGGCGGCGGCGGCAGCGGCGGCGGCGGCAGCGGCGGCGGC<br>GGCAGCGAAATTGTGCTGACCCAGAGCCCGGGCACCCTGAGCCTGAGCC<br>CGGGCGAACGCGCGACCCTGAGCTGCCGCGCGAGCCAGAGCGTGAGCA<br>GCAGCTATCTGGCGTGGTATCAGCAGAAACCGGGCCAGGCGCCGCGCCT<br>GCTGATTTATGGCGCGAGCAGCCGCGCGACCGGCATTCCGGATCGCTTT<br>AGCGGCAGCGGCAGCGGCACCGATTTTACCCTGACCATTAGCCGCCTGG<br>AACCGGAAGATTTTGCGGTGTATTATTGCCAGCAGTATGGCAGCAGCCCG<br>ATGTATACCTTTGGCCAGGGCACCAAACTGGAAATTAAAAGCGCGGCGC<br>GTTTGTGCCGGTGTTTCTGCCGGCGAAACCGACCACCACCCCGGCGCCG<br>CGCCCGCCGACCCCGGCGCCGACCATTGCGAGCCAGCCGCTGAGCCTG<br>CGCCCGGAAGCGTGCCGCCCGGCGGCGGGCGGCGCGGTGCATACCCG<br>CGGCCTGGATTTTGCGTGCGATATTTATATTTGGGCGCCGCTGGCGGGCA<br>CCTGCGGCGTGCTGCTGCTGAGCCTGGTGATTACCCTGTATTGCAACCAT<br>CGCAACCGCAGCAAACGCAGCCGCCTGCTGCATAGCGATTATATGAACAT<br>GACCCCGCGCCGCCCGGGCCCGACCCGCAAACATTATCAGCCGTATGCG<br>CCGCCGCGCGATTTTGCGGCGTATCGCAGCCGCGTGAAATTTAGCCGCA<br>GCGCGGATGCGCCGGCGTATCAGCAGGGCCAGAACCAGCTGTATAACGA<br>ACTGAACCTGGGCCGCCGCGAAGAATATGATGTGCTGGATAAACGCCGC<br>GGCCGCGATCCGGAAATGGGCGGCAAACCGCCGCGCAAAAACCCGCAG<br>GAAGGCCTGTATAACGAACTGCAGAAAGATAAAATGGCGGAAGCGTATAG<br>CGAAATTGGCATGAAAGGCGAACGCCGCCGCGGCAAAGGCCATGATGGC<br>CTGTATCAGGGCCTGAGCACCGCGACCAAAGATACCTATGATGCGCTGCA<br>TATGCAGGCGCTGCCGCCGCGC | 79 |
| PKT7-17 CAR | MALPVTALLLPLALLLHAARPEVQLVQSGGGLVHPGGSLRLSCAGSGFTFSTY<br>LMYWVRQAPGKTLEWVSAIGSGGDTYYADSVKGRFTISRDNAKNSLYLQMN<br>SLRAEDMAVYYCARGLGYWGQGTLVTVSSGGGGSGGGGSGGGGSEIVLTQ<br>SPGTLSLSPGERATLSCRASQSVSSSYLAWYQQKPGQAPRLLIYGASSRATG<br>IPDRFSGSGSGTDFTLTISRLEPEDFAVYYCQQYGSSPMYTFGQGTKLEIKSA<br>AAFVPVFLPAKPTTTPAPRPPTPAPTIASQPLSLRPEACRPAAGGAVHTRGLD<br>FACDIYIWAPLAGTCGVLLLSLVITLYCNHRNRSKRSRLLHSDYMNMTPRRPG<br>PTRKHYQPYAPPRDFAAYRSRVKFSRSADAPAYQQGQNQLYNELNLGRREE<br>YDVLDKRRGRDPEMGGKPRRKNPQEGLYNELQKDKMAEAYSEIGMKGERR<br>RGKGHDGLYQGLSTATKDTYDALHMQALPPR | 80 |
| PTK7-17 scFv | GAAGTGCAGCTGGTGCAGAGCGGCGGCGGCCTGGTGCATCCGGGCGGC<br>AGCCTGCGCCTGAGCTGCGCGGGCAGCGGCTTTACCTTTAGCACCTATCT<br>GATGTATTGGGTGCGCCAGGCGCCGGGCAAAACCCTGGAATGGGTGAGC<br>GCGATTGGCAGCGGCGGCGATACCTATTATGCGGATAGCGTGAAAGGCC<br>GCTTTACCATTAGCCGCGATAACGCGAAAAACAGCCTGTATCTGCAGATG<br>AACAGCCTGCGCGCGGAAGATATGGCGGTGTATTATTGCGCGCGCGGCC<br>TGGGCTATTGGGGCCAGGGCACCCTGGTGACCGTGAGCAGCGGCGGCG<br>GCGGCAGCGGCGGCGGCGGCAGCGGCGGCGGCAGCGAAATTGTG<br>CTGACCCAGAGCCCGGGCACCCTGAGCCTGAGCCCGGGCGAACGCGCG<br>ACCCTGAGCTGCCGCGCGAGCCAGAGCGTGAGCAGCAGCTATCTGGCGT<br>GGTATCAGCAGAAACCGGGCCAGGCGCCGCGCCTGCTGATTTATGGCGC<br>GAGCAGCCGCGCGACCGGCATTCCGGATCGCTTTAGCGGCAGCGGCAG<br>CGGCACCGATTTTACCCTGACCATTAGCCGCCTGGAACCGGAAGATTTTG<br>CGGTGTATTATTGCCAGCAGTATGGCAGCAGCCCGATGTATACCTTTGGC<br>CAGGGCACCAAACTGGAAATTAAA | 81 |
| PTK7-17 scFv (linker underlined) | EVQLVQSGGGLVHPGGSLRLSCAGSGFTFSTYLMYWVRQAPGKTLEWVSAI<br>GSGGDTYYADSVKGRFTISRDNAKNSLYLQMNSLRAEDMAVYYCARGLGYW<br>GQGTLVTVSSGGGGSGGGGSGGGGSEIVLTQSPGTLSLSPGERATLSCRAS<br>QSVSSSYLAWYQQKPGQAPRLLIYGASSRATGIPDRFSGSGSGTDFTLTISRL<br>EPEDFAVYYCQQYGSSPMYTFGQGTKLEIK | 82 |

TABLE 11-continued

CAR Components
CAR Structure:
CD8[signal peptide]-anti-Pkt7[scFV]-CD8[tm]-
CD28[co-stimulatory domain]-CD3ζ; or
CD8[signal peptide]-anti-Pkt7[scFV]-CD8[tm]-
41BB[co-stimulatory domain]-CD3ζ

| Name | Sequence | SEQ ID NO: |
|---|---|---|
| PTK7-17 scFv VH | EVQLVQSGGGLVHPGGSLRLSCAGSGFTFSTYLMYWVRQAPGKTLEWVSAI GSGGDTYYADSVKGRFTISRDNAKNSLYLQMNSLRAEDMAVYYCARGLGY WGQGTLVTVSS | 83 |
| PTK7-17 scFv VL | EIVLTQSPGTLSLSPGERATLSCRASQSVSSSYLAWYQQKPGQAPRLLIYGAS SRATGIPDRFSGSGSGTDFTLTISRLEPEDFAVYYCQQYGSSPMYTFGQGTK LEIK | 84 |
| PTK7-17 VH CDR1 | TYLMY | 85 |
| PTK7-17 VH CDR2 | AIGSGGDTYYADSVKG | 86 |
| PTK7-17 VH CDR3 | GLGY | 87 |
| PTK7-17 VL CDR1 | RASQSVSSSYLA | 88 |
| PTK7-17 VL CDR2 | GASSRAT | 89 |
| PTK7-17 VL CDR3 | QQYGSSPMYT | 90 |
| PTK-17 Donor LHA to RHA | GAGATGTAAGGAGCTGCTGTGACTTGCTCAAGGCCTTATATCGAGTAAAC GGTAGTGCTGGGGCTTAGACGCAGGTGTTCTGATTTATAGTTCAAAACCT CTATCAATGAGAGAGCAATCTCCTGGTAATGTGATAGATTTCCCAACTTAA TGCCAACATACCATAAACCTCCCATTCTGCTAATGCCCAGCCTAAGTTGGG GAGACCACTCCAGATTCCAAGATGTACAGTTTGCTTTGCTGGGCCTTTTTC CCATGCCTGCCTTTACTCTGCCAGAGTTATATTGCTGGGGTTTTGAAGAAG ATCCTATTAAATAAAAGAATAAGCAGTATTATTAAGTAGCCCTGCATTTCAG GTTTCCTTGAGTGGCAGGCCAGGCCTGGCCGTGAACGTTCACTGAAATCA TGGCCTCTTGGCCAAGATTGATAGCTTGTGCCTGTCCCTGAGTCCCAGTC CATCACGAGCAGCTGGTTTCTAAGATGCTATTTCCCGTATAAAGCATGAGA CCGTGACTTGCCAGCCCCACAGAGCCCCGCCCTTGTCCATCACTGGCATC TGGACTCCAGCCTGGGTTGGGGCAAAGAGGGAAATGAGATCATGTCCTAA CCCTGATCCTCTTGTCCCACAGATATCCAGAACCCTGACCCTGCCGTGTA CCAGCTGAGAGACTCTAAATCAGTGACAAGTCTGTCTGCCTATTCACCG ATTTTTGATTCTCAAACAAATGTGTCACAAAGTAAGGATTCTGATGTGTATAT CACAGACAAAACTGTGCTAGACATGAGGTCTATGGACTTCAGGCTCCGGT GCCCGTCAGTGGGCAGAGCGCACATCGCCCACAGTCCCCGAGAAGTTGG GGGGAGGGGTCGGCAATTGAACCGGTGCCTAGAGAAGGTGGCGCGGGG TAAACTGGGAAAGTGATGTCGTGTACTGGCTCCGCCTTTTTCCCGAGGGT GGGGGAGAACCGTATATAAGTGCAGTAGTCGCCGTGAACGTTCTTTTTCG CAACGGGTTTGCCGCCAGAACACAGGTAAGTGCCGTGTGTGGTTCCCGC GGGCCTGGCCTCTTTACGGGTTATGGCCCTTGCGTGCCTTGAATTACTTC CACTGGCTGCAGTACGTGATTCTTGATCCCGAGCTTCGGGTTGGAAGTGG GTGGGAGAGTTCGAGGCCTTGCGCTTAAGGAGCCCCTTCGCCTCGTGCT TGAGTTGAGGCCTGGCCTGGGCGCTGGGGCCGCCGCGTGCGAATCTGG TGGCACCTTCGCGCCTGTCTCGCTGCTTTTCGATAAGTCTCTAGCCATTTAA AATTTTTGATGACCTGCTGCGACGCTTTTTTTCTGGCAAGATAGTCTTGTAA ATGCGGGCCAAGATCTGCACACTGGTATTTCGGTTTTTGGGGCCGCGGG CGGCGACGGGCCCGTGCGTCCCAGCGCACATGTTCGGCGAGGCGGGG CCTGCGAGCGCGGCCACCGAGAATCGGACGGGGGTAGTCTCAAGCTGG CCGGCCTGCTCTGGTGCCTGGCCTCGCGCCGCCGTGTATCCCCGCCC TGGGCGGCAAGGCTGGCCCGGTCGGCACCAGTTGCGTGAGCGGAAAGA TGGCCGCTTCCCGGCCCTGCTGCAGGGAGCTCAAATGGAGGACGCGGC GCTCGGGAGAGCGGGCGGGTGAGTCACCCACACAAAGGAAAAGGGCCTT TCCGTCCTCAGCCGTCGCTTCATGTGACTCCACGGAGTACCGGGCGCCG TCCAGGCACCTCGATTAGTTCTCGAGCTTTTGGAGTACGTCGTCTTTAGGT TGGGGGGAGGGGTTTTATGCGATGGAGTTTCCCCACACTGAGTGGGTGG AGACTGAAGTTAGGCCAGCTTGGCACTTGATGTAATTCTCCTTGGAATTTG CCCTTTTTGAGTTTGGATCTTGGTTCATTCTCAAGCCTCAGACAGTGGTTC AAAGTTTTTTTCTTCCATTTCAGGTGTCGTGACCACCATGGCGCTTCCGGT GACAGCACTGCTCCTCCCCTTGGCGCTGTTGCTCCACGCAGCAAGGCCG GAGGTCCAGCTGGTGCAGAGCGGAGGCGGACTGGTGCATCCTGGAGGC TCCCTGAGACTGTCCTGTGCCGGCAGCGGCTTCACCTTCAGCACCTACCT GATGTACTGGGTGAGACAGGCCCCCGGCAAAACCCTGGAGTGGGTGAGC | 91 |

TABLE 11-continued

CAR Components
CAR Structure:
CD8[signal peptide]-anti-Pkt7[scFV]-CD8[tm]-
CD28[co-stimulatory domain]-CD3ζ; or
CD8[signal peptide]-anti-Pkt7[scFV]-CD8[tm]-
41BB[co-stimulatory domain]-CD3ζ

| Name | Sequence | SEQ ID NO: |
|---|---|---|
| | GCTATCGGCAGCGGCGGAGACACATACTACGCCGACAGCGTGAAGGGCA<br>GGTTCACCATCAGCAGGGACAACGCCAAGAACTCCCTGTACCTGCAGATG<br>AACTCCCTGAGGGCTGAGGACATGGCCGTGTACTACTGCGCTAGAGGCC<br>TGGGCTACTGGGGACAGGGCACACTGGTGACAGTGAGCAGCGGAGGCG<br>GCGGCAGCGGAGGCGGCGGCAGCGGCGGCGGAGGCAGCGAGATCGTG<br>CTGACACAGAGCCCTGGCACCCTGTCCCTGTCCCCTGGCGAAAGGGCCA<br>CCCTGAGCTGTAGGGCCAGCCAGTCCGTGAGCAGCAGCTATCTGGCCTG<br>GTACCAGCAGAAACCCGGCCAGGCCCCTAGACTGCTGATCTACGGCGCC<br>TCCTCCAGAGCCACCGGAATCCCCGATAGATTCAGCGGCTCCGGCAGCG<br>GCACCGATTTCACACTGACCATCAGCAGGCTGGAGCCCGAGGACTTCGC<br>CGTGTATTACTGCCAGCAGTACGGCAGCAGCCCTATGTACACATTCGGCC<br>AGGGCACCAAGCTGGAGATCAAGAGTGCTGCTGCCTTTGTCCCGGTATTT<br>CTCCCAGCCAAACCGACCACGACTCCCGCCCCGCGCCCTCCGACACCCG<br>CTCCCACCATCGCCTCTCAACCTCTTAGTCTTCGCCCCGAGGCATGCCGA<br>CCCGCCGCCGGGGGTGCTGTTCATACGAGGGGCTTGGACTTCGCTTGTG<br>ATATTTACATTTGGGCTCCGTTGGCGGGTACGTGCGGCGTCCTTTTGTTGT<br>CACTCGTTATTACTTTGTATTGTAATCACAGGAATCGCTCAAAGCGGAGTA<br>GGTTGTTGCATTCCGATTACATGAATATGACTCCTCGCCGGCCTGGGCCG<br>ACAAGAAAACATTACCAACCCTATGCCCCCCACGAGACTTCGCTGCGTA<br>CAGGTCCCGAGTGAAGTTTTCCCGAAGCGCAGACGCTCCGGCATATCAG<br>CAAGGACAGAATCAGCTGTATAACGAACTGAATTTGGGACGCCGCGAGGA<br>GTATGACGTGCTTGATAAACGCCGGGGAGAGACCCGGAAATGGGGGGT<br>AAACCCCGAAGAAAGAATCCCCAAGAAGGACTCTACAATGAACTCCAGAA<br>GGATAAGATGGCGGAGGCCTACTCAGAAATAGGTATGAAGGGCGAACGA<br>CGACGGGGAAAAGGTCACGATGGCCTCTACCAAGGGTTGAGTACGGCAA<br>CCAAAGATACGTACGATGCACTGCATATGCAGGCCCTGCCTCCCAGATAA<br>TAATAAAATCGCTATCCATCGAAGATGGATGTGTGTTGGTTTTTTGTGTGT<br>GGAGCAACAAATCTGACTTTGCATGTGCAAACGCCTTCAACAACAGCATTA<br>TTCCAGAAGACACCTTCTTCCCCAGCCCAGGTAAGGGCAGCTTTGGTGCC<br>TTCGCAGGCTGTTTCCTTGCTTCAGGAATGGCCAGGTTCTGCCCAGAGCT<br>CTGGTCAATGATGTCTAAAACTCCTCTGATTGGTGGTCTCGGCCTTATCCA<br>TTGCCACCAAAACCCTCTTTTTACTAAGAAACAGTGAGCCTTGTTCTGGCA<br>GTCCAGAGAATGACACGGGAAAAAAGCAGATGAAGAGAAGGTGGCAGGA<br>GAGGGCACGTGGCCCAGCCTCAGTCTCTCCAACTGAGTTCCTGCCTGCCT<br>GCCTTTGCTCAGACTGTTTGCCCCTTACTGCTCTTCTAGGCCTCATTCTAA<br>GCCCCTTCTCCAAGTTGCCTCTCCTTATTTCTCCCTGTCTGCCAAAAAATC<br>TTTCCCAGCTCACTAAGTCAGTCTCACGCAGTCACTCATTAACCCACCAAT<br>CACTGATTGTGCCGGCACATGAATGCACCAGGTGTTGAAGTGGAGGAATT<br>AAAAAGTCAGATGAGGGGTGTGCCCAGAGGAAGCACCATTCTAGTTGGG<br>GGAGCCCATCTGTCAGCTGGGAAAAGTCCAAATAACTTCAGATTGGAATG<br>TGTTTTAACTCAGGGTTGAGAAAACAGCTACCTTCAGGACAAAAGTCAGG<br>GAAGGGCTCTCTGAAGAAATGCTACTTGAAGATACCAGCCCTACCAAGGG<br>CAGGGAGAGGACCCTATAGAGGCTGGGACAGGAGCTCAATGAGAAAGG | |
| CD8 signal peptide | MALPVTALLLPLALLLHAARP | 93 |
| CD8a transmembrane + 5' Linker (underlined) | GCTGCTGCCTTTGTCCCGGTATTTCTCCCAGCCAAACCGACCACGACTCC<br><u>CGCCCCGCGCCCTCCGACACCCGCTCCCACCATCGCCTCTCAACCTCTTA</u><br>GTCTTCGCCCCGAGGCATGCCGACCCGCCGCCGGGGGTGCTGTTCATAC<br>GAGGGGCTTGGACTTCGCTTGTGATATTTACATTTGGGCTCCGTTGGCGG<br>GTACGTGCGGCGTCCTTTTGTTGTCACTCGTTATTACTTTGTATTGTAATCA<br>CAGGAATCGC | 94 |
| CD8a transmembrane + 5' Linker (underlined) | SAAAFVPVFLPAKPTTTPAPRPPTPAPTIASQPLSLRPEACRPAAGGAVHTRG<br><u>LDFA</u>CDIYIWAPLAGTCGVLLLSLVITLYCNHRNR | 95 |
| CD8a transmembrane (without linker) | TTTGTCCCGGTATTTCTCCCAGCCAAACCGACCACGACTCCCGCCCCGCG<br>CCCTCCGACACCCGCTCCCACCATCGCCTCTCAACCTCTTAGTCTTCGCC<br>CCGAGGCATGCCGACCCGCCGCCGGGGGTGCTGTTCATACGAGGGGCTT<br>GGACTTCGCTTGTGATATTTACATTTGGGCTCCGTTGGCGGGTACGTGCG<br>GCGTCCTTTTGTTGTCACTCGTTATTACTTTGTATTGTAATCACAGGAATCG<br>C | 96 |
| CD8a transmembrane (without linker) | FVPVFLPAKPTTTPAPRPPTPAPTIASQPLSLRPEACRPAAGGAVHTRGLDFA<br>CDIYIWAPLAGTCGVLLLSLVITLYCNHRNR | 97 |

TABLE 11-continued

CAR Components
CAR Structure:
CD8[signal peptide]-anti-Pkt7[scFV]-CD8[tm]-
CD28[co-stimulatory domain]-CD3ζ; or
CD8[signal peptide]-anti-Pkt7[scFV]-CD8[tm]-
41BB[co-stimulatory domain]-CD3ζ

| Name | Sequence | SEQ ID NO: |
|---|---|---|
| CD28 co-stimulatory | TCAAAGCGGAGTAGGTTGTTGCATTCCGATTACATGAATATGACTCCTCGC CGGCCTGGGCCGACAAGAAAACATTACCAACCCTATGCCCCCCCACGAGA CTTCGCTGCGTACAGGTCC | 45 |
| CD28 co-stimulatory | SKRSRLLHSDYMNMTPRRPGPTRKHYQPYAPPRDFAAYRS | 46 |
| 41BB co-stimulatory | AAACGGGGCAGAAAGAAACTCCTGTATATATTCAAACAACCATTTATGAGA CCAGTACAAACTACTCAAGAGGAAGATGGCTGTAGCTGCCGATTTCCAGA AGAAGAAGAAGGAGGATGTGAACTG | 43 |
| 41BB co-stimulatory | KRGRKKLLYIFKQPFMRPVQTTQEEDGCSCRFPEEEEGGCEL | 44 |
| CD3ζ | CGAGTGAAGTTTTCCCGAAGCGCAGACGCTCCGGCATATCAGCAAGGACA GAATCAGCTGTATAACGAACTGAATTTGGGACGCCGCGAGGAGTATGACG TGCTTGATAAACGCCGGGGGAGAGACCCGGAAATGGGGGGTAAACCCCG AAGAAAGAATCCCCAAGAAGGACTCTACAATGAACTCCAGAAGGATAAGAT GGCGGAGGCCTACTCAGAAATAGGTATGAAGGGCGAACGACGACGGGGA AAAGGTCACGATGGCCTCTACCAAGGGTTGAGTACGGCAACCAAAGATAC GTACGATGCACTGCATATGCAGGCCCTGCCTCCCAGA | 98 |
| CD3ζ | RVKFSRSADAPAYQQGQNQLYNELNLGRREEYDVLDKRRGRDPEMGGKPR RKNPQEGLYNELQKDKMAEAYSEIGMKGERRRGKGHDGLYQGLSTATKDTY DALHMQALPPR | 99 |

TABLE 12

Donor Components
Donor structure: TRAC[LHA]-EF1a[promoter]-CAR-polyA-TRAC[RHA]

| Name | Sequence | SEQ ID NO: |
|---|---|---|
| TRAC-LHA | GAGATGTAAGGAGCTGCTGTGACTTGCTC AAGGCCTTATATCGAGTAAACGGTAGTGC TGGGGCTTAGACGCAGGTGTTCTGATTTA TAGTTCAAAACCTCTATCAATGAGAGAGC AATCTCCTGGTAATGTGATAGATTTCCCA ACTTAATGCCAACATACCATAAACCTCCC ATTCTGCTAATGCCCAGCCTAAGTTGGGG AGACCACTCCAGATTCCAAGATGTACAGT TTGCTTTGCTGGGCCTTTTTCCCATGCCT GCCTTTACTCTGCCAGAGTTATATTGCTG GGGTTTTGAAGAAGATCCTATTAAATAAA AGAATAAGCAGTATTATTAAGTAGCCCTG CATTTCAGGTTTCCTTGAGTGGCAGGCCA GGCCTGGCCGTGAACGTTCACTGAAATCA TGGCCTCTTGGCCAAGATTGATAGCTTGT GCCTGTCCCTGAGTCCCAGTCCATCACGA GCAGCTGGTTTCTAAGATGCTATTTCCCG TATAAAGCATGAGACCGTGACTTGCCAGC CCCACAGAGCCCCGCCCTTGTCCATCACT GGCATCTGGACTCCAGCCTGGGTTGGGGC AAAGAGGGAAATGAGATCATGTCCTAACC CTGATCCTCTTGTCCCACAGATATCCAGA ACCCTGACCCTGCCGTGTACCAGCTGAGA GACTCTAAATCCAGTGACAAGTCTGTCTG CCTATTCACCGATTTTGATTCTCAAACAA ATGTGTCACAAAGTAAGGATTCTGATGTG TATATCACAGACAAAACTGTGCTAGACAT GAGGTCTATGGACTTCA | 100 |
| EF1α promoter | GGCTCCGGTGCCCGTCAGTGGGCAGAGCG CACATCGCCCACAGTCCCCGAGAAGTTGG GGGGAGGGGTCGGCAATTGAACCGGTGCC TAGAGAAGGTGGCGCGGGGTAAACTGGGA AAGTGATGTCGTGTACTGGCTCCGCCTTT TTCCCGAGGGTGGGGGAGAACCGTATATA AGTGCAGTAGTCGCCGTGAACGTTCTTTT TCGCAACGGGTTTGCCGCCAGAACACAGG TAAGTGCCGTGTGTGGTTCCCGCGGGCCT GGCCTCTTTACGGGTTATGGCCCTTGCGT GCCTTGAATTACTTCCACTGGCTGCAGTA CGTGATTCTTGATCCCGAGCTTCGGGTTG GAAGTGGGTGGGAGAGTTCGAGGCCTTGC GCTTAAGGAGCCCCTTCGCCTCGTGCTTG AGTTGAGGCCTGGCCTGGGCGCTGGGGCC GCCGCGTGCGAATCTGGTGGCACCTTCGC GCCTGTCTCGCTGCTTTCGATAAGTCTCT AGCCATTTAAAATTTTTGATGACCTGCTG CGACGCTTTTTTTCTGGCAAGATAGTCTT GTAAATGCGGGCCAAGATCTGCACACTGG TATTTCGGTTTTTGGGGCCGCGGGCGGCG ACGGGGCCCGTGCGTCCCAGCGCACATGT TCGGCGAGGCGGGGCCTGCGAGCGCGGCC ACCGAGAATCGGACGGGGGTAGTCTCAAG CTGGCCGGCCTGCTCTGGTGCCTGGCCTC GCGCCGCCGTGTATCGCCCCGCCCTGGGC GGCAAGGCTGGCCCGGTCGGCACCAGTTG CGTGAGCGGAAAGATGGCCGCTTCCCGGC CCTGCTGCAGGGAGCTCAAAATGGAGGAC GCGGCGCTCGGGAGAGCGGGCGGGTGAGT CACCCACACAAAGGAAAAGGGCCTTTCCG TCCTCAGCCGTCGCTTCATGTGACTCCAC GGAGTACCGGGCGCCGTCCAGGCACCTCG ATTAGTTCTCGAGCTTTTGGAGTACGTCG TCTTTAGGTTGGGGGGAGGGGTTTTATGC | 101 |

TABLE 12-continued

Donor Components
Donor structure: TRAC[LHA]-EF1a[promoter]-CAR-polyA-TRAC[RHA]

| Name | Sequence | SEQ ID NO: |
|---|---|---|
| | GATGGAGTTTCCCCACACTGAGTGGGTGG<br>AGACTGAAGTTAGGCCAGCTTGGCACTTG<br>ATGTAATTCTCCTTGGAATTTGCCCTTTT<br>TGAGTTTGGATCTTGGTTCATTCTCAAGC<br>CTCAGACAGTGGTTCAAAGTTTTTTTCTT<br>CCATTTCAGGTGTCGTGA | |
| Synthetic poly(A) signal | AATAAAATCGCTATCCATCGAAGATGGAT<br>GTGTGTTGGTTTTTTGTGTG | 102 |
| TRAC-RHA | TGGAGCAACAAATCTGACTTTGCATGTGC<br>AAACGCCTTCAACAACAGCATTATTCCAG<br>AAGCACCTTCTTCCCCAGCCCAGGTAAG<br>GGCAGCTTTGGTGCCTTCGCAGGCTGTTT<br>CCTTGCTTCAGGAATGGCCAGGTTCTGCC<br>CAGAGCTCTGGTCAATGATGTCTAAAACT<br>CCTCTGATTGGTGGTCTCGGCCTTATCCA<br>TTGCCACCAAAACCCTCTTTTTACTAAGA<br>AACAGTGAGCCTTGTTCTGGCAGTCCAGA<br>GAATGACACGGGAAAAAAGCAGATGAAGA<br>GAAGGTGGCAGGAGAGGGCACGTGGCCCA<br>GCCTCAGTCTCTCCAACTGAGTTCCTGCC<br>TGCCTGCCTTTGCTCAGACTGTTTGCCCC<br>TTACTGCTCTTCTAGGCCTCATTCTAAGC<br>CCCTTCTCCAAGTTGCCTCTCCTTATTTC<br>TCCCTGTCTGCCAAAAAATCTTTCCCAGC<br>TCACTAAGTCAGTCTCACGCAGTCACTCA<br>TTAACCCACCAATCACTGATTGTGCCGGC<br>ACATGAATGCACCAGGTGTTGAAGTGGAG<br>GAATTAAAAAGTCAGATGAGGGGTGTGCC<br>CAGAGGAAGCACCATTCTAGTTGGGGGAG<br>CCCATCTGTCAGCTGGGAAAAGTCCAAAT<br>AACTTCAGATTGGAATGTGTTTTAACTCA<br>GGGTTGAGAAAACAGCTACCTTCAGGACA<br>AAAGTCAGGGAAGGGCTCTCTGAAGAAAT<br>GCTACTTGAAGATACCAGCCCTACCAAGG<br>GCAGGGAGAGGACCCTATAGAGGCCTGGG<br>ACAGGAGCTCAATGAGAAAGG | 92 |

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

What is claimed is:

1. An engineered T cell comprising a nucleic acid encoding a chimeric antigen receptor (CAR) that binds protein tyrosine kinase 7 (PTK7), wherein the CAR comprises an ectodomain comprising an anti-PTK7 single-chain variable fragment (scFv) having the amino acid sequence of SEQ ID NO: 54 and a CD28 co-stimulatory domain.

2. The engineered T cell of claim 1 further comprising a disrupted T cell receptor alpha chain constant region (TRAC) gene.

3. The engineered T cell of claim 2, wherein the nucleic acid encoding the CAR is inserted into the disrupted TRAC gene.

4. The engineered T cell of claim 2, wherein the disrupted TRAC gene comprises the nucleotide sequence of SEQ ID NO: 63.

5. The engineered T cell of claim 1 further comprising a disrupted beta-2-microglobulin (β2M) gene.

6. The engineered T cell of claim 1, wherein the CAR further comprises a CD3 cytoplasmic signaling domain.

7. The engineered T cell of claim 1, wherein the CAR is encoded by the nucleotide sequence of SEQ ID NO: 49 or 112 or a nucleotide sequence comprising a nucleic acid sequence that is at least 90% identical to SEQ ID NO: 49 or 112.

8. The engineered T cell of claim 1, wherein the T cell is a human T cell.

9. A population of cells comprising the engineered T cell of claim 1, wherein at least 25% or at least 50% of engineered T cells of the population express the CAR.

10. A method comprising administering the population of engineered T cells of claim 9 to a subject.

11. The engineered T cell of claim 1, wherein the CAR comprises the amino acid sequence of SEQ ID NO: 50.

12. A population of engineered T cells comprising the engineered T cells of claim 11.

13. A method for producing an engineered T cell, the method comprising
   (a) delivering to a T cell
   (i) a RNA-guided nuclease,
   (ii) a gRNA targeting a TRAC gene, and
   (iii) a vector comprising a donor template that comprises a nucleic acid encoding a CAR that comprise an ectodomain that binds specifically to PTK7, which comprises an anti-PTK7 single-chain variable fragment (scFv); wherein the anti-PTK7 scFv comprises the amino acid sequence of SEQ ID NO: 54; and
   (b) producing an engineered T cell having a disrupted TRAC gene and expressing the CAR.

14. The method of claim 13, wherein the gRNA targeting the TRAC gene comprises the nucleotide sequence of SEQ ID NO: 18 or 19, or targets the nucleotide sequence of SEQ ID NO: 40.

15. The method of claim 13 further comprising delivering to the T cell a gRNA targeting the β2M gene.

16. The method of claim 15, wherein the gRNA targeting the β2M gene comprises the nucleotide sequence of SEQ ID NO: 20 or 21, or targets the nucleotide sequence of SEQ ID NO: 41.

17. The method of claim 13, wherein the CAR further comprises a CD28 co-stimulatory domain or a 41BB co-stimulatory domain.

18. The method of claim 17, wherein the CAR further comprises a CD3 cytoplasmic signaling domain.

19. The method of claim 13, wherein the CAR is encoded by a nucleotide sequence of any one of SEQ ID NOs: 49 and 112 or a nucleotide sequence comprising a nucleic acid sequence that is at least 90% identical to SEQ ID NOs: 49 or 112.

20. The method of claim 13, wherein the nucleic acid encoding the CAR is flanked by left and right homology arms to the TRAC gene.

21. The method of claim 13, wherein the donor template comprises the nucleotide sequence of any one of SEQ ID NOs: 63.

22. An engineered T cell produced by the method of claim 13.

23. A population of cells comprising the engineered T cell of claim 22.

24. A method of treating cancer in a subject, comprising administering to the subject the population of cells of claim 23.

* * * * *